United States Patent [19]
Sgarlato

[11] Patent Number: 5,935,824
[45] Date of Patent: Aug. 10, 1999

[54] PROTEIN EXPRESSION SYSTEM

[75] Inventor: Gregory D. Sgarlato, Los Gatos, Calif.

[73] Assignee: Technologene, Inc., Los Gatos, Calif.

[21] Appl. No.: 08/595,043

[22] Filed: Jan. 31, 1996

[51] Int. Cl.$^6$ .............................. C07K 19/00; C12N 15/62
[52] U.S. Cl. ..................... 435/69.7; 435/69.8; 530/350; 536/23.4
[58] Field of Search .................... 435/69.7, 69.8, 435/207, 68.1; 436/532, 828; 530/387.1, 350, 413, 812, 866, 867; 536/23.4, 23.2, 23.53, 23.7; 935/47

[56] References Cited

U.S. PATENT DOCUMENTS

| | | | |
|---|---|---|---|
| 4,769,326 | 9/1988 | Rutter | 435/68.1 |
| 4,782,137 | 11/1988 | Hopp et al. | 530/328 |
| 4,880,911 | 11/1989 | Brewer et al. | 530/351 |
| 5,013,653 | 5/1991 | Huston et al. | 435/69.7 |
| 5,087,564 | 2/1992 | Mai et al. | 435/69.7 |
| 5,202,239 | 4/1993 | Tarnowski et al. | 435/69.7 |
| 5,225,538 | 7/1993 | Capon et al. | 530/387.3 |
| 5,310,876 | 5/1994 | Bayer et al. | 530/350 |
| 5,409,895 | 4/1995 | Morishita et al. | 514/12 |
| 5,416,007 | 5/1995 | Charette et al. | 435/68.1 |
| 5,447,851 | 9/1995 | Beutler et al. | 435/69.7 |
| 5,482,858 | 1/1996 | Huston et al. | 435/252.33 |
| 5,506,120 | 4/1996 | Yamamoto et al. | 435/69.7 |
| 5,532,142 | 7/1996 | Johnston et al. | 435/69.1 |

OTHER PUBLICATIONS

Maina et al. An *Escherichia coil* vector to express and purify foreign proteins by fusion to and separation from maltose–binding protein. Gene. vol. 74, pp. 365–373, 1988.

*Primary Examiner*—John Ulm
*Attorney, Agent, or Firm*—Medlen & Carroll, LLP

[57] ABSTRACT

The present invention relates to improved recombinant vectors which allow for the production of fusion proteins. The present invention also relates to methods for the expression and purification of authentic recombinant proteins from such fusion proteins. In particular, the present invention relates to fusion proteins wherein additional domains and/or elements are added to the fusion proteins.

23 Claims, 44 Drawing Sheets

LEVEL 1 PROCESSING

LEVEL 2 PROCESSING

1

2

3

4

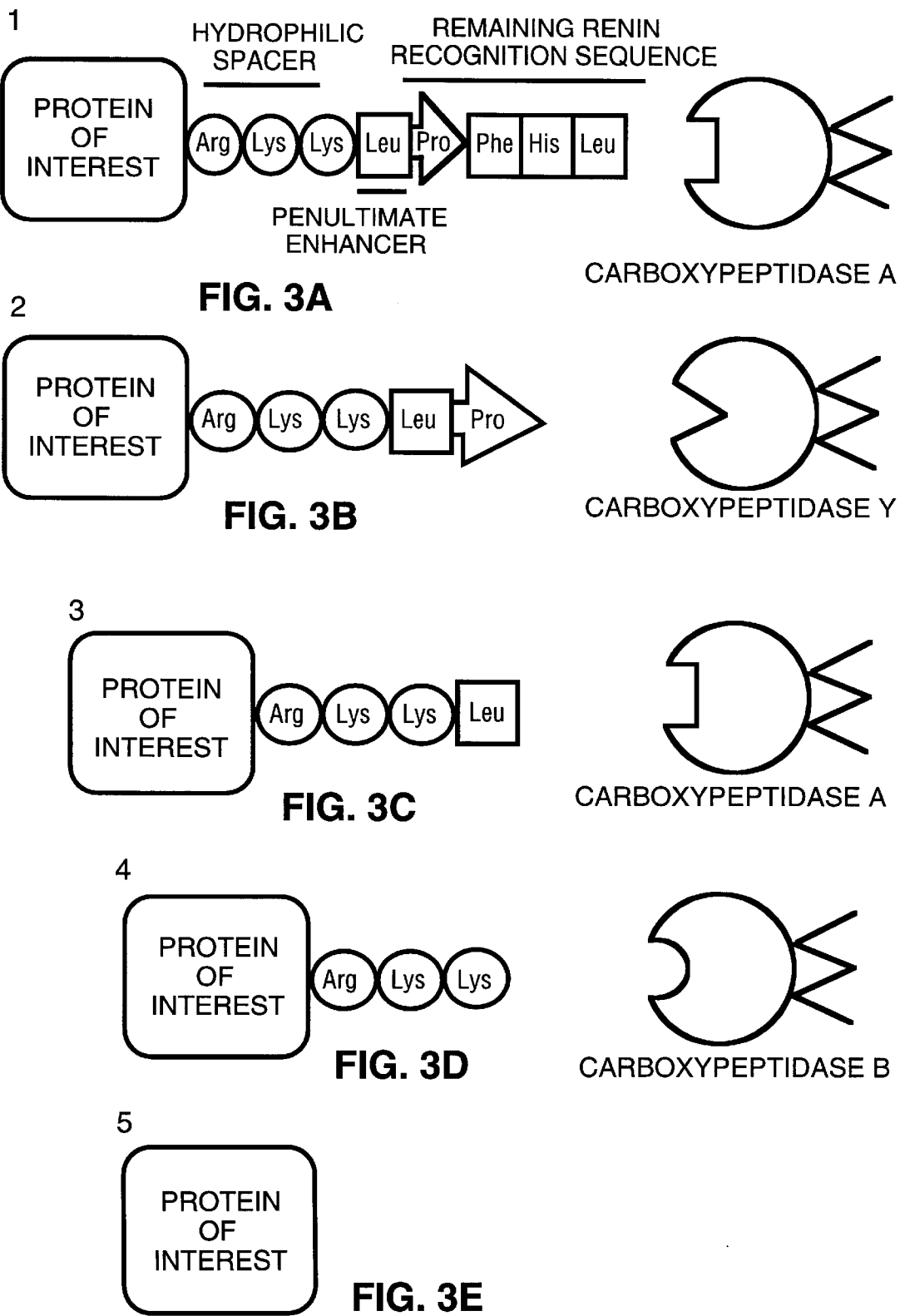

FIG. 10A

HUMAN IgG 1 FRAGMENT
(SEQ ID NO:49,50)

```
       222 223 224 225 226 227 228 229 230 231 232
GAG CCC AAA TCT TGT GAC ACA ACT CAC ACA TGC CCA CCG TGC CCA GCA CCA GAA
CTC GGG TTT AGA ACA CTG TGT TGA GTG TGT ACG GGT GGC ACG GGT CGT GGT CTT
▸Glu Pro Lys Ser Cys Asp Lys Thr His Thr Cys Pro Pro Cys Pro Ala Pro Glu

CTC CTG GGG GGA CCG TCA GTC TTC CTC TTC CCC CCA AAA CCC AAG GAC ACC CTC
GAG GAC CCC CCT GGC AGT CAG AAG GAG AAG GGG GGT TTT GGG TTC CTG TGG GAG
▸Leu Leu Gly Gly Pro Ser Val Phe Leu Phe Pro Pro Lys Pro Lys Asp Thr Leu

ATG ATC TCC CGG ACC CCT GAG GTC ACA TGC GTG GTG GTG GAC GTG AGC CAC GAA
TAC TAG AGG GCC TGG GGA CTC CAG TGT ACG CAC CAC CTG CAC TCG GTG CTT
▸Met Ile Ser Arg Thr Pro Glu Val Thr Cys Val Val Val Asp Val Ser His Glu

GAC CCT GAG GTC AAG TTC AAC TGG TAC GTG GAC GGC GTG GAG GTG CAT AAT GCC
CTG GGA CTC CAG TTC AAG TTG ACC ATG CAC CTG CCG CAC CTC CAC GTA TTA CGG
▸Asp Pro Glu Val Lys Phe Asn Trp Tyr Val Asp Gly Val Glu Val His Asn Ala

AAG ACA AAG CCG CGG GAG GAG CAG TAC AAC AGC ACG TAC CGG GTG GTC AGC GTC
TTC TGT TTC GGC GCC CTC CTC GTC ATG TTG TCG TGC ATG GCC CAC CAG TCG CAG
▸Lys Thr Lys Pro Arg Glu Glu Gln Tyr Asn Ser Thr Tyr Arg Val Val Ser Val

CTC ACC GTC CTG CAC CAG GAC TGG CTG AAT GGC AAG GAG TAC AAG TGC AAG GTC
GAG TGG CAG GAC GTG GTC CTG ACC GAC TTA CCG TTC CTC ATG TTC ACG TTC CAG
▸Leu Thr Val Leu His Gln Asp Trp Leu Asn Gly Lys Glu Tyr Lys Cys Lys Val

TCC AAC AAA GCC CTC CCA GCC CCC ATC GAG AAA ACC ATC TCC AAA GCC AAA GGG
AGG TTG TTT CGG GAG GGT CGG GGG TAG CTC TTT TGG TAG AGG TTT CGG TTT CCC
▸Ser Asn Lys Ala Leu Pro Ala Pro Ile Glu Lys Thr Ile Ser Lys Ala Lys Gly
```

FIG. 10B

```
CAG CCC CGA GAA CCA CAG GTG TAC ACC CTG CCC CCA TCC CGG GAT GAG CTG ACC
GTC GGG GCT CTT GGT GTC CAC ATG TGG GAC GGG GGT AGG GCC CTA CTC GAC TGG
►Gln Pro Arg Glu Pro Gln Val Tyr Thr Leu Pro Pro Ser Arg Asp Glu Leu Thr

AAC CAG GTC AGC CTG ACC TGC CTG GTC AAA GGC TTC TAT CCC AGC GAC ATC
TTG GTC CAG TCG GAC TGG ACG GAC CAG TTT CCG AAG ATA GGG TCG CTG TAG
►Lys Asn Gln Val Ser Leu Thr Cys Leu Val Lys Gly Phe Tyr Pro Ser Asp Ile

GCC GTG GAG TGG GAG AGC AAT GGG CAG CCG GAG AAC AAC TAC AAG ACC ACG CCT
CGG CAC CTC ACC CTC TCG TTA CCC GTC GGC CTC TTG TTG ATG TTC TGG TGC GGA
►Ala Val Glu Trp Glu Ser Asn Gly Gln Pro Glu Asn Asn Tyr Lys Thr Thr Pro

CCC GTG CTG GAC TCC AGG TGG CAG CAG GGG AAC GTC TTC TCA TGC TCC GTG GAC
GGG CAC GAC CTG AGG TCC ACC GTC GTC CCC TTG CAG AAG AGT ACG AGG CAC CTG
►Pro Val Leu Asp Ser Arg Trp Gln Gln Gly Asn Val Phe Ser Cys Ser Val Asp

AAG AGC AGG TGG CAG CAG GGG AAC GTC TTC TCG TAC AGC GTG ATG CAT GAG GCT
TTC TCG TCC ACC GTC GTC CCC TTG CAG AAG AGC ATG TCG CAC TAC GTA CTC CGA
►Lys Ser Arg Trp Gln Gln Gly Asn Val Phe Ser Tyr Ser Val Met His Glu Ala

CTG CAC AAC CAC TAC ACG CAG AAG AGC CTC TCC CTG TCT CCG GGT AAA TGA
GAC GTG TTG GTG ATG TGC GTC TTC TCG GAG AGG GAC AGA GGC CCA TTT ACT
►Leu His Asn His Tyr Thr Gln Lys Ser Leu Ser Leu Ser Pro Gly Lys ***
```

HINGE VARIATIONS/ PCR OLIGOS

SEQ ID NO:51

NgoMI
↓
CCCC CGC CGG CAC ACA TGC CCA CCG TGC CCA GCA
     ▲Arg Arg His Thr Cys Pro Pro Cys Pro Ala

SEQ ID NO:52

SalI
↓
C CCC CGT CGA CGG ACA TGC CCA CCG TGC CCA
     ▲Arg Arg Arg Thr Cys Pro Pro Cys Pro

SEQ ID NO:53

KpnI
↓
GG GGT ACC CAC ACA TGC CCA CCG TGC CCA GCA CCT
   ▲Gly Thr His Thr Cys Pro Pro Cys Pro Ala Pro

FIG. 11 pho SIGNAL SEQUENCE (SEQ ID NO:61)

SEQ ID NO:57

C ATG AAA CAA AGC ACT ATT GCA CTG GCT TTA CTG TTT ACC CCT GTG ACA AA
  TTT GTT TCG TGA TAA CGT GAC CGA AAT GGC AAT GAC AAA TGG GGA CAC TGT TTT CGA
▸Met Lys Gln Ser Thr Ile Ala Leu Ala Leu Pro Leu Phe Thr Pro Val Thr Lys Ala

SEQ ID NO:58

SEQ ID NO:59

SEQ ID NO:60

FIG. 13

THROMBIN LINKER SEQUENCE

SEQ ID NO:68

```
    Nrul
GATCT TCG CGA AAG AAG AAG CTG GTT CCG CGG GGT AC
    A AGC GCT TTC TTC GAC CAA GGC GCC C
      ▸Arg Lys Lys Lys Leu Val Pro Arg Gly
```

SEQ ID NO:69

RENIN LINKER SEQUENCE

SEQ ID NO:64

```
    Nrul
GATCT TCG CGA AAG AAG AAG CTT CCG TTT CAC CTG CTG GTC TAC GGT AC
    A AGC GCT TTC TTC GAA GGC AAA GTG GAC GAC CAG ATG C
      ▸Arg Lys Lys Lys Leu Pro Phe His Leu Leu Val Tyr Gly
```

SEQ ID NO:65

FIG. 22

| >2,000 | >2,000 | >2,000 | >2,000 | >2,000 | >2,000 | >2,00 | >500 | >500 | >500 | >500 |
|---|---|---|---|---|---|---|---|---|---|---|
| Ala-Ala | Ile-Ala | Leu-Ala | Met-Ala | Phe-Ala | Trp-Ala | Val-Ala | Ala-Arg | Ile-Arg | Leu-Arg | Met-Arg |
| Ala-Ile | Ile-Ile | Leu-Ile | Met-Ile | Phe-Ile | Trp-Ile | Val-Ile | Ala-Asn | Ile-Asn | Leu-Asn | Met-Asn |
| Ala-Met | Ile-Met | Leu-Met | Met-Met | Phe-Met | Trp-Met | Val-Met | Ala-Asp | Ile-Asp | Leu-Asp | Met-Asp |
| Ala-Leu | Ile-Leu | Leu-Leu | Met-Leu | Phe-Leu | Trp-Leu | Val-Leu | Ala-Cys | Ile-Cys | Leu-Cys | Met-Cys |
| Ala-Phe | Ile-Phe | Leu-Phe | Met-Phe | Phe-Phe | Trp-Phe | Val-Phe | Ala-Gln | Ile-Gln | Leu-Gln | Met-Gln |
| Ala-Trp | Ile-Trp | Leu-Trp | Met-Trp | Phe-Trp | Trp-Trp | Val-Trp | Ala-Gly | Ile-Gly | Leu-Gly | Met-Gly |
| Ala-Val | Ile-Val | Leu-Val | Met-Val | Phe-Val | Trp-Val | Val-Val | Ala-His | Ile-His | Leu-His | Met-His |
|  |  |  |  |  |  |  | Ala-Lys | Ile-Lys | Leu-Lys | Met-Lys |
|  |  |  |  |  |  |  | Ala-Pro | Ile-Pro | Leu-Pro | Met-Pro |
|  |  |  |  |  |  |  | Ala-Ser | Ile-Ser | Leu-Ser | Met-Ser |
|  |  |  |  |  |  |  | Ala-Thr | Ile-Thr | Leu-Thr | Met-Thr |
|  |  |  |  |  |  |  | Ala-Tyr | Ile-Tyr | Leu-Tyr | Met-Tyr |

| >500 | >500 | >500 | >250 | >250 | >250 | >250 | >216 | >150 | >120 | >120 |
|---|---|---|---|---|---|---|---|---|---|---|
| Phe-Arg | Trp-Arg | Val-Arg | Ser-Ala | Tyr-Ala | Gln-Ala | Asn-Ala | Glu-Ala | Asp-Ala | Gly-Ala | Cys-Ala |
| Phe-Asn | Trp-Asn | Val-Asn | Ser-Ile | Tyr-Ile | Gln-Ile | Asn-Ile | Glu-Ile | Asp-Ile | Gly-Ile | Cys-Ile |
| Phe-Asp | Trp-Asp | Val-Asp | Ser-Met | Tyr-Met | Gln-Met | Asn-Met | Glu-Met | Asp-Met | Gly-Met | Cys-Met |
| Phe-Cys | Trp-Cys | Val-Cys | Ser-Leu | Tyr-Leu | Gln-Leu | Asn-Leu | Glu-Leu | Asp-Leu | Gly-Leu | Cys-Leu |
| Phe-Gln | Trp-Gln | Val-Gln | Ser-Phe | Tyr-Phe | Gln-Phe | Asn-Phe | Glu-Phe | Asp-Phe | Gly-Phe | Cys-Phe |
| Phe-Gly | Trp-Gly | Val-Gly | Ser-Trp | Tyr-Trp | Gln-Trp | Asn-Trp | Glu-Trp | Asp-Trp | Gly-Trp | Cys-Trp |
| Phe-His | Trp-His | Val-His | Ser-Val | Tyr-Val | Gln-Val | Asn-Val | Glu-Val | Asp-Val | Gly-Val | Cys-Val |
| Phe-Lys | Trp-Lys | Val-Lys |  |  |  |  |  |  |  |  |
| Phe-Pro | Trp-Pro | Val-Pro |  |  |  |  |  |  |  |  |
| Phe-Ser | Trp-Ser | Val-Ser |  |  |  |  |  |  |  |  |
| Phe-Thr | Trp-Thr | Val-Thr |  |  |  |  |  |  |  |  |
| Phe-Tyr | Trp-Tyr | Val-Tyr |  |  |  |  |  |  |  |  |

FIG. 30A

| >50 | >50 | >25 | >25 | >25 | >25 | >20 | >10 | <12 | <5 | <5 |
|---|---|---|---|---|---|---|---|---|---|---|
| Thr-Ala | Tyr-Arg | Gln-Arg | Asn-Arg | Pro-Ala | Glu-Arg | Arg-Ala | Gly-Arg | Thr-Arg | His-Arg |
| Thr-Ile | Tyr-Asn | Gln-Asn | Asn-Asn | Pro-Ile | Glu-Asn | Arg-Ile | Gly-Asn | Thr-Asn | His-Asn |
| Thr-Met | Tyr-Asp | Gln-Asp | Asn-Asp | Pro-Met | Glu-Asp | Arg-Met | Gly-Asp | Thr-Asp | His-Asp |
| Thr-Leu | Tyr-Cys | Gln-Cys | Asn-Cys | Pro-Leu | Glu-Cys | Arg-Leu | Gly-Cys | Thr-Cys | His-Cys |
| Thr-Phe | Tyr-Glu | Gln-Glu | Asn-Glu | Pro-Phe | Glu-Gln | Arg-Phe | Gly-Gln | Thr-Gln | His-Gln |
| Thr-Trp | Tyr-Gln | Gln-Gln | Asn-Gln | Pro-Trp | Glu-Glu | Arg-Trp | Gly-Glu | Thr-Glu | His-Glu |
| Thr-Val | Tyr-Gly | Gln-Gly | Asn-Gly | Pro-Val | Glu-Gly | Arg-Val | Gly-Gly | Thr-Gly | His-Gly |
| | Tyr-His | Gln-His | Asn-His | | Glu-His | | Gly-His | Thr-His | His-His |
| | Tyr-Lys | Gln-Lys | Asn-Lys | | Glu-Lys | | Gly-Lys | Thr-Lys | His-Lys |
| | Tyr-Pro | Gln-Pro | Asn-Pro | | Glu-Pro | | Gly-Pro | Thr-Pro | His-Pro |
| | Tyr-Ser | Gln-Ser | Asn-Ser | | Glu-Ser | | Gly-Ser | Thr-Ser | His-Ser |
| | Tyr-Thr | Gln-Thr | Asn-Thr | | Glu-Thr | | Gly-Thr | Thr-Thr | His-Thr |
| | Tyr-Tyr | Gln-Tyr | Asn-Tyr | | Glu-Tyr | | Gly-Tyr | Thr-Tyr | His-Tyr |

| <5 | <1 | <1 | <0.1 |
|---|---|---|---|
| Pro-Arg / Asp-Arg | Lys-Ala | Arg-Arg | Lys-Arg |
| Pro-Asn / Asp-Asn | Lys-Ile | Arg-Asn | Lys-Asn |
| Pro-Asp / Asp-Asp | Lys-Met | Arg-Asp | Lys-Asp |
| Pro-Cys / Asp-Cys | Lys-Leu | Arg-Cys | Lys-Cys |
| Pro-Gln / Asp-Gln | Lys-Phe | Arg-Gln | Lys-Gln |
| Pro-Glu / Asp-Glu | Lys-Trp | Arg-Glu | Lys-Glu |
| Pro-Gly / Asp-Gly | Lys-Val | Arg-Gly | Lys-Gly |
| Pro-His / Asp-His | | Arg-His | Lys-His |
| Pro-Lys / Asp-Lys | | Arg-Lys | Lys-Lys |
| Pro-Pro / Asp-Pro | | Arg-Pro | Lys-Pro |
| Pro-Ser / Asp-Ser | | Arg-Ser | Lys-Ser |
| Pro-Thr / Asp-Thr | | Arg-Thr | Lys-Thr |
| Pro-Tyr / Asp-Tyr | | Arg-Tyr | Lys-Tyr |

FIG. 30B

```
-121                      -110
ATG TCC ATG TTG TTC TAC ACT CTG ATC ACA GCT TTT AAA GAC TAG ATC GGC ATA CAG GCG GAA CCA CAC
TAC AGG TAC AAC AAG ATG TGA GAC TAG TGT CGA AAA TTT CTG ATC TAG CCG TAT GTC CGC CTT GGT GTG
Met Ser Met Leu Phe Tyr Thr Leu Ile Thr Ala Phe Lys Asp * Ile Gly Ile Gln Ala Glu Pro His
                                                                                         -80
-100                   -90
TCA GAG AGC AAT GTC CCT GCA GGA CAC ACC ATC CCC CAA GTC CAC TGG ACT AAA CTT CAG GTC CAT
AGT CTC TCG TTA CAG GGA CGT CCT GTG TGG TAG GGG GTT CAG GTG ACC TGA TTT GAA GTC CAG GTA
Ser Glu Ser Asn Val Pro Ala Gly His Thr Ile Pro Gln Val His Trp Thr Lys Leu Gln Val His
                              -70                                                     -60
TCC CTT GAC ACT GCC CTT CGC AGA GCC CGC GAC GTG GAC CCT CCC CGT GAA GCT GCA CGC GCG GTG
AGG GAA CTG TGA CGG GAA GCG TCT CGG GCG CTG CAC CTG GGA GGG GCA CTT CGA CGT GCG CGC CAC
Ser Leu Asp Thr Ala Leu Arg Arg Ala Arg Asp Val Asp Pro Pro Arg Glu Ala Arg Ala Arg Val
                              -50                                                     -40
GCG GGG CAG ACC CGC AAC ATT ACT GTG CAC CCT CCC GGG CGT GAA CTT GCA GCG GCG ATA CTC CGT
CGC CCC GTC TGG GCG TTG TAA TGA CAC GTG GGA GGG CCC GCA CTT GAA CGT CGC CGC TAT GAG GCA
Ala Gly Gln Thr Arg Asn Ile Thr Val His Pro Pro Gly Arg Glu Leu Ala Ala Ala Ile Leu Arg
                              -30                                              -20
CCC CGT GTG CTG TTT AGC ACC CAG CCT GAC CTG TTT AAA AAG CGG GAC ACT CAG GAT CTG GAC TTC
GGG GCA CAC GAC AAA TCG TGG GTC GGA CTG GAC AAA TTT TTC GCC CTG TGA GTC CTA GAC CTG AAG
Pro Arg Val Leu Phe Ser Thr Gln Pro Asp Leu Phe Lys Lys Arg Asp Thr Gln Asp Leu Asp Phe
                              -10                                    -1   +1
GAG GTC GGT GGT GCT GCC CCC TTC AAC AGG ACT CAC GTG TCC TCG TTC GCC CGG|TCA TCC CAT CCC
CTC CAG CCA CCA CGA CGG GGG AAG TTG TCC TGA GTG CAC AGG AGC AAG CGG GCC|AGT AGG GTA GGG
Glu Val Gly Gly Ala Ala Pro Phe Asn Arg Thr His Val Ser Ser Phe Ala Arg Ser Ser His Pro
```

FIG. 31A

```
ATC TTC CAC AGG GGC GAA CTT TCG GTG TGT GAC AGT GTC AGC TTC AAG AGC GTG CAC ACC TGG GAT AAG ACC
TAG AAG GTG TCC CCG CTT GAA AGC CAC ACA CTG TCA CAG TCG AAG TTC TCA CAC GTG TGG CCC CTA TTC TGG
Ile Phe His Arg Gly Glu Phe Ser Val Cys Asp Ser Val Ser Phe Lys Ser Val His Thr Trp Asp Lys Thr
                  10                              20
ACC GCC ACA GAC TGT ATC TAG ATC AAG GGC AAG GAG TTG GTG ATG TTG AAC CCT CAC GAA GAG CTC TTG AAC AGT
TGG CGG TGT CTG ACA TAG ATC TAG TTC CCG TTC CTC AAC CAC TAC AAC TTG GGA CAT CTG CAC CTC GAG AAC TTG TCA
Thr Ala Thr Asp   Ile  Lys Gly Lys Glu Leu Val Met Val Asn Leu Gly Val Glu Glu Leu Asn Asn Ser
         30                                      40
GTA TTC AAA CAG TAC TTT GAG ACC AAG TGC CGG GAC CCA AAT CCC GTT GAC AGC GGG TGC
CAT AAG TTT GTC ATG AAA CTC TGG TTC ACG GCC CTG GGT TTA GGG CAA CTG TCG CCC ACG
Val Phe Lys Gln Tyr Phe Glu Thr Lys Cys Arg Asp Pro Asn Pro Val Asp Ser Gly Cys
         50                              60
CGG GGC ATT GAC TCA AAG CAC TGG AAC TCA TAT ATA ACC ACG ACT CAC ACC TTT GTC AAG GGG TGC
GCC CCG TAA CTG AGT TTC GTG ACC TTG AGT ATA TAT TGG TGC TGA GTG TGG AAA CAG TTC CCC ACG
Arg Gly Ile Asp Ser Lys His Trp Asn Ser Tyr Cys Thr Thr Thr His Thr Phe Val Lys Gly Cys
         70                    80
CTG ACC ATG GAT GGC AAG CAG GCC TGG ACC GCC TGG CGG ATA GAT ACG GCC TGT GTG TGT
GAC TGG TAC CTA CCG TTC GTC CGG ACC TGG CGG ACC GCC TAT CTA TGC CGG ACA CAC ACA
Leu Thr Met Asp Gly Lys Gln Ala Trp Arg Ala Phe Ile Arg Ile Asp Thr Ala Cys Val Cys
         90                              100                              110
GTG CTC AGC AGG AAG TCC TTC GAG AGA TCT AGA GCC TGA ACT ...
CAC GAG TCG TCC TTC AGG AAG CTC TCT AGA TCT CGG ACT
Val Leu Ser Arg Lys Ser Phe Glu Arg Ser Arg Ala
                                  118
```

```
         -128                                                        -120                                                       -110
        ▶ATG ACC ATC CTT TTC CTT ACT ATG GTT ATT TCA TAC TTT GGT TGC ATG AAG GCT GCC CCC ATG
         TAC TGG TAG GAA AAG GAA TGA TAC CAA TAA AGT ATG AAA CCA ACG TAC TTC CGA CGG GGG TAC
        ▶Met Thr Ile Leu Phe Leu Thr Met Val Ile Ser Tyr Phe Gly Cys Met Lys Ala Ala Pro Met

NcoI
                                             -100                                                       ↓
         AAA GAA GCA AAC ATC CGA GGA CAA GTT CCT GCT GGT GGC TTG GCC TAC CCA GGT GTG CGG ACC CAT GGG ACT
         TTT CTT CGT TTG TAG GCT CCT GTT CAA GGA CGA CCA CCG AAC CGG ATG GGT CCA CAC GCC TGG GTA CCC TGA
        ▶Lys Glu Ala Asn Ile Arg Gly Gln Val Pro Ala Gly Gly Leu Ala Tyr Pro Gly Val Arg Thr His Gly Thr

-80                                                                  -70
         CTG GAG AGC GTG CAC AAT GGG CCC AAG GCA GGT TCA AGA GGC TTG ACA TCA GCT GAC ACT TTC
         GAC CTC TCG CAC GTG TTA CCC GGG TTC CGT CCA AGT TCT CCG AAC TGT AGT CGA CTG TGA AAG
        ▶Leu Glu Ser Val His Asn Gly Pro Lys Ala Gly Ser Arg Gly Leu Thr Ser Ala Asp Thr Phe

-60                                                                  -50
         GAA CAC GTG ATA GAA GAG CTG TTG GAT CTA GAC CAG GAC CTG GTC GTC CAA TTT AAA GTT CGG GCC CCC AAT GAA GAA AAC AAT
         CTT GTG CAC TAT CTT CTC GAC AAC CTA GAT CTG GTC CTG GAC CAG CAG GTT AAA TTT CAA GCC CGG GGG TTA CTT CTT TTG TTA
        ▶Glu His Val Ile Glu Glu Leu Leu Asp Leu Asp Gln Asp Leu Val Val Gln Lys Val Arg Pro Asn Glu Glu Asn Asn

-40                                                                  -30
         AAG GAC GCA GAC TTG TAC ACG TCC AGG GTG ATG TAC CTC AGT AGT TCA AGT AGT TCA CTC CCT TTG GAG CCT
         TTC CTG CGT CTG AAC ATG TGC AGG TCC CAC TAC ATG GAG TCA TCA AGT TCA TCA GAG TGG GAA CTC GGA
        ▶Lys Asp Ala Asp Leu Tyr Thr Ser Arg Val Met Tyr Leu Ser Ser Ser Ser Leu Pro Leu Glu Pro

-20                                                                  -10
         CTT CTC TTT CTG CTG GAG GAA TAC AAA AAT TAC CTA GAT GCT GCA AAC GTG CAA GTG ATG TCC ATG AGG GTC
         GAA GAG AAA GAC GAC CTC CTT ATG TTT TTA ATG GAT CTA CGA CGT TTG CAC GTT CAC TAC AGG TAC TCC CAG
        ▶Leu Leu Phe Leu Leu Glu Glu Tyr Lys Asn Tyr Leu Asp Ala Ala Asn Val Gln Val Met Ser Met Arg Val
```

```
        -1    +1                                                                10
     CGG  CAC  TCT  GAC  CCT  GCC  CGC  CGA  GGG  GAG  CTC  GAC  AGC  GTG  TGT  GAC  AGT  ATT  AGT  GAG  TGG
     GCC  GTG  AGA  CTG  GGA  CGG  GCG  GCT  CCC  CTC  GAG  CTG  TCG  CAC  ACA  CTG  TCA  TAA  TCA  CTC  ACC
   ▶ Arg  His  Ser  Asp  Pro  Ala  Arg Arg  Gly  Glu  Leu  Asp  Ser  Val  Cys  Asp  Ser  Ile  Ser  Glu  Trp 20                                              30                                                 40
     GTA  ACG  GCA  GAC  AAA  GAC  CGT  CTG  GAC  GTG  CAC  CTG  ATG  TCG  GAC  CTG  ACG  GTC  ACA  GTC  GAA
     CAT  TGC  CGT  CTG  TTT  CTG  GCA  GAC  CTG  CAC  GTG  GAC  TAC  AGC  CTG  GAC  TGC  CAG  TGT  CAG  CTT
   ▶ Val  Thr  Ala  Asp  Lys  Asp  Arg  Leu  Asp  Val  His  Leu  Met  Ser  Asp  Leu  Thr  Val  Thr  Val  Leu Glu

50                                                                   NcoI➤
     AAG  GTC  CCT  GTA  TCA  AAA  GGC  CAA  CTG  GAC  GTT  ATA  GAC  TAT  CTG  GAT  AAG  TGC  AAT  CCC  ATG
     TTC  CAG  GGA  CAT  AGT  TTT  CCG  GTT  GAC  CTG  CAA  TAT  CTG  ATA  GAC  CTA  TTC  ACG  TTA  GGG  TAC
   ▶ Lys  Val  Pro  Val  Ser  Lys  Gly  Gln  Leu  Asp  Val  Ile  Asp  Tyr  Leu  Asp  Lys Cys  Asn  Pro  Met

70                           NcoI➤                  80
     GGT  TAC  ACA  AAA  GAA  TGT  AGG  TCC  ACG  CGG  GCC  CTT  ACC  ATG  GAT  AGC  CAT  TGG  AAC  TCC  CAG
     CCA  ATG  TGT  TTT  CTT  ACA  TCC  AGG  TGC  GCC  CGG  GAA  TGG  TAC  CTA  TCG  GTA  ACC  TTG  AGG  GTC
   ▶ Gly  Tyr  Thr  Lys  Glu  Cys  Arg  Ser  Thr  Arg  Ala  Leu  Thr  Met  Asp  Ser  His  Trp  Asn  Ser  Gln 90                                                       100
     ACC  CAG  TCG  TAC  GTG  CAC  GCC  CGG  GCC  CTT  GAA  ATA  GAC  CTG  AAG  TGG  AAA  AAG  AGA  ATT  GGC
     TGG  GTC  AGC  ATG  CAC  GTG  CGG  GCC  CGG  GAA  CTT  TAT  CTG  GAC  TTC  ACC  TTT  TTC  TCT  TAA  CCG
   ▶ Thr  Gln  Ser  Tyr  Val  His  Ala  Arg  Ala  Leu  Glu  Ile  Asp  Leu  Lys Arg His  Lys  Lys Arg Ile 110                                                  119
     AGG  ATA  GAC  ACT  TCT  TGT  ACA  TGT  AAC  TGG  ACC  ATT  AAA  TTT  AGA  GGA  CCT  TCC  CGA  TTC  ATA
     TCC  TAT  CTG  TGA  AGA  ACA  TGT  ACA  TTG  ACC  TGG  TAA  TTT  AAA  TCT  CCT  GGA  AGG  GCT  AAG  TAT
   ▶ Arg  Ile  Asp  Thr  Ser  Cys  Thr  Cys  Asn  Trp  Thr  Ile  Lys Phe  Arg  Gly  Pro  Ser  Arg  Phe  Ile

TAG
                 ATC •••
                 Arg
```

FIG. 32B

PROTEIN EXPRESSION SYSTEM

FIELD OF THE INVENTION

The present invention relates to improved recombinant vectors which allow for the production of fusion proteins and methods for the expression and purification of authentic recombinant proteins from these fusion proteins.

BACKGROUND OF THE INVENTION

The ability to isolate large quantities of recombinant proteins purified to homogeneity is particularly important to the pharmaceutical industry. Recombinant proteins produced for therapeutic applications must be free of antigens and toxins found in the host cell used for protein production. Additionally, the recombinant protein should represent an authentic version of the naturally occurring protein, i.e., a protein having the same primary amino acid sequence as found in the naturally occurring protein.

Proteins encoded by recombinant DNA clones may be expressed and purified using a variety of methods. Recombinant proteins may be expressed in prokaryotic hosts or in eukaryotic hosts, such as yeast or mammalian cell lines. Prokaryotic hosts are more widely used for the expression of recombinant proteins. Prokaryotes, such as *Escherichia coli* (*E. coli*), are well characterized, easy to manipulate and grow in inexpensive media. Expression of recombinant proteins in eukaryotic hosts is attractive particularly when the protein must contain post-translational modifications which do not occur in prokaryotic hosts.

Expression of Recombinant Proteins in Prokaryotic Hosts

*E. coli* is the most widely used host for the expression of recombinant proteins. Early attempts to express foreign proteins in *E. coli* were unsuccessful due in part to rapid proteolytic degradation of the foreign protein. Methods of recombinant protein expression that use a prokaryote as the host cell often employ a technique that expresses a foreign polypeptide fused with a bacterial protein. This is done to stabilize the foreign protein in the host cell line.

Early attempts at the expression of foreign proteins in *E. coli* utilized the bacterial β-galactosidase (β-gal) protein as the fusion partner. Many of the β-gal fusion proteins were insoluble and were found in inclusion bodies [Itakura, K. et al., supra; Young, R. A. and Davis, R. W., *Proc. Natl. Acad. Sci. USA* 80:1194 (1983); Stanley, K. K. and Luzio, J. P., *EMBO J.* 31:429 (1984)]. In some cases, active fusion protein was recovered from the inclusion bodies by solubilization with denaturing reagents [Martson, A. O, *Biochem. J.* 240:1 (1986)]. In other cases, the fusion protein could not be recovered in an active form following denaturation, presumably due to an inability of the denatured protein to correctly refold upon renaturation.

Other bacterial gene products have been used to stabilize the expression of foreign proteins in prokaryotic hosts. These include anthranilate synthetase encoded by the trpE gene product of *E. coli*, staphylococcal protein A, the maltose-binding protein encoded by the malE gene in *E. coli* and glutathione-S-transferase of *Schistosoma japonicum*.

Expression of Recombinant Proteins in Eukaryotic Hosts

Recombinant proteins are expressed in eukaryotic hosts rather than prokaryotic hosts when the recombinant protein requires post-translational modifications such as glycosylation, phosphorylation, disulfide bond formation, oligomerization or specific proteolytic cleavage to produce a biologically active protein. These post-transcriptional processes are not performed by prokaryotic cells. Additionally, some eukaryotic proteins will not fold correctly or efficiently when expressed in a prokaryotic host. Many expression systems have been developed to produce proteins in eukaryotic hosts [For a review see, Sambrook, J. et al., *Molecular Cloning: A Laboratory Manual,* Cold Spring Harbor Laboratory Press, N.Y. (1989) pp. 16.3–16.29]. However, it should be noted that the costs of protein production are often higher when eukaryotic cell lines are employed as the host cell.

To express a DNA sequence encoding a fusion protein in a eukaryotic cell line, a copy of the sequences encoding the fusion protein is inserted into a suitable expression vector and transfected into the desired host cell. When the fusion protein contains a signal sequence at the amino-terminus, the fusion protein may be secreted into the culture media. The generation of such secreted fusion proteins allows for either continuous or batch harvest of fusion protein from eukaryotic cells grown on free flow hollow fiber cartridges.

Purification of Recombinant Fusion Proteins

Affinity purification protocols were developed to facilitate the isolation of large amounts of fusion proteins. Typically, a ligand capable of binding with high specificity to an affinity matrix is chosen as the fusion partner. For example, p-aminophenyl-β-D-thiogalactosidyl-succinyldiaminohexyl-Sepharose selectively binds to β-galactosidase allowing the purification of β-gal fusion proteins [Germino, J., et al., *Proc. Natl. Acad. Sci. USA* 80:6848 (1983)]. Other expression systems which permit the affinity purification of fusion proteins include fusion proteins made with glutathione-S-transferase, which are selectively recovered on glutathione-agarose [Smith, D. B. and Johnson, K. S., *Gene* 67:31 (1988)]. IgG-Sepharose can be used to affinity purify fusion proteins containing staphylococcal protein A [Uhlen, M. et al., *Gene* 23:369 (1983)]. The maltose-binding protein domain from the malE gene of *E. coli* has been used as a fusion partner and allows the affinity purification of the fusion protein on amylose resins. Fusion proteins having the hydrophilic octapeptide Asp-Tyr-Lys-Asp-Asp-Asp-Asp-Lys (SEQ ID NO:1) at the amino-terminus can be affinity purified on an immuno-affinity resin containing an antibody specific for the octapeptide [Hopp, T. P., et al., *Biotechnology* 6:1204 (1988); Prickett, K. S., et al., BioTechniques 7:580 (1989); U.S. Pat. No. 4,851,341, the disclosure of which is herein incorporated by reference].

Other means of purifying fusion proteins include the poly-arginine system, in which the fusion protein is selectively purified on a cation exchange resin [Sassenfeld, H. M. and Brewer, S. J. BioTechnology 2:76 (1984); U.S. Pat. No. 4,532,207, the disclosure of which is herein incorporated by reference]. Sassenfeld and Brewer reported a carboxy-terminal extension of five arginine residues fused to a protein of interest (urogastrone). This basic polyarginine extension allowed the purification of the fusion protein on a SP-Sephadex resin. An analogous protein expression and purification system employs a polyhistidine tract or tag at either the amino- or carboxy-terminus of the fusion protein. The fusion protein is purified by chromatography on a $Ni^{2+}$ metal affinity resin [Porath, J., *Protein Expression and Purification* 3:7995 (1992)]. The use of small polypeptides as fusion partner (e.g., the polyarginine or polyhistidine tag) may be insufficient to stabilize a wide variety of foreign proteins in prokaryotes since a fusion protein construct with only ten amino acids from β-gal was insufficient to stabilize somatostatin [K. Itakura et al., *Science* 198:1056 (1977)].

Another means of achieving partial purification of foreign proteins in prokaryotes is the addition of signal sequences to the foreign protein such that the protein is exported to the periplasmic space in *E. coli* [Grey, G. L. et al., *Gene* 39:247 (1985); Baty, D. et al., *Gene* 16:79 (1981); Inouye, H. et al., *J. Bacteriol.* 149:434 (1982); Kato, C. et al., *Gene* 54:197 (1987)]. As the periplasm contains fewer proteins than does the cytoplasm, a partial purification is achieved by export alone.

Cleavage of Recombinant Fusion Proteins

The ability to express recombinant proteins as fusion proteins is useful in that it allows the stable expression and affinity purification of the foreign proteins in eukaryotic and prokaryotic hosts. However, in many cases it is desirable that the foreign protein be recovered free from its stabilizing fusion partner. In some cases, the addition of the fusion protein to the protein of interest destroys the activity of the foreign protein. When the foreign protein is to be used for therapeutic purposes, the presence of the bacterial gene product can illicit an undesirable immune response against the entire fusion protein in the recipient.

To address these problems, expression systems were developed where the protein of interest could be separated from all or a majority of the bacterial protein sequences. Many of these systems provide for the generation of a tripartite hybrid protein in which a site for the proteolytic or chemical cleavage is inserted between the protein of interest and the fusion partner. Sites for cleavage by collagenase [Germino J. and Bastis, D., *Proc. Natl. Acad. Sci. USA* 81:4692 (1984)], renin [Haffey, M. L. et al., *DNA* 6:565 (1987)], Factor Xa protease [Nagai, K. and Thogersen, H. C., *Nature* 309:810 (1984); Smith, D. B. and Johnson, K. S. *Gene* 67:31 (1988)], thrombin (Smith, D. B. and Johnson, K. S., supra) and enterokinase [Hopp, T. P. et al., supra; Prickett, K. S., *Biotechniques* 7:580 (1989); U.S. Pat. No. 4,851,341, the disclosure of which is herein incorporated by reference] have been inserted between the fusion partner and the gene of interest.

The collagenase-based cleavage system inserts the protein of interest at the amino-terminal end of the fusion protein followed by 60 amino acids from chicken proB-2 collagen followed by the entire β-galactosidase protein (Germino, J. and Bastis, D., supra). The tripartite fusion protein is affinity purified on p-aminophenyl-β-D-thiogalactosidyl-succinyldiaminohexyl-Sepharose. The protein of interest is cleaved from the rest of the fusion protein by controlled digestion with collagenase. Collagenase cleaves following the X and Y residues in following sequence: -Pro-X-Gly-Pro-Y- (where X and Y are any amino acid) (SEQ ID NO:2).

Several limitations exist with the collagenase/β-gal fusion system. Collagenase digestion does not remove all of the chicken collagen sequence from the carboxy-terminus of the protein of interest, several amino acids (<10) remain. The presence of extra amino acids is undesirable when the protein of interest is to be used for therapeutic applications. Additional limitations to the system include, the use of a collagen linker between the protein of interest and the β-gal protein requires that the protein of interest not contain an internal collagenase recognition sequence. Also, the use of β-gal as the fusion partner increases the likelihood that the fusion protein will be insoluble [Shen, S. -H., *Proc. Natl. Acad. Sci. USA* 81:4627 (1987) and Marston, F. A. O., *Biochem. J.* 240:1 (1986)].

A fusion protein cleavable by the endopeptidase renin was reported by Haffey, M. L. et al., *DNA* 6:565 (1987). Renin cleaves between the leucine residues in the following sequence: Pro-Phe-His-Leu-Leu-Val-Tyr (SEQ ID NO:3). A tripartite fusion protein consisting of an Epstein-Barr virus membrane antigen protein (EBV-MA), the recognition sequence for renin and the coding sequence for β-gal was produced. The fusion protein could be cleaved by treatment with renin between the EBV-MA and β-gal proteins. Cleavage with renin was reported to be efficient and specific. However, the use of a linker encoding a renin recognition site results in the production of a cleaved protein of interest which contains either three or four linker-encoded amino acid residues (four residues remain on the carboxy-terminus of the protein domain comprising the amino-terminal portion of the fusion protein and three residues remain on the amino-terminus of the cleaved protein domain comprising the carboxy-terminal portion of the fusion protein). Thus, with the fusion system reported by Haffey et al., supra it is not possible to generate an authentic recombinant protein of interest.

The recognition sequence for Factor Xa protease (i.e., the activated form of Factor X) has been used to cleave the protein of interest from a fusion partner. Factor Xa protease cleaves after the Arg in the following sequences: Ile-Glu-Gly-Arg-X; Ile-Asp-Gly-Arg-X; and Ala-Glu-Gly-Arg-X, where X is any amino acid except proline or arginine, (SEQ ID NOS:4–6, respectively) (Nagai, K. and Thogersen, H. C., supra). A fusion protein comprising the 31 amino-terminal residues of the cII protein, a Factor Xa cleavage site and human β-globin was shown to be cleaved by Factor Xa and generate authentic β-globin [Nagai, K. and Thogersen, H. C., *Nature* 308: 810–812 (1984)].

Smith and Johnson, supra, developed a fusion system in which the amino-terminus of the fusion protein was comprised of the glutathione-S-transferase (GST) protein followed by the Factor Xa protease recognition sequence which in turn was followed by the protein of interest. The Factor Xa sequence was followed by a polylinker encoding several restriction enzyme sites to allow for the insertion of the gene encoding the protein of interest. Depending upon the restriction endonuclease site chosen for the insertion of the DNA encoding the protein of interest, the cleaved protein may or may not have non-native amino acids at its amino-terminus. The use of GST as the fusion partner appears to result in a majority of cases (36/47 reported fusions) in the production of fusion proteins which are wholly or partly soluble. Thus, the use of GST rather than β-gal as the fusion partner is an improvement.

Guan and Riggs [*Gene* 67:21 (1987)] developed a fusion system utilizing the Factor Xa cleavage site in which the amino-terminus of the fusion protein was derived from the maltose-binding protein (MBP) of *E. coli*. The presence of the MBP on the fusion protein allows for affinity purification on amylose resins. The MBP sequences are followed by the Factor Xa cleavage site which in turn is followed by the protein of interest at the carboxy-terminus of the fusion protein. The number of non-native amino acids added to the protein of interest as a result of cleaving the fusion partner from the fusion protein is a function of the primary and secondary structure of the junction site. Thus, limitation imposed by the design of the junction site preclude the universal use of the Factor Xa system of Smith and Johnson to generate an authentic recombinant protein.

Two different versions of the MBP vectors exist. One version contains the signal sequence of the malE gene. The presence of this sequence directs the fusion protein to the periplasm. The other version lacks this signal sequence so that the fusion protein remains in the cytoplasm. Vectors which direct the MBP fusion protein to the cytoplasm generally give higher yields than do the vectors which allow for export to the periplasm. However, since some foreign proteins will not fold properly in the reducing environment of the *E. coli* cytoplasm, transport to the less reducing environment of the periplasm often will allow proper folding. The use of a vector which produces a fusion protein exported to the periplasm is usually preferred for foreign proteins that are secreted or contain disulfide bonds [Riggs, P., *Curr. Protocols Mol. Biol.* 16.6.12 (1990)].

The use of GST or MBP as the fusion partner is an improvement over the use of β-gal which was used in the collagenase cleavage system. However, cleavage by Factor Xa is inefficient for many fusion proteins. It is reported that only about 50% of the fusions made with Factor Xa cleavage sites and MBP are cleaved by Factor Xa following affinity purification [P. Riggs, *Curr. Protocols Mol. Biol.*, supra]. It has been postulated that inefficient Factor Xa cleavage is the result of inaccessibility of the cleavage site within the fusion protein.

In order to cleave some fusion proteins which contain a Factor Xa cleavage site, denaturation of the fusion protein is required. It is likely that denaturation of the fusion protein permits the protease to gain access to the cleavage site. The need to treat fusion proteins with harsh denaturants, such as guanidine hydrochloride or urea, is undesirable. Furthermore, exposing the recombinant protein to harsh denaturants may alter the functional activity and/or the antigenicity of the purified protein. In addition, once denatured, many proteins do not renature (i.e., they become irreversibly denatured or unfolded).

The insertion of a linker or spacer between the Factor Xa site and the protein of interest has been reported to facilitate the cleavage of some fusion proteins. However, the insertion of the linker results in the addition of extra amino acids (i.e., not naturally occurring) at the amino terminus of the protein of interest (Riggs, P., supra at 16.6.13). Another limitation of the Factor Xa-based fusion systems is the fact that Factor Xa has been reported to cleave at arginine residues that are not present within in the Factor Xa recognition sequence [Nagai, K. and Thogerson, H. C., supra; Lauritzen, C. et al., *Prot. Expr. and Purif.* 2:372 (1991)]. Additionally, Factor Xa will not cleave at the recognition site if the site is followed by a proline or arginine residue (Riggs, P., supra at 16.6.13).

Smith and Johnson, supra, also reported the generation of GST fusion proteins which contained a cleavage site for thrombin in place of the Factor Xa site. Thrombin cleaves Arg-X and Lys-X bonds (where X is any amino acid). Preferred cleavage sites for thrombin are (1) P4-P3-Pro-Arg-P1'-P2', where P3 and P4 are hydrophobic amino acids and P1' and P2' are nonacidic amino acids and (2) P2-Arg-P1', where P2 or P1' are Gly (Chang, J. -Y., *Eur. J. Biochem.* 151:217 (1985)]. Smith and Johnson utilized the following thrombin cleavage site: Leu-Val-Pro-Arg-Gly-Ser (SEQ ID NO:7). Cleavage by thrombin was noted to be faster and more efficient than cleavage of analogous fusion proteins containing the Factor Xa site. The chief drawback to the use of this vector system in producing recombinant proteins is that typically, extra amino acids remain at the amino-terminus of the protein of interest after cleavage (as is the case for the GST/thrombin fusions). This occurs because thrombin has a requirement for particular amino acid residues surrounding the Arg or Lys residue where cleavage occurs.

A fusion system which uses chemical cleavage rather than an enzymatic cleavage has been reported [for a review see, Nilsson, B., *Meth. Enz.* 198:3 (1991)]. In this system, staphylococcal protein A (SpA) forms the amino-terminal portion of the fusion protein facilitating affinity purification on IgG-Sepharose. The vector used to generate the fusion protein contains sequentially (amino to carboxy-terminus) the signal sequence of protein A, two copies of the IgG binding domains of protein A, followed by the protein of interest. The signal sequence of protein A facilitates the appearance of the fusion protein in the culture medium. After purification, the protein of interest is cleaved from the fusion protein by treatment with hydroxylamine, cyanogen bromide (CNBr) or N-chlorosuccinamide. Hydroxylamine cleaves between the sequence Asn-Gly and thus requires that the first amino acid of the protein of interest be glycine. CNBr cleaves at methionine residues and therefore when the protein of interest contains internal methionine residues a partial digestion must be performed. N-chlorosuccinamide cleaves on the carboxy-terminal side of tryptophan residues and therefore the protein of interest must not contain tryptophan residues. Thus, the use of SpA fusion system in conjunction with chemical cleavage of the fusion protein is limited. Chemical cleavage requires the absence of specific residues internal to the protein of interest or the presence of specific amino acids in the sequence at the junction between the protein of interest and the linker sequences.

The art needs a fusion and cleavage system which allows for the efficient cleavage and generation of authentic proteins of interest that do not contain extraneous (i.e., non-naturally occurring) amino acids.

SUMMARY OF THE INVENTION

The present invention relates to compositions and methods for producing authentic proteins by recombinant means. The invention provides novel fusion proteins and recombinant DNA vectors encoding the same, as well as, methods for the production of authentic proteins from the novel fusion proteins. In one embodiment the invention provides fusion proteins comprising three domains joined together in order from amino-terminus to carboxy-terminus of a first domain comprising a protein of interest, a second domain comprising a hydrophilic spacer, and an affinity domain, each domain comprising amino acid residues. It is not required that each of these domain be contiguous with one another. The invention contemplates fusion proteins wherein additional domains and/or elements (e.g., a penultimate enhancer and/or a CPB terminator) are inserted between the three domains described above. The invention further contemplates a fusion protein wherein the hydrophilic spacer is an arginine residue and the hydrophilic spacer and the affinity domain are separated by a domain comprising 1 to 19 amino acid residues wherein these 1 to 20 residues are capable of removal by a means for selective amino acid removal. In a preferred embodiment these 1 to 20 residues are removable by a selective endoprotease cleavage and/or a carboxypeptidase, the latter is preferably selected from the group comprising carboxypeptidase A, carboxypeptidase B and carboxypeptidase Y.

The fusion proteins of the present invention comprise a domain comprising a hydrophilic spacer. In a particularly preferred embodiment, the amino acids of the hydrophilic spacer are susceptible to removal by a means for selective amino acid removal. In yet another preferred embodiment, the means for selective amino acid removal comprise a carboxypeptidase, the latter are preferably selected from the group comprising carboxypeptidase A, carboxypeptidase B and carboxypeptidase Y.

In particularly preferred embodiment, the susceptible amino acids of the hydrophilic spacer are selected from the group consisting of arginine and lysine. In one embodiment, the susceptible amino acids of the hydrophilic spacer have the sequence selected from the group comprising SEQ ID NOS:16–37. The hydrophilic spacers of the novel fusion proteins may comprise an extended hydrophilic spacer. In a preferred embodiment, the extended hydrophilic spacer comprises the amino acid sequence of either SEQ ID NOS:18 or 19 joined to the carboxy-terminus of an amino acid sequence selected from the group comprising SEQ ID NOS:16–37 such that either SEQ ID NOS:18 or 19 is located between said SEQ ID NOS:16–37 and the affinity domain.

The fusion proteins of the present invention may further comprise a signal peptide sequence located at the amino-terminus of the fusion protein and joined to the first domain (i.e., the protein of interest). In a preferred embodiment, the signal sequence is sequence of SEQ ID NO:61.

In a particularly preferred embodiment, the fusion protein comprises an endoprotease recognition sequence joined to the second domain (i.e., the hydrophilic spacer) between the second domain and the affinity domain. In yet another preferred embodiment, the fusion protein containing an endoprotease recognition sequence comprises a CPB terminator joined to the first domain comprising the protein of interest between the first domain and the second domain comprising the hydrophilic spacer.

In still another preferred embodiment, the fusion protein containing an endoprotease recognition sequence further comprises a penultimate enhancer joined to the second domain comprising the hydrophilic spacer and between the second domain and the endoprotease recognition sequence.

The invention also provides recombinant DNA vectors having a nucleotide sequence encoding a fusion protein comprising three domains joined together in order, from amino-terminus to carboxy-terminus, of a first domain comprising a protein of interest, a second domain comprising a hydrophilic spacer, and an affinity domain, each domain comprising amino acid residues. In a preferred embodiment, the recombinant DNA vector encodes a fusion protein wherein the amino acids of the encoded hydrophilic spacer are susceptible to removal by a means for selective amino acid removal, the later preferably being a carboxypeptidase. In another preferred embodiment, the amino acids comprising the encoded hydrophilic spacer are removable using a carboxypeptidase selected from the group comprising carboxypeptidase A, carboxypeptidase B and carboxypeptidase Y. In yet another preferred embodiment, the recombinant vector encodes a fusion protein wherein the susceptible amino acids of the encoded hydrophilic spacer are selected from the group consisting of arginine and lysine; particularly preferred encoded hydrophilic spacers comprises sequences selected from the group comprising SEQ ID NOS:16–37. The encoded hydrophilic spacer may comprise an extended hydrophilic spacer; in a preferred embodiment the encoded extended hydrophilic spacer comprises the amino acid sequence of either SEQ ID NOS:18 or 19 in combination with any of SEQ ID NOS:16–37 wherein SEQ ID NOS:18 or 19 are linked via their amino-terminus to the carboxy-terminus of SEQ ID NOS:16–37 and joined via their carboxy-terminus to the affinity domain.

The invention further provides a method of producing authentic recombinant proteins of interest, comprising: a) providing: i) a recombinant DNA vector encoding a fusion protein comprising three domains joined together in order from amino-terminus to carboxy-terminus of a first domain comprising a protein of interest, a second domain comprising a hydrophilic spacer, a third domain comprising an endoprotease recognition sequence and an affinity domain, each domain comprising amino acid residues; ii) host cell suitable for expressing said fusion protein encoded by said recombinant DNA vector; iii) an endoprotease capable of cleaving said fusion protein within said endoprotease recognition sequence; iv) an affinity resin capable of interacting with said affinity domain on said fusion protein; and v) a means for removing non-authentic amino acids from said first domain comprising said protein of interest; b) introducing said vector into said host cell under conditions such that said fusion protein is expressed; c) purifying said expressed fusion protein by means of interaction of said affinity domain on said fusion protein with an affinity resin; d) cleaving said purified fusion protein with said endoprotease to generate a released protein of interest; and e) removing any non-authentic amino acids present at the carboxy-terminus of said released protein of interest with said removal means to produce an authentic protein of interest. The invention is not limited to the use of fusion proteins wherein the hydrophilic spacer and the endoprotease domain are two separate domains. As discussed below, in some cases the hydrophilic spacer may also serve as the endoprotease domain.

In a preferred embodiment, the method of producing an authentic protein of interest employs a removal means which comprises at least one carboxypeptidase and the removal comprises contacting the released protein of interest with at least one carboxypeptidase under conditions such that the non-authentic amino acids are removed to generate the authentic protein of interest.

The methods of the invention are not limited to the use of a particular affinity domain. In one embodiment, the affinity domain comprises a portion of the Fc domain of human IgG1; in this case, the fusion protein is purified using an affinity resin selected from the group comprising protein A and protein G. In another embodiment, the affinity domain comprises a portion of the protein glutathione-S-transferase; in this case, the fusion protein is purified on a glutathione resin. In yet another embodiment, the affinity domain comprises a portion of the maltose binding protein; in this case, the fusion protein is purified on an amylose resin. In still another embodiment, the affinity domain comprises a portion of the staphylococcal protein A; in this case the fusion protein is purified on an IgG resin. In another embodiment, the affinity domain comprises a portion of the protein β-galactosidase; in this case, the fusion protein is purified on p-aminophenyl-β-D-thiogalactosidyl-succinyldiaminohexyl-Sephahrose.

DESCRIPTION OF THE DRAWINGS

FIG. 3 provides a schematic illustrating the processing of fusion proteins having Level 3 linker designs.

FIG. 10 depicts the nucleotide (SEQ ID NO:49) and amino acid sequence (SEQ ID NO:50) of the hinge and Fc portion of the human IgG 1 molecule.

FIG. 11 depicts the nucleotide and amino acid sequence of three oligonucleotides used in the construction of vectors having three variations of the hinge region of the IgG1 molecule.

FIG. 13 depicts the nucleotide sequence of and the amino acid sequence encoded by the pho signal formed by the annealing of four oligonucleotides.

FIG. 22 depicts the nucleotide sequence of and the amino acid sequence encoded by the thrombin and renin linker sequences.

FIG. 30 is a table showing the relative rates of release (hydrolysis) for carboxy-terminal amino acids from various dipeptides.

FIG. 31 depicts the nucleotide and amino acid sequence of human preproNGF.

FIG. 32 depicts the nucleotide and amino acid sequence of human preproBDNF.

DEFINITIONS

Figure 1A:
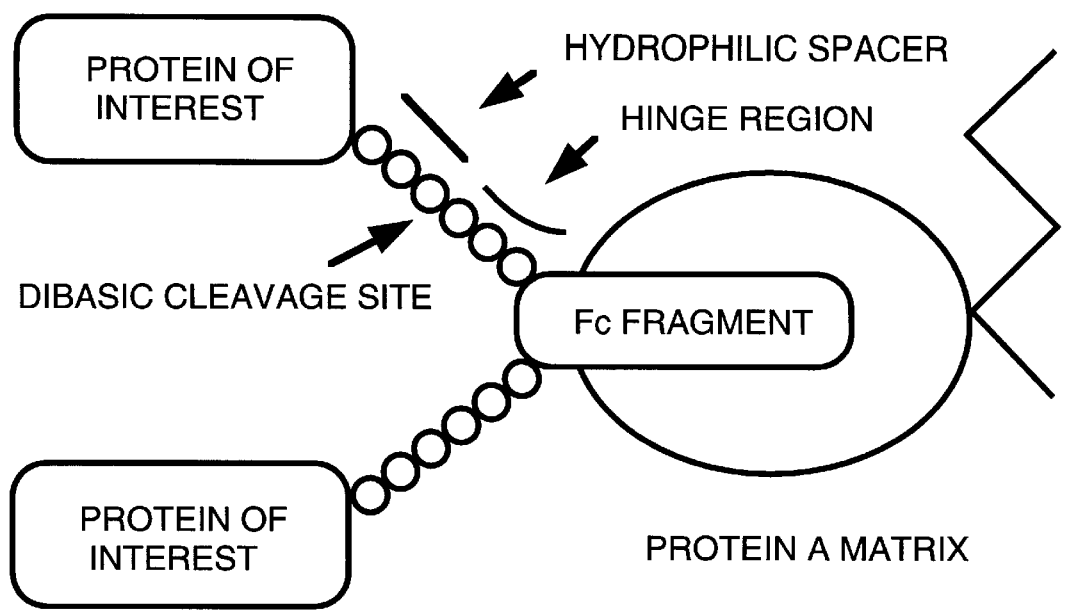
FIG. 1 provides a schematic illustrating the processing of fusion proteins having Level 1 linker designs.

To facilitate understanding of the invention, a number of terms are defined below.

The term "in operable combination" as used herein refers to the linkage of nucleic acid sequences in such a manner that a nucleic acid molecule capable of directing the synthesis of a desired protein molecule is produced. The term also refers to the linkage of amino acid sequences in such a manner that a functional protein is produced.

The term "recombinant DNA molecule" as used herein refers to a DNA molecule which is comprised of segments of DNA joined together by means of molecular biological techniques.

The term "recombinant protein" as used herein refers to a protein molecule which is expressed from a recombinant DNA molecule.

The term "expression vector" as used herein refers to nucleic acid sequences containing a desired coding sequence and appropriate nucleic acid sequences necessary for the expression of the operably linked coding sequence in a particular host organism. Nucleic acid sequences necessary for expression in prokaryotes include a promoter, a ribosome binding site, optionally an operator sequence and possibly other sequences. Eukaryotic cells utilize promoters, and often enhancers and polyadenlyation signals.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

The term "hydrophilic" when used in reference to amino acids refers to those amino acids which have polar and/or charged side chains (i.e., R groups). Hydrophilic amino acids include lysine, arginine, histidine, aspartate (i.e., aspartic acid), glutamate (i.e., glutamic acid), glycine, serine, threonine, cysteine, tyrosine, asparagine and glutamine.

The term "means for selective amino acid removal" refers to means, such as enzymes, which are capable of removing specific amino acid residues but which do not remove or can be prevented from removing other amino acid residues which comprise the authentic protein of interest. Carboxypeptidases, such as CPA, CPB and CPD-Y, are particularly preferred means for selective removal of the amino acid residues comprising the hydrophilic spacers of the present invention. Amino acid residues which can be removed (i.e., hydrolyzed or digested) by a carboxypeptidase are said to be susceptible to removal by that carboxypeptidase. Carboxypeptidases comprise a group of enzymes that hydrolyze peptide bonds one amino acid at a time, from the carboxy-terminus of a polypeptide.

The term "hydrophilic spacer" refers to combinations of 1 to 5 predominantly hydrophilic amino acids present within the fusion proteins of the present invention, wherein at least one of the amino acid residues is an arginine residue. Preferred hydrophilic spacers comprise 3 to 5 hydrophilic amino acids. The term "extended hydrophilic spacer" refers to combinations of 6 to 8 predominantly hydrophilic amino acids. Particularly preferred hydrophilic spacers and/or extended hydrophilic spacers comprise only arginine and lysine residues; arginine and lysine residues are effectively removed by CPB. The hydrophilic spacers of the present invention contain at least one arginine residue; the arginine residues provide barriers or termination points for CPA digestions (i.e., CPA cannot remove arginine residues). Authentic proteins of interest are generated from the fusion protein by selective removal of non-authentic amino acids from the carboxy-terminus of the fusion protein (after the fusion protein has been cleaved by the desired endoprotease). The arginine residue(s) within the hydrophilic spacer acts as a barrier to excessive digestion (i.e., digestion into the protein of interest) of the fusion protein by CPA. When CPA encounters an arginine residue it cannot proceed. At that point CPB, which can only remove arginine and lysine residues, is used to digest the remaining arginine and/or lysine residues of the hydrophilic spacer to generate the authentic protein of interest. As discussed further below, doublets of lysine residues, which are extremely resistant to carboxypeptidase Y (CPD-Y) digestion, may be employed in the hydrophilic spacers. Hydrophilic spacers containing lysine doublets are employed in level 3 linker processing designs which requires the use of CPD-Y to the generation of authentic proteins.

In addition to providing a means for generating authentic proteins by providing residues which are capable of selective removal (e.g., using carboxypeptidases), the hydrophilic and basic nature of arginine and lysine residues causes them to be orientated within exposed regions of the fusion protein. This increases the likelihood that the hydrophilic linker (i.e., the hydrophilic spacer and the endoprotease site) will be accessible to digestion with endoproteases.

The term "penultimate enhancer" refers to a single amino acid residue which increases the rate or efficiency at which the amino-terminal residue of the endoprotease recognition sequence is removed during the carboxypeptidase reactions of level 2 or 3 linker designs. Particularly preferred penultimate enhancers comprise hydrophobic aliphatic resides (e.g., leucine, isoleucine, valine) because they are preferred in the penultimate position by both CPD-Y and CPA. Hydrophobic aliphatic residues are preferred penultimate enhancers in linker designs when the fusion protein is to be expressed in a host cell which produces furin. Because the hydrophilic spacers bear a resemblance to the furin recognition site, a hydrophobic aliphatic residue is positioned after the carboxy-terminal residue in the hydrophilic spacer to prevent any aberrant furin cleavage. When host cells are used which do not produce furin (e.g., AG1 E. coli cells), the penultimate enhancer may comprise any amino acid residue which is efficiently removed by CPA and which, when present in the penultimate position, is favored by CPD-Y (i.e., phenylalanine, tryptophan, leucine, isoleucine, valine, alanine and methionine).

If the junction between the endoprotease site and the hydrophilic spacer is formed by the juxtapositioning of an amino acid residue which is slowly released from the endoprotease recognition sequence (the amino-terminal residue of the endoprotease site) with an amino acid residue at the carboxy-terminal position of the hydrophilic spacer that is also slowly released (e.g., arginine and/or lysine residues), the result is an amino acid pair that is processed extremely slowly in the carboxypeptidase reaction (CPD-Y and CPA). In order to increase the speed and efficiency of transition from CPD-Y to CPA to CPB digestion, a preferred amino acid (i.e., a penultimate enhancer) is added at the junction between the hydrophilic spacer and the endoprotease recognition sequence (see FIG. 36 for an example). The residue which functions as the penultimate enhancer will increase the rate at which the amino-terminal residue of the endoprotease site is removed by digestion with carboxypeptidase.

The term "CPB terminator" refers to a single amino acid that prevents the digestion of any authentic protein sequences when removing the amino acid residues comprising the hydrophilic spacer with carboxypeptidase B (CPB). CPB removes only arginine and lysine residues. Amino acids which are particularly preferred as CPB terminators are hydrophobic aliphatic residues (e.g., leucine, isoleucine, valine) as these residues are removed quickly by carboxypeptidase A (CPA) and carboxypeptidase Y (CPD-Y). A hydrophobic aliphatic residue at this position will also prevent any cleavage at the authentic molecule linker junction site by furin should the design be used in a mammalian host system and the desired molecule contain a furin recognition motif directly at its carboxy-terminus. When the protein of interest to be expressed in the fusion protein does not contain a furin recognition site or when a non-furin producing host cell is employed, any amino acid that is rapidly released by CPA and that is not released by CPB can be used as a CPB terminator (i.e., phenylalanine, tryptophane, leucine, isoleucine, valine, alanine and methionine). A CPB terminator is employed in the linker design when the protein of interest contains an arginine or lysine at its carboxy terminus; the CPB terminator is located on the carboxy-terminal side of the authentic arginine or lysine, between the authentic protein of interest and the hydrophilic spacer (see FIG. 34 for an example).

The term "endoprotease recognition sequence" refers to a defined amino acid sequence that allows cleavage of a protein or peptide containing this sequence by an endoprotease.

The terms "hydrophilic linker" or "linker" refers to a functional unit present on the fusion proteins of the invention which comprises a hydrophilic spacer and an endoprotease recognition site; the linker may also contain a CPB terminator and/or a penultimate enhancer element. The hydrophilic spacer joins or links the protein of interest to the affinity domain. The term linker is also used to refer to DNA sequences encoding the amino acids comprising the hydrophilic spacer, endoprotease recognition site, CPB terminator and penultimate enhancer; it is clear from the context in which this term is used whether the linker comprises amino acid or DNA sequences. The present invention provides for three levels of hydrophilic linker (i.e., linker) designs as discussed in detail below.

The term "fusion protein" as used herein refers to a polypeptide which comprises protein domains from at least two different proteins.

The term "control fusion protein" refers to a fusion protein which is generated from a recombinant DNA molecule encoding two different protein domains that are joined together without the presence of an amino acid sequence comprising the recognition site for a site-specific protease.

The term "fusion partner" refers to components of a fusion protein which are fused to the amino acids comprising the protein of interest; these components include affinity domains such as portions of Ig molecules, MBP, GST, etc.

The term "carboxy-terminal fusion protein" refers to a fusion protein in which the protein of interest is located at the amino-terminal portion of the fusion protein; the fusion partner components are joined to the carboxy-terminus of the protein of interest.

The term "amino-terminal fusion protein" refers to a fusion protein in which the protein of interest is located at the carboxy-terminal portion of the fusion protein; the fusion partner components are joined to the amino-terminus of the protein of interest.

The term "authentic protein" or "authentic recombinant protein" as used herein refers to a protein having the same primary amino acid sequence as that encoded by the native gene sequences, i.e., the recombinant protein does not contain any non-native amino acids. In contrast, a "non-authentic" protein contains at least one amino acid not found in the naturally occurring protein (i.e., not encoded by the native gene sequences). During the processing of the fusion proteins of the present invention, non-authentic proteins containing additional amino acids (i.e., not encoded by the native gene), typically at the carboxy-terminal end of the authentic protein sequence, are generated. These additional amino acids are removed using carboxypeptidase(s) to generate authentic recombinant proteins.

The terms "protein of interest" or "desired protein" as used herein refer to the protein whose expression is desired within the fusion protein. In a fusion protein the protein of interest will be joined or fused with another protein or protein domain, the fusion partner, to allow for enhanced stability of the protein of interest and/or ease of purification of the fusion protein. In the fusion proteins of the invention, the desired protein or protein of interest may comprise either the amino- or carboxy-terminal portion of the fusion protein; however, fusion proteins which contain the protein of interest as the amino-terminal protein of the fusion protein are particularly preferred.

The terms "authentic protein of interest" or "authentic recombinant protein of interest" refer to proteins produced by recombinant means which contains only native or naturally-occurring amino acids.

The term "affinity domain" as used herein refers to a domain present on a fusion protein which permits purification of the fusion protein on an affinity resin. For example, the $F_C$ domain of immunoglobulins may be used as the affinity domain on the fusion proteins of the invention; the $F_c$ domain allows purification of the fusion protein on protein A or protein G chromatography resins.

The term "signal peptide sequence" refers to an approximately 16–40 amino acid stretch present on the amino-terminus of a protein which directs the nascent protein to the periplasm (prokaryotic cells) or permits the secretion of the protein (eukaryotic cells). The signal peptide is cleaved from the protein once the protein has been directed to its desired location (i.e., periplasm, secretory granule, etc.). The terms "signal peptide," "signal peptide sequence" and "leader sequence peptide" are used interchangeably in the art.

Many proteins, in particular secretory proteins, are synthesized as larger precursors which are cleaved at one or a few specific peptide bonds to produce the mature form of the protein. The larger precursor forms are referred to as either preproproteins or proproteins. The term "preproprotein" refers to a precursor protein which undergoes at least two successive proteolytic cleavages to produce the mature protein. For example, preproalbumin contains an 18 amino acid signal sequence at the amino-terminus which is cleaved to generate proalbumin. Proalbumin is then cleaved to generate albumin.

The term "proprotein" refers to a precursor protein which undergoes proteolytic processing to generate the mature form of the protein. When the active protein is an enzyme the precursor is referred to as a "proenzyme" or "zymogen."

The terms "site-specific protease" or "site-specific endoprotease" are used interchangeably and refer to an endoprotease which cleaves at a specific set of amino acid sequences. For example, the endoprotease renin cleaves between the two leucine residues in the following sequence: Pro-Phe-His-Leu-Leu-Val-Tyr (SEQ ID NO:3).

The term "endoprotease" or "endopeptidase" as used herein refers to a protease capable of hydrolysing interior peptide bonds of a polypeptide, at points other than the terminal bonds (i.e., the peptide bonds of the terminal amino acid).

The term "exoprotease" or "exopeptidase" as used herein refers to a protease capable of hydrolysing peptide bonds at points only at the terminal bonds of a polypeptide.

The term "carboxypeptidase" as used herein refers to an exoprotease that hydrolyses only the peptide bond of a terminal amino acid containing a free carboxyl group. Carboxypeptidases are used to remove amino acids from the carboxy-terminus of a peptide chain.

The term "promoter DNA sequence" as used herein refers to a DNA sequence that precedes a gene in a DNA polymer and provides a site for initiation of the transcription into mRNA.

The term "terminator DNA sequence" as used herein refers to a DNA sequence that follows a gene in a DNA polymer and provides a signal for termination of the transcription into mRNA.

Eucaryotic expression vectors may also contain "viral replicons" or "viral origins of replication." Viral replicons are viral DNA sequences which allow for the extrachromosomal replication of a vector in a host cell expressing the appropriate replication factors. Vectors which contain either the simian virus 40 (SV40) or polyoma virus origin of replication replicate to high copy number (up to $10^4$ copies/cell) in cells that express the appropriate viral T antigen. Vectors which contain the replicons from bovine papillomavirus or Epstein-Barr virus replicate extrachromosomally at low copy number (approximately 100 copies/cell).

The term "stable transfection" or "stably transfected" refers to the introduction and integration of foreign DNA into the genome of the transfected cell. The term "stable transfectant" refers to a cell which has stably integrated foreign DNA into the genomic DNA.

The term "selectable marker" as used herein refers to the use of a gene which encodes an enzymatic activity that confers resistance to an antibiotic or drug upon the cell in which the selectable marker is expressed. Selectable markers may be "dominant"; a dominant selectable marker encodes an enzymatic activity which can be detected in a cell line. Examples of dominant selectable markers include the bacterial aminoglycoside 3' phosphotransferase gene (also referred to as the neo gene) which confers resistance to the drug G418 in mammalian cells. Additional examples of a dominant selectable marker are the bacterial hygromycin G phosphotransferase (hyg) gene which confers resistance to the antibiotic hygromycin and the bacterial xanthine-guanine phosphoribosyl transferase gene (also referred to as the gpt gene) which confers the ability to grow in the presence of mycophenolic acid.

Other selectable markers are not dominant in that their use must be in conjunction with a cell line that lacks the relevant enzyme activity. Examples of non-dominant selectable markers include the thymidine kinase (tk) gene which is used in conjunction with tk- cell lines, the CAD gene which is used in conjunction with CAD-deficient cells and the mammalian hypoxanthine-guanine phosphoribosyl transferase (hprt) gene which is used in conjunction with hprt- cell lines. A review of the use of selectable markers in mammalian cell lines is provided in Sambrook, J. et al., Molecular Cloning: A Laboratory Manual, pp. 16.9–16.15.

The terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DESCRIPTION OF THE INVENTION

The invention provides reagents and methods which permit the production of authentic recombinant proteins (i.e., an authentic protein produced by recombinant means). The methods of the invention include the construction of expression vectors which permit the expression of fusion proteins capable of isolation by affinity chromatography (i.e., affinity-purifiable fusion proteins) in procaryotic or eucaryotic cells. The affinity-purifiable fusion proteins comprise the following domains, from amino- to carboxy-termini: 1) the protein of interest, 2) a hydrophilic spacer, 3) an endoprotease recognition site and 4) an affinity-purifiable domain (i.e., the affinity domain). The fusion proteins of the present invention may contain additional elements such as CPB terminators and/or penultimate enhancers (discussed below). It is noted that the hydrophilic spacer and the endoprotease recognition site may comprise a single element as discussed in Level 1 linker designs below.

In order to produce authentic recombinant protein from the fusion proteins of the present invention, the fusion proteins are expressed in an appropriate host cell, purified by affinity chromatography and then processed to remove the affinity domain, the endoprotease site and hydrophilic spacer (and any additional elements present which comprise amino acids not present in the authentic protein). The removal of amino acids comprising the endoprotease site and hydrophilic spacer is accomplished using carboxypeptidases. Carboxypeptidases are enzymes which remove (i.e., hydrolyze) protein chains beginning at the carboxy-terminal end of the chain and liberate amino acids one at a time. In the methods of the present invention, various carboxypeptidases are used singly, sequentially, or in combination to generate authentic proteins from the fusion proteins of the present invention. The processing of the fusion proteins of the invention is described in detail below.

The hydrophilic spacers of the present invention comprise one to five arginine and/or lysine residues. Extended hydrophilic spacers comprise six to eight arginine and/or lysine residues. The hydrophilic spacers serve several functions. The hydrophilic amino acids which comprise the hydrophilic spacer serve to orient this portion of the fusion protein toward the exterior of the molecule in aqueous solutions; this increases the exposure and accessibility of the nearby endoprotease recognition site. The hydrophilic spacers also allow for the physical separation of the domain comprising the protein of interest from the affinity domain. This separation ensures that the affinity domain is free to interact with the affinity resin as the possibility of steric hinderance from the protein of interest is reduced. In addition, the hydrophilic spacers allow for the physical separation of the endoprotease recognition site from the carboxy-terminal portion of the protein of interest. This separation is advantageous as the carboxy-terminal portion of the protein of interest may limit access of the endoprotease to the endoprotease recognition site if located in close proximity.

The fusion proteins comprising the hydrophilic spacer and endoprotease recognition site are purified using an affinity resin which binds to the affinity domain of the fusion protein. The affinity domain is generally removed from the purified fusion protein by digestion with the endoprotease whose recognition site is present in the hydrophilic spacer/ endoprotease recognition site domain of the fusion protein (the affinity domain may also be removed from the fusion protein by chemical cleavage using methods known to the art). The domain comprising the cleaved protein of interest (i.e., that portion of the fusion protein containing the protein of interest following digestion of the fusion protein with an endoprotease) is then processed to remove any amino acids which comprise the hydrophilic spacer and/or the endoprotease recognition site. Digestion with the endoprotease may occur while the fusion protein is still bound to the affinity resin or alternatively, the fusion protein may be eluted from the affinity resin and then digested with the endoprotease. When the fusion protein is eluted from the affinity chromatography column prior to digestion with the endoprotease, the cleaved affinity domain may be removed from the cleaved protein of interest by selective binding to the affinity resin. The efficiency of the endoproteolytic or chemical cleavage of the recombinant fusion protein is determined by the amino acid sequence located at the junction between the fusion partner and the protein of interest.

The cleaved protein of interest may contain amino acids at the carboxy-terminus which comprise all or a portion of the hydrophilic spacer and/or endoprotease recognition site. These amino acids are sequentially removed from the carboxy-terminus of the protein of interest by digestion with carboxypeptidases to generate an authentic protein of interest. Carboxypeptidases comprise a group of enzymes that hydrolyze peptide bonds one amino acid at a time, from the carboxy-terminus of a polypeptide.

In the present invention, synthetic oligonucleotides (termed "linkers") are used to join sequences coding for the protein of interest to sequences encoding the affinity domain. By varying the triplet DNA sequence representing specific amino acids (i.e., codons) in the linker design, it is possible to create restriction sites for enzymes that recognize and cleave those designed sequences without changing the amino acid sequence of the encoded protein of interest. The use of sequences encoding recognition sites for restriction enzymes having a minimum of 6 bases in the recognition site is preferred; this reduces the chance that multiple restriction enzyme cleavage sites will be present in both the vector and the sequences encoding the protein of interest.

The ends which result from the digestion of DNA by restriction endonucleases may be joined if the overhanging ends are compatible (i.e., capable of hybridizing). The ends produced by restriction digests that leave blunt DNA ends are compatible with all other blunt ended DNA. Ends may be compatible as a result of digestion with isocaudamers or they may be made compatible by partially or completely filling in the ends using the Klenow enzyme or T4 DNA polymerase. Ligation of a pair of filled in ends generally does not recreate either restriction site but this technique greatly increases the possible combinations of sequences that can be combined. Overhanging termini produced by digestion of DNA with restriction endonucleases may be removed to generate blunt ends by treatment of the DNA with S1 nuclease.

An example of this technique would be the joining of the DNA coding sequences for proteins 1 and 2 (Genes 1 and 2) such that the resulting fusion is orientated 5' 1→2 3' in its open reading frame using synthetic DNA. A restriction site close to the 3' end of the Gene 1 sequence is determined by analysis of the nucleic acid sequence. Preferentially, the enzyme of choice will produce an overhang to facilitate cloning. Similar analysis is performed for the 5' sequence of Gene 2. Once the restriction sites have been determined, synthetic oligonucleotides are designed to be complementary to each other and code for the sequence that is removed as the result of the restriction digest. Hybridized oligonucleotides (comprising the linker) will have compatible overhangs for ligation to the 3' of Gene 1 and the 5' of Gene 2. The linkers are phosphorylated, hybridized and ligated to Gene 1. Restriction digests are used to cleave off multiple oligonucleotides and generate compatible overhangs for the Gene 2 ligation. Size exclusion chromatography is used to separate free linker molecules from Gene 1 molecules ligated to linker. Gene 1 with ligated linker is then ligated directly to Gene 2. The resulting fusion can be identified and isolated using restriction digestion and isolation of the desired product on a low melting temperature agarose gel.

Synthetic DNA can also be used to change or add additional sequences between the two sequences encoding the two protein domains by ligating an oligonucleotide comprising the desired sequence between two protein domain-encoding sequences. Site directed mutagenesis can be used to create restriction sites at or near the termini of the sequences to be joined.

PCR is also an effective tool for cloning known genes (into blunt or sticky sites). Primers can code for 25–40 bases of known sequence and the resulting PCR product can be cloned into a digested vector having blunt ends by removing any possible 3' overhangs with T4 DNA polymerase. Another method of linking sequences with the use of the PCR reaction is to create restriction sites at the end(s) of the amplified DNA. These restriction sites are easily added to the 5' ends of the primers used for amplification. Digestion of the purified PCR products will produce ends for ligation to other DNA having compatible termini.

In a preferred embodiment, the invention comprises a vector for the production of recombinant proteins in procaryotic or eukaryotic hosts comprising: (1) a controllable transcriptional promoter which, upon activation (by induction or release of repression), directs the transcription of large amounts of mRNA from the cloned gene; (2) translational control sequences, such as a ribosome binding site; (3) a prokaryotic or eukaryotic signal sequence which directs the transport of the protein across the inner membrane into the periplasmic space in bacterial host cells; in a eukaryotic host cell, the signal sequence directs the secretion of the protein; (4) a DNA sequence encoding a protein of interest; (5) a linker sequence which encodes a hydrophilic amino acid sequence (e.g., a hydrophilic linker which encodes a hydrophilic spacer) attached to the 3' end of the sequences encoding the protein of interest; (6) sequences encoding an endoprotease recognition (i.e., cleavage) site; and (7) a DNA sequence encoding an affinity domain (e.g., at least a portion of the hinge and Fc domains of an immunoglobulin molecule) attached to the 3' end of the sequences encoding the linker. The fusion protein produced by such a vector will comprise the protein of interest at the amino-terminus of the fusion protein followed by the hydrophilic spacer and endoprotease site; the immunoglobulin hinge and Fc domains will form the carboxy-terminus of the fusion protein. The fusion protein may also contain a CPB terminator and/or a penultimate enhancer in the junction between the authentic protein and the endoprotease recognition site.

Transcriptional Control of Recombinant Fusion Protein Expression

The mere insertion of a gene sequence into a vector is generally insufficient to permit the expression of an exogenous gene in a host cell line. The structural gene sequences must be operably linked to appropriate transcriptional control signals to permit expression of the encoded protein in either a prokaryotic and eukaryotic host. In prokaryotes, a number of promoter sequences have been identified. Of particular use are those promoters which can be controlled (an "inducible" promoter); transcription from an inducible promoter occurs at low levels unless a particular molecule is present or until a repressor of the promoter is removed. Examples of these types of inducible promoters include:

1) The tac promoter is a hybrid of the trp and lac promoters [Amann, E. et al., *Gene* 40:183 (1985); de Boer, H. A. et al., *Proc. Natl. Acad. Sci. USA* 80:21 (1983)]. The tac promoter is regulated by the lac repressor. Transcription from the tac promoter is repressed in *E. coli* strains, such as RB791 (ATCC No. 53622), which make high levels of the lac repressor. The lac repressor may be provided by placing a copy of the lacI$^q$ gene on the plasmid carrying the gene of interest; this allows for host-independent repression of the tac promoter. Transcription from the tac promoter is induced (i.e., repression is relieved) by the addition of isopropylthio-β-D-galactoside (IPTG);

2) The bacteriophage λ $P_L$ promoter which is regulated by a temperature-sensitive repressor, cIts857 [Sambrook, J. et al., supra, p. 17.11]. Repression occurs at low temperatures (30° C.) and is relieved by a shift to higher temperatures (40–45° C.). The ability to use heat to induce expression from a promoter is advantageous in terms of cost; no compounds must be added to the culture. However, the shift to a higher temperature may also activate heat shock proteins, some of which encode proteases. This potential drawback may be eliminated by selecting a host strain which is deficient in the expression of these proteases. For example, *E. coli* strains Y1089r- (Stratagene) and BL21 (Novagen) are deficient in expression of the La protease due to mutations in the lon gene. Expression of the La protease is induced by heat shock. *E. coli* strains carrying mutations in the lon gene have been shown to limit proteolysis of intracellular proteins [Buell, G., et al., *Nucleic Acid Res.*, 13, 1923 (1985)]. Alternative means of induction of the λ $P_L$ promoter include the use of mitomycin C or nalidixic acid, neither of which induce heat shock proteins;

3) The bacteriophage T7 promoter [Studier, F. W. and Moffatt, B. A., *J. Mol. Biol.* 189:113 (1986) and Tabor, S. and Richardson, C. C., *Proc. Natl. Acad. Sci. USA* 83:561 (1985)]. This promoter is recognized only by T7 RNA polymerase and expression from the T7 promoter requires a two component system: T7 RNA polymerase which can be provided from a copy of the gene inserted into the *E. coli* chromosome on an infecting bacteriophage B vector and a plasmid vector containing the T7 promoter upstream of the gene to be expressed.

The above described promoters are preferred, as they are known to direct high levels of transcription in prokaryotic hosts. However, many other prokaryotic promoters are known to the art and the invention is not limited by the choice of promoter selected.

Transcriptional control signals in eukaryotes are comprised of promoter and enhancer elements. Promoters and enhancers consist of DNA sequences that interact specifically with proteins involved in transcription [Maniatis, T., et al., *Science* 236:1237 (1987)]. These elements have been isolated from a variety of sources including genes in yeast, insect and mammalian cells and viruses. The selection of a particular promoter and enhancer depends on the cell type which is to be used to express the protein of interest. Some eukaryotic promoters and enhancers have a broad host range while others are functional in a limited subset of cell types [for review see, Voss, S. D., et al., *Trends Biochem. Sci.*

11:287 (1986) and Maniatis, T., et al., (1987), supra]. For example, the SV40 early gene enhancer is very active in a wide variety of cell types from many mammalian species and has been widely used for the expression of proteins in mammalian cells [Dijkema, R. et al., *EMBO J.* 4:761 (1985)]. Two other examples of promoter/enhancer elements active in a broad range of mammalian cell types are those from the long terminal repeats of the Rous sarcoma virus [Gorman, C. M., et al., *Proc. Natl. Acad. Sci. USA* 79:6777 (1982)] and from the human cytomegalovirus [Boshart, M., et al., *Cell* 41:521 (1985)]. The SV40 enhancer/promoter and the CMV enhancer/promoter are preferred transcriptional control sequences when the protein is to be expressed in mammalian cells.

Efficient expression of recombinant DNA sequences in eukaryotic cells requires signals directing the efficient termination and polyadenylation of the resulting transcript. Transcription termination signals are generally found downstream of the polyadenylation signal and are a few hundred nucleotides in length. The term "poly A site" or "poly A sequence" as used herein denotes a DNA sequence which directs both the termination and polyadenylation of the nascent RNA transcript. Efficient polyadenylation of the recombinant transcript is desirable as transcripts lacking a poly A tail are unstable and are rapidly degraded. The poly A signal utilized in an expression vector may be "heterologous" or "endogenous." An endogenous poly A signal is one that is found naturally following the coding region of a given gene in the genome. A heterologous poly A signal is one which is isolated from one gene and placed 3' of another gene. A commonly used heterologous poly A signal is the SV40 poly A signal.

When the fusion proteins of the present invention are to be expressed in mammalian or insect cells lines, stable transformants containing DNA sequences encoding the fusion protein are preferably generated. However, the invention is not limited to the expression of fusion proteins in stably transformed cells. The art is aware of several transient transfection systems which may be employed for the expression of the fusion proteins of the present invention. For example, the use of an expression vector containing the SV40 origin of replication in conjunction with a cell line which stably expresses the SV40 T antigen, such as the COS-1 or COS-7 cell lines may be used for the expression of fusion proteins in mammalian cells. Vectors which contain the SV40 origin of replication will replicate to high copy number in host cells which express the SV40 large T antigen, such as the COS-1 (ATCC CRL 1650) [Gluzman, Y. (1981) *Cell* 23:175] and COS-7 (ATCC CRL 1651) [Gluzman, supra] cell lines. Vectors containing the polyoma virus origin of replication will replicate to high copy number in cells, such as WOP cells, which express polyoma virus large T antigen [Dailey, L. and Basilico, C. J., *Virol.,* 54:739 (1985)]. Another example of a replication transient transfection system is the bovine papilloma virus (BPV) system.

Use of Signal Peptides to Translocate Expressed Proteins

Sequences encoding signal peptides may be joined to sequences encoding the fusion proteins of the present invention. The use of a signal sequence may be advantageous for expression of recombinant proteins in either prokaryotic or eukaryotic hosts. Secretion signals are relatively short (16–40 amino acids) in most species. The presence of a signal sequence on the protein permits the transport of the protein into the periplasm (prokaryotic hosts) or the secretion of the protein (eukaryotic hosts). Signal sequences from bacterial or eukaryotic genes are highly conserved in terms of function, although not in terms of sequence, and many of these sequences have been shown to be interchangeable [Grey, G. L. et al., *Gene* 39:247. (1985)].

In prokaryotes, the signal sequence directs the nascent protein across the inner membrane into the periplasmic space. It has been found that transport to the periplasm will allow proper folding of some proteins which cannot fold properly in the cytoplasm. Transport to the periplasmic space also functions as a partial purification step, as the periplasm contains fewer proteins than does the cytoplasm. Proteins present in the periplasm may be released by a mild osmotic shock of the bacterial cells. *E. coli* cells which express the kil gene product may be used to achieve the secretion of proteins transported to the periplasm without the need for cell lysis or osmotic shock [Kobayashi, T. et al., *J. Bacteriol.* 166:728 (1986)]. The kil gene product causes an increase in the permeability of the outer membrane allowing the secretion of periplasmic proteins into the culture medium.

The presence of a signal sequence on a protein expressed in a eukaryotic host results in the transport of the nascent protein across the lumen of the rough endoplasmic reticulum which may allow for eventual secretion of the protein into the culture medium. In both prokaryotes and eukaryotes, the signal sequence is removed from the amino-terminus of the protein molecule by enzymatic cleavage during transport of the polypeptide through the membrane.

While some signal sequences have been shown to be interchangeable, the use of specific signal sequences in a particular host may increase expression of the fusion protein. For example, when the fusion protein to be expressed comprises a human pre-protein and the host cell is a bacterial cell, the naturally occurring human secretion signal is replaced with an efficient bacterial signal sequence. Among the preferred bacterial signal sequences are those derived from the β-lactamase and phosphatase (pho) genes that have been genetically engineered or synthesized to have an NcoI or NdeI site at the ATG start codon and another restriction site at the 3' end of the signal sequence to be used to link the DNA encoding the mature protein of interest. A phoA mediated expression system which utilizes the pho signal sequence followed by a multiple cloning site has been reported [Oka T., et al., Proc. Natl. Acad. Sci. USA 82: 7212 (1985)].

Immunoglobulin Hinge/Fc Domains and Other Fusion Partners

The expression of exogenous gene products in host cell lines is facilitated by the use of fusion proteins comprising sequences encoding the protein of interest linked via a hydrophilic spacer sequence to a fusion partner (as discussed below the spacer comprises hydrophilic amino acid residues). The fusion partner functions to stabilize the protein of interest as well as to provide a domain which permits the affinity chromatographic purification of the recombinant protein. The present invention is not limited by the nature of the affinity domain chosen.

A preferred affinity domain (i.e., fusion partner) comprises the immunoglobulin hinge and Fc domains (the nucleotide and amino acid sequence of the hinge/Fc domain of human IgG1 is given in SEQ ID NOS:49 and 50, respectively). The use of these protein domains is advantageous. The hinge region of the immunoglobulin molecules is known to be flexible and accessible to proteases. Sites for cleavage by papain and pepsin are present in the hinge region. The use of the flexible hinge region to join the protein of interest with the ligand for the affinity matrix, the Fc region, may allow the independent folding of the two domains. Protein A- and Protein G-Sepharose (Pharmacia Biotech) bind to the Fc domain of immunoglobulin G of many species with high affinity allowing for the purification of the fusion protein. Other classes of immunoglobulins, such as IgM, IgA and IgE, may be used as the donor of the Fc region and purified on anti-IgM, A or E resins.

It is known that IgG Fc can be expressed in E. coli and that proper disulfide bond formation occurs when the protein is directed across the inner membrane into the periplasmic space [Kitai, K., et al., Appl. Microbiol. Biotechnol. 28:52 (1988)]. The hinge and Fc domains of IgG were used to create a CD4/IgG fusion protein for therapeutic use in humans [Capon, D. J. et al., Nature 337:525 (1989) and Mayforth, R. D. and Quintans, J., N. Eng. J. Med. 323:173 (1990)]. The CD4/IgG fusion protein was produced in a human embryonic kidney-derived cell line. The CD4/IgG fusion protein was not designed to be cleaved into the separate protein components since the investigators fused the IgG sequences to a soluble form of CD4 to increase the half-life of soluble CD4 in the serum of patients.

While the use of the hinge and Fc regions of immunoglobulin molecules is advantageous for the reasons discussed above, the invention is not limited by the use of these immunoglobulin regions as a means to affinity purify the fusion protein. The invention contemplates the improvement of other protein fusion systems which use other means of providing an affinity-purifiable domain on the fusion protein. For example, sequences encoding the novel hydrophilic spacers of the invention may be inserted between the sequences encoding the malE gene product, which provides the MBP domain for affinity purification on amylose resins, and the protein of interest. It is desirable that the protein of interest be expressed as the amino-terminal portion of the fusion protein; in contrast existing MBP fusion systems express the MBP domain at the amino-terminus of the fusion. As discussed below, there are advantages to having the protein of interest emerge from the ribosome first.

The invention also contemplates the use of the novel hydrophilic spacers (described in detail below) joined to the hinge region of an immunoglobulin which is then joined to any protein domain capable of providing a means of affinity purification of the fusion protein. Again, the protein of interest is inserted in front of the spacer sequences such that the protein of interest forms the amino-terminal domain and the affinity ligand-binding domain forms the carboxy-terminus of the fusion protein. The addition of the hydrophilic spacer and the hinge region of an immunoglobulin would greatly improve the efficiency of cleavage of existing fusion systems and provide a means to consistently generate authentic recombinant proteins.

Additionally, the invention contemplates the improvement of existing fusion/cleavage systems by the addition of the novel hydrophilic spacers of the invention to a cleavage site for a site-specific endoprotease. The hydrophilic spacer is added to the amino-terminal side of the endoprotease cleavage site so that an authentic carboxy-terminus of the protein of interest may be generated. Again, the fusion protein is preferably designed so that the protein of interest is located on the amino-terminal side of the hydrophilic spacer. This allows for the generation of authentic recombinant proteins following endoproteolytic cleavage and carboxypeptidase digestion. Existing cleavage/fusion systems which express the affinity-purifiable domain at the amino-terminal end of the fusion protein may also be further modified to express the protein of interest at the amino-terminal domain of the fusion protein. However, even if this is not done, the addition of the hydrophilic spacer to the site-specific endoprotease cleavage site is still an improvement to existing cleavage/fusion systems since increased efficiency of cleavage will result by the addition of the hydrophilic spacer. This spacer will increase the physical separation between the protein of interest and the endoprotease cleavage site and thereby increase the accessibility of the cleavage site by the endoprotease.

The invention also contemplates the use of the novel hydrophilic spacers followed by a cleavage site for a site-specific endoprotease followed by a hydrophilic domain other than the hinge region of an immunoglobulin followed by an affinity domain. It is not necessary that only the hinge region of an immunoglobulin molecule be used to provide a endoproteolytically susceptible domain which allows for increased accessibility of the cleavage site to the endoprotease.

For example, an endoproteolytically susceptible stretch comprising the sequence Gln-Gly-Pro-Gly-(Gln-Lys)$_n$ (SEQ ID NO:90), where n equals 1 to 5 and where n equals 3 to 5 is preferred, may be used to separate the protein of interest from an affinity domain other than the hinge/Fc region of an immunoglobulin, such as β-galactosidase [Germino, J. and Bastia, D., Cell 32,131–140 (1983)], the B domain of staphylococcal protein A, the S-peptide of ribonuclease S [Doria, H., et al., Bio/Technology 12, 890–897 (1994)], the GST protein (Smith, supra) and the mature streptavidin gene product [aa 1–160, Argarana, C. E., et al., Nucleic Acids Res. 14, 1871–1882 (1986)]. This stretch was designed to be both hydrophilic (the use of glutamine and lysine residues enhances solubility) and to expose the proteolytic site for the chosen endoprotease. This sequence is used to provide the a stretch of amino acids which serve a function similar to that provided by the hinge region of the immunoglobulin molecule when the affinity domain chosen is not the hinge/Fc domain of IgG. When an endoproteolytically susceptible stretch such as SEQ ID NO:90 is employed, the fusion protein will comprise the following domains in order, from the amino- to carboxy-terminus: a domain comprising the protein of interest, a domain comprising a hydrophilic spacer a domain comprising an endoproteolytically susceptible stretch (e.g., SEQ ID NO:90), and the chosen affinity domain (other than a portion of IgG).

For example, the spacer comprising Gln-Gly-Pro-Gly-(Gln-Lys)$_n$ may be used in the production of recombinant human growth hormone (hGH) in E. coli using the GST protein as a carboxy terminal affinity tail (hGH is used as the protein of interest for illustrative purposes; any protein of interest may be produced as described herein using an affinity domain other than the Fc or hinge domain of IgG). The carboxy-terminal phenylalanine (hGH) is linked to a thrombin site using a hydrophilic spacer sequence [e.g., Arg-Arg-Lys-Lys-Lys (SEQ ID NO:32)]. The carboxyl side of the thrombin site is linked to the amino-terminus of the GST protein with the above described spacer [Gln-Gly-Pro-Gly-Gln-Lys-Gln-Lys-Gln-Lys (SEQ ID NO:8)]. The resulting fusion protein is very soluble and the thrombin site is extremely vulnerable to the endoprotease (thrombin), resulting in very efficient separation of hGH from the fusion partner. Authentic hGH is generated by carboxypeptidase digestion of the remaining thrombin recognition sequence and the hydrophilic spacer.

Vectors containing DNA sequences encoding the following proteins which may be employed as affinity domains are commercially available: β-galactosidase (the lacZ gene product), the B domain of staphylococcal Protein A, the maltose binding protein (MBP) (the malE gene product) and *Schistosoma japonicum* glutathione-S-transferase. Vectors containing the lacZ gene sequences are available from Pharmacia Biotech (pCH110 and pMC1871; GenBank Accession Nos: U13845 and L08936, respectively). Fusion proteins containing β-galactosidase sequences can be affinity purified on aminophenyl-β-D-thiogalactosidyl-succinyldiaminohexyl-Sepharose. Vectors containing *Schistosoma japonicum* glutathione-S-transferase (GST) gene sequences are available from Pharmacia Biotech (the pGEX series which have GenBank Accession Nos.: U13849 to U13858). Fusion proteins containing GST sequences can be affinity purified on glutathione resins [e.g., glutathione Sepharose 4B (Pharmacia Biotech)]. Vectors containing malE gene sequences encoding the MBP are available from New England Biolabs (pMAL-c2 and pMAL-p2). Fusion proteins containing MBP sequences can be affinity purified on amylose resin (New England Biolabs). A Vector containing sequences encoding the IgG binding domains of Protein A is available from Pharmacia Biotech (pRIT2T; GenBank Accession No. U13864). Fusion proteins containing the IgG binding domains of Protein A can be affinity purified on IgG resins [e.g., IgG Sepharose 6FF (Pharmacia Biotech)].

When any of the above listed proteins (including the hinge/Fc domains of human IgG1) are used as affinity domains, it is not required that the entire protein be used as the affinity domain. Portions of these proteins may be used as the affinity domain provided the portion selected is sufficient to permit interaction of a fusion protein containing the portion of the protein used as the affinity domain with the desired affinity resin.

Site-Specific Endoproteases

The fusion proteins of the present invention comprise a protein of interest linked to an affinity domain via a hydrophilic spacer and an endoprotease site. Following affinity purification of the fusion protein, the affinity domain is removed from the fusion protein by endoproteolytic cleavage. Amino acid sequences which remain on the carboxy-terminal end of the protein of interest (derived from the endoprotease cleavage site and/or the hydrophilic spacer) are then removed by treatment with carboxypeptidase(s), as discussed below.

The following are preferred site-specific endoproteases:

1) Papain, which cleaves on the carboxy-terminal side of Arg-X, Lys-X, His-X and Phe-X (where X is any amino acid) [Carrey, E. A. (1989) Protein Structure: A Practical Approach, T. E. Creighton ed., IRL Press, Oxford, pp.117]. Papain is preferred for cleavage of fusions protein when the protein of interest is linked directly to the hinge region of an immunoglobulin molecule and is not susceptible to papain cleavage in its natural folded state. The hinge region is naturally accessible to papain and cleavage occurs at the following the histidine residue at position 225 of human IgG1 (see FIG. 10). Papain is a relatively mild protease, is commercially available in a highly purified form, and is available attached to solid supports (Sigma). The advantage of using a protease attached to a solid support is that this allows the complete and easy removal of the protease following digestion.

2) Protease VII and the ompT protease from *E. coli*, which cleave between Arg-Arg, Lys-Lys and Lys-Arg residues [Sugimura, K. and Higashi, N., *J. Bacteriol.* 170:3650 (1988) and Grodberg, J. and Dunn, J., *J. Bacteriol.* 170:1245 (1988)].

3) Clostropain, which cleaves on the carboxy-terminal side of arginine residues, with the preferred sequence being Arg-Tyr.

4) Trypsin, which cleaves on the carboxy-terminal side of arginine and lysine residues.

5) Yeast Protease Kex2 [Julius D., et.al., *Cell* 37, 1075–1089 (1984)], which recognizes and cleaves at the carboxy side of paired basic residues of Lys-Arg and Arg-Arg.

6) Kallikrein, which preferentially cleaves on the carboxy-terminal side of arginine within the recognition sequence Phe-Arg-Ser-Val (SEQ ID NO:9). When kallikrein is used as the protease for cleavage, the preferred linker sequence is Val-Pro-Phe-Arg-Ser (SEQ ID NO:10). The valine residue present in SEQ ID NO:10 functions as a penultimate enhancer thereby enhancing the removal of the proline residue by CPD-Y.

7) Thrombin, which cleaves on the carboxy-terminal side of arginine in the following sequence: Leu-Val-Pro-Arg-Gly-X, where X is a non-acidic amino acid (SEQ ID NO:11) [Chang, *Eur. J. Biochem.* 151:217 (1985)].

8) *Xenopus leavis* skin Arg-X'-Val-Arg-Gly (SEQ ID NO:12) endoprotease which cleaves between the arginine and glycine residues with the preferred X' being Leu, Phe, Ile, Val, Ala or Trp [Kuks, P., et al., *J. Biol. Chem.* 264:14609 (1989)].

9) Factor Xa, which cleaves between the arginine and glycine residues in the following sequences: Ile-Glu-Gly-Arg-X (SEQ ID NO:4), Ile-Asp-Gly-Arg-X (SEQ ID NO:5), and Ala-Glu-Gly-Arg-X (SEQ ID NO:6), where X is any amino acid except proline or arginine.

10) Enterokinase, which cleaves after the lysine residue in the following sequence: Asp-Asp-Asp-Asp-Lys (SEQ ID NO:13).

11) Renin, which cleaves between the leucine residues in the following sequence: Pro-Phe-His-Leu-Leu-Val-Tyr (SEQ ID NO:3).

12) Collagenase, which cleaves following the X residue in following sequence: Pro-X-Gly-Pro-Y where X and Y are any amino acid (SEQ ID NO:2) [Steinbrink R. D., et al., *J. Biol. Chem.* 260:2771 (1985)].

Hydrophilic Spacer Design

The placement of the protein of interest within the fusion construct is important for efficient generation of authentic recombinant proteins of interest. Placement of the protein of interest at the amino-terminus of the fusion protein has certain advantages. The protein of interest will be the first amino acid sequences produced on the ribosome. The fact that the protein of interest emerges from the ribosome before the fusion partner increases the likelihood that the protein of interest will fold properly. The amino-terminal peptide begins to fold as soon as it emerges from the ribosome without the interference of the fusion partner [Georgiou G. and Bowden G. A., Inclusion Body Formation and the Recovery of Aggregated Recombinant Proteins, in *Recombinant DNA Technology and Applications*, pp 333–356 McGraw Hill, Inc. (1991)]. The invention provides hydrophilic linkers which encode hydrophilic spacers that permit the construction of expression vectors encoding fusion proteins in which sequences encoding the protein of interest are located at the 5' end of the coding region. The sequences encoding the protein of interest are linked to sequences encoding the fusion partner domain through the hydrophilic linker in such a way as to facilitate the generation of authentic recombinant proteins of interest.

The hydrophilic spacers of the present invention serve several purposes, including a physical separation between the signal sequence-tagged protein of interest and the affinity domain (e.g., immunoglobulin domains). The amino acids of the spacer are designed to be highly hydrophilic, thus encouraging the appearance of the spacer towards the exterior of the desired molecule thereby increasing its exposure and availability for enzymatic cleavage. The sequence encoding the recognition sequence for any known site-specific endoprotease can be placed following the hydrophilic spacer. The specific endoprotease site chosen depends upon the proteolytic susceptibility of the protein of interest. The hydrophilic spacer/endoprotease site design generates a fusion protein in which it is possible to completely remove the immunoglobulin domain from the protein of interest. The physical separation provided by the hydrophilic spacer between the protein of interest and the affinity domain ensures the spatial availability of the affinity domain to interact with the affinity matrix as the possibility of steric hindrance from the protein of interest is reduced.

Parameters for the design of the hydrophilic spacers are deduced from the substrate specificities of the known carboxypeptidases. These enzymes have different preferences for particular amino acids when located at the ultimate position (i.e., the last residue) of the carboxy-terminus. The penultimate amino acid (i.e., the next to the last residue) also greatly influences the rate of hydrolysis. A review of the specificities of the serine carboxypeptidases has been published [Breddam K., *Carlsberg Res. Commun.* 51, 83–128 (1986)] and the specificities of the metallocarboxypeptidases A and B have been reviewed [R. P. Ambler, *Methods Enzymology* 25:262 (1972)].

The hydrophilic spacer joined to a specific endoprotease site forms a functional unit. This unit has a higher than normal probability of cleavage by endoproteases (due to the hydrophilic nature of the spacer sequences) and the amino acids remaining on the desired protein (post-cleavage) can be removed to generate authentic proteins. The protein which is generated by endoproteolytic cleavage of the fusion protein is referred to as the "released protein of interest." This term indicates that the protein of interest has been separated or "released" from the affinity domain.

Three levels of hydrophilic spacer/endoprotease site (i.e., linker) designs are provided in the present invention. The choice of a particular linker design depends on 1) the nature of the carboxy-terminus of the protein of interest and 2) the specific endoprotease chosen for cleavage of the fusion molecule. The term "level" refers to the level of processing required to generate the authentic protein of interest following cleavage of the fusion protein.

In Level 1, the processing of the cleaved or "released" protein of interest to generate authentic protein requires either 1) no further treatment or 2) treatment with carboxypeptidase B. In Level 2, the cleaved or "released" protein of interest is treated with carboxypeptidase A and carboxypeptidase B. In Level 3, the released protein of interest is treated with carboxypeptidase A, carboxypeptidase B and carboxypeptidase Y.

Three levels of hydrophilic spacer/endoprotease site designs are provided; these three levels permit the production of most authentic proteins by recombinant means. It is noted that the vast majority of proteins to be produced using the methods of the present invention will utilize a Level 2 or 3 design due to the increased specificity of the endoprotease used.

Level 1 Linker Designs

The Level 1 linker design is the simplest functional unit in which the endoprotease site and the hydrophilic spacer comprise the same amino acids. The Level 1 design is employed when endoproteases which cleave basic amino acid residues are employed for the removal of the affinity domain. Table 1 provides a list of endoproteases suitable for cleavage of Level 1 design fusion proteins. In Table 1, "X" refers to any amino acid, the arrow indicates the site of cleavage and the use of a slash between two amino acid residues indicates that either of these residues may be present at that position. For example, furin will cleave at either Arg-X-Arg-Arg (SEQ ID NO:14) or Arg-X-Lys-Arg (SEQ ID NO:15).

TABLE 1

| Hydrophilic Spacer | Endoprotease | Resulting COOH |
| --- | --- | --- |
| Arg↓ or Lys↓ | Trypsin | Arg or Lys |
| Arg/Lys-Arg↓ | Yeast Kex2 | Lys-Arg or Arg-Arg |
| Arg/Lys↓-Arg or Lys↓-Lys | OmpT, Protease VII | Arg or Lys |
| Arg↓-Tyr | Clostropain | Arg |
| Arg-X-Arg/Lys-Arg↓ | Furin | Arg-X-Arg/Lys-Arg |

The endoproteases shown in Table 1 are listed in order of those requiring the least number of specific amino acids residues in the cleavage site to those requiring the greatest number of specific residues. It is noted that trypsin will cleave at the recognition site for all of the endoproteases listed in Table 1. The yeast Kex2, OmpT and protease VII proteases are referred to as "dibasic recognition" or "dibasic" proteases; these enzymes require two adjacent basic amino acid residues for cleavage. The sites cleaved by furin can also be cleaved by the dibasic proteases and trypsin.

The Level 1 linker design is employed when the protein of interest is not susceptible to digestion by one of the endoproteases listed in Table 1 and either 1) the naturally occurring carboxy-terminal amino acid of the protein of interest is an arginine or a lysine or 2) a spacer comprising basic amino acids is used to link the protein of interest and the affinity purifiable domain. When the protein of interest naturally terminates in an arginine or lysine residue, a Level 1 linker can be employed which places an arginine or lysine residue next to the carboxy-terminal residue of the protein of interest; in this way a cleavage site for OmpT and/or protease VII is created. Cleavage of such a fusion protein with the OmpT protease or protease VII will generate an authentic protein of interest without the need to further treat the released protein of interest. When the protein of interest is not susceptible to digestion by one of the endoproteases listed in Table 1 but does not contain a carboxy-terminal arginine or lysine residue, a Level 1 linker is employed to join the protein of interest to the affinity domain. In this case, sequences encoding the affinity domain are joined to sequences encoding the protein of interest using a linker which encodes basic amino acid residues.

Figure 1B:
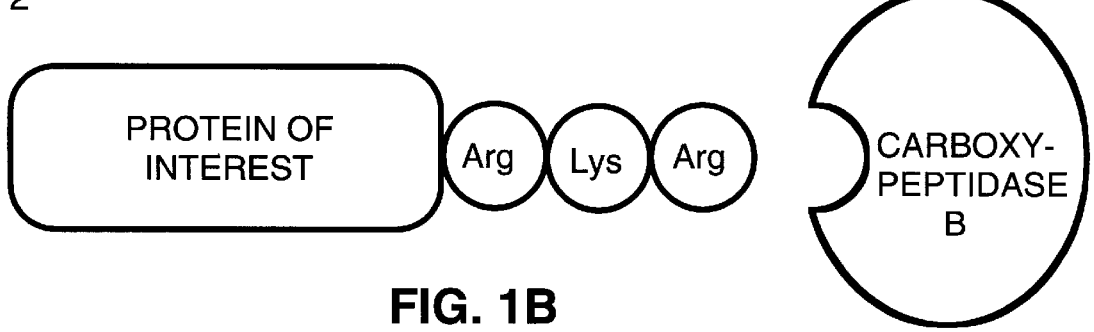
Figure 1C:
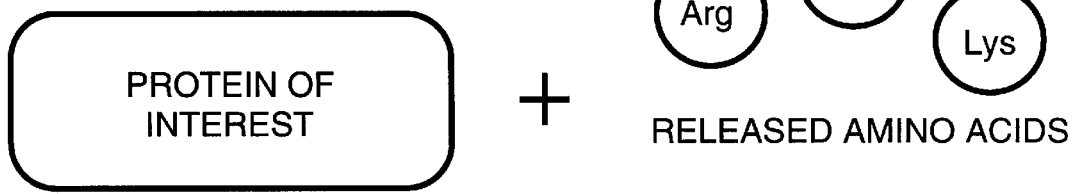
Figure 2A:
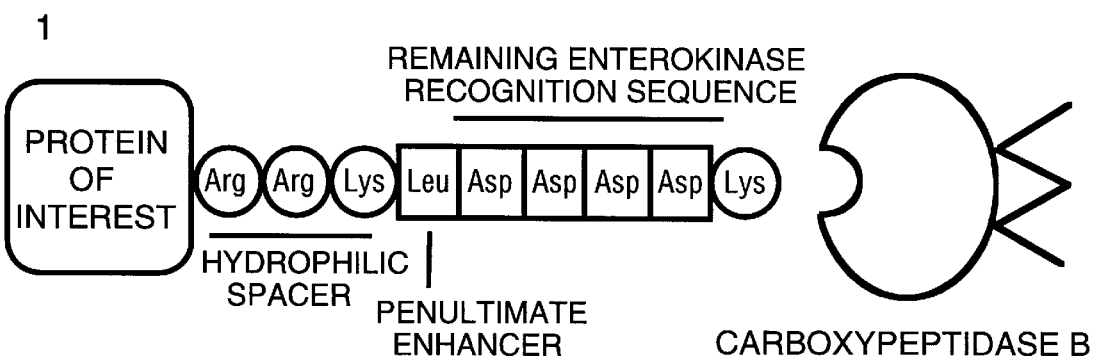
FIG. 2 provides a schematic illustrating the processing of fusion proteins having Level 2 linker designs.
Figure 2B:
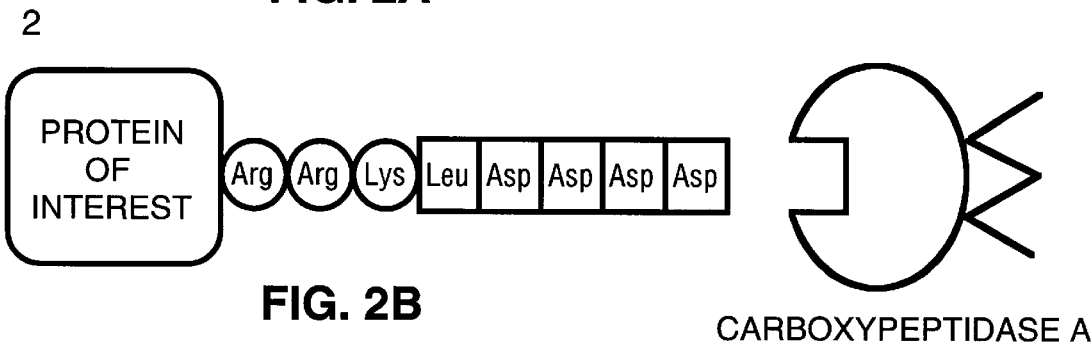
Figure 2C:
Figure 2D:

FIG. 1 provides a schematic illustrating Level 1 processing. FIG. 1 shows an exemplary case where the hydrophilic spacer/endoprotease site employed contains a recognition site for a dibasic protease and the affinity domain comprises the hinge and Fc domains of a IgG. In FIG. 1, step 1 shows the fusion protein (as a dimer of two molecules as the IgG sequences are capable of dimerization) bound to the affinity resin (e.g., protein A-Sepharaose). In Level 1 processing, cleavage of the fusion protein generates a released protein of interest which contains either an arginine or a lysine residue at the carboxy-terminus (FIG. 1, step 2). Authentic protein of interest is generated from the released protein of interest by removal of the linker-encoded arginine or lysine residues (i.e., the residues comprising the hydrophilic spacer) by digestion with carboxypeptidase B.

There are processing advantages to using the enzymes listed in Table 1 above. These enzymes recognize the amino acids arginine and/or lysine without the requirement for specific amino acids in positions located toward the amino-terminus of the substrate. As discussed below, generation of authentic amino acid products is achieved by incubating the cleaved fusion protein with immobilized carboxypeptidase B, thus removing the amino acids comprising the hydrophilic spacer. Dibasic recognition proteases (i.e., yeast Kex2, OmpT and protease VII) are preferred over trypsin due their increased specificity. The OmpT protease is a dibasic recognition protease which is readily isolated from the outer membrane of any *E. coli* K strain which expresses the protease, such as LE 392 (Stratagene), by incubating whole cells with 30 mM n-octylglucoside [Grodberg J. and Dunn J. J., *J. Bacteriol.* 170:1245 (1988)].

Another advantage of using proteolytic enzymes specific for Arg-Arg or Lys-Arg (i.e., a dibasic recognition protease) is that many proteins are synthesized as precursor molecules (e.g., prohormones) that require proteolytic processing to produce the active or mature form of the protein. Specialized secretory cells are required to process these proteins during secretion [Thomas G. et al., *Science* 232:1641 (1986)]. Prokaryotic and some eukaryotic cells are not capable of processing secretory proteins. The processing of the prohormone to the hormone form of peptide hormones involves the cleavage after a pair of basic amino acid residues (i.e., a dibasic Kex2 site). These dibasic sites comprise Arg-Arg or Lys-Arg. Thus, when the protein of interest is a peptide hormone, the expression vector will contain sequences encoding the prohormone form of the protein of interest, a Level 1 spacer and the affinity domain. When the resulting fusion protein is separated from the affinity domain by digestion with the Kex2 dibasic recognition protease, the mature form of the hormone is also generated by cleavage of the dibasic site internal to the prohormone.

Level 2 Linker Designs

Level 2 spacer/endoprotease site (i.e., linker) designs are used in combination with endoproteases that leave a portion of their recognition sequence behind after proteolytic cleavage. This remnant, because of its amino acid sequence, can be removed by sequential treatment with carboxypeptidase A (CPA) and carboxypeptidase B (CPB). CPB removes carboxy-terminal arginine or lysine residues only. CPA can rapidly digest or remove carboxy-terminal tyrosine, phenylalanine, tryptophan, leucine, isoleucine, methionine, threonine, glutamine, histidine, alanine and valine residues. CPA removes carboxy-terminal asparagine, serine and lysine slowly; glycine, aspartic acid, glutamic acid and cysteine derivatives (e.g., $CySO_3H$ and S-carboxymethylcycteine) are removed very slowly by CPA; CPA cannot cleave or remove arginine and proline residues.

Thus, using CPA and CPB in combination all amino acids can be removed from the released protein of interest except for proline, which neither CPB or CPA can remove. Combination of amino acids which are released very slowly or not at all released amino acids (proline or arginine) in the penultimate positions will generally decrease the rate of release of carboxy-terminal amino acids [Ambler, supra]. The addition of the leucine residue into the enterokinase linker allows CPA to proceed smoothly to the arginine residue by avoiding the extremely slow step of Arg-Asp (the CPA digestion is conducted at 37° C.).

Table 2 below provides examples of Level 2 linker designs for use with specific endoproteases. In Table 2 underlining is used to indicate amino acid residues provided by the hydrophilic spacer (the hydrophilic spacer may contain additional hydrophilic amino acid residues). In Table 2, bold type is used to indicate the penultimate enhancer. Penultimate enhancers are an element used to promote the efficient removal of the amino-terminal residue of the proteolytic recognition sequence during carboxypeptidase reactions of level 2 or 3 designs. Specific endoprotease recognition sites are provided and the arrow indicates the location of the cleavage within these sites.

TABLE 2

| Spacer/Endoprotease Site | Endoprotease | Digestion Protocol[a] |
|---|---|---|
| Arg-Lys-Lys-Ile-Glu-Gly-Arg↓ | Factor Xa | CPB, CPA, CPB |
| Arg-Lys-Arg-Phe-Val-Arg↓-Gly | *X. leavis* protease[b] | CPB, CPA, CPB |
| Arg-Lys-Lys-Leu-Asp-Asp-Asp-Asp-Lys↓ | Enterokinase | CPB, CPA, CPB |

↓cleavage site
[a]sequential digestion using the indicated enzymes in an immobilized form
[b]RXVRG-endoprotease from X. leavis FIG. 2 provides a schematic which represent the generation of authentic protein using the Level 2 spacer design. In FIG. 2, basic amino acids which can be removed by CPB are represented by the circles and amino acids which can be removed by CPA are represented by the squares. Level 2 processing is illustrated using a hydrophilic spacer which comprises the sequence Arg-Arg-Lys (SEQ ID NO:16); the spacer is followed by a leucine residue which functions as a penultimate enhancer; the penultimate enhancer is followed by the recognition site for the endoprotease enterokinase [Asp-Asp-Asp-Asp-Lys (SEQ ID NO:13)]. Step 1 of FIG. 2 shows the released protein of interest generated by digestion of the fusion protein with enterokinase (enterokinase cleaves on the carboxy-terminal side of the lysine residue present in the enterokinase recognition site); the released protein is then treated with CPB to remove the terminal lysine residue. Step 2 of FIG. 2 shows the released protein of interest following treatment with CPB and indicates that the released protein of interest is now to be treated with CPA to remove the asparagine and leucine residues. In all Level 2 and 3 designs, the preferred hydrophilic spacer has a lysine residue at its carboxy terminal position to allow efficient transition from CPA digestion to CPB digestion. Carboxy terminal lysine residues can be removed with CPA and/or CPB. The lysine residues allow CPA to proceed completely through the remaining exoprotease recognition sequence or penultimate enhancer without any inhibition. An arginine residue in the same position would slow the reaction and therefore is not preferred. Complete efficient removal of the remaining exoprotease recognition sequence or penultimate enhancer ensures that the hydrophilic spacer will be available for CPB digestion. Following treatment with CPA, the released protein of interest is treated again with CPB to remove any remaining lysine residues and the arginine residues (step 3) to generate the authentic protein of interest (step 4). As discussed in greater detail below, removal of the amino acids which comprise the endoprotease site and the hydrophilic spacer can be achieved using immobilized forms of the carboxypeptidases. The use of immobilized enzymes is advantageous as this obviates the need to remove the carboxypeptidases from the final preparation of the authentic protein and allows the sequential digestion of the released protein of interest with the carboxypeptidases.

Level 2 designs are used when the protein of interest would be susceptible to the cleavage protocol described above for the Level 1 design. Level 1 linkers comprise hydrophilic spacer sequences that do not require additional endoprotease sequences because the endoproteases used in the Level 1 design recognize and cleave the hydrophilic spacers. Level 2 linkers encode protease recognition sites for proteases that leave amino acids on the carboxy-terminus of the protein of interest which cannot be removed by digestion with CPB. Level 2 denotes that additional in vitro processing steps are needed to generate authentic protein molecules, specifically CPA digestion(s) is required. Due to the specificities of the carboxypeptidases and the digestion conditions utilized in conjunction with the Level 2 and 3 linkers it is not possible to generate authentic proteins that have carboxy terminal lysine residues using carboxypeptidases to digest non-authentic amino acid residues from the protein of interest. All of the currently characterized carboxypeptidases can remove lysine residues under the conditions described herein. However, the Level 1 linker design that inserts a single arginine residue after the naturally-occurring lysine residue to create an OmpT/proteases VII cleavage site permits the generation of authentic proteins which terminate (carboxy-terminus) with lysine.

Arginine residues at the authentic proteins carboxy terminus of Level 2 or 3 linkers can be handled one of two ways. The first method adds a hydrophilic spacer that is composed of lysine only [e.g., Lys-Lys-Lys (SEQ ID 18)]. This hydrophilic spacer is placed following the natural arginine, and allows the hydrophilic spacer to be removed during the CPA digestion without the requirement of a CPB digestion. The second method adds a hydrophilic spacer that contains arginine residues and requires alternating CPA and CPB digestions to generate authentic protein with a carboxyterminal arginine. A leucine residue is placed between the natural arginine and the arginine represented in the hydrophilic spacer Arg-Lys-Lys SEQ ID 16) in order to act as a termination point for the CPB digestion. CPB is used as described to remove the hydrophilic spacer, stopping at the inserted leucine residue. A final CPA digestion is used to remove the leucine residue and generate an authentic protein.

Level 3 Linker Designs

The Level 3 linker designs take into consideration the fact that many specific endoproteases require proline residues in their recognition sequence for optimum activity. Since proline cannot be removed using CPA or CPB, another carboxypeptidase with this capability must be used. Carboxypeptidase Y (CPD-Y) is chosen due to the well characterized preference of this enzyme for hydrophobic amino acids [Breddam and Ottesen, *Carlsberg Res Commun.* 52:55 (1987)]. This yeast carboxypeptidase can digest all naturally occurring amino acids but it has a preference for hydrophobic amino acids in both the ultimate and penultimate positions. A general preference profile for the CPD-Y enzyme at pH 6.5 has been described [Breddam, *Carlsberg Res Commun.* 51:83 (1986)] and is shown below:

| | |
|---|---|
| penultimate | Phe > Leu > Ala > His > Glu > Gly > > Lys |
| ultimate | Met, Ile, Leu > Phe > Ala > Arg > Ser > Pro > Lys > Asn > Gly > Asp |

The above preferences for the CPD-Y enzyme are listed in order of decreasing $K_{cat}/K_m$ values. In cases where the values deviate by less than 20%, a comma is used in place of the greater than symbol (>).

CPD-Y can digest every amino acid, although the different amino acids are removed with varying rates. In order to selectively remove a proline residue from the carboxy-terminus of a population of molecules comprising the released protein of interest without proceeding into the protein of interest itself, the hydrophilic linker must also provide protection against excessive carboxy-terminal degradation by CPD-Y. There are sequences that are reported to be resistant to CPD-Y digestion (at pH 4.5), namely Arg-Arg and Lys-X [Klarskov et al., *Analytical Biochem.* 180: 28–37 (1989)]. These sequences are accordingly incorporated into the hydrophilic spacer region when designing the Level 3 linkers which encode the hydrophilic spacers.

Table 3 provides examples of Level 3 linker designs for use with specific endoproteases. In Table 3 underlining is used to indicate amino acid residues provided by the hydrophilic spacer (the hydrophilic spacer may contain additional hydrophilic amino acid residues). In Table 3, bold type is used to indicate the penultimate enhancer. Penultimate enhancers are an element used to promote the efficient removal of the amino-terminal residue of the proteolytic recognition sequence during carboxypeptidase reactions of level 2 or 3 linkers. Specific endoprotease recognition sites are provided and the arrow indicates the location of the cleavage within these sites.

TABLE 3

| Spacer/Endoprotease Site | Endoprotease | Digestion Protocol[a] |
|---|---|---|
| <u>Arg-Arg</u>-Leu-Val-Pro-Arg↓-Gly | Thrombin | CPB, CPD-Y[a], CPA, CPB |
| <u>Arg-Arg-Lys-Lys-Lys</u>-Leu-Val-Pro-Arg↓-Gly | Thrombin | CPB, CPD-Y[a], CPA, CPB |
| <u>Arg-Lys-Lys</u>-Val-Pro-Phe-Arg↓-Ser | Kallikrien | CPB, CPD-Y[a], CPA, CPB |
| <u>Arg-Lys-Lys</u>-Leu-Pro-Leu↓-Gly-Pro | Collagenase | CPA, CPD-Y[a], CPA, CPB |
| <u>Arg-Lys-Lys</u>-Leu-Pro-Phe-His-Leu↓-Leu-Val-Tyr | Renin | CPA, CPD-Y[a], CPA, CPB |

↓ cleavage site
[a] immobilized enzyme limited flow digest

The penultimate enhancers shown above in the collagenase and renin linkers allow CPD-Y to remove the proline residues present in the endoprotease recognition sequence after cleavage more efficiently than if the endoprotease site sequence were to be directly linked to the hydrophilic spacer sequence. The lysine residue present in the hydrophilic spacers listed above is the residue least preferred by CPD-Y (when the lysine is present in the penultimate position shown above). The direct linking of lysine to proline would result in an extremely slow digestion step during the CPD-Y flow digestion. In order to significantly raise the $K_{cat}/K_m$ for proline removal, an amino acid which is preferred by CPD-Y when in the penultimate position (i.e., phenylalanine or leucine) is inserted between the lysine of the hydrophilic spacer and the proline of the endoprotease recognition sequence. Leucine is the preferred amino acid to be inserted after the hydrophilic spacer because it also prevents cleavage after the carboxy-terminal hydrophilic spacer residue by precursor processing enzymes, such as furin/PACE and PC1/PC3 [Nakayama, et al., *J. Biol. Chem.* 267:16335 (1992)].

FIG. 3 provides a schematic which represents the generation of authentic protein using the Level 3 linker design. In FIG. 3, basic amino acids (i.e., amino acids having positively charged side chains) which can be removed by CPB are represented by the circles; amino acids which can be removed by CPA are represented by the squares; residues which are removed by CPD-Y (e.g., proline) are represented by an arrowhead. The term "penultimate enhancer" refers to the use of a non-hydrophilic amino acid (e.g., leucine) which when located next to a carboxy-terminal proline residue will enhance the removal of proline by CPD-Y.

In FIG. 3, Level 3 processing is illustrated using a fusion protein which contains a hydrophilic spacer comprises the sequence Arg-Lys-Lys (SEQ ID NO:17); the spacer is followed by a leucine residue which serves as a penultimate enhancer allowing the efficient removal of the proline residue by CPD-Y. The penultimate enhancer is followed by the recognition site for the endoprotease renin [Pro-Phe-His-Leu↓-Leu-Val-Tyr (SEQ ID NO:3); the arrow indicates the site of cleavage].

Step 1 of FIG. 3 shows the released protein of interest generated by digestion of the fusion protein with renin (renin cleaves on the carboxy-terminal side of the first leucine residue present in the renin recognition site); this protein is then treated with CPA to remove the leucine, histidine and phenylalanine residues which remain after digestion of the fusion protein with renin. This first CPA digestion is allowed to go to completion as the proline residue will halt digestion by CPA. The CPA-treated released protein is then treated with CPD-Y to remove the terminal proline residue (Step 2 of FIG. 3); the use of the leucine residue as a penultimate enhancer allows the efficient digestion of proline by CPD-Y. Following treatment with CPD-Y, the protein of interest is treated with CPA to remove the leucine residue. The lysine and arginine residues of the hydrophilic spacer are then removed by digestion with CPB (Step 4) to generate the authentic protein of interest (Step 5).

The above discussion provides guidance for the selection of a particular design of spacer/endoprotease sites to be used to join the protein of interest with the affinity domain. More guidance is provided below.

The following are preferred forms of hydrophilic spacer sequences: Arg-Arg-Lys (SEQ ID NO:16); Arg-Lys-Lys (SEQ ID NO:17); Lys-Arg-Lys (SEQ ID NO:18); Lys-Lys-Lys (SEQ ID NO:19); Arg-Arg-Arg-Lys (SEQ ID NO:20); Arg-Arg-Lys-Lys (SEQ ID NO:21); Lys-Arg-Arg-Lys (SEQ ID NO:22); Arg-Lys-Arg-Lys (SEQ ID NO:23); Arg-Lys-Lys-Lys (SEQ ID NO:24); Lys-Arg-Lys-Lys (SEQ ID NO:25); Lys-Lys-Arg-Lys (SEQ ID NO:26); Arg-Arg-Arg-Arg-Lys (SEQ ID NO:27); Arg-Arg-Arg-Lys-Lys (SEQ ID NO:28); Arg-Arg-Lys-Arg-Lys (SEQ ID NO:29); Arg-Lys-Arg-Arg-Lys (SEQ ID NO:30); Lys-Arg-Arg-Arg-Lys (SEQ ID NO:31); Arg-Arg-Lys-Lys-Lys (SEQ ID NO:32); Arg-Lys-Arg-Lys-Lys (SEQ ID NO:33); Arg-Lys-Lys-Arg-Lys (SEQ ID NO:34); Lys-Arg-Arg-Lys-Lys (SEQ ID NO:35); Lys-Arg-Lys-Arg-Lys (SEQ ID NO:36); Lys-Arg-Lys-Lys (SEQ ID NO:37); and Arg-Lys-Lys-Lys-Lys (SEQ ID NO:38). These preferred hydrophilic spacers can be used in Level 1, 2 or 3 linker designs; these spacers can be used when the fusion protein is to be expressed in non-endocrine mammalian cell lines. Fusion proteins comprising proteins of interest which end in an arginine or lysine residue require the insertion of a leucine residue between the carboxy-terminal arginine or lysine of the protein of interest and the hydrophilic spacer (as described above for Level 2 designs).

The above listed sequences represent preferred spacer sequences which should be adequate for separating the desired endoprotease site from the carboxy-terminus of the protein of interest. The invention also contemplates the insertion of hydrophilic triplets such as Lys-Lys-Lys (SEQ ID NO:19) and Lys-Arg-Lys (SEQ ID NO:18) to the amino-terminal end of any of the above-listed spacers to generate extended hydrophilic spacers. These longer (i.e., extended) spacers are employed when the carboxy-terminus of the protein of interest is sufficiently buried within the hydrophobic interior of the protein so as to structurally inhibit the removal of any remaining endoprotease recognition sequences and/or the penultimate enhancer by CPA digestion. Traditional approaches to dealing with the cleavage of fusion proteins having a buried carboxy-terminus of the protein of interest employ the use of denaturant during the digestion of the fusion protein. This approach is not appropriate when CPA is to be employed as CPA loses most of its activity under denaturing conditions. The use of the "extended hydrophilic spacers" is appropriate when the protein of interest is large and has a hydrophobic carboxy-terminus. The use of the additional hydrophilic triplets will extend the amino acids of the remaining endoprotease recognition sequence and/or penultimate enhancer towards the hydrophilic exterior of the protein thereby allowing digestion of these sequences with CPA under non-denaturing conditions. The extended hydrophilic spacer can be removed by digestion with CPB under denaturing conditions (e.g., in the presence of 2–6 M urea) [Sassenfeld, H. M. and Brewer S. J. Bio/Technology, January, p. 76 (1984)]. Proteases that cleave to leave a lysine residue are the preferred method for removal of the affinity domain until carboxypeptidases which cannot remove lysine residues become available.

Host Cells and the Use of Level 1, 2 or 3 Designs

The production of recombinant proteins often involves the use of protease inhibitors to prevent the degradation of the recombinant protein (e.g., fusion protein) before it can be isolated in a purified form. Numerous protease inhibitors are known to the art and include, but are not limited to leupeptin, pepstatin A, antipain, aprotinin, PEFABLOC (Pentapharm Ltd., Basel, Switzerland), chymostatin, trypsin inhibitor from soybean, FBS-d-PI, phenylmethylsulfonyl fluoride (PMSF) and (4-amidinophenyl) methane sulfonyl fluoride (APMSF). Due to the design of the hydrophilic spacers of the present invention, it is required that steps are taken to inhibit trypsin and other serine proteases that recognize arginine and/or lysine residues to prevent the cleavage of the fusion proteins. In selecting a cell line to be used as a host cell for the production of fusion proteins, the cell line is screen for the ability to produce and/or secrete proteases which can cleave the hydrophilic spacers of the invention. In addition, medium supplements should also be monitored for the presence of these proteases. Cell lines (and culture supernatant from cell lines) and medium supplements can be monitored using commercially available synthetic peptide substrates. Four particularly useful synthetic substrates are N-benzoyl-Val-Lys-Lys-Arg-4-methoxy-B-napthyamide, N-t-Boc-Glu-Lys-Lys-7-amido-4-methycoumarin, N-t-Boc-Gly-Arg-Arg-7-amido-4-methylcoumarin and N-t-Boc-Gly-Lys-Arg-7-amido-4-methylcoumarin [Mizuno et al., *Biochem. Biophys. Res. Commun.* 144:807 (1987)]; all of these substrates are available from Sigma. Cell lines and medium supplements which express the least amount of protease activity on these type of substrates (i.e., substrates containing arginine and/or lysine residues) are preferred.

Protease activity capable of producing detectable cleavage of the above synthetic substrates and/or of the hydrophilic linker of the fusion proteins of the invention, which is present in cell lines and medium supplements to be used, may be inhibited by the inclusion of one or more protease inhibitors in the growth medium and in all solutions used for the harvesting and processing of the fusion protein until the fusion protein has been subjected to purification steps which remove proteases (e.g., affinity purification). When protease inhibitors are to be added to the growth medium, the following proteases inhibitors derived from natural sources are preferred: aprotinin (Sigma) derived from bovine lung [Weidle, et al. Gene 73:439 (1988)], trypsin inhibitor from soybean and FBS-d-PI which is present fetal bovine serum [Shinommura, et al. Cytotechnology 6:1 (1911)]. Inclusion of one or more of these preferred protease inhibitors in the growth medium will prevent or minimize the cleavage of secreted fusion proteins prior to the isolation of culture supernatant containing the fusion protein.

The hydrophilic spacers of the present invention are suspectable to cleavage by the dibasic proteases present in a variety of host cells. The cell lines used for expression of the fusion proteins must lack proteases which can cleave the hydrophilic linker sequences. Expression of the fusion proteins in bacterial cells requires the use of bacterial strains which lack the OmpT protease [e.g., C1757, B834 (Novagen), UT4400 and BL21 (Novagen); Grodberg and Dunn, J. Bacteriol. 170:1245 (1988)]. The AG1 strain (Stratagene) is a derivative of the DH1 strain which contains very low levels of OmpT protease. Expression of the fusion proteins in yeast may be achieved using S. cerevisiae kex2 mutant strains [e.g., XBH16-15A, RW427 and RW433; Julius D., et al., Cell 37:1075 (1984)].

Insect cells which lack protease activity have not been reported. Accordingly, when fusion proteins are to be expressed in insect cells [e.g., Sf9, Sf21 and MG1 cells (Stratagene)] the following hydrophilic spacers are used: Arg-Lys-Lys (SEQ ID NO:17), Arg-Lys-Lys-Lys (SEQ ID NO:24) and Arg-Lys-Lys-Lys-Lys (SEQ ID NO:38). If an extended hydrophilic spacer is to be employed for the expression of fusion proteins in insect cells, the lysine triplet (SEQ ID NO:19) can be added to the carboxy-terminal end of the above 3 spacers. The ability of the Sf9 insect cell line to at least partially process proNGF into authentic, active NGF by cleavage of the naturally occurring proprocessing site Arg-Ser-Lys-Arg (SEQ ID NO:39) (U.S. Pat. No. 5,272, 063, the disclosure of which is herein incorporated by reference) limits the use of hydrophilic spacers to those containing Arg-Lys and Lys-Lys amino acid combinations and those lacking Arg-Arg and Lys-Arg combinations.

Expression of the fusion proteins of the present invention in mammalian cell lines requires the use of cell lines which have a limited ability to cleave dibasic residues. The enzymes responsible for the dibasic processing of prepro precursor molecules of the endocrine system have been termed PC2 and PC1/PC3. These enzymes are part of the regulated secretion pathway and are expressed only in the secretory cells of the endocrine system. These enzymes have the ability to cleave dibasic (e.g., Lys-Arg and Arg-Arg) and monobasic sites (Arg-X-X-Arg) (SEQ ID NO:40) [Molly, et al. J. Biol. Chem., 267:16396 (1992)]. Cell lines derived from secretory cells of the endocrine system (e.g., AtT-20 mouse pituitary) should be avoided when the fusion proteins are to be expressed in mammalian host cells.

Most mammalian cell lines have enzymes which process proproteins into mature proteins during the export of the protein in a constitutive secretion pathway. The isozymes of the constitutive secretion pathway are termed PACE (paired basic amino acid cleaving enzyme)/furin and PACE4; these enzymes are ubiquitously expressed and are present at varying levels in most mammalian cell lines. The substrate specificity of furin [recognition site: Arg-X-Arg/Lys-Arg (SEQ ID NOS:14 and 15)] has been studied using a variant synthetic peptides based on the N-terminal sequence of human proalbumin [Brennan and Nakayama, FEBS Letters 347:80 (1994)]. These experiments concluded that furin could not cleave in the middle of a tetra-basic sequence which indicates that the protease cannot cleave between two basic residues. Another established substrate specificity requirement prevents the cleavage of a furin recognition motif (Arg-X-Arg/Lys-Arg-Y) where Y is a hydrophobic aliphatic residue (i.e., leucine, isoleucine, valine) [Nakayama, et al., J. Biol. Chem. 267:16335 (1992)]. These sequence requirements were used as guidelines in the design of hydrophilic spacers of the present invention to prevent the cleavage of fusion proteins during secretion in mammalian host cell lines. These sequence requirements were used as guidelines in the design of hydrophilic spacers to prevent the cleavage of fusion proteins during secretion in mammalian host cell lines.

When fusion proteins containing Lys-Arg or Arg-Arg in the hydrophilic linker region are to be expressed in mammalian cells, non-endocrine cell lines, such as monkey kidney derived cell lines [CV-1 (ATCC CCL 70), COS-1 (ATCC CRL 1650) or COS-7 (ATCC CRL 1651)] or a Chinese hamster ovary cell line [CHO-K1 (ATCC CCL 61)] are employed to prevent cleavage of the fusion protein in vivo (i.e., prior to affinity purification).

Several cell lines of higher eukaryotes cannot correctly process pro-insulin (i.e., COS and CV-1) [Laub O., J. Biol. Chem. 258:6043 (1983)] or preproglucagon [BHK fibroblasts (ATCC 6281)] [Drucker D. J., J.Biol.Chem 261:9637 (1986)]; the inability to process these proteins suggests that these cell lines are deficient in the enzymes that are responsible for the proteolytic processing which occurs in the specialized secretory cells of the endocrine system. Cell lines which have been previously shown to lack the ability to process molecules at their natural dibasic sites preferred cell lines for the production of recombinant fusion proteins which contain Lys-Arg or Arg-Arg in the hydrophilic linker region.

The presence of a dibasic recognition site alone is not sufficient to allow proteolytic cleavage as many hormones and growth factors have internal dibasic sites (i.e., sites located within the sequences encoding the mature form of the protein) that are not cleaved during secretion. A study of sequences encoding prosomatostatin derived from several species suggests that the general exposure (i.e., location on the exterior of the molecule) and conformation of the dibasic site may influence whether a particular site is susceptible to cleavage [Warren, Cell 39:547 (1984)]. The enzymes responsible for dibasic cleavage in the constitutive secretion pathway (i.e., non-regulated secretion) have been characterized; these enzymes are termed furin or PACE. Furin and PACE require an arginine at the P4 site for cleavage [Hatsuzawa et al., J. Biol. Chem. 267:16094 (1992)]. The specificities of furin and PC1/PC3 enzymes from the endocrine system have been compared [Nakayama, J. Biol. Chem. 267:16335 (1992)] and found to be similar [the recognition sequence for furin is Arg-X-Lys/Arg-Arg (SEQ IS NOS:14 and 15); the recognition site for PC1/PC3 is Arg-X-X-Arg (SEQ ID NO:40). Therefore, furin-like activity is found in both endocrine and constitutive secretion systems.

Expression in Non-Endocrine Mammalian Cell Lines

The NIH3T3, HepG2, COS-7 and CHO cell lines are examples of constitutively secreting cell lines that produce furin in varying amounts to process pro-regions at the motif Arg-X-Lys/Arg-Arg (Yanagita M., supra). Proteins that naturally have amino terminal pro regions are ideal candidates for the carboxy-terminal fusion designs of the present invention. High level expression levels of pro-proteins can overwhelm the amount of natural furin activity, but when furin is cotransfected with pro-protein fusion this limitation can be overcome (Hatsuzawa K. et al., supra). The optimum motif for furin cleavage is Arg-X-Lys/Arg-Arg and although most proproteins produced by the constitutive secretion pathway contain this recognition sequence, proproteins of the endocrine secretory route do not. Secreted molecules of the endocrine system can be produced in constitutive secretion cells according to the methods of the present invention by fusing the carboxy-terminus of the mature protein to the hydrophilic spacers described and joining that fusion to the KpnI site of the IgG1 fragment (discussed in detail below). The amino-terminal pro cleavage site would be modified in these cases to represent a furin cleavage motif.

By combining the expression of preproprotein fusion molecules with a host that contains a high level of furin activity, the resulting secreted product will be affinity purified from the media with a processed amino-terminus. Separation of the desired molecule from the affinity domain by a specific protease results in a purified, naturally folded and glycosylated protein. The remaining hydrophilic spacer and endoprotease sequence can be sequentially removed by digestion with carboxypeptidase A, carboxypeptidase Y and/ or carboxypeptidase B.

Generation of Authentic Proteins Using Carboxypeptidases

Recognition sequences of more specific proteases are used when the desired product is susceptible to proteolytic degradation by the Arg and/or Lys proteases. Removal of the carboxy-terminal hydrophilic linker and remaining proteolytic recognition sequence is accomplished sequentially with carboxypeptidases with varying specificities. Enzymes that can be used are, but not limited to, carboxypeptidase B, carboxypeptidase A, carboxypeptidase Y, carboxypeptidase C, cathepsin A, malt carboxypeptidases I/II and carboxypeptidase P. All of these enzymes exhibit preferences for amino acids in the ultimate and penultimate positions of the substrate. A review of serine carboxypeptidases is given concerning P1 (penultimate) and P1' (ultimate) specificities and preferences [Breddam K. Carlsberg Res. Comm. 51, 83–128 (1986)].

The present invention uses immobilized carboxypeptidases to sequentially and specifically remove amino acids from the carboxy-termini of recombinant fusion proteins following cleavage with endoproteases. CPA releases different amino acids at different rates (Ambler, supra). The following amino acids are releases rapidly by CPA: tyrosine, phenylalanine, tryptophan, leucine, isoleucine, methionine, threonine, glutamine, histidine, alanine, valine and homoserine. The following amino acids are releases slowly by CPA: asparagine, serine, lysine (the rate of lysine release may be modified by changing the pH of the digestion) and MetSO$_2$. The following amino acids are released very slowly by CPA: glycine, aspartic acid, glutamic acid, CySO$_3$H and s-carboxymethylcysteine. The following amino acids are not released by CPA: proline, hydroxyproline and arginine. The presence of an amino acid which is either very slowly released or not released in the penultimate position will generally decrease the rate of release of the carboxy-terminal residue by CPA. CPB has a much more narrow specificity as compared to CPA; CPB removes only arginine and lysine residues rapidly (Ambler, supra).

CPA and CPB have defined limitations as to their removal of carboxy-terminal amino acids and are used to digest remaining linker sequence to completion, therefore traditional immobilization media such as activated CNBr agarose beads can be used. Immobilized CPA digestions can be incubated to completion because the hydrophilic spacers protect the protein of interest by encoding an arginine residue which CPA cannot remove. (All hydrophilic spacers contain at least one arginine; the lysine triplet used to generate an extended hydrophilic spacer is used in combination with spacers which contain an arginine or alternatively may be used as the spacer when the protein of interest terminates with an arginine residue). Alternate immobilization media is needed to control the hydrolysis of the carboxy-terminal amino acids when CPD-Y is used as the exoprotease, because CPD-Y does not have the specific substrate limitations of CPA and CPB. CPD-Y attached to traditional immobilization media (e.g., agarose) produces a wide variety of digestion products. This heterogenous population of digested products is useful when attempting to determine the organization of amino acids at the carboxy terminus (i.e., for determination of protein sequences). Extensive proteolytic digestion is likely to occur as result of the peptide entering into diffusion zones were the enzyme concentration is high and the rate of diffusion is slow. The desired effect when performing CPD-Y digestions is a uniform, but limited, removal of a specific amino acid (proline) from a large homogenous population of molecules. This can only be accomplished by limiting the time that a high uniform concentration of the CPD-Y enzyme is allowed to interact with limiting concentrations (i.e., below the $K_m$) of substrate.

To achieve uniform processing the immobilization media must have limited diffusion zones for the substrate to enter and provide a high enzyme binding capacity. Examples of media meeting these requirements are nitrocellulose and nylon sheets with 0.45 micron pores (Schleicher & Schuell), "Spectra/mesh Nylon" filters with a percent open area of less than 10% (Spectrum), and Acti-Disk /Acti-Mod cartridges (Arbor Technologies and U.S. Pat. Nos. 3,862,030 and 4,169,014; the disclosures of these patents is hereby incorporated by reference). All of these media have sites available for the preferred enzyme immobilization method via reductive amination using glutaraldehyde as a linker/functional group [Hermanson, Mallia and Smith, Chapter 2, *Immobilized Affinity Ligand Techniques,* Academic Press Inc., San Diego, Calif. (1992)].

Enzymes immobilized to these limited-diffusional matrices provide excellent control over the amount of time the substrate is exposed to the enzyme. Immobilization of proteolytic enzymes to a limited-diffusional matrix allows selective, uniform proteolytic processing based on the controlled exposure of substrate to enzyme. Digestion rates for each carboxypeptidase are controlled by changing salt concentration, pH and flow rates past the immobilized enzyme.

Carboxypeptidase A can release a wide variety of amino acids from the carboxy terminus at varying rates, except proline and arginine (Ambler R. P., supra). The strategy of alternating between carboxypeptidase A and B is used when the cleavage sequence does not contain any prolines. The enterokinase recognition sequence used in Level 2 designs is an example of this strategy. The sequence Arg-Arg-Lys-Leu-Asp-Asp-Asp-Asp-Lys (SEQ ID NO:41) remains after cleavage of the fusion protein (see FIG. 2). The lysine residue can be removed by digestion with CPA or CPB at pH 8.0 at 25° C. The release of the lysine, asparagine and leucine residues by CPA is very slow at room temperature, but the reaction rate can be increased by raising the temperature to 37° C. and lowering the pH to less than 6.2 (Ambler R. P., supra). The reaction can be allowed to go to completion (stopping at the arginine residues) as long as suitable protease inhibitors are present (i.e., disopropylflourophosphate). Authentic protein is generated by removing the remaining arginine residues with carboxypeptidase B.

In circumstances where carboxypeptidase A cannot remove the remaining amino acids from the protease recognition sequence, alternate digestion protocols are used. Since the sequence of amino acids to be removed from the protein of interest is known, the enzymes used are chosen based on their specificity. For example, cleavage of the thrombin site results in the following amino acids remaining attached to the protein of interest: Arg-Lys-Lys-Lys-Leu-Val-Pro-Arg (SEQ ID NO:42). Carboxypeptidase B is used to remove terminal arginine. Carboxypeptidase Y is used to remove the proline residue. This reaction is slow, but having a valine residue in the penultimate position enhances the binding and cleavage rate. The lysine triplet not only provides a hydrophilic spacer, it also provides a barrier to excessive carboxypeptidase Y digestion. Lysine is removed very slowly, and is also the least preferred amino acid to have in the penultimate position. Thus, the lysine pair is a formidable obstacle for CPD-Y digestion. Multiple passes (about 3 or 4) of the cleaved protein through an immobilized carboxypeptidase Y medium at a rate suitable to remove the carboxy-terminal proline insures that the digestion will go to completion (i.e., approximately 100% past proline and approximately 0% past arginine). Immobilized CPA is used to remove any remaining leucine, valine and lysine residues and a final digestion with CPB is used to generate the authentic protein.

Expression and Purification of the Recombinant Fusion Protein

Once a suitable recombinant DNA vector encoding the desired fusion protein has been constructed, the vector is introduced into the desired host cell. DNA molecules are transfected into prokaryotic hosts using standard protocols. Briefly, the host cells are made competent by treatment with calcium chloride solutions (competent bacteria cells are commercially available and are easily made in the laboratory). This treatment permits the uptake of DNA by the bacterial cell. Another means of introducing DNA into bacterial cells is electroporation in which an electrical pulse is used to permit the uptake of DNA by bacterial cells.

Standard protocols exist for the introduction of DNA molecules into eukaryotic hosts, including yeast and higher eucaryotes. DNA may be efficiently transferred into eukaryotic cells by calcium phosphate-DNA co-precipitation, DEAE-dextran-mediated transfection, electroporation, microinjection, lipofection, protoplast fusion, retroviral infection, particle bombardment (e.g., biolistics) and the like.

Following the introduction of DNA into a host cell, selection pressure may be applied to isolate those cells which have taken up the DNA. Prokaryotic vectors will contain an antibiotic-resistance gene, such as ampicillin, kanamycin or tetracycline resistance genes. Growth in the presence of the appropriate antibiotic indicates the presence of the vector DNA. Selectable markers exist for yeast and higher eukaryotic cells as well. In yeast, the DNA vector typically contains a gene encoding an essential metabolite which the host cell lacks. The ability of the transformed yeast cell to grow in the absence of that metabolite indicates the presence of the DNA in the yeast cell. In mammalian cells genes encoding selectable markers such as aminoglycoside phosphotransferase, which confers resistance to neomycin, hygromycin B phosphotransferase, which confers resistance to hygromycin, thymidine kinase, dihydrofolate reductase, xanthine-guanine phosphoribosyl transferase, adenosine deaminase, CAD, and asparagine synthetase are used to isolate cells which have incorporated vector sequences (for review see Sambrook, J. et al., supra at 16.8–16.15).

Following the isolation of host cells harboring the DNA vector sequences, the protein encoded by the vector may be expressed. In prokaryotic hosts the bacteria are grown to a suitable density ($OD_{600}$ 0.4–0.6) and then transcription from the promoter is induced. The manner of induction will vary depending upon which promoter is selected. When the tac promoter is utilized, induction is achieved by the addition of 0.1 M IPTG to the medium and the cells are grown for two hours to allow the expression of the fusion protein [Riggs, P., Current Protocols Mol. Biol. 19:16.6.1–16.6.14 (1990)]. When the lambda $P_L$ promoter is utilized, induction is achieved by a shift in temperature from 30° C. to 40–45° C. [Shatzman, A. R. et al., Curr. Protocols Mol. Biol. 11:16.3.1–16.3.11 (1990)]. The induction of other prokaryotic promoters is well known in the art.

Following the induction of protein expression from the vector, the fusion protein is harvested from the bacteria. If the fusion protein was secreted into the periplasmic space, then bacteria are pelleted by centrifugation and the supernatant is discarded. The fusion protein is released from the periplasm by a cold osmotic shock (Riggs, P., supra at 16.6.7). The pelleted cells are resuspended in 30 mM Tris-Cl/20% sucrose, pH 8.0 (Tris/sucrose). Thirty milliliters of Tris/sucrose is added per gram of cells (wet weight) and EDTA is added to a final concentration of 1 mM. The cells are incubated at room temperature for 5–10 minutes without shaking or stirring. The cells are then centrifuged and then resuspended in 80 ml per gram of ice-cold 5 mM $MgSO_4$ and shaken or stirred for 10 minutes while kept at 5° C. using an ice bath. The cells are then centrifuged and the resulting osmotic shock fluid (supernatant) is then subjected to affinity purification to isolate the fusion protein. If the fusion protein was secreted into the culture medium, the bacteria are removed by centrifugation and the culture supernatant is retained for affinity purification of the secreted fusion protein.

The choice of the affinity matrix depends upon the fusion partner used to create the fusion protein. When the Fc domain of an immunoglobulin G molecule is utilized, the affinity matrix selected is either protein A- or protein G-Sepharose. Protein A and protein G bind with high affinity to the Fc domain of IgG. Well characterized purification protocols are available for protein A and protein G and the corresponding Sepharose resins are commercially available (Pharmacia). If the fusion partner is GST, the affinity matrix used is glutathione-agarose. When MBP is utilized as the fusion partner, the fusion protein is affinity purified on an amylose resin.

Following affinity chromatography the protein of interest is separated from the fusion partner by proteolytic cleavage. The site-specific protease used for the cleavage will depend upon which cleavage site was used in the vector. A vector containing the protein of interest and the fusion partner without the cleavage site for the site-specific protease is used to express a control fusion protein. The control fusion protein is used to test for the ability of the site-specific protease to cleave at residues internal to the protein of interest. This control protein need only be produced in a small culture to provide enough protein for a test of cleavage by the desired protease.

Protocol Overview

The invention is illustrated by the following examples in which MBP/Ig, NGF/Ig and BDNF/Ig fusion proteins are expressed and used to generate authentic MBP, NGF and BDNF. However, the invention is not limited to the production of any specific recombinant protein. To generate any desired fusion protein capable of producing an authentic protein of interest, the following steps are taken:

1. Insertion of a DNA sequence encoding the protein of interest into a vector containing the DNA sequences encoding the desired hydrophilic spacer sequence and the desired fusion partner. The sequences encoding the protein of interest are inserted upstream of the linker sequence such that the resulting fusion protein comprises the protein of interest at the amino-terminus.

2. Insertion of a DNA sequence encoding the protein of interest into a vector lacking DNA sequences encoding the desired linker sequence and containing the DNA sequences encoding the desired fusion partner. This vector is constructed to provided a control fusion protein which lacks the cleavage site for the site-specific protease present in the linker sequences of the vector in step 1. The control fusion protein is digested with site-specific protease designed to cleave within the linker sequences. No cleavage should occur unless a site for cleavage appears internal to the protein of interest. In such a case, a different protease site is selected by inserting the DNA encoding the protein of interest into a vector harboring a different linker.

3. The vector containing the protein of interest is transferred into the desired prokaryotic or eukaryotic host. Appropriate selective pressure is applied to isolate hosts containing the vector sequences. For example, if the vector is used to transform E. coli and the vector contains the ampicillin resistance gene, the transformed bacteria are grown in the presence of 20–60 $\mu$g/ml ampicillin to select for those bacteria which have taken up the vector sequences. If the vector contains the neomycin resistance gene and is introduced into a eukaryotic host, such as a mammalian cell line, the cell line is grown in the presence of 200–400 $\mu$g/ml G418 to select for those cells which have taken up the vector sequences.

4. Transcription is induced if a controllable promoter is used. If the promoter used is the tac promoter then IPTG is added to a final concentration of 0.3 mM. If the promoter used is the lambda $P_L$ promoter, induction is achieved by increasing the temperature the bacteria are grown at from 30° C. to 40 to 45° C.

5. Following induction, the host cells are grown for an appropriate period of time to allow for the expression of the fusion protein. In the case of bacterial hosts, the induced bacteria are typically grown for 2–4 hours before the bacteria are harvested by centrifugation for 10 min at 7000×g at 4° C. If the fusion protein is transported to the periplasm, the supernatant is discarded and the fusion protein is released from the bacteria by a cold osmotic shock. The shock fluid is then subjected to affinity resin chromatography to isolate the fusion protein. In cases where the protein is secreted into the medium, the supernatant is saved and the protein is concentrated by ammonium sulfate precipitation in preparation for affinity resin chromatography.

When eukaryotic hosts such as mammalian cell lines are used, clones which stably express the fusion protein are isolated (i.e., stable transformants or stable clones) and induction may not be necessary (i.e., the promoter is constitutively transcribed). If the fusion protein contains a signal sequence, it will be secreted into the culture medium in which the mammalian cell is grown. In this case, the stable clone may be expanded into batch cultures from which the fusion protein can be isolated from the spent medium every 2–4 days depending on the growth characteristics of the established stably transformed cell line. Batch growths are typically maintained for 10–30 days depending on the growth characteristic of the stably transformed cell line.

In a preferred embodiment, a fusion protein composed of the protein of interest and a portion of an immunoglobulin molecule is expressed. The fusion protein will form a dimer between the immunoglobulin domains creating a product having a molecular weight of greater than 50 kD. Such a large protein will be retained inside the lumen of the hollow fiber reactor with a molecular weight cutoff greater than 50 kD (Unisyn Technologies, Tustin, Calif.) permitting the batch harvest of concentrated product from the interior of the hollow fiber with limited amounts of low molecular weight contaminants. The use of hollow fiber reactors with large molecular weight cutoffs are preferred because they allow for the batch harvesting of fusion protein. The large pores present in these hollow fiber reactors allow the exchange of essential nutrients and waste products between the growth medium and the lumen of the fiber. This structure permits an increase in the growth rate of the cells and thereby increases production of the fusion protein.

If the fusion protein is not secreted, the eukaryotic cells are harvested using any appropriate method. If the cells grow attached to the culture dish, they are harvested by treatment with trypsin or by manually scrapping the cells from the culture vessel. The cells are pelleted by centrifugation and washed three time with PBS, pH 7.2. [If the cells are released from the dish by treatment with trypsin, the trypsin is removed from the cell pellet by washing the cells (three times with PBS, pH 7.2) following collection by centrifugation. Soybean trypsin inhibitor (Sigma) and/or aprotinin (Sigma) may also be included at a concentration of 1–2 $\mu$g/ml.] The pelleted cells are then lysed by mechanical disruption or chemical treatment. The cell debris is removed by centrifugation and the supernatant is subjected to affinity resin chromatography to isolate the fusion protein.

6. Affinity purification of fusion proteins: the supernatant containing the fusion protein (shock fluid, culture medium, supernatant from disrupted cells) is applied to an appropriate affinity matrix to isolate the fusion protein. For example, if the fusion partner utilized is the IgG Fc domain then a SPA-Sepharose resin (Pharmacia) is used to selectively bind the fusion protein. The supernatant is applied to the resin, the resin is washed to remove proteins which do not bind and then the fusion protein is eluted from the resin using an appropriate agent. In the case of the SPA-Sepharose resin, elution is achieved with 0.1 M citric acid, pH 2.8 or other low pH buffer such as 0.1 M glycine-HCl, pH 3.0. The purified fusion protein is then cleaved with an endoprotease to generate authentic protein of interest. In a preferred embodiment, the desired protein is released from the immobilization matrix by digestion with the specific endoprotease that cleaves between the affinity domain and the desired protein. This eliminates the need to reabsorb the affinity domain after proteolytic separation and avoids the harsh low pH elution step.

7. Endoprotease cleavage of fusion proteins: if the purified fusion protein contains a Ig hinge region, it is first digested with a site-specific endoprotease which cleaves at a sequence located within either the hydrophilic spacer or within the hinge region of Ig. Both the fusion protein containing the site for a site-specific endoprotease and the corresponding control fusion protein lacking the cleavage site are digested with the endoprotease. This is done to test whether the protein of interest is cleaved by the site-specific endoprotease at a site internal to the protein of interest. Generally the amino acid sequence of the protein of interest is known and a site-specific endoprotease is selected which does not have a recognition site internal to the protein of interest. However, different preparations of endoproteases may contain other protease activities (present as a contaminant) or the site-specific endoprotease may cleave at a non-preferred site located within the protein of interest. The fusion protein is cleaved into its parts once a suitable site-specific endoprotease is found which cleaves only at the desired site.

Cleavage with the site-specific endoprotease may leave extra amino acids on the carboxy-terminal end of the protein of interest (i.e., for Level 2 and 3 designs). These amino acids remain as a result of the amino acids present on the amino-terminal side of the cleavage site for the site-specific endoprotease as well as those within the hydrophilic spacer. These undesirable (i.e., non-authentic) amino acids are removed by digestion with carboxypeptidases. Carboxypeptidases cleave carboxy-terminal amino acids. Carboxypeptidase A cleaves carboxy-terminal amino acids other than arginine or proline. Carboxypeptidase B cleaves only carboxy-terminal arginine or lysine residues. For example, if the fusion protein is cleaved at the following thrombin site: Leu-Val-Pro-Arg-Gly-Thr (SEQ ID NO:43) located within the following sequence: Protein of interest-Arg-Arg-Lys-Lys-Lys-Leu-Val-Pro-Arg-Gly-Thr-IgG hinge/Fc, then following cleavage with thrombin, the protein of interest will have the following extra carboxy-terminal amino acids: Protein of interest-Arg-Arg-Lys-Lys-Lys-Leu-Val-Pro-Arg. Treatment with immobilized carboxypeptidase B will remove the first arginine residue. Digestion with carboxypeptidase Y at pH 5.75 will remove the proline residue and most of the valine and leucine residues. Digestion with carboxypeptidase A at pH 6.0 will remove the remaining valine and leucine residues; the enzyme will slow down at the lysine residues. Digestion with carboxypeptidase B will remove any remaining lysine residues and the arginine tail yielding an authentic carboxy-terminus of the protein of interest. Alternating carboxypeptidase digestions can be use to generate an authentic protein of interest when the linker utilized contains arginine and/or lysine residues following the carboxy-terminus of the protein of interest.

When the natural carboxy-terminus of the protein of interest comprises an arginine residue, the linker utilized will contain a leucine, valine or isoleucine residue between the naturally occurring arginine on the protein of interest and the arginine/lysine residues in the spacer. These residues (Leu, Val, Ile) are preferred when expression of the fusion protein is achieved in a mammalian cell line in order to prevent the possibility of undesirable cleavage of the fusion protein by furin after the arginine located at the carboxy-terminus of the protein of interest. During processing of the released protein of interest, carboxypeptidase B will proceed through the hydrophilic spacer residues until it reaches the leucine or tyrosine residue (referred to as a CPB terminator). Carboxypeptidase A is then used to efficiently remove the leucine, valine or isoleucine residue while leaving the naturally occurring arginine residue intact as the carboxy-terminal residue of the protein of interest.

8. Purification of the authentic proteins of interest: following carboxypeptidase digestion to remove extra carboxy-terminal amino acids, a final purification step using cation exchange and gel filtration chromatography is employed to remove released amino acids and separate any undigested fusion protein and partially processed protein of interest from the authentic protein of interest.

9. Confirmation of the carboxy-terminal residues of the protein of interest may be obtained by analysis of purified and cleaved protein using known automated carboxy-terminal amino acid sequence analysis methods [e.g., Miller, C. G. and Bailey, J. M. (1994) Genetic Eng. News, Sep. 15, 1994, p. 16]. The processed fusion proteins may be subjected to automated C-terminal protein sequence analysis according to the manufacturer's instructions [e.g., Hewlett-Packard G1009A C-terminal protein sequencing system; Miller, et al., *Techniques in Protein Chemistry VI* (1995) Academic Press, Inc., pp. 219–227].

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); ° C. (degrees Centigrade); AMP (adenosine 5'-monophosphate); cDNA (copy or complimentary DNA); dNTP (deoxyribonucleotide triphosphate); PBS (phosphate buffered saline); OD (optical density); HEPES (N-[2-Hydroxyethyl]piperazine-N-[2-ethanesulfonic acid]); HBS (HEPES buffered saline); SDS (sodium dodecylsulfate); Tris-HCl (tris[Hydroxymethyl]aminomethane-hydrochloride); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); ORI (plasmid origin of replication); lacI (lac repressor); ATCC (American Type Culture Collection, Rockville, Md.); Clontech (Clontech Laboratories, Inc., Palo Alto, Calif.); HyClone (HyClone, Logan, Utah); NEB (New England Biolabs, Inc., Beverly, Mass.); Novagen (Novagen, Inc., Madison, Wis.); Operon (Operon Technologies, Alameda, Calif.); Sigma (Sigma Chemical Co., St. Louis, Mo.); Stratagene (Stratagene Cloning Systems, LaJolla, Calif.). All restriction enzymes were purchased from New England BioLabs and were used according to the manufacturer's instructions, unless otherwise noted.

Unless otherwise specified, protein or peptide sequences are written from amino to carboxy-termini and nucleic acid sequences are listed in the 5' to 3' direction.

For the production of recombinant proteins using this invention, it is necessary to use a strain of bacteria carrying some mutation that prevents the expression of the omp T locus [Grodberg and Dunn, supra]. Strains B834 (Novagen), BL21 (Novagen), and C1757 are preferred due to their inability to cleave the proteolytically susceptible dibasic Lys-Arg site at 172–173 of T7 RNA polymerase. A derivative of the DH1 strain, the AG1 strain (Stratagene) was used for experiments due to its commercial availability and limited ability to cleave the hydrophilic spacer/endoprotease regions during the isolation of fusion product. B strains of *E. coli* are preferred due the lon deficiency.

EXAMPLE 1

Expression of a MBP/IgG Fusion Protein in *E. coli*

The following experiments were conducted to demonstrate the advantages provided by the use of the hydrophilic spacers and endoprotease sites in conjunction with the hinge and Fc domain of IgG in the design of a fusion protein. A fusion protein comprising the secreted form of the maltose-binding protein (MBP) as the protein of interest linked to an IgG affinity tag via an Arg-Arg-Thrombin linker (a Level 3 design) was produced. The vector pMA2TH-9 was constructed to produce this MBP/IgG fusion protein. This example involved a) the construction of the pMA2TH-9 expression vector, b) expression and affinity purification of the MBP/IgG fusion protein, c) cleavage of the MBP/IgG fusion protein with thrombin and d) cleavage of the MBP/IgG fusion protein while immobilized on a Protein A resin.

a) Construction of pMA2TH-9

Figure 4:
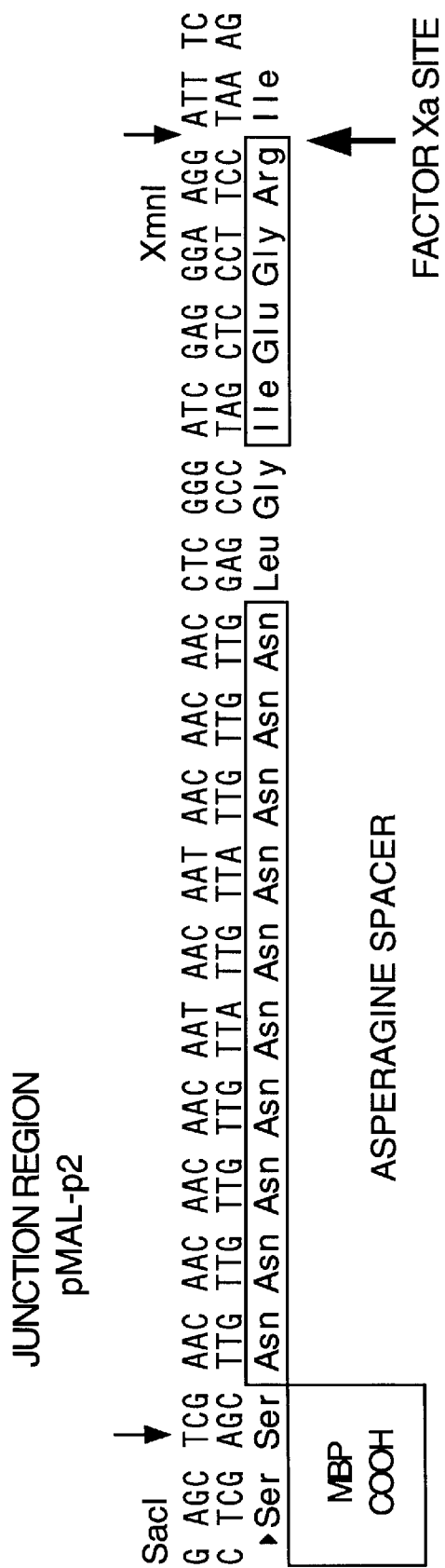
FIG. 4 depicts the junction region of the pMa1-p2 vector.

The pMAL-p2 vector was designed to allow the expression of fusion proteins in bacteria. pMA2TH-9 was derived from the commercially available pMAL-p2 vector (New England BioLabs). pMAL-p2 encodes the maltose-binding protein (MBP) under the transcriptional control of the inducible tac promoter. The pMAL-p2 vector encodes the lac repressor (lacI$^q$ gene) which suppresses transcription until IPTG is added to the culture medium. The pMAL-p2 vector contains sequence encoding the naturally occurring signal sequence of the MBP (i.e., the malE signal sequence) which allows the MBP to be exported into the periplasmic space of the host cell. The vector is design such that the protein of interest is inserted downstream (i.e., on the carboxy-terminal side) of the sequences encoding the MBP in pMAL-p2. The resulting fusion protein is then purified using an amylose resin which binds the MBP. An asparagine linker, a Factor Xa protease site and a polylinker are positioned between the MBP sequences and the inserted protein of interest in the pMAL-p2 vector; this region of pMAL-p2 is termed the junction region and is shown in FIG. 4. These sequences were removed in the modified vector.

The pMAL-p2 vector was used as the starting vector because it encodes a secretory protein (the MBP with the malE signal sequence), an example of the type of proteins ideally suited for production using the expression systems of the present invention. In the modified vector, the MBP acts as the protein of interest rather than as the fusion partner and affinity domain (as is the case in the pMAL-p2 system).

pMAL-p2 was modified as follows. The unique NgoMI site, located at position 4778 on the map of pMAL-p2, was removed by ligating an excess of a self-annealed A1 oligonucleotide termed A1 which has the sequence 5'-CCGGGCGCGCGCGC-3' (SEQ ID NO:44) into 200 ng of NgoMI digested pMAL-p2. Subclones containing the desired modification were identified by restriction analysis. The selected clone contained a BssHII restriction site in place of the original NgoMI site and was designated pM-Ng (−). The asparagine linker and polylinker cloning sites were removed from pM-Ng(−) by digestion with SacI and HindIII. Following the digestion reaction, the plasmid was purified from the released fragment using a CHROMA SPIN-400 gel filtration column (Clontech) using the manufacturers protocol.

A conversion linker next inserted into the pM-Ng(−) vector; this conversion linker serves several functions. The linker encodes the hydrophilic spacer (Arg-Arg) and the endoprotease site (thrombin) and it contains recognition sites for SalI, EcoRI and NheI which permit the insertion of sequences encoding various amounts of the IgG hinge/Fc fragment (the affinity domain). The conversion linker was formed by annealing the complementary oligonucleotides B1 and B2. The B1 oligonucleotide comprises the sequence 5'-CGTTTCGCCGGCTGGTTCCGCGGGGTCGACGGA-TTCAGCTAGCA-3' (SEQ ID NO:45). The B2 oligonucleotide comprises the sequence 5'-AGCTTGCT-AGCTGAATCCGTCGACCCCGCGGAACCAGCCGGC-GAAACGAGCT-3' (SEQ ID NO:46). The annealed B1/B2 oligonucleotide pair generates the following sequence which contains recognition sites for NgoMI, SalI, EcoRI and NheI:

```
5'-CGTTTCGCCGGCTGGTTCCGCGGGGTCGACGAATTCAGCTAGCA-3'
3'-TCGAGCAAAGCGGCCGACCAAGGCGCCCCAGCTGCTTAAGTCGATCGTTCGA-5'
```

The B1 and B2 oligonucleotides were annealed by placing 10 μl of each oligonucleotide (100 μM) in a 100 μl total volume in a buffer comprising 20 mM Tris-HCl (pH 8.0), 100 mM NaCl, 12 mM MgCl$_2$. The mixture was placed in a 500 μl microcentrifuge tube and heated for 10 minutes at 95° C., the reaction was slowly cooled to 60° C. for 1 hour and then allowed to slowly cool to room temperature over a three hour period. The annealed conversion linker was then ligated to the SacI/HindIII digested pM-Ng(−) plasmid as follows.

The conversion linker was ligated to the SacI/HindIII digested pM-Ng(−) using 200 ng of purified digested plasmid and the hybridized complementary oligonucleotides B1 and B2 in a 3:1 insert to vector ratio; the resulting plasmid was termed pMA2-TH. A schematic representation of the pMA2-TH plasmid is shown in FIG. 5.

Figure 5:
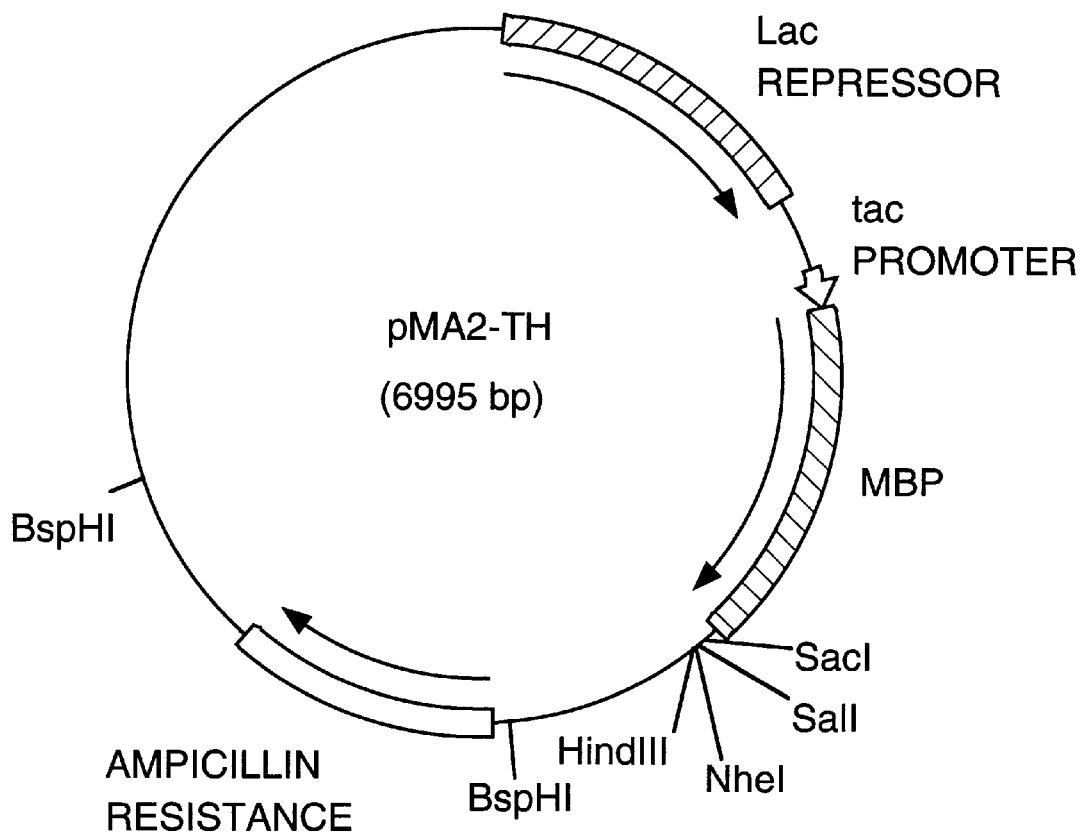
FIG. 5 provides a map of the pMA2-TH vector.

In FIG. 5, the location of the conversion linker downstream of the MBP coding region is indicated by the cluster of restriction sites. The coding regions for the lac repressor (lacI$^q$), MBP and ampicillin resistance gene (β-lactamase) are shown and the direction of transcription is indicated by the arrows. The tac promoter is also indicated (open arrowhead).

The B1/B2 oligonucleotide pair creates compatible overhangs for SacI and HindIII at the 5' and 3' end, respectively. These restriction sites allow for the directional ligation of the conversion linker and also place a phenylalanine residue at the carboxy-terminus of the MBP protein. This phenylalanine provides an easily characterized amino acid to allow for ease in monitoring of the subsequent carboxy-terminal digestion reactions (by fluorescence; phenylalanine emission is detected at OD$_{228}$).

Figure 6:
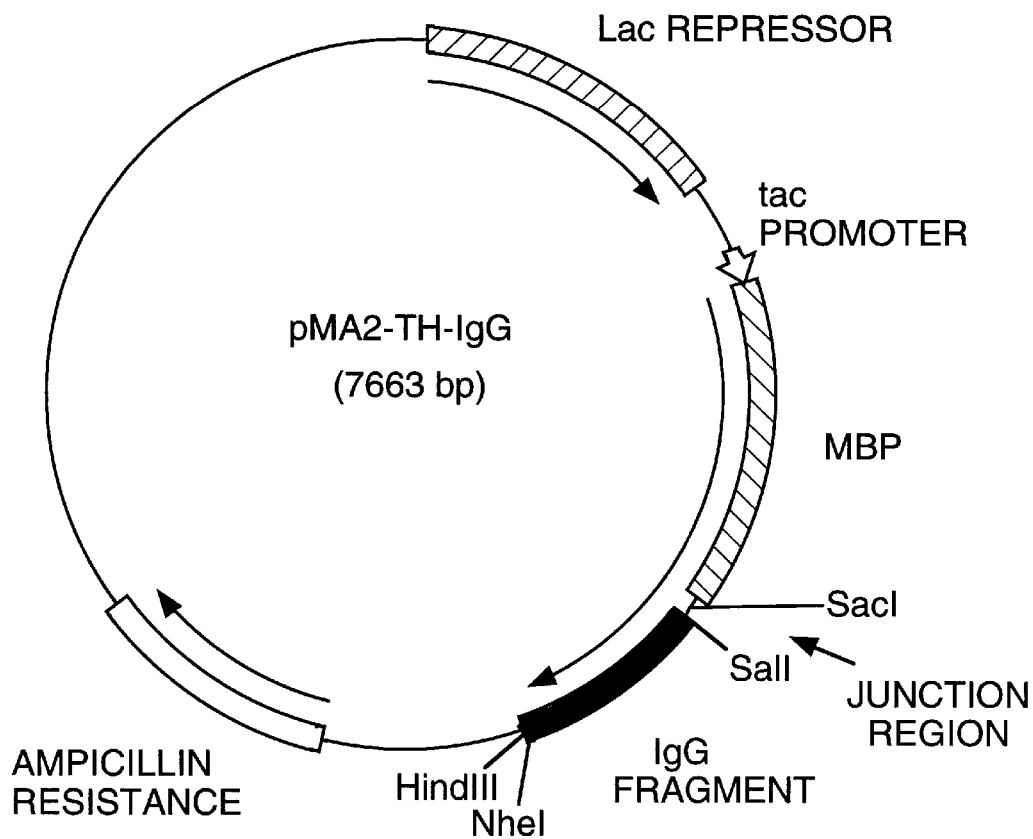
FIG. 6 provides a map of the pMA2-TH-IgG vector.

A 0.7 kb SalI/NheI fragment encoding the hinge and Fc domains of human IgG were inserted into the pMA2-TH vector to provide an affinity-purifiable domain on the fusion protein. The IgG domain was isolated using PCR as described below in Example 3. The SalI/NheI IgG fragment was inserted into pMA2-TH digested with SalI and NheI to generate pMA2-TH-IgG. FIG. 6 provides a schematic representation of pMA2-TH-IgG.

In FIG. 6, the coding regions for the lac repressor (lacI$^q$), MBP, the IgG fragment and ampicillin resistance gene (β-lactamase) are shown and the direction of transcription is indicated by the arrows; selected restriction sites are indicated. The tac promoter is also indicated (open arrowhead). The location of the junction region is indicated.

The insertion of the IgG fragment into SalI and NheI-digested pMA2-TH was achieved as follows. An equimolar ratio of vector and IgG fragment were used in the ligation. The ligation products were used to transform competent AG1 cells (Stratagene) and 10 clones containing inserts of the proper size were isolated; these clones were designated pMA2-TH-IgG 1–10.

The pMA2-TH-IgG clones were screened for the stable production of the fusion protein by the detection of human IgG. Briefly, the ten pMA2-TH-IgG clones were grown overnight in LB and used to inoculate 5 ml of LB containing 100 μg/ml of ampicillin in a 50 ml conical tube. The 5 ml cultures were incubated at 37° C., shaking at 235 rpm for 90 min. IPTG was added to 1 mM final concentration and growth was continued for an additional 90 min. The induced cultures were pelleted, resuspended in 500 μl PBS, pH 7.4 and sonicated using a SONIPREP sonicator at a power setting that allowed maximum membrane disruption for 4 pulses of 20 sec. The sonicated cells were clarified by centrifugation at 12,000×g for 10 minutes at 4° C. and the supernatants were collected. Five microliters of the clarified extracts were spotted onto dry nitrocellulose strips and allowed to air dry. Positive controls containing known concentrations of human IgG were used as standards (Sigma). The strips were then incubated for 30 minutes in blocking solution (PBS containing 5% non-fat dry milk). The strips were transferred into blocking solution containing 5 μg/ml of a horseradish peroxidase-labeled anti-human IgG, Fc-specific goat antibody [Rockland, Gilbertsville, Pa.]. The strips were incubated with the anti-Ig antibody for 1 hour at room temperature while rocking. The strips were washed 3 times in PBS, pH 7.4 and developed using a DAB/$H_2O_2$ solution until color appeared on the positive control dots. Relative amounts of IgG in the sonicated extracts were determined by comparison of the signal intensity relative to the positive controls. Detection of IgG molecules is simplified due to the commercial availability of Fc-specific preconjugated antibodies which subsequently allow for a direct assay for fusion protein expression. Clone pMA2-TH-IgG-9 was chosen for expression and isolation studies due to its high levels of expressed IgG.

Figure 7:
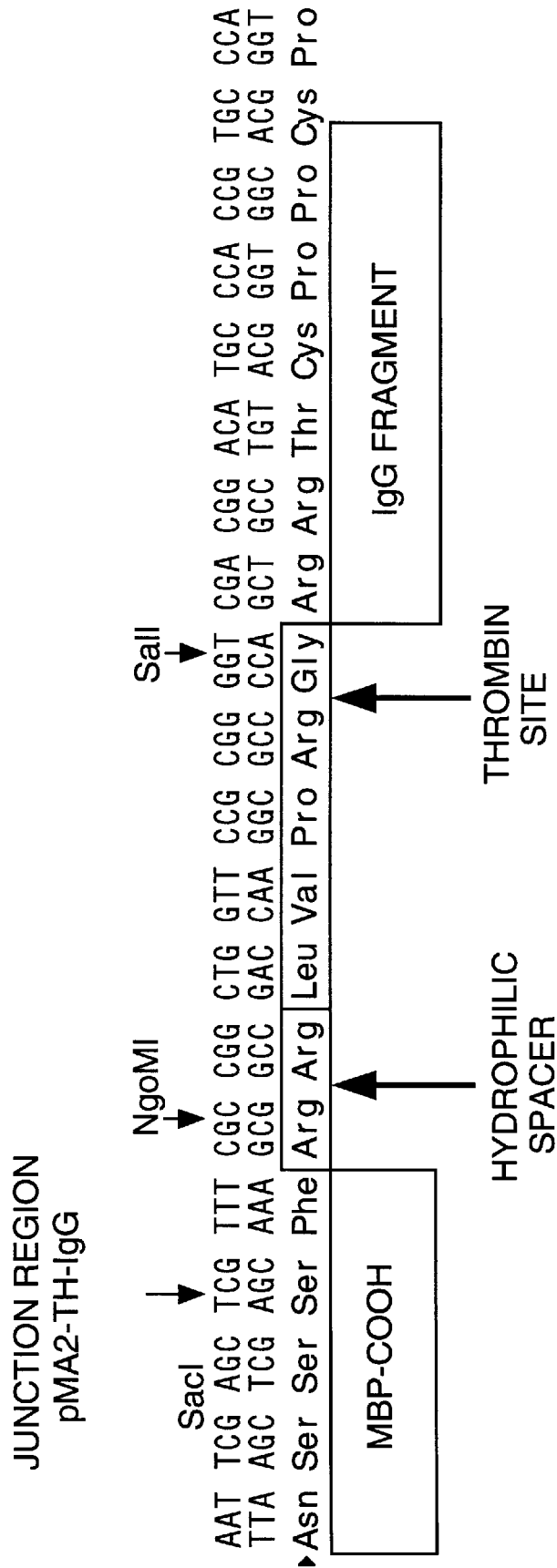
FIG. 7 depicts the junction region of the pMA2-TH-IgG vector.

The junction region (i.e., the region which joins the protein of interest with the affinity domain) present in pMA2-TH-IgG is shown in FIG. 7. The first 5 amino acid residues shown comprise the carboxy-terminal end of the MBP (the phenylalanine is encoded by the conversion linker as described above). The hydrophilic spacer (Arg-Arg) and thrombin recognition site are boxed and labeled; the cleavage site for thrombin is indicated by the arrow placed between the Arg and Gly residues. The phenylalanine residue, the hydrophilic spacer and the thrombin site [Leu-Val-Pro-Arg-Gly (SEQ ID NO:11)] are encoded by the conversion linker. The conversion linker sequences also encode two arginine residues located immediately downstream of the thrombin recognition site; these arginines are followed by sequences comprising the hinge region of IgG. The pairs of arginine residues surrounding the thrombin site in the linker were designed to allow for maximal exposure of the endoproteolytic site, increasing the removal efficiency of the affinity domain from the protein of interest.

The junction region of pMA2-TH-IgG can be easily modified to replace the existing hydrophilic spacer and/or endoprotease recognition site with other spacers and endoprotease sites; this is achieved by digestion of pMA2-TH-IgG with the SalI and NgoMI and insertion of the desired sequences.

b) Expression and Affinity Purification of the MBP/IgG Fusion Protein pMA2-TH-IgG-9 was used to express the MBP/IgG fusion protein in *E. coli*. Bacteria (*E. coli* strain AG1) harboring the plasmid were grown and induced using protocols developed for the pMAL-p2 vector [Riggs in *Curr. Protocols Mol. Biol.*, at p. 16.6.12 (1990)] with minor modifications which permitted maximum expression of the IgG carboxy fusion constructs. Briefly, all ampicillin resistant colonies were grown in LB containing 100–150 μg/ml ampicillin to maintain plasmid stability. All cultures were grown at 37° C., shaking at 225–250 rpm. Glucose was not included in expression growth experiments because it has been shown to cause leakage of fusion proteins from the cell by making the outside membrane semi-permeable. The growth conditions and protocol for the most efficient expression of the pMA2-TH-IgG-9 fusion protein at the 1 liter scale were as follows: 100 mls of LB containing 120 μg/ml ampicillin (LB-Amp 120) in a 250 ml flask was inoculated with a single colony from a fresh plate. The culture was then grown to mid-log phase (i.e., for less than 12 hrs.). Mid-log cultures were then used to inoculated 1 liter of prewarmed LB-Amp 120 in a 2.8 liter culture flask (Fisher Scientific). Cultures were grown at 37° C. with vigorous shaking (240–260 rpm) until an O.D.$_{600}$ of 0.600 was reached. Cultures were then induced by the addition of 440 μl of 1 M IPTG and incubation was continued for 2.5–3.0 hours.

Induced cultures were harvested by centrifugation at 4° C. in 500 ml bottles for 30 min at 4000×g in a GSA rotor (Sorvall). The pelleted cells were then disrupted by treatment with lysozyme as described below; alternatively, the cells may be disrupted by sonication or the fusion protein may be isolated from osmotic shock fluid.

The pelleted cells were resuspended at 1/50 the original volume in Lysis Buffer (50 mM Tris-Cl, pH 8.0, 100 mM NaCl, 1 mM $ZnCl_2$ and 10% sucrose). Freshly prepared lysozyme (10 mg/ml in 10 mM Tris-HCl, pH 8.0) was added to a final concentration of 0.5 mg/ml and the solution was incubated on ice for thirty minutes with inversion every 5 minutes. The lysozyme-treated cells were pelleted at 15,000×g for 30 minutes at 4° C. in an SS34 rotor. The supernatant was pooled and stored at −20° C. until affinity chromatography was performed.

Immobilized Protein A was used to isolate the carboxy-terminal IgG fusion proteins. Immobilized Protein A was obtained from two manufacturers, Protein A Sepharose-6B (Pharmacia) and Affinica Protein A Agarose (Schleicher and Schuell). Disposable 10 ml, 1.0 cm diameter Affinica columns (Schleicher and Schuell) were used to hold 1–2 ml of the Protein A matrix. The protein was applied to the Protein A columns using binding and wash buffers comprising Tris-HCl (50 mM), phosphate (100 mM) or carbonate (100 mM) buffers at pH 8.0 containing 450 mM NaCl. Elution buffers included 0.1 M glycine-HCl, pH 2.3 and 0.4 M citrate buffer, pH 2.8. The citrate buffer was preferred because it did not interfere with measurement of protein concentration in the eluted fractions using the BCA protein assay (Pierce). Eluted fusion protein was neutralized with either ¼ volume of 0.5 M sodium phosphate buffer, pH 7.7 or 1/10 volume 1 M Tris-HCl, pH 9.0.

After cell extracts were prepared from induced bacterial cells (as described above), the resulting supernatants were prepared for chromatography by passage through a 0.44 micron filtration cartridge which included a prefilter matrix to prevent clogging [Uniflow Plus, (Schleicher and Schuell)]. The supernatant was the then brought to 450 mM NaCl by adding an appropriate volume of 5 M NaCl. The sample was applied to a 2.0 ml protein A column which had been pre-equilibrated with 5 volumes of binding buffer (50 mM Tris pH 8.0, 450 mM NaCl). The sample was applied at a flow rate of approximately 0.5 ml/min using only gravity. The flow-through was collected and reapplied to the column. The column was washed with 10 volumes of binding buffer and the fusion protein was eluted by the addition of 5 column volumes of elution buffer (0.04 M Citrate buffer, pH 2.8). Fractions (1 ml) were collected into microcentrifuge tubes containing 100 µl of neutralizing buffer (1 M Tris-HCl, pH 9.0) and protein levels were monitored using a micro protein assay kit based on brilliant blue G (Coomassie blue) interaction with protein to produce a blue colored complex (Sigma). Fractions containing eluted protein were pooled and run on an 4–15% precast SDS-PAGE mini gradient gel (Schleicher & Schuell) to determine purity. Samples were boiled for two minutes after adding an equal volume of 2× loading buffer (0.5 M Tris-HCl, pH 6.8, 4% SDS, 20% glycerol, and 0.01% bromphenol blue). Visual inspection of the PAGE gel after staining with Coomassie brilliant blue dye showed that the fusion protein was isolated in both monomeric and dimeric forms and was greater than 95% pure (gels run under non-denaturing conditions were used to estimate the percentage of protein present as a dimer). These results demonstrate that both monomeric and dimeric IgG hinge/Fc regions can bind to protein A. Furthermore, the results show that affinity purification of the fusion protein from total cellular extracts is specific for the MBP/IgG fusion protein.

c) Cleavage of the MBP/IgG Fusion Protein With Thrombin

The affinity purified MBP/IgG fusion protein was cleaved with the endoprotease thrombin as follows. The eluted fusion protein was mixed with an equal volume of 2×thrombin cleavage buffer (50 mM Tris-HCl, pH 8.0, 300 mM NaCl, 5 mM $CaCl_2$) and thrombin (Sigma) was added at 1:100 molar ratio (thrombin:fusion protein). The digestion reaction was incubated at room temperature and 50 µl aliquots were removed at 5, 15, 30 and 60 minutes to determine the efficiency of thrombin digestion. The removed samples (50 µl) were added to 50 µl of 2× SDS reducing buffer (0.5 M Tris-HCl pH 6.8, 4% SDS, 2% β-mercaptoethanol, 20% glycerol, and 0.01% bromphenol blue) and boiled immediately to inactivate the thrombin enzyme. Time course digestion samples were analyzed on a 10% SDS-PAGE gel. From visual inspection of the gel, it was estimated that 75% of the fusion protein was cleaved after 5 minutes and complete digestion was achieved after 15 minutes of incubation in the presence of a 1:100 molar ratio of thrombin to fusion protein.

Following digestion with thrombin, a sample containing 2 mg of the digested MBP/IgG fusion protein was brought to 450 mM NaCl and was applied to a fresh protein A column in order to remove the IgG domain released by the thrombin digestion from the protein of interest (the MBP portion of the fusion protein). Dot blot analysis using anti-IgG-HRPO showed that the second protein A column efficiently removed the majority of the free IgG. The re-chromatography of the thrombin-digested sample on protein A removes free IgG domains from cleaved fusion protein as well as any undigested MBP/IgG fusion protein.

The thrombin-IgG fusion plasmid pMA2-TH-IgG-9 represents an example of a hydrophilic spacer/specific endoprotease site organization that allows efficient proteolytic separation and isolation of the desired production molecule using affinity chromatography. Previously researchers have reported problems cleaving a MBP fusion protein (Riggs, P., supra at 16.6.13). Steric hindrance from the amino-terminus of the protein of interest and solubility are the most common problems encountered when cleaving fusion proteins using the pMAL/Factor Xa expression system.

Solutions to this problem involve the denaturation of the fusion molecule with guanadinium HCl or 8 M urea before enzymatic cleavage (Riggs, supra). However, the use of harsh denaturants can significantly decrease or eliminate the functional activity of the desired protein. Alternatively, other proteases have been used that more efficiently cleave fusion molecules as the result of the cleavage site being towards the middle of a recognition sequence rather than following a recognition sequence (for example, thrombin, renin, Igase). However, these proteases do not generate authentic proteins as following endoprotease digestion amino acids contributed by the endoprotease recognition site remain on the protein of interest.

In contrast, the hydrophilic spacers of the present invention physically separate the natural conformation of a desired molecules carboxy-terminus from the designed proteolytic site and provide enhanced solubility because of their hydrophilic nature. The hydrophilic spacer permits the removal of any residual proteolytic recognition sequence that remains at the carboxy-terminus of the authentic protein after the specific cleavage of designed fusion protein. The arginine residue(s) present in the hydrophilic spacer provide a barrier to prevent the removal of residues from the carboxy-terminus of the authentic protein of interest by CPA (Ambler, supra) and allows for the removal of any amino acids derived from the endoprotease recognition site which remain on the carboxy-terminus of the protein of interest following endoprotease digestion of the fusion protein.

d) Cleavage of the Fusion Protein While Immobilized on the Protein A Resin

Crystallographic studies of protein A bound to Fc fragments of IgG indicate that the major binding site on the IgG molecule occurs at the junction between the CH2 and CH3 regions of the IgG molecule [Deisenhofer, *Biochem.* 20:2361 (1981)]. These crystallization studies suggested that endoproteolytic site located on the carboxy-terminal IgG fusion proteins of the present invention would be available for proteolytic cleavage while the fusion protein was immobilized on the protein A matrix. This hypothesis was tested by performing the following experiment.

Bacteria containing the pMA2-TH-IgG-9 plasmid were grown and induced as described in section b) above. Supernatant from cell extracts was prepared and applied to a protein A column as described above. The column was washed with binding buffer to remove any non-specific proteins bound to the column. Five column volumes of thrombin cleavage buffer were then applied to the column. The lower salt concentration present in the thrombin cleavage buffer did not release any of the bound fusion protein as determined by assaying the wash for the presence of IgG. Four column volumes of thrombin buffer containing enough thrombin for the cleavage of a maximally bound matrix (10 mg fusion protein/ml matrix or 10 ng thrombin/mg fusion protein) were then added to the column. The column matrix was gently shaken to create a suspension and the top and bottom of the column were sealed. The column was then placed on a rocker for 20 minutes at room temperature.

The column was then placed upright and the cleavage buffer was collected. The column was then washed with 2 column volumes of wash buffer (50 mM Tris-HCl, pH 8.0, 100 mM NaCl, 20 mM EDTA). The flow-through containing the cleavage buffer and the wash buffer was pooled (these fractions contain the cleaved protein of interest). The IgG portion of the digested fusion protein was eluted as described above and all protein containing fractions were analyzed on an SDS-PAGE gel. The results of the SDS-PAGE analysis showed that all fusion molecules were cleaved by this method (i.e., no intact fusion protein was eluted from the column following thrombin digestion) and the resulting MBP was substantially purer than that from previous isolations as described in section b. That is, the cleavage of the fusion protein while immobilized (bound) to the protein A resin eliminated the minor quantities of non-specific proteins that were present during the previously described low pH elution of intact fusion protein.

Cleavage of the fusion protein while immobilized to the column resin under mild conditions is a preferred method of protein isolation as this eliminates the need to remove the free IgG domain from the protein of interest following protease digestion thereby decreasing the number of processing steps.

EXAMPLE 2

The Use of the Kanamycin-Resistance Gene in Place of the Ampicillin-Resistance Gene Improves the Yield of Periplasmic IgG Fusion Protein Experiments growing and inducing bacteria containing pMA2-TH-IgG-9 showed that high concentrations of ampicillin were needed to maintain plasmid stability and to generate consistently high levels of the fusion protein. Glucose was eliminated from the growth media during the IPTG induction of pMA2-TH-IgG-9 to prevent the recombinant product from escaping from the periplasmic space into the media. These problems may be directly associated with the use of a modified pMAL vector since induction of the unmodified commercial pMAL-p2 clones is noted by the manufacturer to be lethal and our immunoblotting control experiments showed a consistent, low level of transcription in the absence of IPTG. Conversely, the IgG portion of the fusion protein may contribute to this instability and leakage.

Ampicillin-resistance is conferred by the presence of the β-lactamase gene product in the periplasmic space. Secretion of proteins into the periplasmic space occurs by a regulated transport process and may be rate-limiting for the production of secreted fusion products. Additionally, if the presence of the fusion protein makes the outer membrane unstable, the action of β-lactamase may be hindered. To eliminate these concerns, the ampicillin-resistance gene present on pMA2-TH-IgG was replaced by the kanamycin-resistance gene. The β-lactamase promoter was used to express the kanamycin-resistance gene. The kanamycin-resistance gene was chosen to replace the β-lactamase gene because kanamycin-resistance gene product is not secreted.

The kanamycin-resistance gene was isolated from the eukaryotic vector pBK-RSV (Stratagene). Two micrograms of each pBK-RSV and pM-TH (described in Example 1a) were digested with BspHI to completion. The digestion products were concentrated by ethanol precipitation and run on a 1.5% low-melting temperature agarose (LMA) gel using TAE buffer (40 mM Tris-acetate, 2 mM EDTA). The approximately 1.8 kb fragment containing the kanamycin-resistance gene from pBK-RSV and the approximately 5.6 kb pM-TH vector fragment were excised from the gel and digested with Gelase (Epicentre Technologies) according to the manufacturer's protocol. Two hundred nanograms of purified vector DNA was combined with 200 ng of insert DNA in a final volume of 20 μl and ligated at 17° C. in the presence of T4 DNA ligase and 1 mM ATP. The ligation products were used to transform competent AG1 cells (Stratagene). Transformants were grown on plates containing 50 μg/ml kanamycin. Four clones were picked and analyzed by restriction enzyme digestion. All four clones contained the kanamycin-resistance gene in the desired orientation. The resulting plasmid was called pMA2TH-Kan.

To investigate whether replacement of the ampicillin-resistance gene with the kanamycin-resistance gene would lead to improved expression of periplasmic fusion proteins, the IgG domain was inserted downstream of the malE gene in pMA2TH-Kan to generate the pM-Col-K vector which encodes a MBP/IgG fusion protein. The thrombin site and the hydrophilic spacer (Arg-Arg) were replaced with a hydrophilic spacer resistant to proteolytic cleavage (the control spacer) in order to eliminate any possible degradation of fusion protein during the quantitation experiments. This spacer was designed to give large proteins sufficient range of rotation around the Fc tail by including glycine and proline residues.

Insertion of the linker encoding the spacer was accomplished as follows. pMA2-TH vector (2.0 μg) was digested with SacI and NheI to remove the thrombin site. The digested plasmid was purified by ethanol precipitation. The oligonucleotide pair comprising ColF1: 5'-CGTTTAAAAAGAAACCGCGGGGCCCGGGTAC-3' (SEQ ID NO:47) and ColR1: 5'-CCGGGCCCCGCGGTTTCTTTTTAAACGAGCT-3' (SEQ ID NO:48) was annealed by incubating 10 μl of each oligonucleotide (100 μM) in 100 μl of hybridization solution (10 mM Tris-HCl, pH 8.0 and 50 mM NaCl) at 90° C. for 10 min and then allowing the solution to cool to room temperature over a period of 2 hours. The KpnI/NheI digested IgG PCR product (described below in Example 3) was ligated to an excess of the annealed ColF1/ColR1 oligonucleotide pair.

Following the ligation reaction, the products were purified on a CHROMA SPIN-400 column (Clontech) and ligated into the SacI/NheI-digested pMA2TH-Kan vector. The ligation products were used to transform competent AG1 cells. Transformants were selected by the ability to grow in the presence of 50 μg/ml kanamycin. Kanamycin-resistant clones were screened for inserts and the ability to produce IgG as described above in Example 1. Clones which expressed IgG were designated pM-Col-K(1–4); the numbers are used to indicate unique isolates. To provide a control plasmid, the KpnI/NheI IgG fragment was cloned into the ampicillin-resistant version of pMA2-TH using the above protocol and this plasmid was designated pM-Col-A(1–4).

Figure 8:
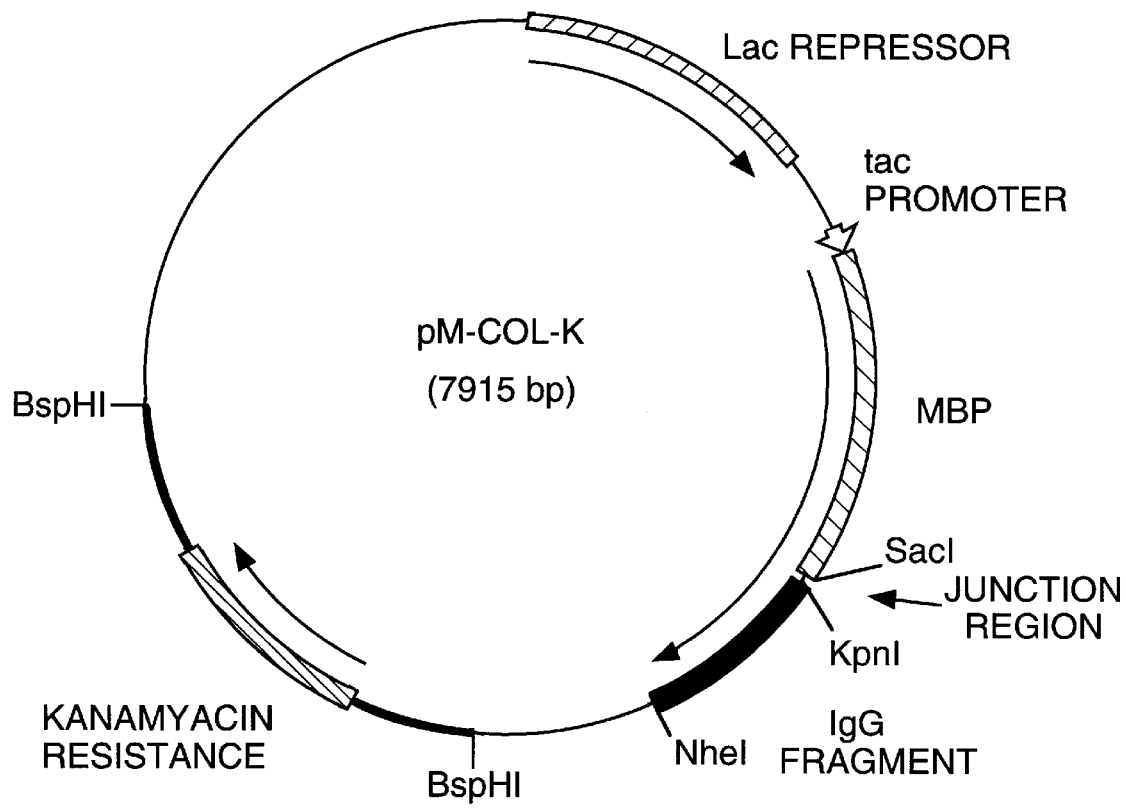
FIG. 8 provides a map of the pM-Col-K vector.

FIG. 8 provides a schematic map of pM-Col-K. In FIG. 8, the coding regions for the lac repressor (lacI$^q$), MBP, the IgG fragment and kanamycin resistance gene are shown and the direction of transcription is indicated by the arrows; selected restriction sites are indicated. The tac promoter is also indicated (open arrowhead). The location of the junction region is indicated.

Figure 9:
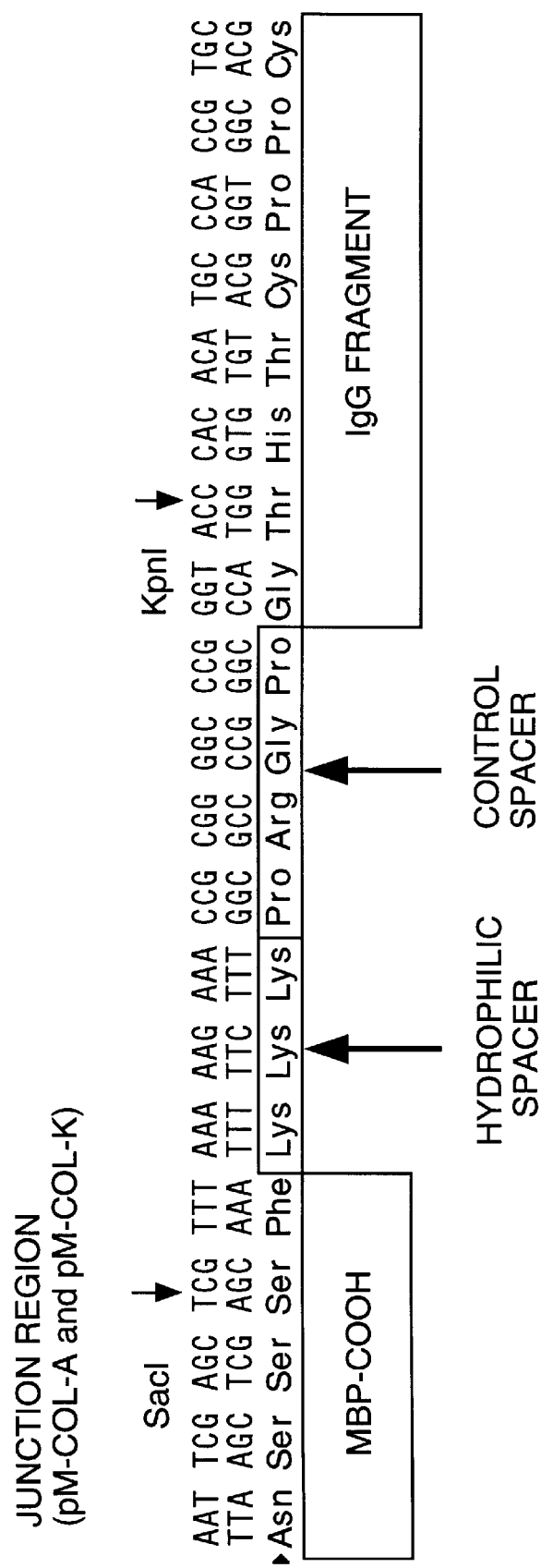
FIG. 9 depicts the junction region present in the pM-Col-A and pM-Col-K vectors.

The sequences comprising the junction region present in pM-Col-K and pM-Col-A are shown in FIG. 9. Sequences comprising the carboxy-terminus of the MBP, the hydrophilic spacer, the control spacer and the amino-terminal portion of the IgG hinge region are indicated. The site of cleavage for the restriction enzymes SacI and KpnI are indicated by the arrowheads.

Bacteria harboring either pM-Col-K or pM-Col-A were induced by growth in the presence of IPTG in order to compare the amount of recombinant fusion protein expressed by each plasmid. The resulting fusion protein was affinity purified on protein A columns as described above. Briefly, overnight cultures (200 ml) of bacteria containing either pM-ColK or pM-ColA were grown in LB containing either 50 µg/ml kanamycin or 120 µg/ml ampicillin, respectively. These overnight cultures were used to inoculate 2.8 liter flasks containing 1 liter of the appropriate LB media prewarmed to 37° C. The cultures were grown at 37° C. in a shaker incubator with a rotation speed of 260 rpm until an $OD_{600}$ of 0.6 was reached. IPTG was added to a final concentration of 0.4 mM and growth was continued for 2.5 hours. The cells were harvested by centrifugation and lysed with lysozyme as described in Example 1. The lysates were adjusted to 450 mM NaCl, filtered and applied to 2 mls of prewashed immobilized Protein A in separate 10 ml disposable Affinica columns (Schleicher & Schuell). The columns were washed with 10 mls of binding buffer (20 mM Tris-HCl, pH 8.0, 450 mM NaCl, 5 mM EDTA) and the fusion protein was eluted with 100 mM NaCitrate buffer, pH 2.8. One milliliter fractions were collected and assayed for protein content using the BCA assay (Pierce). Fractions containing protein were pooled and the yield of fusion protein produced by the two plasmids was calculated. The results of these experiments are summarized below.

Recombinant fusion protein yields were increased two fold using the kanamycin-resistant constructs as compared to the ampicillin-resistant constructs. Greater than 20 mg of fusion protein per liter of induced culture was isolated from the pM-Col-K vector. In comparison, only about 10 mg of fusion protein per liter of induced culture was produced by the pM-Col-A vector. In addition, growth rates were much slower for the pM-Col-A vector; bacteria containing this plasmid required nearly twice as much time to reach an $OD_{600}$ of 0.6 as compared to bacteria containing the pM-Col-K vector.

These results demonstrate that the use of the kanamycin-resistance gene is preferred for the production of fusion proteins which are secreted into the periplasmic space in prokaryotic hosts.

EXAMPLE 3

Construction of an IgG Affinity Domain

The hinge and Fc portion of the human IgG molecule were isolated to provide DNA sequences encoding a protein domain which would allow for the affinity purification of fusion proteins (i.e., an affinity domain).

The IgG1-secreting human plasma cell line ARH-77 (ATCC CRL 1621) [Burk, et al., *Cancer Res.* 38:2508 (1978)] was used as the source of RNA for the isolation of cDNA clones encoding the hinge-CH2-CH3 (i.e., Fc) region of IgG1. ARH-77 cells were grown in RPMI 1640 medium (GIBCO) containing 10% FCS (GIBCO) in 125 ml tissue culture flasks (Fisher). The cells were allowed to grow to confluency and then were harvested by centrifugation at 300×g in 50 ml conical tubes (Fisher). The cell pellet was washed with 40 ml PBS, pH 7.4 and resuspended in a final volume of 10 ml PBS, pH 7.4.

Total cellular RNA was isolated from the ARH-77 cell pellet using a Total RNA Isolation Kit (Clonetech) according to the manufacturer's instructions. Briefly, 10 ml of denaturing solution (6 M guanidinum-HCl) was added to the pooled, washed cells (10 ml) and incubated for 10 minutes at room temperature. The following reagents were added in the stated order with gentle mixing: 1.0 ml 2 M NaOAc pH 4.5, 10 ml water-saturated phenol and 2 ml chloroform/isoamyl alcohol (29:1). The tube was shaken and stored on ice for 10 minutes. The tube was then centrifuged for 15 minutes in an SS34 rotor (Sorvall) at 5000×g at 4° C. The aqueous phase (supernatant) was removed and 10 ml of isopropanol was added to precipitate the nucleic acids.

The tube was stored at −20° C. overnight. The RNA was then pelleted by centrifugation at 5000×g in a SS34 rotor at 4° C. The RNA pellet was resuspended in 0.5 ml of denaturing solution and transferred to a 1.5 ml siliconized microcentrifuge tube (Fisher). The RNA was precipitated by the addition of 0.6 ml of isopropanol and incubation of the tube at −20° C. for 1 hour. RNA was pelleted gently in a Eppendorf microcentrifuge at 5,000×g for 10 min at 4° C., resuspended in 75% ethanol and stored at −20° C. until needed.

Poly $A^+$ RNA was isolated from the above total RNA preparation as follows. The total RNA was pelleted by centrifugation in a microfuge; the pellet was partially air-dried. The RNA was resuspended in 1.0 ml DEPC-treated $H_2O$. Four hundred microliters were removed and the RNA was saved as an EtOH precipitate by the adding of 800 µl ethanol; the tube was stored at −20° C. The remaining 600 µl were brought to 955 µl by adding 355 µl TE buffer, pH 8.0. Magnetic beads covalently linked to streptavidin and biotinylated oligo $dT_{(n)}$ [Magna Poly AAA+RNA Isolation Kit (Clonetech)] were then used to isolate the poly $A^+$ RNA. The RNA suspension (955 µl) was incubated at 65° C. for 5 min and 25 µl of sample buffer (provided in the kit) and 20 µl of biotinylated oligo-dT were added and the reaction was cooled to 4° C.

To this mixture, magnetic streptavidin beads were added and the mixture was incubated at room temperature for 10 min, according to the manufacturer's protocol. The tube was placed against a magnetic rack to allow separation of the poly $A^+$ RNA-magnetic streptavidin complexes. The complexes were washed with binding buffer (provided by the kit) 3 times while in the magnetic rack. Poly $A^+$ mRNA was released from the magnetic beads by washing the beads with 1.5 ml of $H_2O$. The eluted poly $A^+$ RNA was divided into three aliquots and stored as ethanol precipitates at −20° C. until used.

First strand cDNA was synthesized using the poly $A^+$ RNA isolated above and a First Strand Synthesis Kit (Stratagene). Briefly, a single tube of the isolated poly $A^+$ RNA was pelleted by centrifugation at 12,000×g in a microfuge at 4° C. The poly $A^+$ RNA was resuspended in 32 µl of DEPC-treated $H_2O$ and 3 µl of oligo dT primer (provided in the kit) was added. The tube was heated to 65° C. for 5 min and allowed to cool slowly to room temperature. 10× buffer, RNAse Block, dNTPs and 20 units MMLV reverse transcriptase were added as indicated by the manufacturer (all reagents were provided in the kit) and the reaction was incubated at 37° C. for 1 hour. Completed reactions were stored in 3 µl aliquots at −20° C. in a Stratacooler (Stratagene).

A cDNA clone containing the hinge and Fc domains was isolated by PCR amplification of the first strand cDNA. Reagents for PCR amplification were obtained as follows: Taq Polymerase and Core reagent Buffers (Perkin-Elmer), dNTPs (New England Bio-Labs), Pfu polymerase (Stratagene) and synthetic oligonucleotides (National Biosciences). Pfu polymerase was used to generate functional clones because of its increased fidelity compared to Taq polymerase. Temperature cycling was performed using a Perkin-Elmer thermocycler (N801-0150).

FIG. 10 provides the nucleotide and amino acid sequence of the human IgG1hinge/$F_C$ region (SEQ ID NOS:49 and 50, respectively). In FIG. 10, selected amino acid residues are numbered to facilitate the discussion below (the initiator methionine located at the amino-terminus of the molecule in the $V_H$ domain is residue number 1).

The IgG hinge/$F_C$ domain was amplified using three different oligonucleotides to prime separate PCR reactions at the 5' end of the hinge region. All three 5' oligonucleotides contain approximately 20 bases of sequence complimentary to the IgG hinge region linked to nucleotides comprising either a NgoMI, KpnI or SalI restriction site at the 5' end of the oligonucleotide primer. The sequence of these three 5' primers is shown in FIG. 11.

In FIG. 11, the bases present in the three 5' primers which correspond to sequences located in the human IgG1 hinge region are underlined. The location of the restriction sites present at the 5' end of the primers is indicated and the cleavage site is marked by an arrowhead.

As shown in FIG. 11, these three oligonucleotide primers introduce different amino acids at the 5' end of the hinge region. The IG5NGO oligonucleotide (SEQ ID NO:51) contains the recognition site for NgoMI and introduces two arginine residues immediately upstream of the histidine residue located at amino acid position 225 in the human IgG1 molecule. The IG5ARS oligonucleotide (SEQ ID NO:52) contains the recognition site for SalI and introduces two arginine residues at the 5' end of the hinge region (immediately upstream of the threonine residue located at amino acid position 226 in the human IgG 1 hinge region). The IG5KPN oligonucleotide (SEQ ID NO:53) contains a KpnI site and introduces a glycine residue in the hinge region (immediately upstream of the threonine residue located at amino acid position 224 in the human IgG hinge region).

A single 3' oligonucleotide was used to prime the PCR reactions. This oligonucleotide was termed IG3NHE and comprises the following sequence: 5'-CCCCCGCTAGCGTCATTTACCCGGAGACAGGGA-GA-3' (SEQ ID NO:54). The IG3NHE oligonucleotide contains an NheI site to allow for the directional cloning of the isolated PCR products. Sequences present in the IG3NHE oligonucleotide which hybridize to sequences present at the 3' end of the human IgG1 $F_C$ domain are underlined in FIG. 10.

The resulting 0.7 kb PCR products contain three variations of the hinge domain. They are designed to allow the naturally occurring proteolytic cleavage site of the hinge maximum exposure (see FIG. 10). The SalI-IgG product was designed to be very hydrophilic; this product is generated using primers comprising SEQ ID NOS:52 and 54. Two arginine residues encoded by the 5' primer (SEQ ID NO:52) were used to replace the naturally occurring Thr(224) and His(225) to make the region more hydrophilic. In the KpnI-IgG fragment a glycine residue encoded by the 5' primer (SEQ ID NO:53) replaces the naturally occurring Lys(223) amino acid to allow for maximum rotation of the protein of interest and attached endocleavage site, Thr(224) and His(225) were not disturbed. The KpnI-IgG fragment is generated using primers comprising SEQ ID NOS:53 and 54.

In the NgoI-IgG fragment, the threonine (at position 224) was replaced with an arginine residue to make the hinge region more hydrophilic. A glycine codon (GGG) can be created by using a cloning linker that terminates with GG and has an NgoI compatible 5' overhang to provide additional flexibility.

Thermocycling was performed using the following conditions: 95° C. for 1 min 30 sec, 37° C. for 1 min and 72° C. for 2 min sec for 30 cycles. Following amplification, each PCR product was isolated on a low-melt agarose gel in order to remove primers and incomplete products. Nearly 100% recovery of products from the gel was accomplished using Gelase (Epicenter), an enzyme that degrades agarose to saccharides, following the manufacturer's protocol. After treatment with Gelase, the PCR fragments were isolated by EtOH precipitation. The IgG fragments (i.e., the NgoMI/ NheI-, SalI/NheI- or KpnI/NheI-IgG fragment) were digested with NgoMI and NheI, SalI and NheI, or KpnI and NheI then inserted into the desired vectors digested with the appropriate restriction enzymes.

EXAMPLE 4

Construction of Fusion Proteins Expression Vectors for Use in a Variety of Host Cell Types To produce the fusion proteins comprising the hydrophilic spacers of the present invention in any desired host cell, expression vector constructs have to be made that will satisfy the various genetic requirements of the system. Genes encoding the protein of interest need to be inserted into vectors containing the appropriate transcription and translation sequences. Moreover, those control elements must be linked to the carboxy-terminal fusion partner (e.g., the hinge and Fc domain of IgG) via the chosen hydrophilic spacer and endoprotease site. This configuration may be achieved by modification of any commercially available expression vector using standard techniques of molecular biology.

Synthetic linkers encoding the desired hydrophilic spacer and endoprotease site are used to join the 3' end of the gene encoding the protein of interest to the 5' end of the IgG gene fragment. This construction must maintain a single open reading frame so that the hydrophilic spacer, endoprotease site and affinity domain are properly expressed (i.e., no premature stop codons are generated and no shifts in reading frame occurs). Examples are herein provided demonstrating how such constructs are made in order to generate vectors suitable for expression of fusion proteins in prokaryotic cells and eukaryotic cells such as mammalian cells or insect cells.

All of these exemplary vectors use the Kpn/NheI-IgG fragment (described above in Example 3) as the carboxy-terminal fusion partner, but it is noted that the invention is not limited to the use of this particular affinity domain. These exemplary vectors do not specify a particular endoprotease site or a particular hydrophilic linker sequence to be used. These elements are selected based on the amino acids present in naturally occurring carboxy terminus of the protein of interest and the proteolytic susceptibility as discussed in the Description of the Invention above.

a) Prokaryotic Expression Vectors: Construction of pTVkIg-1

The expression vector pTVkIg-1 was constructed to allow the expression of fusion proteins containing the hydrophilic spacers in prokaryotic hosts such as *E. coli*. This vector contains the strong tac promoter to allow for high level transcription and the lacO operator to allow for transcriptional regulation in the presence of the lac repressor. The lacI$^q$ repressor gene encoded by pTVkIg-1 allows for regulation of expression in any *E. coli* strain. An optimized ribosome binding site is present to allow for efficient initiation of translation.

To construct pTVkIg-1, the commercially available vector pSE380 (Invitrogen) was modified as follows. The Superlinker cloning site of pSE380 was removed by digesting pSE380 with NcoI and HindIII. A polylinker containing multiple restriction sites was inserted by ligation of the following annealed oligonucleotide pair: VNH1: 5'-CATGGACTGAAAGCTTGACGGTACCTGAGCTAGCT-3' (SEQ ID NO:55) and VNH2: 5'-AGCTAGCTAGCTCAGGTACCGTCAAGCTTTCAGTC-3' (SEQ ID NO:56). This oligonucleotide pair contains the recognition sites for NcoI, HindIII, KpnI and NheI. When this pair of oligonucleotides is annealed, a 5' overhang compatible with NcoI ends and a 3' overhang compatible with HindIII ends are created. Generation of the modified vector is confirmed by restriction analysis (absence of deleted Superlinker sites and presence of NcoI, HindIII, KpnI and NheI) and is designated pST-1.

The sequences encoding the hinge and Fc ($C_H2$ and $C_H3$) regions of the human IgG1 molecule contained on a 0.7 kb KpnI/NheI fragment (described in Example 3) was inserted into pST-1 as follows. pST-1 was digested with KpnI and NheI and the 0.7 kb KpnI/NheI IgG fragment was ligated into the digested pST-1 vector using a 2:1 ratio of insert to vector. A clone containing the IgG insert was confirmed by restriction analysis and was designated pSTIg-1. A map of pSTIg-1 is provided in FIG. 12.

Figure 12:
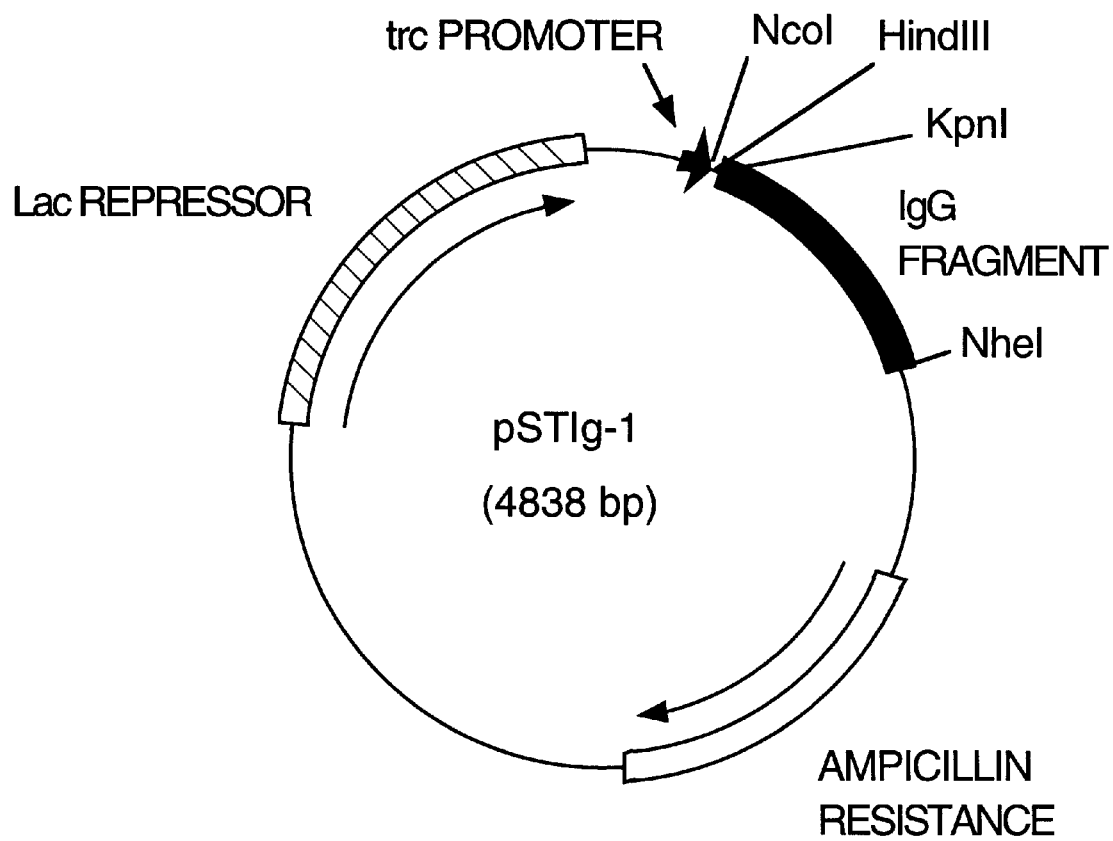
FIG. 12 provides a map of the pSTIg-1 vector.

In FIG. 12, the location of the trc promoter, the KpnI/NheI IgG fragment, the ampicillin-resistance gene and the $lacI^q$ gene are indicated; selected restriction sites are also indicated.

To provide a signal sequence which is efficiently utilized by prokaryotic cells, a signal peptide sequence derived from the bacterial phosphatase (pho) gene was then inserted into pSTIg-1. This improved signal peptide sequence contains a NcoI site at the ATG codon and a HindIII site at the 3' end. These engineered sites allow the insertion of the signal sequence into the expression vector and allows the addition of sequences encoding the desired protein of interest at the 3' end of the signal peptide sequence. When secreted eukaryotic proteins of interest are to be expressed in prokaryotic hosts, the naturally occurring signal sequence is deleted from the eukaryotic gene and is replaced with the modified pho signal sequence.

The pho signal sequence was generated by annealing the following four oligonucleotides together. pho F1: 5'-CATGAAACAAAGCACTATTGCACTGGCTGTC-3' (SEQ ID NO:57). pho F2: 5'-TTACCGTTACTGTTTACCCCTGTGACAAA-3' (SEQ ID NO:58). pho R1: 5'-AGCTTTTGTCACAGGGGTAAACAGTAACGGTAAGACAGC-3' (SEQ ID NO:59). pho R2: 5'-CAGTGCAATAGTGCTTTGTTT-3' (SEQ ID NO:60). Oligonucleotides pho F2 and pho R2 contained 5'-phosphate groups; pho F1 and pho R2 were nonphosphorylated.

FIG. 13 shows the double-stranded sequence generated by annealing of the four pho oligonucleotides; the amino acid sequence encoded by the annealed oligonucleotides is shown below the nucleotide sequence; the amino acid sequence of the pho signal sequence is also listed in SEQ ID NO:61.

Annealing was accomplished as follows. Each of the four oligonucleotides was suspended at a concentration of 40 μM in 50 mM Tris-HCl, pH 8.0, 20 mM KCl and 1 mM EDTA. Twenty-five microliters of each oligonucleotide solution was combined and heated to 90° C. and then allowed to slow cool to room temperature over 120 min. The reaction was then placed at 17° C. and $MgCl_2$ (10 mM final concentration), ATP (1 mM final concentration) and T4 DNA ligase was added. The ligation reaction was incubated for 1 hour at room temperature and then stored at −20° C.

To insert the pho signal sequence into pSTIg-1, the vector was digested with NcoI and HindIII. A 3 fold molar excess of the annealed signal sequence and the digested pSTIg-1 vector are ligated together in a final reaction volume of 20 μl using T4 DNA ligase at 17° C. Insertion of the signal sequence into pSTIg-1 was confirmed by restriction analysis (lack of the NcoI site). The resulting vector containing the pho signal sequence and the IgG fragment was designated pTVkIg-1. A map of pTVkIg-1 is shown in FIG. 14.

Figure 14:
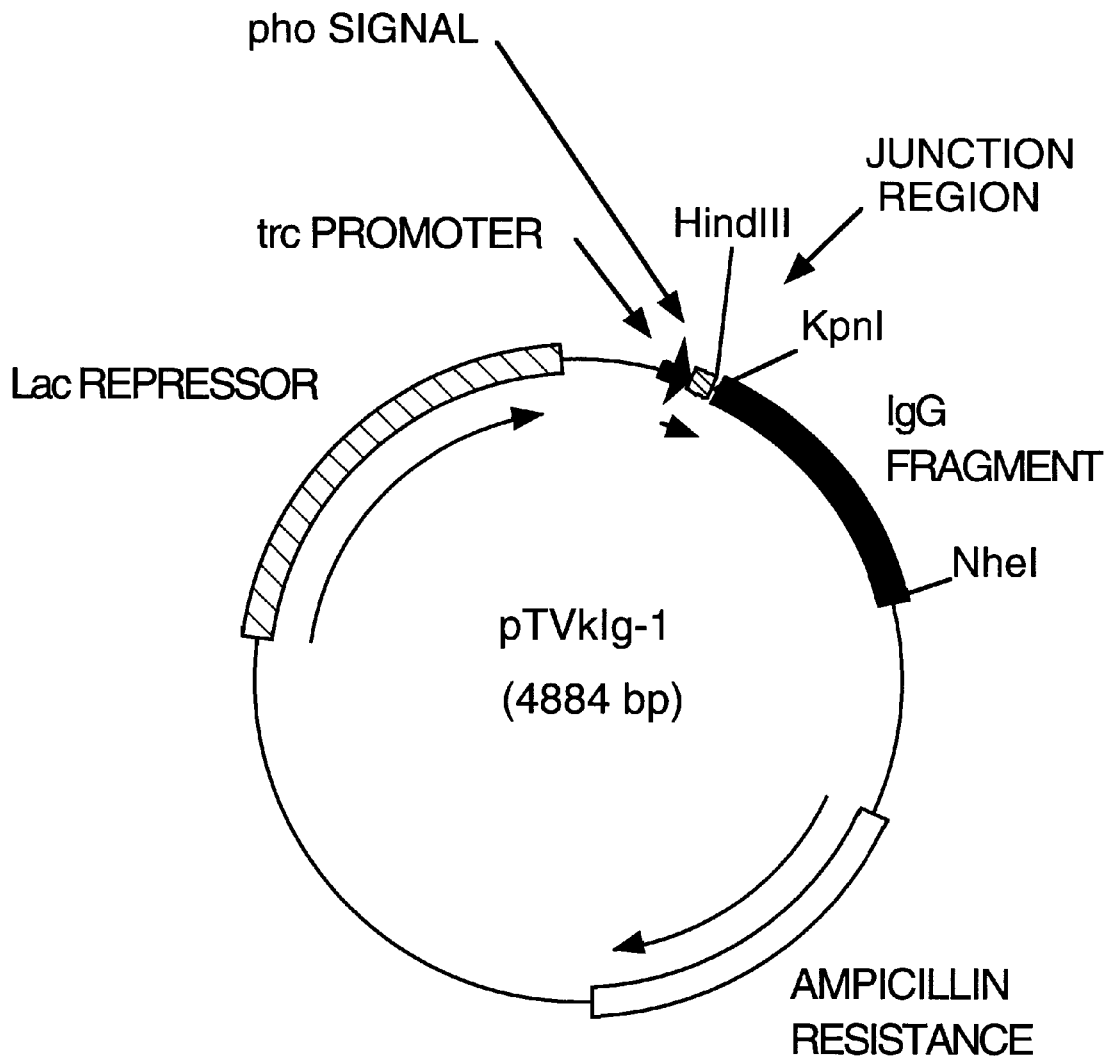
FIG. 14 provides a map of the pTVkIg-1 vector.

In FIG. 14, the location of the trc promoter, the pho signal sequence, the junction region, the KpnI/NheI IgG fragment, the ampicillin-resistance gene and the lac repressor ($lacI^q$) gene are indicated; selected restriction sites are also indicated.

Figure 15:
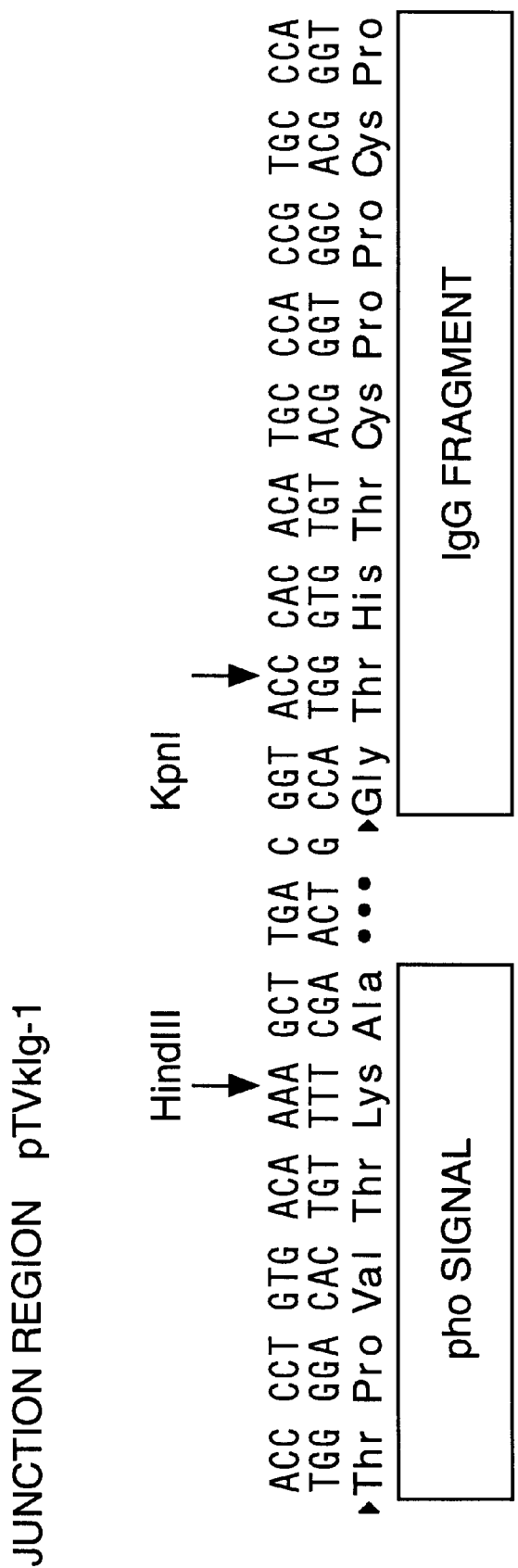
FIG. 15 depicts the junction region of the pTVkIg-1 vector.

As shown in FIG. 15, pTVkIg-1 contains a HindIII and a KpnI site between the pho signal peptide sequences and the IgG sequences to allow for the insertion of sequences encoding the desired protein of interest. Additionally, when desired, sequences encoding a hydrophilic spacer and endoprotease site may be inserted into the junction region (see FIGS. 14 and 15) between the 3' end of the desired protein and the 5' end of the IgG nucleic acid sequences.

The pTVkIg-1 vector was engineered to provide a number of advantages for the expression of fusion proteins. The pho signal peptide or secretion sequence is followed by a stop codon so that the downstream IgG sequences are not expressed in clones which lack an insert encoding the protein of interest (see FIG. 15). This design allows for the expression screening of clones containing sequences encoding the protein of interest inserted into the HindIII and KpnI sites of pTVkIg-1 using anti-Fc antibodies. Only those clones containing sequences encoding the protein of interest correctly joined to sequences encoding the hydrophilic spacer and affinity domain will result in the production of the Fc portion of the IgG molecule. Sequences encoding the protein of interest can be inserted into the HindIII and KpnI sites of pTVkIg-1 using a variety of techniques including the use of linkers and adapters and the generation of compatible ends through the use of primers having the desired restriction sites in a PCR. Additionally, the HindIII site in pTVkIg-1 can be made blunt by incubation of the digested plasmid with the Klenow fragment of E. coli DNA polymerase and dNTPs. This fill-in reaction will produce a blunt end which is in frame with the desired codons in the protein of interest.

The sequences encoding the IgG affinity domain were designed so that the KpnI site at the 5' end of the IgG sequences introduces a glycine residue into the hinge region of the IgG sequences. This provides flexibility to the hydrophilic region allowing for enhanced accessibility of this region of the fusion protein to the endoprotease. The use of NheI as the restriction site at the 3' end of the IgG sequence provides an additional stop codon to prevent any read through translation.

b) Eukaryotic Expression Vectors
i) Mammalian Expression Vectors: Construction of pTVMam-Ren Numerous eukaryotic expression vectors are currently available. Most provide for high levels of constitutive transcription from mammalian enhancer/promoter sequences and contain appropriate transcription termination and polyadenylation signal sequences. Sequences which allow for the replication of the vector in appropriate mammalian cell lines (e.g., the SV40 origin of replication and COS cells) may be present. Sequences encoding a selectable marker, such as the neo gene, may be utilized to allow for the isolation of stable mammalian cell lines expressing the vector sequences. The pcDNA3 vector (Invitrogen) was used to illustrate the modification of a mammalian expression vector to allow for the production of the improved fusion proteins of the present invention.

The NruI and KpnI sites are deleted from pcDNA3 to prepare for the construction of pTVMam-Ren. The NruI site is eliminated by ligating a self-annealing 8-mer that codes for the NotI recognition sequence [GCGGCCGC (NEB)] into NruI-digested pcDNA3. The KpnI site is eliminated by treating the modified pcDNA3 vector with KpnI followed by treatment with T4 DNA polymerase at 25° C. in the presences of dNTPs. Religation (i.e., circularization) of the blunted vector will result in the loss of the KpnI site.

The modified pcDNA3 vector is then ready for insertion of the KpnI/NheI IgG fragment (described in Example 3) into a unique XbaI site located at the 3' end of the multiple cloning site (i.e., polylinker) in pcDNA3. The NheI end present on the KpnI/NheI IgG fragment is compatible with the downstream XbaI overhang present in the digested pcDNA3 vector (this ligation will destroy both the NheI and XbaI sites). The KpnI end on the IgG fragment is connected to the upstream XbaI overhang through the use of a linker which contains a single-stranded extension at the 5' end which is compatible with XbaI ends and a single-stranded extension at the 3' end which is compatible with KpnI ends. The linker sequences also encode a hydrophilic spacer and an endoprotease site.

A suitable linker (termed the 5' linker) is formed by annealing the oligonucleotide pair XKf2 and XKr2 (SEQ ID NOS:62 and 63, respectively) together to generate the following double-stranded sequence:

```
5'-CTAGCTGATCGCGAAAGAAGCTGCCGTTCCACCTGCTGGTGTACGGTAC-3'  (XKf2)
      3'-GACTAGCGCTTTCTTCGACGGCAAGGTGGACGACCACATGC-5'  (XKr2)
```

The above linker is compatible with NheI ends at the 5' and with KpnI ends at the 3' end; this allows the linker to be inserted into the upstream XbaI site of pcDNA3 and allows the linker to be ligated to the KpnI/NheI IgG fragment through the KpnI ends; the NheI end present on the IgG fragment is capable of ligation into the downstream XbaI site on pcDNA3. The above linker encodes a hydrophilic spacer comprising the sequence Arg-Lys-Lys (SEQ ID NO:17), a penultimate enhancer (leucine) and the recognition site for the endoprotease renin [Pro-Phe-His-Leu-Leu-Val-Tyr (SEQ ID NO:3)]

The 5' linker used to join the IgG fragment to the vector and provide the spacer and endoprotease site may be designed such that additional arginine, lysine and tyrosine residues may be placed upstream of the endoprotease site. Insertion of the IgG fragment into the XbaI site in the above described manner allows the remaining sites in the multiple cloning site to be utilized for insertion of sequences encoding the gene of interest. The above-described linker contains a NruI site (TCGCGA) which produces a blunt end upon digestion. The resulting blunt end has CGA as its first three nucleotides which encodes the first arginine residue of the hydrophilic spacer. The sequence following this CGA can be varied to generate the desired hydrophilic linker and endoprotease site.

To construct pTVMam-Ren, 2 μg of pcDNA3 is digested with XbaI. The 5' linker is formed by annealing equimolar ratios of unphosphorylated XKf2 and XKr2 oligonucleotides at a concentration 10 μM in a total volume of 100 μl as described in Example 1a. The annealed XKf2/XKr2 oligonucleotide pair is ligated in excess (10 fold) to the KpnI/NheI IgG fragment (Example 3). Linkers ligated to the 3' NheI end of the IgG fragment (via the compatible XbaI overhang on the 5' linker) are removed by digestion with NheI and passing the reaction products through a CHROMA SPIN 100 column (Clontech). The purified insert is then ligated to 200 ng of XbaI-digested pcDNA3 vector using a 3:1 insert:vector ratio. The ligation products are used to transform competent E. coli cells. Ampicillin-resistant colonies are screened for inserts in the proper orientation by restriction analysis (a double digestion using with ApaI and NruI). Clones having inserts in the proper orientation are isolated and their plasmids are purified. The exemplary vector, pTVMam-Ren is shown in FIG. 16.

Figure 16:
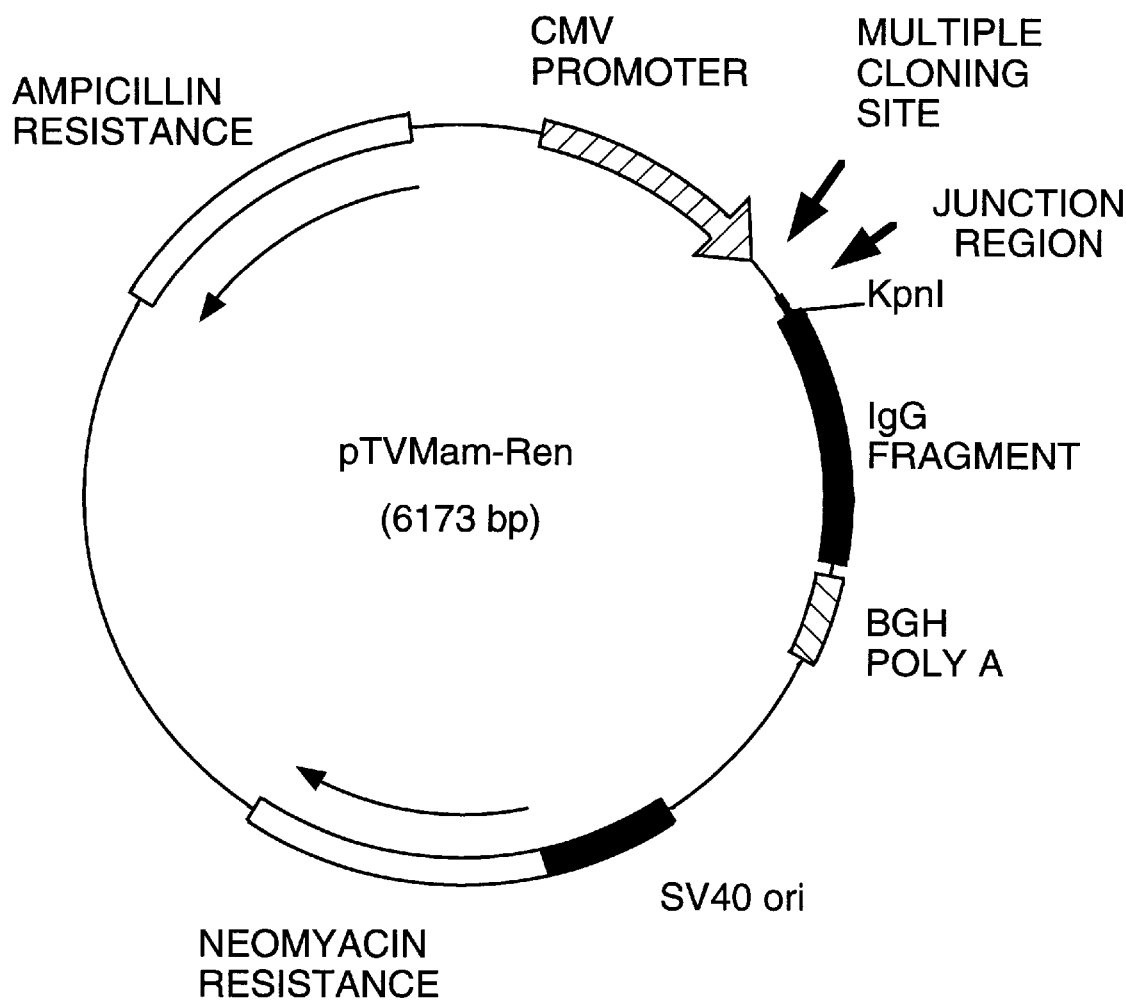
FIG. 16 provides a map of the pTVMam-Ren vector.

In FIG. 16, the location of the cytomegalovirus (CMV) promoter, the multiple cloning site, the junction region, the KpnI/NheI IgG fragment, the bovine growth hormone polyadenylation site ("BGH poly A"), the SV40 origin of replication, the neomycin-resistance gene and the ampicillin-resistance gene are indicated; the direction of transcription is indicated by the arrows; selected restriction sites are indicated.

Figure 17:
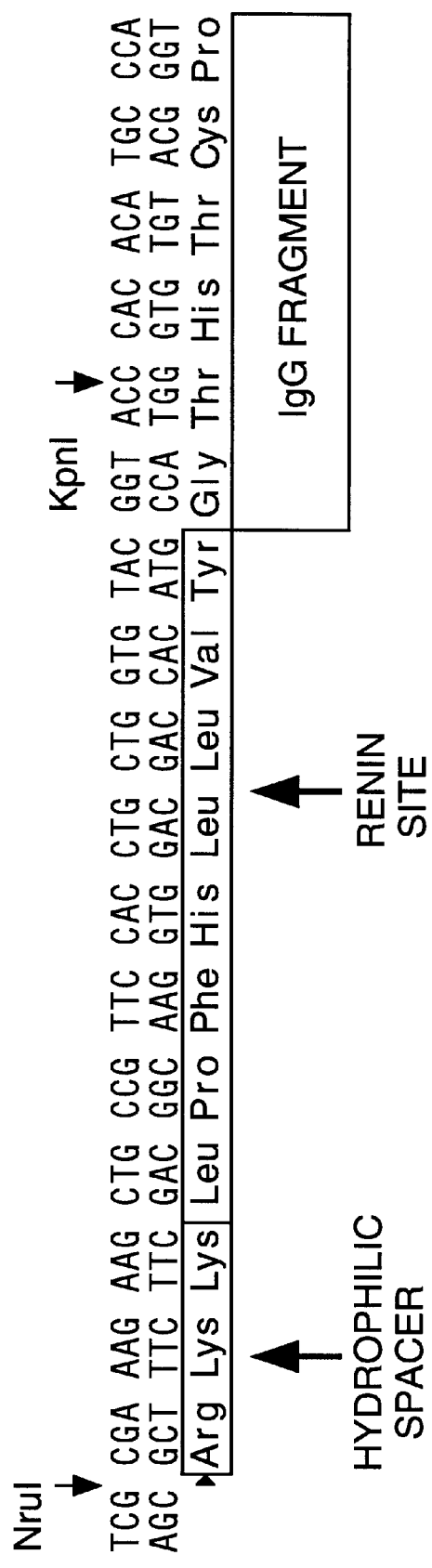
FIG. 17 depicts the junction region of the pTVMam-Ren vector.

FIG. 17 provides a diagram showing the sequences comprising the junction region which contains the hydrophilic spacer and renin endoprotease site present on pTVMam-Ren; a portion of the sequences encoding the IgG hinge region are also shown. Sequences encoding the protein of interest are inserted upstream of the sequences encoding the hydrophilic spacer (See FIG. 18). The location of the NruI and KpnI restriction sites are indicated by the arrowheads; the location of the cleavage site for renin is indicated by the arrow pointing between the adjacent leucine residues.

Figure 18:
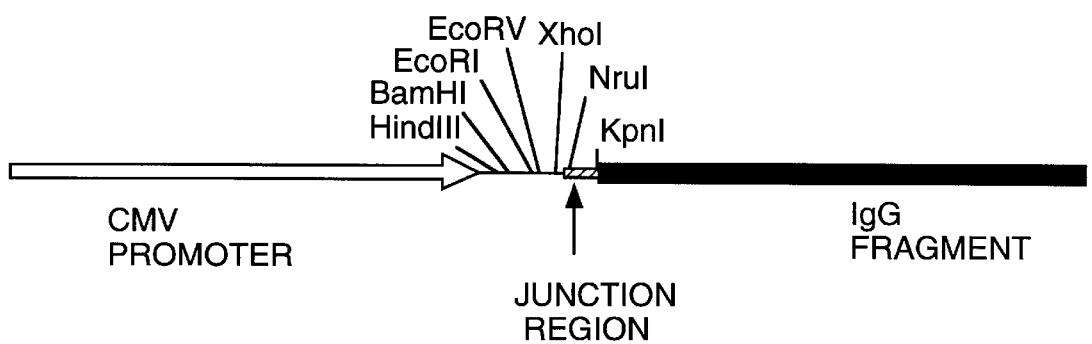
FIG. 18 depicts the multiple cloning site present in the pTVMam-Ren vector.

As shown in FIG. 18, vectors constructed in this manner have a multiple cloning site available for ligation to the 5' end of the sequences encoding the protein of interest. FIG. 18 depicts a portion of the pTVMam-Ren vector containing the CMV promoter, the multiple cloning site (indicated by the cluster of restriction sites), the junction region and the IgG fragment. The NruI site present in the junction region produces a blunt end for the ligation of the 3' end of the sequences encoding the protein of interest. The sequences encoding the protein of interest must contain an ATG initiation site and have a full codon represented at its 3' blunt end to enable the production of IgG fusion molecules in mammalian cells using the pTVMam-Ren vector.

ii) Baculovirus Expression Vectors: Construction of pTVBac-kIg

A number of vectors are commercially available for the expression of fusion proteins in insect cells including the pBlueBacHis vectors and the pVL1393 vector (Invitrogen). The pVL1393 vector is modified to permit the expression of the fusion proteins of the present invention as follows. Several restriction sites are present in the pVL1393 vector that allow for efficient cloning of inserts. The KpnI/NheI IgG fragment (see Example 2) and a desired linker sequence are inserted into the pVL1393 vector while maintaining the availability of the multiple cloning sites for ligation to the 5' end of sequences encoding the gene of interest. In this example the linker encodes a hydrophilic linker comprising the sequence Arg-Lys-Lys-Lys (SEQ ID NO:24), a penultimate enhancer (Leu) and a renin endoprotease recognition site. However, other combinations of hydrophilic spacers and endoprotease sites may be employed.

pVL1393 was modified generate pTVBac-kIg as follows. Due to the presence of KpnI sites within the vector (pVL1393), linkers are used to clone the KpnI/NheI IgG fragment into the Bg/II site at the 3' end of the multiple cloning site in pVL1393. The KpnI/NheI IgG fragment is isolated from the pM-Col-K vector (described in Example 2). Digestion of pM-Col-K with KpnI and NheI releases the KpnI/NheI IgG fragment which is then purified on a LMA gel as described in Example 3. This IgG fragment has been previously shown to encode authentic and functional form of the KpnI IgG molecule.

Synthetic linkers (a 5' and a 3' linker) are used to insert the IgG fragment into the Bg/II site of pVL1393. The 5' linker encodes the hydrophilic spacer and endoprotease site (renin); this linker has single-stranded extension at the 5' end which is compatible with a BglII overhang and a single-stranded extension at the 3' end which is compatible with a KpnI overhang. The 5' linker is used to join the IgG fragment via the KpnI site to the upstream BglII overhang on the digested pVL1393 vector. A 3' linker which comprises a NheI overhang on the 5' end and a BglII overhang on the 3' end is used to join the IgG fragment via NheI site to the downstream BglII overhang on the digested pVL1393 vector.

A suitable 5' linker is created by annealing together the BKRENf (SEQ ID NO:64) and BKRENr (SEQ ID NO:65) oligonucleotide pair (see FIG. 22) to each other at a concentration of 20 μM (in 20 mM Tris-HCl, pH 8.0, 50 mM NaCl, 1 mM EDTA), by heating to 95° C. for 5 minutes and slow cooling to room temperature over 60 minutes. A suitable 3' linker is formed by annealing the NBf [CTAGCCCCC (SEQ ID NO:66)] and NBr [GATCGGGGGG (SEQ ID NO:67)] oligonucleotides together as follows. The NBf and NBr oligonucleotides are hybridized at a concentration of 20 μM (20 mM Tris-HCl, pH 8.0, 500 mM NaCl, 1mM EDTA) by heating to 80° C. for 5 minutes and slow cooling to 20° C. over 60 minutes. The use of this 3' linker converts the NheI site present at the 3' end of the KpnI/NheI IgG fragment into an BglII overhang while eliminating the BglII site).

The 5' and 3' non-phosphorylated linkers are then ligated to the IgG fragment and the linkers are removed with a CHROMA SPIN-400 column pre-equilibrated with 500 mM NaCl. The purified fragment contains BglII compatible ends and is ligated to into BglII digested pVL1393 vector. The ligation products are used to transform competent bacterial cells [e.g., JM101 (Stratagene)]. Clones are screened for the presence of the IgG insert in the desired orientation by restriction enzyme analysis. The desired clone can be identified by a double digestion with NheI and EcoRI; clones containing a single copy of linker-adapted IgG fragment in the proper orientation will produce a 747 bp NheI/EcoRI fragment. A map of the pTVBac-kIg vector is shown in FIG. 19.

Figure 19:
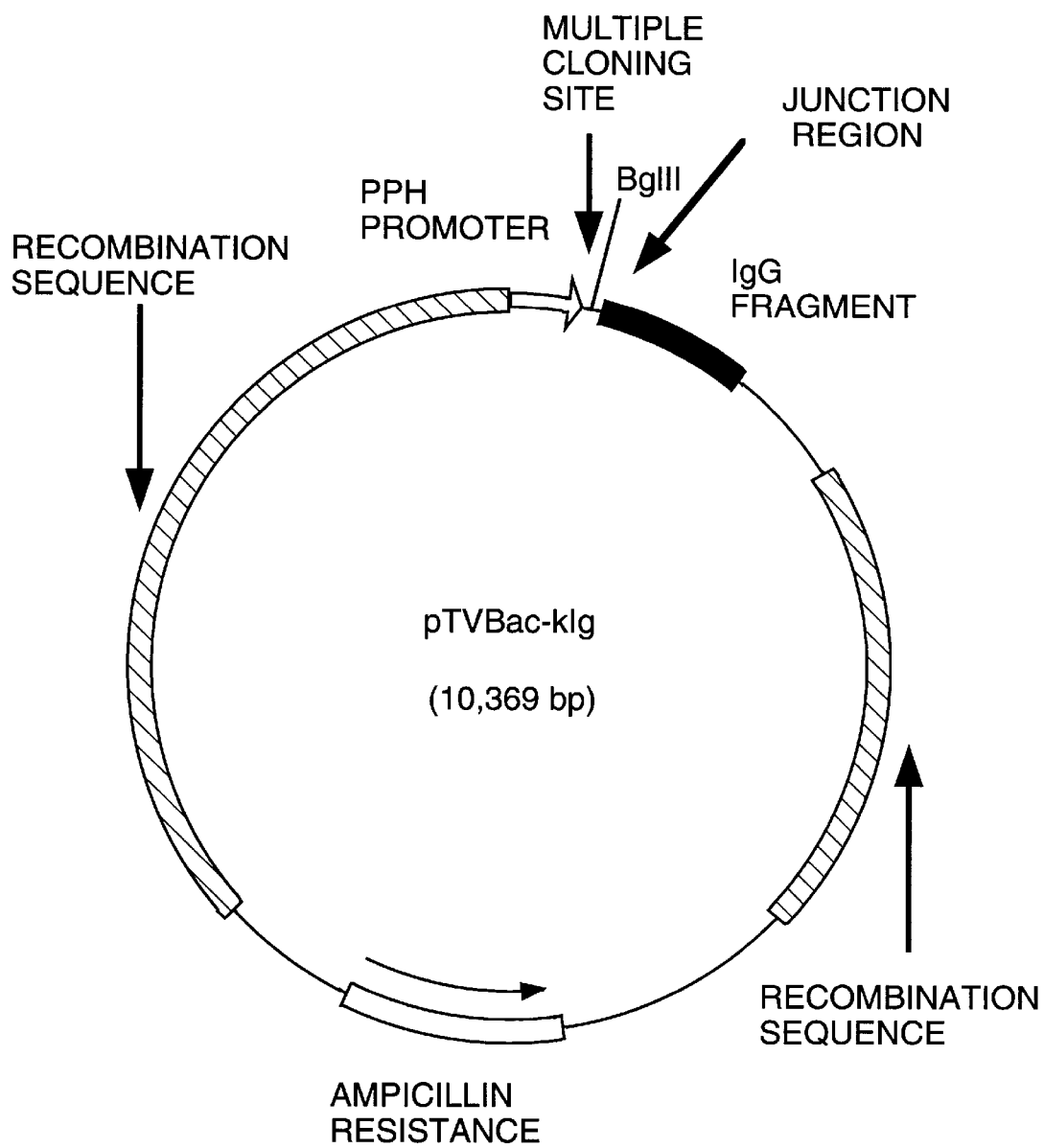
FIG. 19 provides a map of the pTVBac-kIg vector.

In FIG. 19, the location of polyhedron (PPH) promoter, the multiple cloning site, the junction region, the IgG fragment, the ampicillin-resistance gene and recombination sequences are indicated. The recombination sequences are sequences that flank the polyhedron gene in the wildtype AcMNPV which are used in the pTVBac-kIg transfer vector to permit a homologous recombination event to generate a recombinant virus which contains the PPH promoter and the inserted gene sequences; this recombination event is achieved by cotransfection of the pTVBac-kIg vector with AcMNPV DNA (Invitrogen) into suitable host cells such as Sfp cells (Invitrogen).

Figure 20:
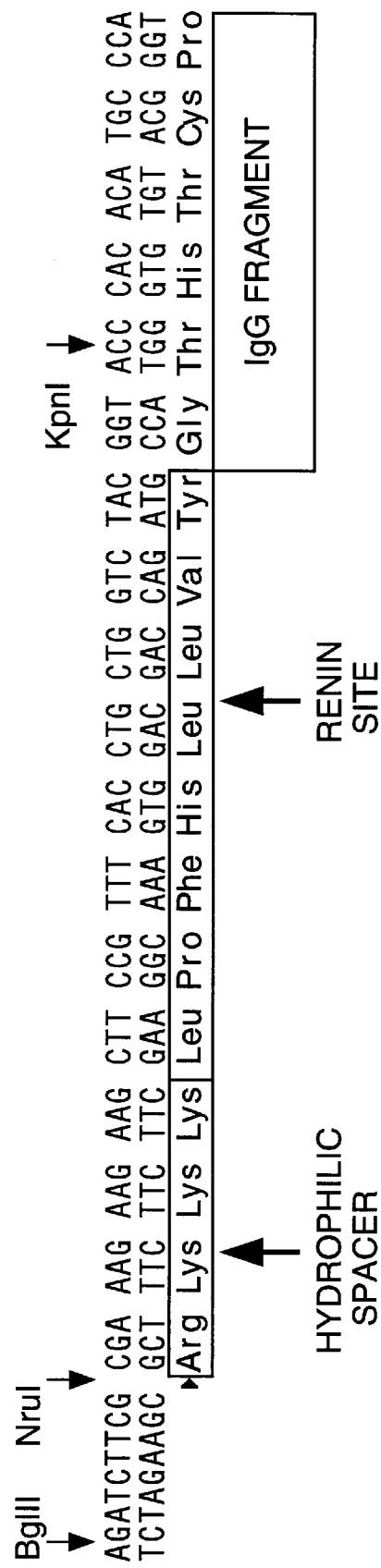
FIG. 20 depicts the junction region of the pTVBac-kIg vector.

FIG. 20 provides a diagram showing the sequences present in the junction region of pTVBac-kIg. The hydrophilic spacer is boxed and comprises the sequence Arg-Lys-Lys-Lys (SEQ ID NO:24); the penultimate enhancer (leucine) is indicated and the renin site is enclosed in a box and the site of cleavage is indicated by the arrow pointing between the adjacent leucine residues. The first 6 amino acids of the IgG fragment is shown. The site of cleavage for BglII, NruI and KpnI is indicated by the arrowheads.

Figure 21:
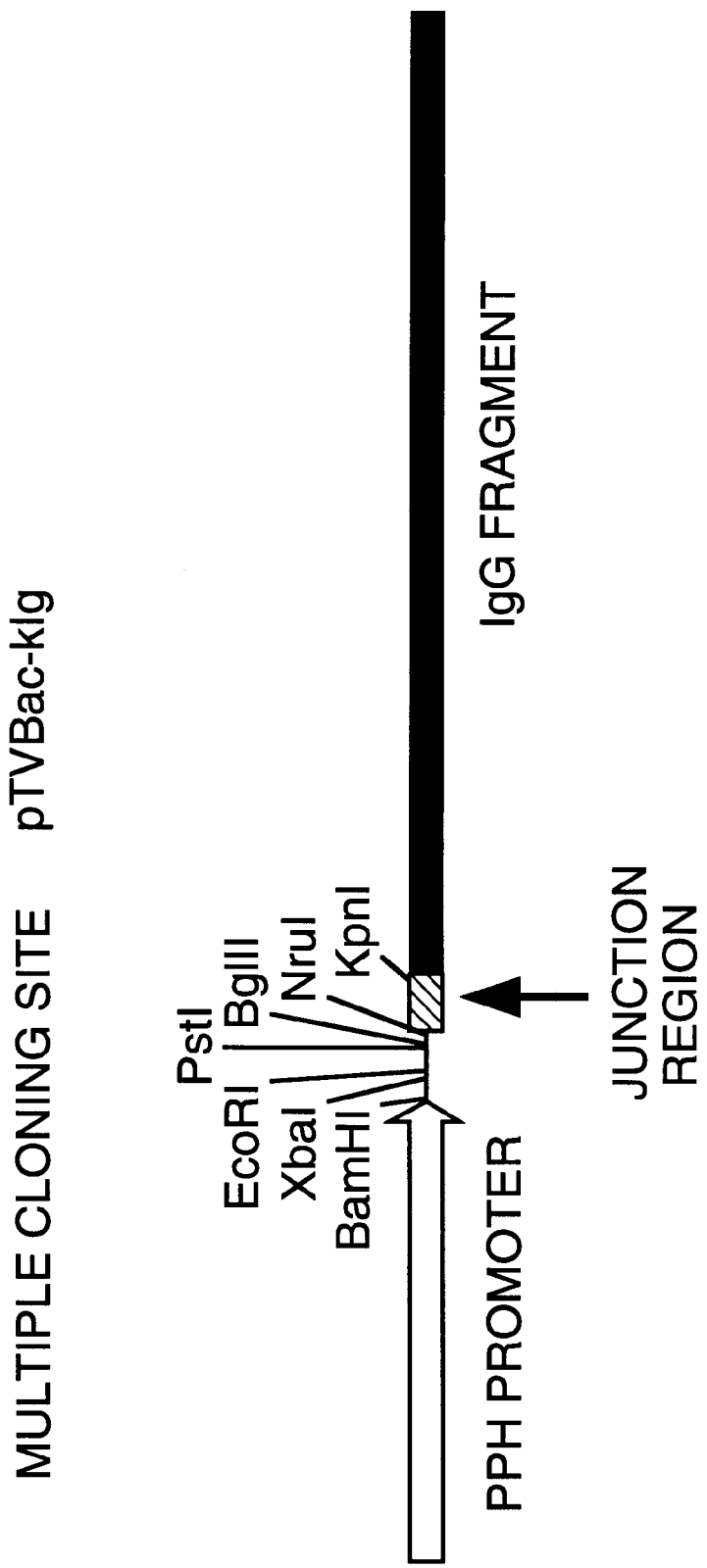
FIG. 21 depicts the multiple cloning site present in the pTVBac-kIg vector.

FIG. 21 depicts a portion of the pTVBac-kIg vector containing the PPH promoter, the multiple cloning site (indicated by the cluster of restriction sites), the junction region and the IgG fragment.

As shown in FIG. 21, pTVBac-kIg retains most of the cloning sites present in the multiple cloning site of the original vector; these sites are available for insertion of the 5' end of the sequences encoding the protein of interest. The translation initiation codon (ATG) must be provided by the sequences encoding the protein of interest. NruI digestion of pTVBac-kIg provides a blunt end for the ligation of the 3' end of the inserted gene while preserving the first arginine residue of the hydrophilic spacer. Several variations of hydrophilic spacers and endoprotease sites can be engineered using the approach described above to create specific vectors for the production of fusion proteins which can be isolated using IgG affinity chromatography (i.e., use of Protein A and/or G resins).

For example, the following oligonucleotide pair can be annealed to provide a thrombin site within the hydrophilic linker in pTVBac-kIg. The thrombin linker is formed by the TBKF (SEQ ID NO:68) and TBKR (SEQ ID NO:69) oligonucleotide pair.

FIG. 22 provides a diagram showing the annealed TBKF and TBKR oligonucleotides which comprise the thrombin linker. The annealed BKRENf (SEQ ID NO:64) and BKRENr (SEQ ID NO:65) oligonucleotide pair which comprises the renin linker used in the construction of pTVBac-kIg (described above) is also shown in FIG. 22. Both the thrombin linker and the renin linker have compatible ends for insertion into the BglII and KpnI sites of the vector.

Vectors constructed with these specific linkers are suitable for the expression of sequences encoding proteins of interest which are not susceptible to thrombin and renin cleavage, respectively. The desired gene is cloned into the appropriate vector using the techniques described above. The vector contains sequences that allow for replication and identification of the desired clones in a commercially available bacterial strain such as JM101 (Stratagene).

Once a construct comprising the sequences encoding the desired fusion protein is isolated, the bacterial cell harboring this construct is grown, isolated and purified by standard techniques (e.g., cesium chloride density gradient centrifugation). The baculovirus transfer vector (e.g., pTVBac-kIg) is used with AcMNPV DNA to cotransfect Sf9 cells to generate a recombinant baculovirus expressing the fusion protein using procedures known to the art. For example, procedures for transformation, growth and selection of insect cells expressing recombinant nerve growth factor (NGF) using baculovirus vectors have been described [U.S. Pat. No. 5,272,063, the disclosure of which is herein incorporated by reference].

Briefly, log phase *Spodoptera frugiperda* (Sf9) cells (Invitrogen) at a density of $2.0 \times 10^6$ cells/ml are allowed to attach to 60 mm² tissue culture plates. One microgram of linearized AcMNPV DNA and 3 µg of purified pTVBac-KIgG plasmid containing the desired gene are mixed together in 1 ml Graces medium without added protein supplement (Invitrogen). Twenty microliters of Insectin™ liposomes (Invitrogen) are then added and the mixture is vortexed (this comprises the transfection mixture). All medium is removed from the attached growing insect cells (60 mm² plate) and the transfection mixture (1 ml) is added to the cells which are then incubated on a rocker platform for 4 hours at room temperature. The virus-containing medium is then removed and 1 ml of fresh protein supplemented (3.62 g/500 ml) Graces medium (Invitrogen) is added and the plate is incubated at 27° C. in a humidified environment for 48 hours. Fresh medium is added and within 4 days of incubation of the cells at 27° C., culture supernatants are harvested and titrated on confluent monolayers of Sf9 cells. Plaques exhibiting no occlusion bodies are picked and replaqued to generate polyhedron negative recombinant viruses. Large scale high titer virus stocks ($10^7$–$10^8$ pfu/ml) are prepared from several isolated recombinant plaques to insure that a high producing virus is isolated.

Production of desired proteins with the titered recombinant virus is conducted as described [Chan H. W., supra]. Briefly, insect cells (Sf9, Invitrogen) are propagated in serum free medium XL-400 (JR Scientific, Woodland Calif.) at 27° C. to a density of $2.0 \times 10^6$ per ml. The medium is removed and replaced with serum-free medium containing plaque-purified recombinant virus (using a multiplicity of infection or "MOI" of 0.01–5.0). The medium containing the recombinant virus is removed after 1 hour of incubation at 27° C. and is replaced with 5 volumes of fresh medium to give a density of $0.4 \times 10^6$ cells/ml. When the fusion protein encoded by the recombinant baculovirus contains a secretion signal at its amino-terminus, the log phase cells are infected at a MOI from 0.01 to 0.2 pfu/cell and the media is harvested 3–4 days post infection. A higher MOI (5.0 p.f.u./cell) is used to infect cells when the fusion protein does not contain a secretion signal and the cells are harvested before the 72 hour post infection time point.

To harvest fusion protein from the recombinant baculovirus-infected cells, the cells are removed from the plates and collected by centrifugation. The cell pellet is resuspended in one-fiftieth (⅟₅₀) the original culture volume in binding buffer (50 mM Tris-HCl, pH 8.0, 450 mM NaCl and 5 mM EDTA) and subjected to repeated cycles of freezing and thawing (at −70° C. and 42° C., respectively). Insoluble debris is removed by centrifugation of the mixture at 10,000×g in an SS34 rotor (Sorvall). DNA present in the sample is sheared by passing the supernatant through an 18 gauge needle. Lysates are passed though a 1 micron filter to remove any debris that may clog the affinity matrix and the fusion protein is isolated by chromatography on a protein A resin as described in Example 1.

EXAMPLE 5

Generation of Authentic Protein by Carboxypeptidase Digestion

The enzymatic removal of carboxy-terminal amino acids from cleaved fusion proteins to generate authentic proteins is accomplished by taking advantage of the substrate specificities of the various carboxypeptidases. The most extensively characterized carboxypeptidases are the mammalian metallo carboxypeptidases A and B (CPA and CPB) and the serine carboxypeptidase Y from yeast (CPD-Y). The inability of CPA and CPB to remove carboxy-terminal arginines or prolines [Ambler A. P., *Methods Enzymol.*, 25:271 (1972)] played a key role in the design of the hydrophilic spacers described in the present invention. Carboxypeptidase Y has a broad specificity (i.e., they can remove a wide variety of amino acids) including the ability to remove proline.

Carboxypeptidases immobilized to either a diffusional or a limited diffusional matrix are employed. These enzymes are immobilized on insoluble supports. Insoluble supports have gained popularity in immobilized enzyme applications because immobilized enzymes remain active for long periods of time and are recoverable from the reaction mixture (reduces cost). Most commercially available matrices comprise synthetic supports produced by the polymerization of functional monomers to produce an interconnected beaded matrix which is suitable for affinity chromatography and most enzymatic applications. The critical characteristics of a particular matrix to consider are 1) particle size (average dimension of a single bead); 2) pore size (exclusion limit); surface area (M2/gram) and 4) mass transfer effect (diffusional or flow through/non-diffusional). The mass transfer effect of a matrix depends on the nature of the pores on the beads. If the pores connect through the beads and a solution can flow through the pores, the matrix is considered non-diffusional. If the pores of the beads are dead ends and solution cannot flow through the pores, the matrix is considered to be diffusional.

Diffusional matrices are ideal for CPA and CPB digestions as employed in the methods of the present invention. While not limiting the present invention to any particular theory, an explanation of the interaction between the fusion proteins and immobilized CPA or CPB matrices is provided. The majority of the enzyme activity is located within the large surface area of the pores when CPB is immobilized to Sepharose 4B (Pharmacia). When a released protein of interest containing an exposed hydrophilic spacer at the carboxy-termninus are incubated with the CPB-Sepharose matrix, the proteins diffuse into the pores of the matrix and are acted upon by the immobilized enzyme. Because the diffusion process is slow compared to the enzymatic reaction, the probability that the multiple arginine and/or lysine residues of the spacer will be removed while the protein of interest is in the pore is high. This is advantageous when CPA or CPB digestions are to be performed as spacer designs which require treatment with these enzymes require that the reaction go to completion in order to generate authentic protein of interest.

In contrast, CPD-Y digestions, which are used to remove proline residues present in the endoprotease sites used in Level 3 designs cannot utilize diffusional matrices. Because CPD-Y can effectively remove all amino acid residues (present in any combination) given enough time and proper reaction conditions, digestion with CPD-Y must be controlled to prevent the removal of residues present on the authentic protein of interest. The approach chosen to control the extent of digestion with CPD-Y was to use CPD-Y immobilized to a limited diffusional matrix. U.S. Pat. Nos. 3,862,030 and 4,169,014 describe suitable limited diffusional matrices (the disclosure of these patents is herein incorporated by reference). Enzymatic incubation times are adjusted by varying the flow rate over the thin limited diffusional matrix containing immobilized CPD-Y.

The experiments described below were designed to confirm that control of flow rate could be used to control the extent of CPD-Y digestion. Two forms of immobilized carboxypeptidase were used. The first form comprised a commercially available immobilized carboxypeptidase Y in which the immobilization media comprised 4% beaded agarose. Carboxypeptidases cross-linked to agarose are commercially available and are commonly used for the carboxy-terminal sequencing of proteins; these protein sequencing protocols involve the sequential removal of amino acids from the carboxy-terminus of proteins. CPD-Y immobilized to 4% agarose has been traditionally used for the determination of the amino acid sequence of peptides and proteins (carboxy-terminal sequencing). The molar concentration of CPD-Y used in sequencing reactions is kept low compared to the concentration of substrate (1:1000 to 1:400) in order to promote a non-uniform digestion which allows a determination of the order of removal of the amino acids.

In contrast, high enzyme to substrate ratios [greater than 1:10 (enzyme:substrate)] were used in the following experiments in order to promote uniform digestion of the substrate. Flow rates were adjusted to limit the amount of time that the substrate was exposed to the immobilized enzyme in order to limit the extent of digestion by CPD-Y.

The following reagents were used in the experiments described below: immobilized carboxypeptidase Y, 12.5 units/ml cross-linked 4% beaded agarose (Pierce; a diffusional matrix); 22 mm ×0.5 mm Acti-Disk, GTA-activated (Arbor Technologies, Inc, Pine Brook, N.J.; a limited diffusional matrix); carboxypeptidase Y, 100 units/mg (Sigma); Hytach Peptide Column (C-18, 2 B nonporous matrix, 105×4.6 mm) [Hewlett-Packard]; unless otherwise stated, all other chemicals referred to below were obtained from Sigma.

A synthetic 12 residue peptide containing mostly hydrophilic residues was synthesized (Analytical Biotechnology Services, Boston, Mass.). This peptide comprises the following sequence: Ala-Leu-Lys-Asp-Ala-Gln-Thr-Asn-Ser-Ser-Ser-Phe (SEQ ID NO:70); this peptide is referred to as the control peptide. This peptide represents the carboxy-terminal control peptide that would be generated by digestion of authentic MBP by *Staphylococcus aureus* V8 (see Example 1). As described below, this peptide proved to be an excellent substrate for controlled carboxypeptidase digestion experiments.

Ten milliliters of a solution containing 100 µg/ml of the control peptide in PBS (pH 6.5) was repeatedly passed through 1 ml of a matrix consisting of CPD-Y immobilized on cross-linked agarose (12.5 U/ml, Pierce). The 10 ml sample was applied to the top of a 1.0 cm Affinica column (Schleicher & Schuell) containing 1.0 ml of the immobilized CPD-Y/agarose and allowed to flow by gravity. An aliquot (100 µl) of the digestion reaction were taken and the remaining sample was reapplied to the column as the previous sample approached the matrix (i.e., the sample was recirculated through the column). Aliquots (100 µl) were removed after 1, 5, 11 and 17 passes over the immobilized CPD-Y/agarose column; 20 µl of these aliquots were analyzed by high pressure liquid chromatography (HPLC) using a TFA/acetonitrile gradient and a C-18 column (Hytach protein column). A Shimadzu HPLC spectrophotometer equipped with a UV recorder was adjusted to analyze the digestion products at 210 nm. The following buffers were used for the HPLC analysis. Buffer A consisted of 1.125% TFA and Buffer B consisted of 1.0% TFA in 80% acetonitrile. To achieve separation of the peptides produced by CPD-Y digestion of the control peptide, a gradient of 0–30% B buffer was applied over a 30 minute period.

Figure 23:
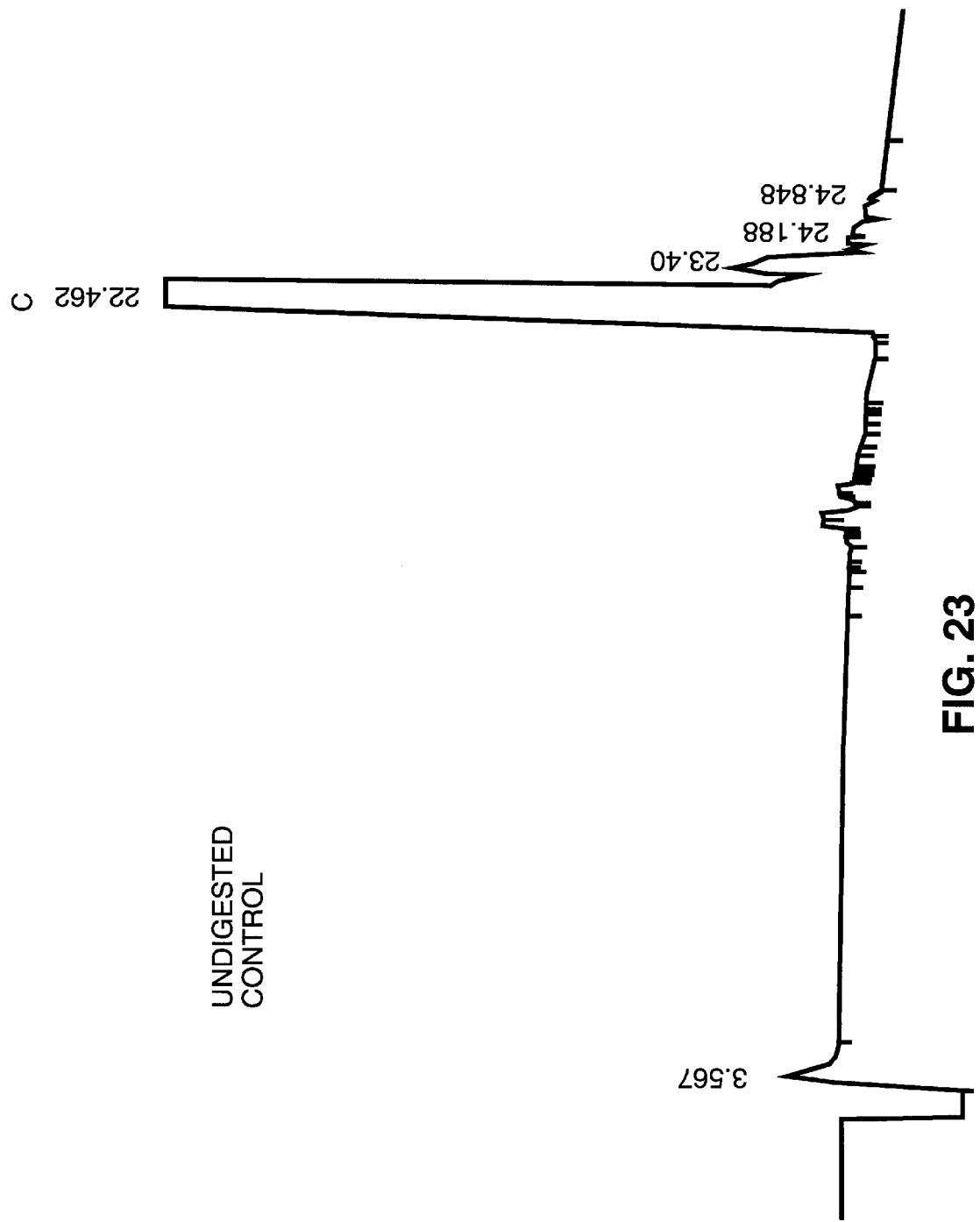
FIG. 23 is a chromatograph generated by an HPLC spectrophotometer.
Figure 24A:
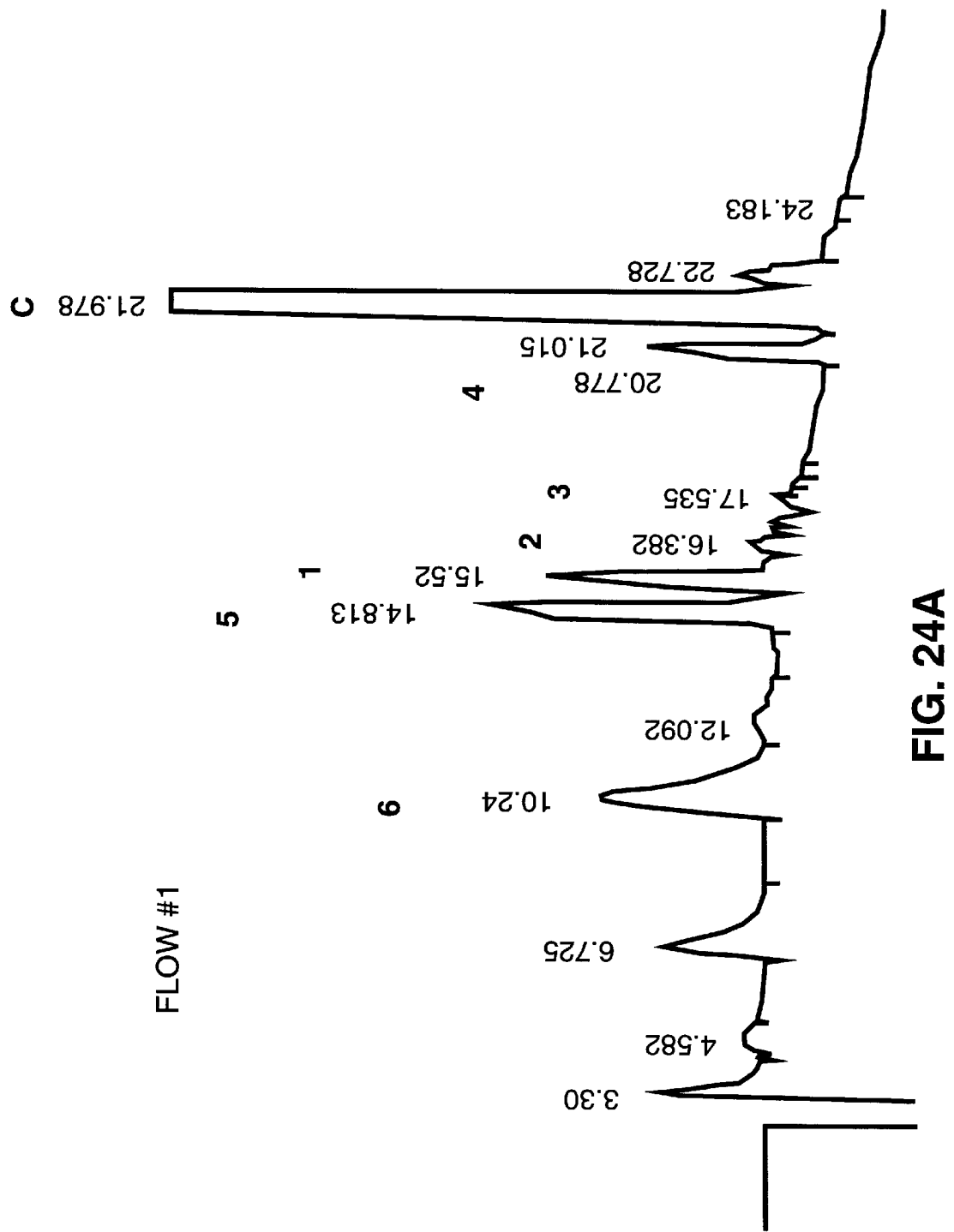
FIG. 24A is a chromatograph generated by an HPLC spectrophotometer.
Figure 24B:
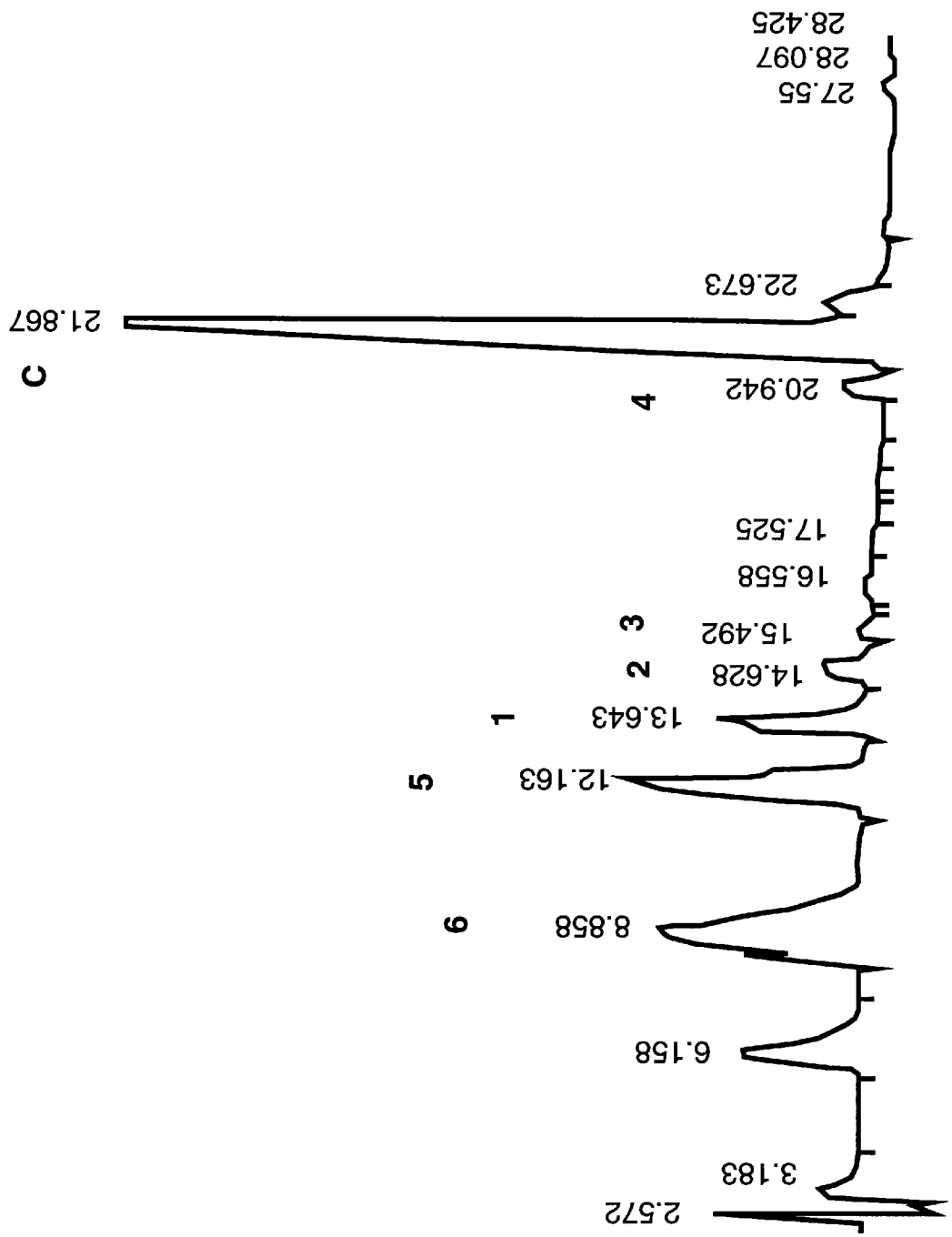
FIG. 24B is a chromatograph generated by an HPLC spectrophotometer.

FIGS. 23–25 depict chromatographs generated by the Shimadzu HPLC spectrophotometer. In FIGS. 23–25, the numbers appearing over a given peak ($OD_{210}$) represents the retention time (in minutes) for a given peptide. FIG. 23 shows the retention time for the undigested control peptide; the large peak seen at 22.4 minutes corresponds to the full-length control peptide ("C"). FIG. 24 shows the retention times for the peptides generated by passing the control peptide once (FIG. 24A) or five (FIG. 24B) times over the CPD-Y/agarose column. In FIG. 24A, the peaks labelled "C" correspond to full-length control peptide; the peaks labelled (in bold) 1, 2, 3, 4, 5, and 6 correspond to the control peptide minus 1, 2, 3, 4, 5, or 6 amino acids, respectively.

Figure 25A:
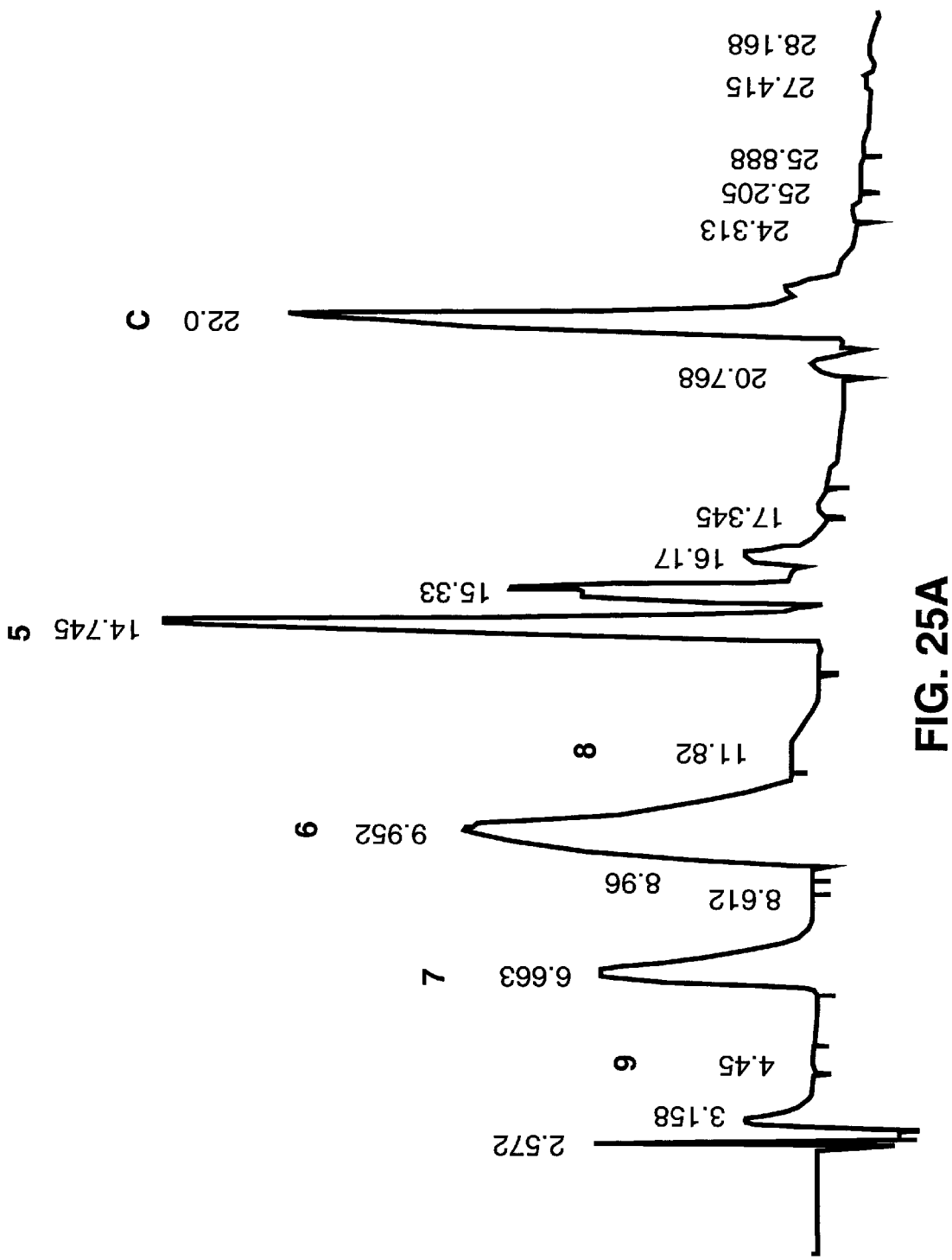
FIG. 25A is a chromatograph generated by an HPLC spectrophotometer.
Figure 25B:
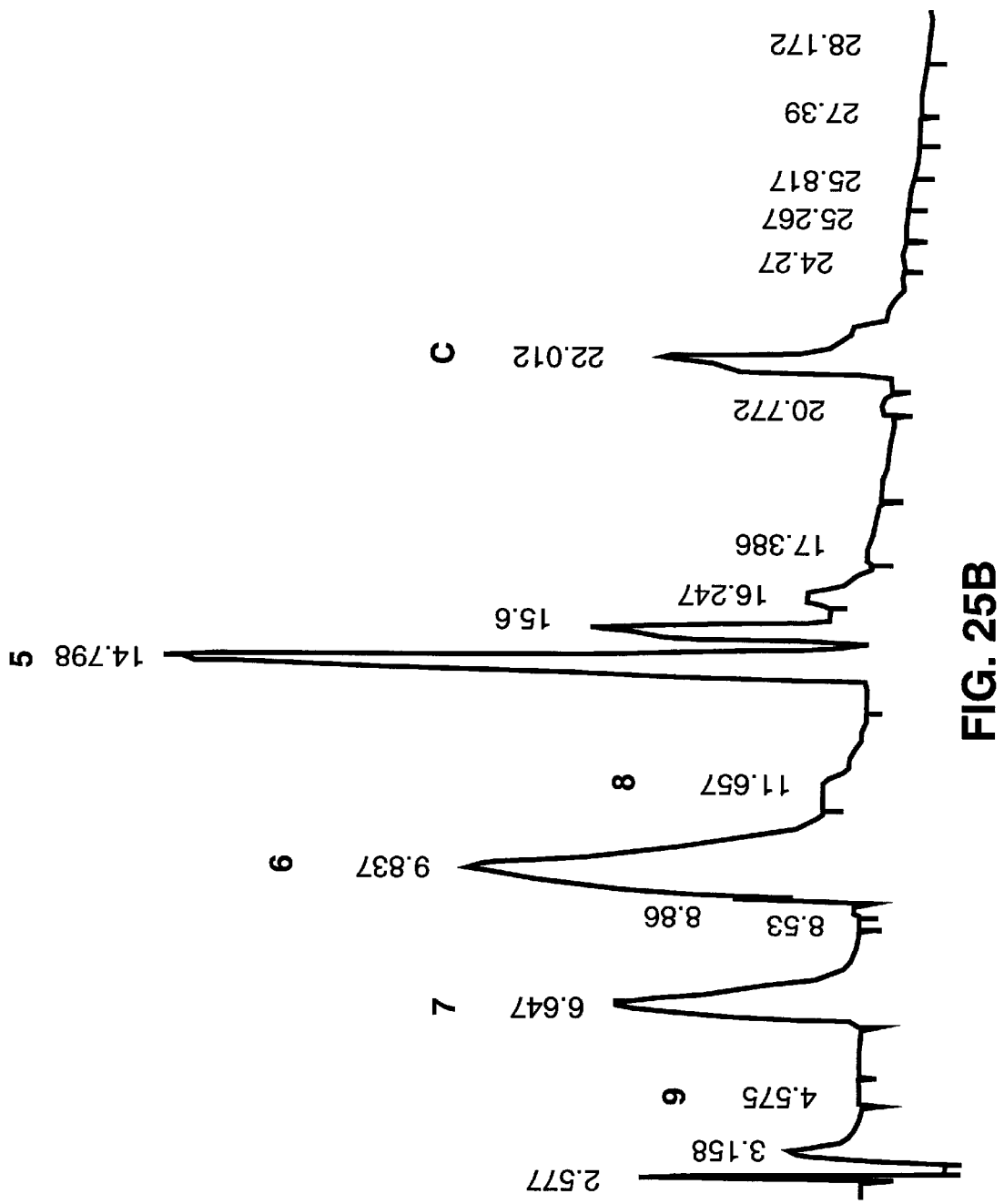
FIG. 25B is a chromatograph generated by an HPLC spectrophotometer.

FIG. 25 shows the retention times for the peptides generated by passing the control peptide eleven (FIG. 25A) or seventeen (FIG. 25B) times over the CPD-Y/agarose column. In FIG. 25 the peaks labelled "C" correspond to full-length peptide; the peaks labelled (in bold) 5, 6, 7, 8 or 9 correspond to the control peptide minus 5, 6, 7, 8 or 9 amino acids, respectively.

The results of the flow digestion using immobilized CPD-Y/agarose shown in FIGS. 23–25 demonstrate the limitations of traditional matrices such as 4% agarose; specifically these results show the lack of control possible when using a diffusional matrix. The data shown in FIGS. 23–25 indicated that multiple amino acids were released from the carboxy-terminus of the control peptide on a single pass (see FIG. 24), based on the appearance of multiple peaks. Surprisingly, it took more that 15 passes through the CPD-Y/agarose matrix to substantially decrease the amount of full length peptide (FIG. 25B); even after 11 passes through the CPD-Y/agarose column, the full-length control peptide comprised a large percentage of the molecules present (FIG. 25A). These results were surprising because CPD-Y has the highest affinity for phenylalanine (the carboxy-terminal peptide on the undigested control peptide) of all the amino acids present in the control peptide; therefore it was expected that the phenylalanine residue would be rapidly removed from the control peptide as it was applied to the CPD-Y/agarose matrix. However, it was found that the phenylalanine residues were not being removed from significant percentage of the molecules while other less preferred residues were being removed.

Experiments in which the control peptide concentration (100 µg/ml) was reduced to 50 µg/ml or 10 µg/ml had little influence on the peak pattern seen when an equal amount (1 µg) was analyzed by reverse phase HPLC as described above. The flow rate was also varied; the flow rate was slowed from gravity flow (approximately 0.5 ml/min) to 100 µg/ml by attaching an adapter for silicon tubing to the top of the Affinica column which was then attached to a peristaltic pump. Lowering the flow rate of the substrate through the Affinica column containing 1 ml of CPD-Y/agarose decreased the amount of intact (full-length) peptide seen on the resulting chromatograph but did not change the peak pattern. Control experiments were run using the above buffer (i.e., PBS, pH 6.5) containing 6 M urea to determine if there were conformational structures limiting the access of the CPD-Y enzyme to the carboxy-terminus of the small control peptide. The urea samples were digested at slower rates due to the reduced efficiency of the enzyme in the urea buffer, but the same multiple peak pattern was observed indicating the absence of conformational limitations. Analysis of the chromatographs of the digestion products revealed that 9 major peaks were identified; the accumulation of the peak at 9.9 min. is the 3-mer Ala-Leu-Lys which would be expected after the complete digestion of the control peptide with CPD-Y under these reaction conditions because CPD-Y cannot hydrolyze dipeptides and is very slow at removing tripeptides.

To achieve limited, specific digestion of the control peptide (i.e., removal of the phenylalanine residue only) approximately 4 mg of CPD-Y (Sigma) was immobilized to a pre-activated (GTA) Acti-Disk Cartridge (25 mm; Arbor Technologies). The silicon-based matrix within the Acti-Disk is described in U.S. Pat. No. 3,862,030, the disclosure of which is herein incorporated by reference. Essentially, this matrix is a microporous fluid-permeable filter that has finely divided hydrophilic filler particles dispersed throughout a microporous matrix which are capable of binding large amounts of protein or enzyme. The matrix has an extremely large surface area (80 m$^2$/gram) attributed to a large number of interconnected pores of non-uniform size distribution. The matrix is 60% porous and is commercially available in a wide variety of sizes and thicknesses for scale-up. This matrix represents a limited-diffusional matrix.

Immobilization of CPD-Y to the Acti-Disk cartridge was accomplished by recirculating 10 mls of a solution containing 1 mg/ml CPD-Y in 100 mM Na Citrate (pH 6.0) through the Acti-Disk according to the manufacturers protocol for 90 minutes at room temperature. The OD$_{280}$ of the CPD-Y solution was measured before and after the immobilization procedure. The disk was washed extensively with 100 mM Tris-HCl (pH 8.0), 500 mM NaCl buffer until no protein was detected in the wash. The final concentration of enzyme per available fluid volume within the disk (65 nmoles/115 $\mu$l) was 0.565 mM (35 mg/ml). The porous nature of the Acti-Disk matrix immobilizes the carboxypeptidase enzyme on the exterior of the matrix allowing a more consistent exposure of the substrate to enzyme than do the traditional cross linked agarose matrixes.

The control peptide (SEQ ID NO:70), at a concentration of 100 $\mu$g/ml, was passed through the CPD-Y Disk at flow rates ranging from 4 ml/min to 100 $\mu$l/min; a periplasmic pump (Pharmacia) was used to regulate the flow. A 2 ml sample of the flow digestion at 4 ml/min was collected. The setting on the peristaltic pump was changed to 3 ml/min and the reaction was allowed to equilibrate. Five milliliters of the solution containing the control peptide processed at the lower flow rate (3 ml/min) was allowed to pass through the exit tubing before another 2 ml sample was collected. This procedure was repeated at each designated flow rate. An aliquot (25 $\mu$l) of each sample was run on the Hytach protein column as described above. The results of these digestions are summarized in Table 4 below. In Table 4 the time refers to time spent in the reaction chamber (i.e., the Acti-Disk).

TABLE 4

| Flow Rate (ml/min) | % Product Remaining | Time (sec) | Product ($\mu$M) |
| --- | --- | --- | --- |
| 0.25 | 8.3 | 27.6 | 72 |
| 0.50 | 14.0 | 13.8 | 68 |
| 1.0 | 25.6 | 6.9 | 59 |
| 1.5 | 32.4 | 4.6 | 54 |
| 2.0 | 38.7 | 3.45 | 48 |
| 2.5 | 42.8 | 2.76 | 45 |
| 3.0 | 46.4 | 2.3 | 43 |
| 4.0 | 51.5 | 1.73 | 39 |

The flow digestion experiments using the control peptide show that CPD-Y immobilized to the Acti Disk matrix allows for effective control of the incubation time that the substrate is exposed to the immobilized enzyme. The control peptide was exposed to the enzyme only long enough to remove one amino acid. This is in contrast to the cross-linked agarose matrix which did not allow for such strict control of digestion times due to the diffusional characteristics of the immobilization matrix.

Figure 26:
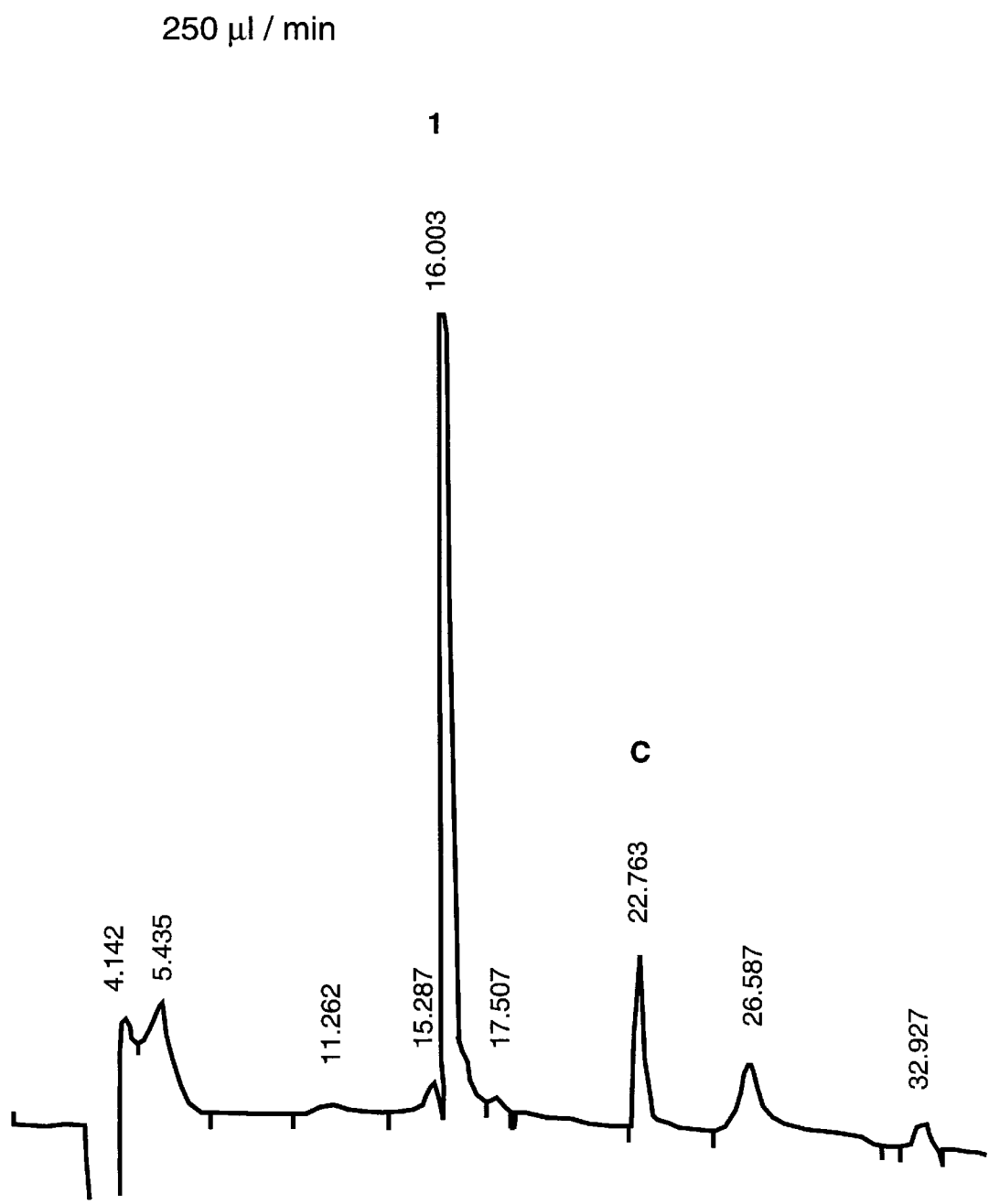
FIG. 26 is a chromatograph generated by an HPLC spectrophotometer.
Figure 27:
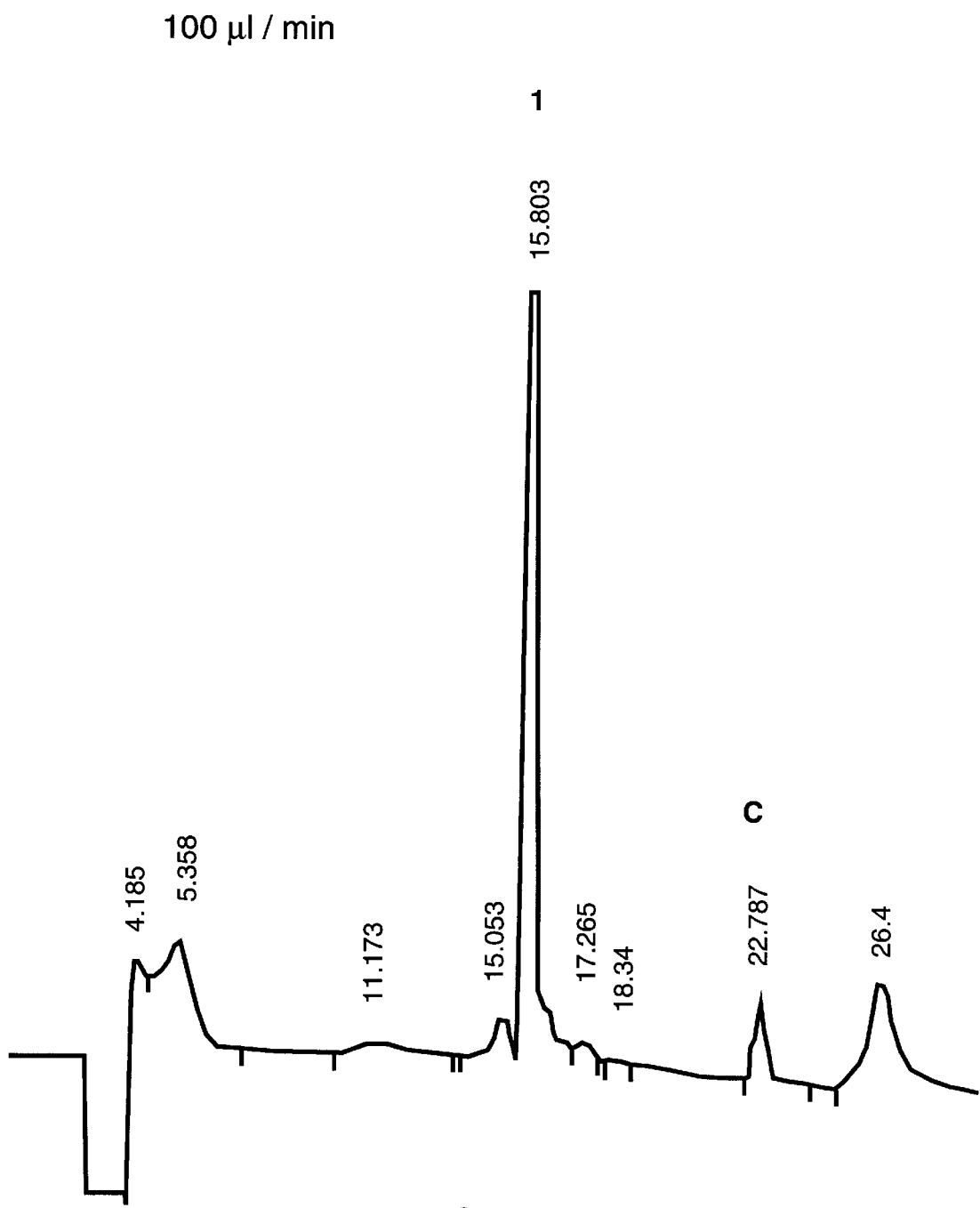
FIG. 27 is a chromatograph generated by an HPLC spectrophotometer.

By varying the flow rate and substrate concentration, it was possible to remove the carboxy-terminal phenylalanine residue from approximately 96% of the control peptide molecules with very little degradation beyond this point (see FIGS. 26 and 27).

FIGS. 26 and 27 depict chromatographs generated by the Shimadzu HPLC analyzer; the numbers appearing over a given peak (OD$_{210}$) represent the retention time for a given peptide. FIG. 26 shows the retention times for the peptides generated using the CPD-Y Acti Disk and a flow rate of 250 $\mu$l/min; FIG. 27 shows the retention times for the peptides generated using the CPD-Y Acti Disk and a flow rate of 100 $\mu$l/min.

The data shown in FIGS. 26 and 27 demonstrates nearly complete processing of a more favorable substrate (high K$_{cat}$) without significant processing of the less favorable substrate (low K$_{cat}$). These chromatographs (FIGS. 26 and 27) have an additional peak at 26.4 minutes which has been determined to be free CPD-Y enzyme that is being released from the matrix. This leaking of enzyme from the matrix was eliminated when a new CPD-Y Acti-Disk was produced by the previously described protocol, followed by a neutralization/reduction step.

Briefly, a 2 mg/ml solution of CPD-Y was continuously passed through a pre-activated GTA Acti-Disk for 90 minutes. The disk was then washed sequentially with 10 mls of water and 10 mls of 1 M NaCl. The remaining aldehyde groups were blocked and the Schiff bases were reduced by recirculating 0.1 M ethanolamine containing 50 mM sodium cyanoborohydride through the Acti Disk matrix for two hours at 1 ml/min. The disk was then washed with 30 mls of 100 mM potassium phosphate, pH 6.2. The final 2 ml of this 30 ml wash were collected and analyzed on a Beckman DU 7000 spectrophotometer in scanning wavelength mode (190 nm to 600 nm) and no peaks were seen when compared to the buffer only sample.

In order to estimate the activity of the CPD-Y immobilized to the Acti Disk matrix the following experiments were conducted.

a) Use of N-CBZ-Dipeptides for the Quantitation of Immobilized Enzyme Activity

The reported K$_m$ values for CPD-Y have been generated using extremely low enzyme concentration compared to substrate concentration. The value for K$_m$ represents the concentration of substrate that will produce ½ the maximum velocity for the initial reaction rates. During the testing of the immobilized CPD-Y enzyme disks with various dipeptide substrates, the maximum flow rate that can be achieved without any substantial increase in the pressure of the solution, is 4 ml/min. At this flow rate, the substrate remains within the immobilized enzyme matrix for 1.74 seconds. This value is determined by dividing the internal porous volume of the matrix to which the enzyme is immobilized (115 $\mu$L/4000 $\mu$L, min$^{-1}$). Due to the high concentration of enzyme (565 $\mu$M) within the limited volume of the immobilization matrix (115 $\mu$l) a very high percentage of the substrate was hydrolyzed even at these short incubation times which prevents the accurate determination of actual K$_m$ values for the individual substrates. The high level of activity also limits the which N-CBZ dipeptides can be used to determine first order reaction rate kinetic constants to those dipeptides that do not exhibit substrate inhibition (e.g., N-CBZ-Glu-Tyr, N-CBZ-Ala-Pro, N-CBZ-Ala-Leu and N-CBZ-Pro-Phe).

The following experiments were designed to characterize the enzymatic properties and the activity of the Acti Disk-immobilized CPD-Y. All substrates and reagents were purchased from Sigma.

Standard ninhydrin assay: Hydrolysis of the non-proline containing N-CBZ-dipeptides was determined by assaying the amount of free amino acid released by a colorometric ninhydrin reaction at a pH greater than 5.2. One gram of ninhydrin was dissolved in 50 ml ethylene glycol monomethyl ether containing 0.03% ascorbic acid. This ninhydrin solution was made fresh daily. A 0.4 M Citrate buffer, pH 5.2 was made by adjusting the pH of ACS grade citric acid with NaOH. Two hundred microliter samples at pH greater than 5.2 were mixed with an equal volume of ninhydrin reagent and incubated at 100° C. for 20 minutes. When 200 µl samples below pH 5.2 were to be assayed, 100 µl of 0.4 M Citrate buffer was included prior to heating the sample to 100° C. Samples were then cooled to room temperature and 600 µl of 60% ethanol was added as the diluent and the absorbance was read at 570 nm on a Beckman DU 7000 spectrophotometer.

Proline ninhydrin assay: Hydrolysis of proline-containing N-CBZ-dipeptides were measured with a modified version of the assay described by Magne and Larher [Anal. Biochem., 200:115 (1982)]. Briefly a ninhydrin reagent containing 2% ninhydrin prepared in glacial acetic acid:water 60:40 (v/v) was prepared. Five hundred microliter samples were combined with 500 µl glacial acetic acid and 500 µl ninhydrin reagent was added. The sample was subsequently boiled for one hour. One milliliter of analytical grade toluene was then used to extract the chromophore and the absorbance was read at 520 nm.

Concentrations of N-CBZ-Ala-Pro ranging from 4 mM to 100 µM (100 mM citrate, 100 mM NaCl, pH 5.75) were passed through a CPD-Y Acti Disk at a flow rate of 2.0 ml/min. Reaction rates were determined by assaying the appropriate dilutions of the various substrates using the above described proline ninhydrin assay specific of free proline to obtain $OD_{570}$ readings below 1.5. The results obtaining using the N-CBZ-Ala-Pro dipeptide are summarized in Table 5 below.

TABLE 5

| Substrate Concentration | Velocity |
| --- | --- |
| 100 µM | 170 nM/min |
| 200 µM | 344 nM/min |
| 300 µM | 503 nM/min |
| 500 µM | 846 nM/min |
| 1000 µM | 1684 nM/min |

Reaction rates were directly dependent on substrate concentration (when using less than 1 mM substrate) which defines the flow digestion as first order reactions at these concentrations.

N-CBZ-Ala-Pro (dissolved in 100 mM citrate, 100 mM NaCl, pH 5.75) at a concentration of 200 µM, was passed through the same CPD-Y Acti Disk at flow rates ranging from 2 ml/min to 175 µl/ min. Five milliliters of each specific flow rate were collected and assayed by the proline ninhydrin assay in order to determine the relative percentage of substrate that was hydrolyzed using the various flow rates. In order to characterize the amount of substrate hydrolyzed per unit of time, flow rates are converted to amount of time that the substrate is within the immobilized enzyme matrix (Acti Disk). The amount of time the substrate is within the immobilized enzyme matrix at a given flow rate is shown below in Table 6.

TABLE 6

| Flow Rate | Log S/S-P | Seconds |
| --- | --- | --- |
| 2000 ml/min | .560 | 3.45 |
| 1000 µl/min | .672 | 6.90 |
| 350 µl/min | 1.022 | 19.7 |
| 175 µl/min | 1.541 | 36.4 |

Figure 28:
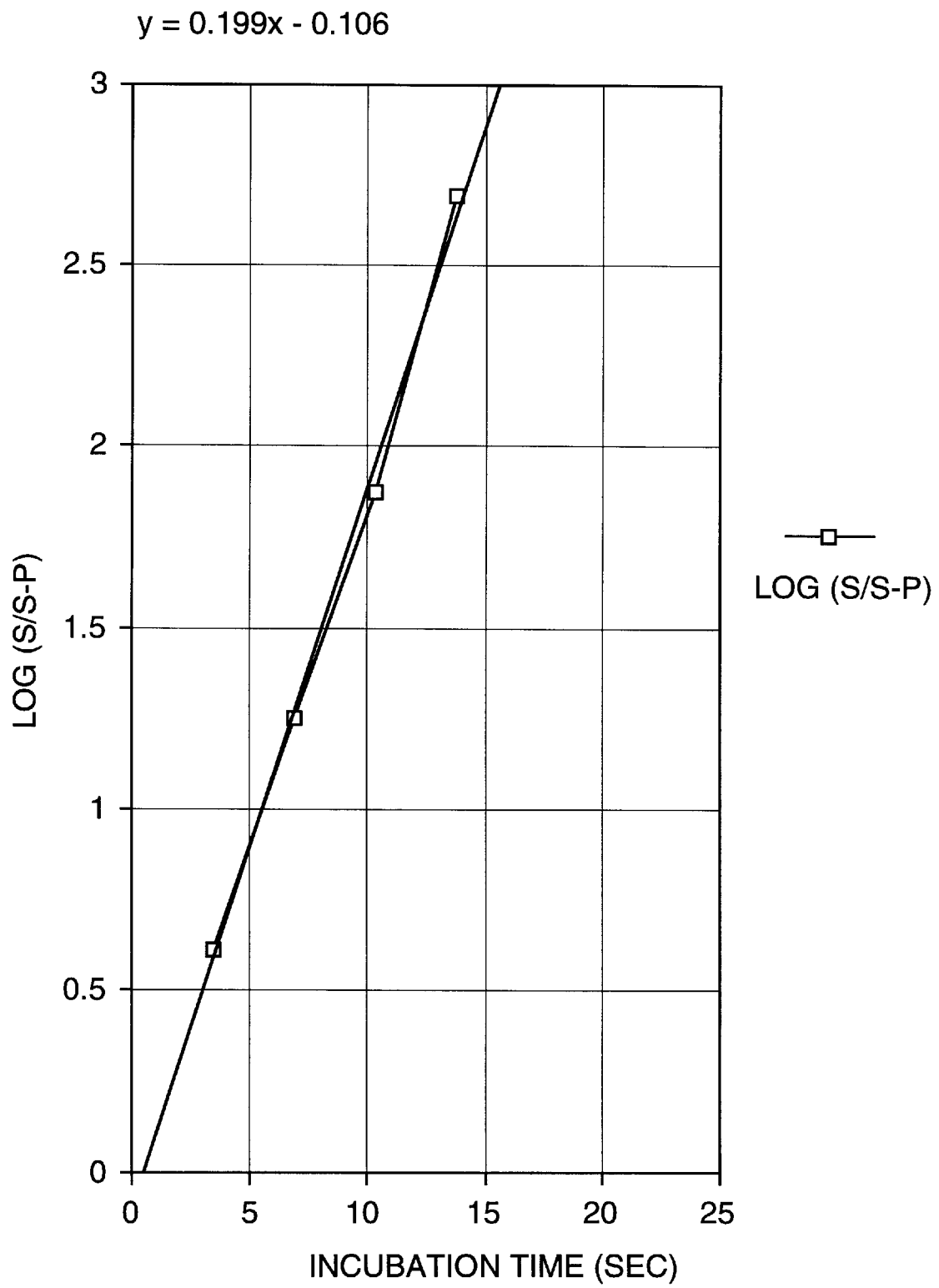
FIG. 28 is a plot of the log S/S-P versus time (seconds) using the N-CBZ-Ala-Pro substrate.

The log of the [Substrate]/[Substrate]-[Product] over seconds was plotted and yielded a line that intersected the Y axis at 0.458 and has a slope of 0.030. The slope of 0.030 is equal to the first-order rate reaction constant divided by 2.3 according to the derivatized first-order rate equation ($k^1 t =$ 2.3 log [S]/[S]-[P]). This rate constant is determined (0.069) and has the units of seconds$^{-1}$. This value is converted to minutes$^{-1}$ by multiplying by 60 (60×0.064=3.84 min$^{-1}$). The fact that this line does not intersect the Y axis at 0 is an indication that the reaction initially has a higher rate constant in the initial stages of the reaction and levels off at a reduced reaction rate constant after the first couple of seconds. This variation of first order kinetics was not present when 500 µM N-CBZ-Ala-Pro in the same buffer (100 mM citrate, 100 mM NaCl, pH 5.75) was repeatedly passed through the matrix at the same flow rate (2000 µl/min). Plotting of the log [S]/[S]-[P] versus seconds yielded a line that has a slope of 0.199 and nearly intersects the x/y axis (FIG. 28). Table 7 below summarizes the log (S/S-P) obtained when the N-CBZ-Ala-Pro substrate was passed over the CPD-Y Acti Disk matrix 1 to 3 times at a flow rate of 2000 µl/min.

TABLE 7

| Number of Passes | Log (S/S-P) | Time (sec) |
| --- | --- | --- |
| 1 | .614 | 3.45 |
| 2 | 1.236 | 6.90 |
| 3 | 1.870 | 10.35 |

These experiments showed that the alanine-proline bond was successfully hydrolyzed as it flowed through the CPD-Y Acti Disk matrix. The first order rate constant determined for the N-CBZ-Ala-Pro substrate is applicable only as a reference for comparison to other N-CBZ-dipeptide first order rate constants. N-CBZ-Phe-Ala is the substrate used by Sigma to characterize the activity of CPD-Y at 100 units per milligram, 1 unit can hydrolyze 1 µmol of N-CBZ-Phe-Ala per minute. A 20 mM solution of N-CBZ-Phe-Ala in 100 mM Citrate buffer, pH 5.75 containing 100 mM NaCl was passed though a CPD-Y Acti-Disk at flow rates of 1, 2, 3 and 4 ml per minute. Although the N-CBZ-Phe-Ala substrate displays substrate inhibition, the two shortest incubation times (3 and 4 ml/min) produced consistent kinetic constants ($K^1$ min=2.3 log [S]/[S]-[P]) which indicates that substrate inhibition had not yet taken effect and that the reaction was still governed by first order kinetics. The rate of digestion of the N-CBZ-Phe-Ala substrate at the flow rate of 4 ml/minute was 41.96 µmole/min. This value was calculated by multiplying the concentration released alanine (10.49 mM) by the liters of sample that were processed (0.004) in one minute.

First order rate constants were approximated for a number of N-CBZ-dipeptides by passing them through the CPD-Y Acti Disk matrix at a flow rate of 2 ml/min. The amount of free amino acid released was determined by the previously described ninhydrin assays. Initial substrate concentrations and the concentration of free amino acid released are represented in Table 8 below as log S/S-P values which are used to obtain first order reaction constants at 3.45 seconds of incubation (2 ml/min flow rate). All reactions were performed in the same buffer (100 mM Citrate buffer, 100 mM NaCl, pH 5.75) at room temperature (~25° C.).

TABLE 8

| Substrate | Log S/S-P | $K^1$ min$^{-1}$ |
|---|---|---|
| N-CBZ-Gly-Pro | 0.004 | 0.160 |
| N-CBZ-Pro-Phe | 0.037 | 1.480 |
| N-CBZ-Ala-Pro | 0.560 | 22.40 |
| N-CBZ-Glu-Tyr | 0.606 | 24.24 |
| N-CBZ-Ala-Leu | 0.688 | 27.52 |

The rate constants shown in Table 8 above are applicable for comparison to each other only and are substantially lower than the published rate constants due to the inability to saturate the high enzyme concentrations present within the Acti Disk matrix.

Results from the hydrolysis of N-CBZ-Ala-Pro in the flow digestion system confirm that the alanine-proline bonds is a sufficiently favorable substrate (high $K_{cat}$) to be hydrolysed within the CPD-Y Acti Disk matrix under the flow conditions described. The N-CBZ-dipeptides provided no information as to whether a particular substrate could be multiply hydrolyzed as it passed through the limited thickness of the Acti Disk matrix. In order to test the immobilized system for multiple hydrolysis events, a unique substrate was needed. N-CBZ-Gly-Pro-Leu-Ala-Pro was purchased from Sigma for this experiment because proline and alanine/leucine amino acids could be separately quantitated using the above described specific ninhydrin assays. This N-CBZ-pentapeptide proved to be an excellent substrate for CPD-Y digestion.

The N-CBZ-Gly-Pro-Leu-Ala-Pro substrate was suspended at a concentration of 200 μM in 100 mM Citrate buffer, 100 mM NaCl, pH 5.75 and subjected to flow digestions using flow rates of either 2 ml/min, 1 ml/min or 250 μl/min. Samples were collected after one pass through the disk with the exception of the experiment using a flow rate of 2 ml/min in which a sample was collected after 1 or 2 passes. Five milliliter from each flow digestion rate were saved and each was assayed by both the standard and proline ninhydrin assays. The relative concentration of amino acids from the assay results are listed below in Table 9.

TABLE 9

| Flow rate (ml/min) | 2.0 | 1.0 | 0.25 | 2 × 2 ml/min |
|---|---|---|---|---|
| Standard | 265.7 μM | 315.9 μM | 384.0 μM | 353.4 μM |
| Proline | 197.0 μM | 196.5 μM | 212.5 μM | 195.6 μM |

A number of conclusions can be inferred by the analysis of the results obtained using the N-CBZ-pentapeptide. Hydrolysis of the N-CBZ-dipeptides is substantially slower than when an amino acid is in the N-CBZ position in a tripeptide or quadrapeptide. This difference can be approximated by comparing the rate that the N-CBZ-Pro-Phe dipeptide was hydrolyzed to the rate that the proline-leucine bond in the tripeptide position of the pentapeptide was hydrolyzed. The analysis of the second flow at 2 ml/min using the pentapeptide provides the necessary information when a couple of assumptions are made. On the first pass of the substrate though the CPD-Y Acti-Disk matrix nearly all of the primary proline and alanine residues were released. This is a logical assumption because the CPD-Y enzyme can release amino acids sequentially one at a time. The proline ninhydrin assay indicates that nearly equimolar amounts of proline to substrate were released and the hydrolysis rate of the leucine-alanine bond can approximated from the earlier dipeptide kinetic data to be 20 times faster than the subsequent proline-leucine bond. It has been previously demonstrated that phenylalanine and leucine have nearly equal kinetic constants when they are in the ultimate (P1) position of N-CBZ-Gly-X dipeptides [Kuhn, Biochem. 13:3871 (1974)]. Assuming nearly all the amino acid released by the second flow at 2.0 ml/min through the matrix to be the result of the hydrolysis of the remaining Pro-Leu bond, a kinetic constant can be calculated as previously for the N-CBZ-dipeptides (134.3 μM→46.6 μM=87.7 μM product in 3.45 seconds, k=18.39). The rate constant is over ten times higher for the N-CBZ-tripeptide compared to the N-CBZ-dipeptide. Another observation that N-CBZ-pentapeptide flow digestion confirms is that a second pass of the substrate through the CPD-Y Acti Disk matrix at the same flow rate (2 ml/min) results in more hydrolysis than does a single pass which allows twice the incubation time (i.e., using ½ flow rate).

The above results provide guidance for the maximization and control of the rate of hydrolysis through the adjustment of the primary amino acid sequence when designing the spacer and junction regions as described by this invention. As can be summarized from the inherent preferences of both CPA and CPD-Y for hydrophobic aliphatic amino acids, the ideal endoprotease for use in this invention would cleave at the amino side of at least three base specificity and prefer arginines and lysines adjacent to the amino terminal cleavage site. This would allow the generation of authentic proteins by a simple CPB digestion. Alternatively, a preferred endoprotease could cleave at the carboxy side of a specific hydrophobic sequence that can be efficiently removed by the combination of CPD-Y and CPA digestions, followed by a CPB digestion to generate the authentic molecule. Two original designed, preferred examples are listed below for thrombin and collagenase which have been deduced from known substrate specificities for the indicated endoprotease combined with the substrate specificity of the carboxypeptidases that are used to remove the residual endoprotease recognition sequence.

| Thrombin | Phe-Leu-Ala-Pro-Arg-Gly-Thr (SEQ ID NO:71) |
|---|---|
| | P5 P4 P3 P2 P1 P1' |
| [Chang, Eur. J Biochem. 151:217 (1985)] | |
| Collagenase | Ala-Pro-Tyr-Gly-Pro-Pro (SEQ ID NO:72) |
| | P3 P2 P1 P1' P2' P3' |
| [Steinbrink, Bond, and Van Wart, J Biol. Chem. 260:2771 (1985)] | | b) Determination of the Rate of Hydrolysis for the Lys-Lys Pair Represented in the Preferred Hydrophilic Spacer A good approximation of the rate of hydrolysis of the Lys-Lys bond of the hydrophilic spacer is needed to insure that the flow rates used to generate authentic proteins do not allow for hydrolysis events which extend past the point of the hydrophilic spacer. Since the dipeptide hydrolysis data did not give reasonable approximations of the hydrolysis rates of peptides, a specific peptide terminating with a carboxy terminal lysine pair was analyzed. The peptide sequence is Pro-Leu-Ser-Arg-Leu-Ser-Val-Ala-Lys-Lys (SEQ ID NO:73) (Sigma; herein after referred to as the Lys-Lys peptide). Analysis of the of the reaction rates required the use of a modified ninhydrin assay developed by Doi, et al. for the analysis of peptidase activity [Anal. Biochem. 118:173 (1981)]. Compared to the ninhydrin assays described above, the pH of the ninhydrin solution is reduced (pH=4.6) and the heating time is shortened (less than or equal to 20 minutes) such that only free amino acids react at appreciable rates. Incubation times were strictly controlled by performing incubation at elevated temperatures in a programmable thermocycler (Hybaid). The fact that the peptide had a proline residue at its amino terminus significantly lowered any possible peptide background.

The Lys-Lys peptide was suspended at a concentration of 400 μM in 100 mM Citrate buffer, 100 mM NaCl, pH 5.75 and subjected to flow digestions at 2 ml/min and 500 μl/min. The amount of free lysine released was quantified by mixing 200 μl of flow sample with 200 μl 0.2 M NaCitrate, pH 4.6 and 100 μl of 2.5% ninhydrin in methyl cellusolve (Sigma), 0.03% ascorbic acid. Samples, control peptide only and known standards were incubated at 98° C. for 20 minutes, cooled to room temperature and 600 μl of 60% ethanol was added as the diluent. The $OD_{570}$ was determined and the values were converted to μM of product in order to determine the first order rate constant for the Lys-Lys bond in the CPD-Y Acti Disk flow digestion (k=0.160). This is the same value determined for the N-CBZ-Gly-Pro dipeptide. This extremely low hydrolysis rate constant for the Lys-Lys peptide bond allows protein samples to be passed through the CPD-Y Acti Disk matrix twice at a flow rate of 2 ml/min without measurable digestion beyond the Lys-Lys pair. Samples are passed through the CPD-Y Acti Disk matrix twice in order to insure the complete removal of proline residues.

The estimated $K_m$ pk for the Ser-Phe bond is 0.69 mM and the $K_{cat}$ is 400/min [Khun, Biochem. 13:3871 (1974)]; the Ser-Phe bond is the first bond to be cleaved during hydrolysis of the control peptide. Actual reaction rates obtained for CPD-Y immobilized to the Acti-Disk indicated that less than 20% of the enzyme activity was present after the immobilization process. This value was determined by comparing the initial velocity of the control peptide CPD-Y-Acti-Disk flow digestion to the manufacturer's specific activity for free enzyme (i.e., enzyme present in solution) through the use of the Michaelis-Menton rate equation. The specific activity for Phe-Ala substrate 100 μmoles/mg (Sigma) was converted to activity by multiplying by the amount of enzyme immobilized within the Acti-Disk matrix (4 mg). The catalytic constant for the Phe-Ala substrate was calculated by dividing the μmoles of activity (400 μmoles/min) by the μmoles of enzyme (0.065 μmole: 4 mg), $K_{cat}$=6200/min. This value compares well to the value that can be approximated from the $K_{cat}$ data provided by Kuhn. The $K_{cat}$ value for the cleavage of the Ser-Phe bond by free CPD-Y can be deduced from Kuhn's data to be approximately 400/min and this value was used to calculate the maximum initial velocity ($V_o$ at [S]=79 μM) for 100% activity of the immobilized enzyme. The $V_{max}$ for 100% activity is calculated by multiplying $K_{cat}$ (400/min) by the enzyme concentration (0.065 μmoles/115 μL=0.565 mM), $V_{max}$=226 mM/min. 100% activity (Vo) for 79 μM flow digestion experiments is calculated using the theoretical $K_M$=0.69 mM deduced from Kuhn's data, Vo=23.2 mM/min. Initial velocity Vo for control peptide flow experiments were determined by plotting μM of product produced versus seconds of incubation within the immobilization matrix of the Acti-Disk (see FIG. 29).

Figure 29:
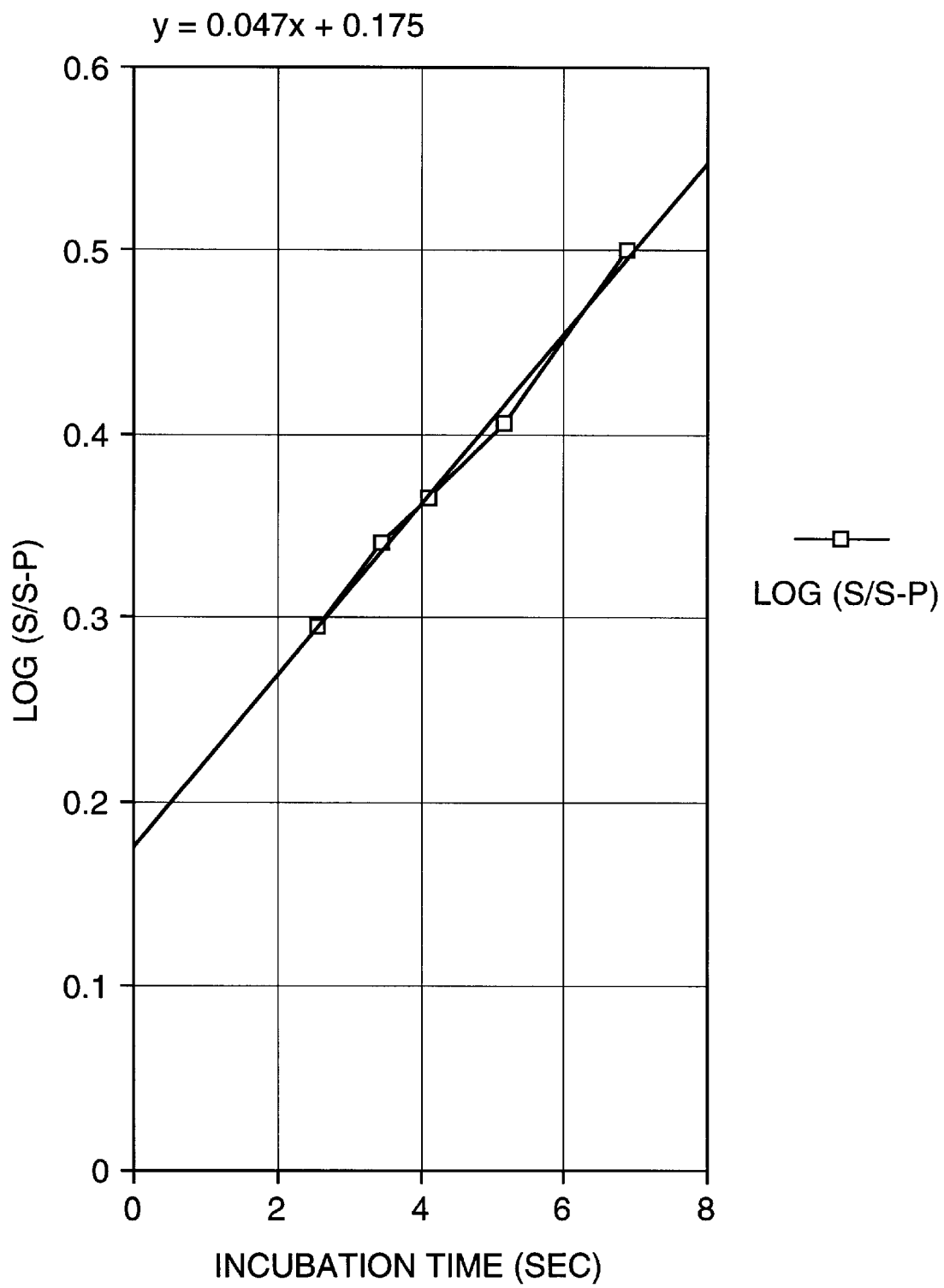
FIG. 29 is a plot of the log S/S-P versus time (seconds) of incubation of the control peptide substrate in the CPD-Y Acti-Disk matrix.

In FIG. 29, the log ([S]/[S]−[P]) (in μM) is plotted against the incubation time (in seconds). For the results shown in FIG. 29, the following calculations apply: the 4000 μl/min flow rate through 115 μl reaction matrix equals 1.73 seconds within the matrix. The initial reaction rate ($V_o$) was approximated from the initial slope (3.6 mM/min) of a logarithmic curve that fit the data points (y=3.074+28.866°LOG(x)). This nearest fit curve was necessary because the reaction proceeded to over 45% completion at the first observed time point (1.73 seconds). Comparison of the observed $V_o$ (3.6 mM/min) to the maximum $V_o$ (23.2 mM) for 100% activity of the immobilized enzyme allowed the determination that the immobilized enzyme had approximately 15.5 percent of the free enzyme activity.

The calculations made above were used to approximate the activity of the immobilized CPD-Y Acti-Disk. There are many reasons why the immobilized enzyme could show such a decrease in activity compared to the manufacturer's (Sigma) specific activity based on dipeptide cleavage. The observed reduced rates can result from higher $K_M$S and lower $K_{CAT}$S for the control peptide as compared to dipeptide results. The hydrophobicity of the control peptide may influence its ability to bind to the enzyme, but may also interact with the immobilization matrix and limit accessibility to the enzyme. These effects and others have been described in the literature [Goldstein, Methods Enzymol. 44;397 (1976) and Laidler and Bunting, Methods Enzymol. 64:227 (1980)].

The use of a high concentration of enzyme relative to the substrate allowed the hydrolysis of the carboxy-terminal phenylalanine with a single pass of the substrate past the immobilized enzyme because the following serine-serine bond is cleaved with less efficiency. Under these conditions where the second bond of the peptide is substantially less preferred than the first, multiple passes can be used to get the first reaction to go to completion without cleavage of the second less preferred bond. An experiment where 5 ml of the control peptide (100 μg/ml) was recirculated through the CPD-Y Acti-Disk at a flow rate that cleaved 86% of the ultimate bond (Ser-Phe) in a single pass (flow rate of 500 μl/ml) resulted in 96% cleavage without cleavage of the second bond (Ser-Ser). The control peptide was subjected to a single pass through the reaction disk (at a flow rate of 500 μl/ml) and was followed by 20 minutes of recirculation at the same flow rate [i.e., the first pass of a twenty minute recirculation experiment (5 mls=10 passes through the matrix)]. This experiment varied from the recirculation experiment described above for the column recirculation (using the CPD-Y/agarose matrix). In this experiment (using the CPD-Y/Acti-Disk matrix), the sample volume was 5 ml, the flow loop was 2 ml; recirculation using a peristaltic pump in the conformation described above results in the dilution of the 3 ml single flow continuously with secondary flow at the rate of 500 μl/min. After 3 minutes, the single flow has been diluted in half with secondary flow and there is now tertiary flow entering the system. Under these reaction conditions, the Ser-Ser bond of the control peptides is not detectably cleaved at this flow rate.

It is not possible to selectively remove the ultimate amino acid from all amino acid combinations one at a time. The digestion of the control peptide's ultimate residue (phenylalanine) using immobilized CPD-Y demonstrates the degree of control over the hydrolysis of favorable amino acids (low $K_M$ value) over unfavorable amino acids (high $K_M$ value). This control allows for the removal of the remaining endoprotease recognition sequence without the digestion of the hydrophilic spacer. It has been reported that the activity and specificity of carboxypeptidase Y for various substrates under modified conditions (i.e., pH 4.3 vs. pH 7.0) enhances or retards relative reaction rates for particular amino acids [Breddam and Ottesen, Carlsberg Res. Commun. 52,55-63 (1987)].

FIG. 30 provides a summary of the relative rates of release for carboxy-terminal amino acids from various di-peptides; these rates were deduced from reviews of CPD-Y digestions of various substrates and previously described P1 and P1' substrate preferences [Breddam and Ottesen, supra; Breddam, *Carlsberg Res. Commun.* 51:838 (1986); Martin, et al., *Carlsberg Res. Commun.* 42:99 (1977); Klarskov, et al., *Anal. Biochem.* 180:28 (1989); Kuhn, et al., *Biochem.* 13(19):3871 (1974); Hayashi, et al., *J. Biol. Chem.* 248(7):2296 (1973); Hayashi, *Methods Enzymol.* 47:84 (1977)]. The values listed in FIG. 30 are estimates of the $K_{CAT}/K_M (mM^{-1}, min^{-1})$ for peptides normal digestion conditions based on the $K_{CAT}/K_M$ for dipeptides based upon experimental data from the above references and from the previously described experiments. These values are used to standardize the relative activities of CPD-Y-Acti-Disks. The sequences listed in bold type at the bottom of FIG. 30 have the lowest values and represent those sequences that are present within the described hydrophilic spacers. The values listed are for N-CBZ-dipeptides and are not directly applicable to reaction rates that apply to the hydrolysis of proteins or polypeptides (larger than a dipeptide). Each protein substrate to be digested by the immobilized CPD-Y disk will be tested independently for the relative rate of hydrolysis of its carboxy-terminal amino acids using a CPD-Y-Acti-Disk which has been previously standardized.

Each prepared CPD-Y Acti-Disk must be assayed to determine its maximum activity. Control peptides or dipeptides having substantially similar $K_{cat}/K_m$ values to the amino acid pair which is to be removed (FIG. 30) are used to determine relative flow rates that will be used to selectively remove greater than 90% of the ultimate amino acids from a uniform population of desired protein substrate in a single pass through a particular CPD-Y Acti-Disk.

The substrate used in the control digestion model (Ser-Phe; bolded and underlined in FIG. 30) is not the most nor the least preferred substrate of the enzyme (refer to FIG. 30). Carboxypeptidase Y has a preference for particular amino acids in the ultimate and penultimate positions. Relative rates of digestion for particular pairs of amino acids can range several fold based on specific affinity ($K_M$) and the pairs influence on hydrolysis rates ($K_{CAT}$). The flow digestion example demonstrates the selective removal of a preferred amino acid when the remaining amino acid is less preferred without any significant product inhibition. In cases were the leaving amino acid of the substrate is less preferred than the carboxy-terminal amino acid of the product there will be a reduction in the rate of cleavage of the original substrate due to competition from the product. The product competition in the first flow of a CPD-Y digestion will be very limited due to lack of product entering the reaction chamber. On the second pass of the target molecule through the reaction chamber the competition will be significant because of the high ratio of product (P1) to original substrate. The competing reaction will be completely processed to another product (P2) which may or may not significantly compete for the immobilized enzyme. In either case, the sample is passed through the reaction matrix again. When the P2 substrate is less favorable (hydrophilic spacer) compared to the original substrate, the original substrate is substantially processed. When the P2 substrate is more favorable, it is processed into P3 and subjected to another pass through the reaction chamber until a less favorable bond is reached (FIG. 30).

The competition from products in the CPD-Y flow digestion model is of minimal consequence because the amino acids comprising the hydrophilic spacers of the present invention are much less preferred and cannot be digested at the flow rates used to remove proline residues of endoprotease recognition sequences. In the cases were the penultimate amino acid pair is more preferred, the substrate is passed through the immobilized CPD-Y Acti-Disk multiple times to insure the complete removal of the ultimate amino acid. Multiple Acti-Disk matrixes (0.5 mm thickness) can be stacked in a single reaction chamber to provide longer incubation times (see U.S. Pat. No. 4,169,014) for the slower amino acid pairs of FIG. 30, values below 100 mM/min.

EXAMPLE 6

Expression of Fusion Proteins Derived From the NGF/BDNF Family of Proteins

This example describes the expression of fusion proteins comprising the NGF/BDNF family of neurotrophic proteins to further illustrate the use of the hydrophilic spacers of the present invention and to highlight the factors which are considered when selecting a spacer design for the expression of a desired protein.

Neurotrophic factors are proteins which function to promote the survival and maintenance of the phenotypic differentiation of nerve and/or glial cells. Two neurotrophic factors have been described that are closely related in amino acid sequence but which affect different, although partially overlapping, sets of responsive neurons. These two neurotropic factors are: 1) nerve growth factor (NGF) and 2) brain-derived neurotrophic factor (BDNF).

NGF is a neurotrophic factor for cholinergic neurons in the basal forebrain. BDNF is a neurotrophic factor for sensory neurons in the peripheral nervous system. BDNF has been proposed to be useful for the treatment of the loss of sensation associated with damage to sensory nerve cells that occurs in various peripheral neuropathies [U.S. Pat. No. 5,235,043 to Collins et al., the disclosure of which is herein incorporated by reference].

The gene encoding NGF has been isolated from humans and various animals, including mice; the gene encoding BDNF has been isolated from pigs and humans. There is significant similarity in amino acid sequences between mature NGFs and mature BDNF, including the relative position of all six cysteine residues, which is identical in mature NGFs and BDNF from all species examined. This suggests that the three-dimensional structure of these two proteins is similar. Both mature proteins also share a basic isoelectric point. Both NGF and BDNF are neurotrophic factors for different, although partially overlapping, sets of responsive neurons.

Based on the above characteristics, it has been proposed that NGF and BDNF define a family of structurally related neurotrophic proteins. Additional members of this family have been isolated and include NGF-2 and NGF-3.

Both NGF and BDNF are synthesized as larger precursor forms (termed preproNGF and preproBDNF) which are then processed by proteolytic cleavages, to produce the mature neurotrophic factor. These prepro regions are located at the amino terminus of the precursor molecule and are needed for proper folding and secretion of these proteins. The mature forms of NGF and BDNF have arginine residues at their carboxy termini which requires that a leucine residue be inserted between the naturally occurring arginine and the hydrophilic spacer. This leucine residue is called a CPB terminator because it prevents CPB from removing authentic amino acids from the natural protein; the CPB terminator can be removed with CPA to generate authentic molecules.

The precursor preproNGF molecule is also proteolytically modified at its carboxy terminus to generate the mature arginine-terminating NGF molecule. The human gene sequence for the carboxy terminus of the precursor NGF molecule is shown below to code for an extra arginine and alanine residues. These two amino acids are removed to generate mature NGF by the dibasic proteolytic activity of the gamma NGF subunit.

Coding Region

TGT GTG TGT GTG CTC AGC AGG AAG GCT GTG AGA AGA GCC TGA

Cys Val Cys Val Leu Ser Arg Lys Ala Val Arg <u>Arg Ala</u> Stop

Mature Carboxy-Terminus Of The Human NGF Protein

Cys Val Cys Val Leu Ser Arg Lys Ala Val Arg

Both NGF and BDNF require proteolytic processing and formation of the correct intramolecular disulfide bonds to produce mature fully-biologically-active or mature forms of these proteins. Previous attempts to produce these molecules in bacterial hosts required the expression of truncated mature NGF sequences in bacteria (i.e., sequences which lack the pro regions) and further required inefficient in vitro refolding steps to generate active molecules [See, U.S. Pat. No 5,235,043 and European Patent Application No. 336, 324]. The use of eucaryotic cells such as mammalian cells permits the proper proteolytic processing of NGF molecules encoded by the pre-proprotein forms of the gene; however, the expression of the full length preproNGF protein in mammalian systems produces low yields of active secreted mature NGF and the use of mammalian cells for the production of proteins is costly [Edwards, et.al., *Mol. Cell. Biol.* 8:2456 (1988)]. Therefore, it is desirable to produce members of the NGF/BDNF family of proteins in inexpensive host cells such as bacteria. The following example provides methods for the production of human NGF in bacterial host cells without the need to use inefficient in vitro refolding procedures to generate biologically-active (i.e., correctly processed and folded) proteins.

FIGS. 31 and 32 provide the nucleic acid and amino acid sequences of human preproNGF and preproBDNF, respectively. The nucleic acid sequence and amino acid sequence of preproNGF are listed in SEQ ID NOS:74 and 75, respectively. The nucleic acid sequence and amino acid sequence of preproBDNF are listed in SEQ ID NOS:76 and 77, respectively. The sequence of the mature form of NGF and BDNF is indicated by the use of the large box which encloses the nucleic and amino acid sequences in each figure. In FIGS. 31 and 32, underlining is used to indicated sequences which correspond to sequences present in oligonucleotide primers can be used to generate a DNA sequence encoding the preproNGF and preproBDNF, respectively. In FIGS. 31 and 32, amino acids present in the mature form of NGF and BDNF are labeled with positive numbers; negative numbers indicate amino acid residues which are removed during proteolytic processing to generate the mature form of NGF and BDNF. Boxes which enclose amino acid residues only indicate sites susceptible to cleavage by dibasic proteases and/or furin.

NGF and BDNF are examples of the preproproteins which have a furin recognition motif at the proprotein/active protein junction. The pro regions of these molecules allow for efficient secretion and proper folding of these molecules into active forms. The production of preproproteins as properly folded biologically active molecules with removable carboxy-terminal affinity tails would be a considerable improvement over other recombinant production methods devised for these molecules As shown in FIGS. 31 and 32, these two members of the NGF/BDNF family of proteins contain hydrophilic arginine residues at their carboxy-termini making it necessary to adjust the composition of the hydrophilic spacer designs when expressing these proteins as fusions with carboxy-terminal affinity domains (e.g., the hinge and $F_c$ portion of IgG). These adjustments allow the carboxypeptidase reaction to generate authentic carboxy termini and can prevent aberrant cleavages by endogenous proteases present in the production host (i.e., furin in mammalian cells).

The nucleotide and amino acid sequences corresponding to the preproprotein forms of human NGF and BDNF are shown in FIGS. 31 and 32, respectively. The amino acid sequence of the mature forms of these molecules are outlined by a thin lined box in FIGS. 31 and 32. The bold boxes represent proteolytic sites within the mature protein that are susceptible to the Kex2 protease used in the dibasic cleavage protocol. The bold boxes immediately preceding the mature protein sequence represent the recognition sites for the protease that naturally cleaves at junction of the mature protein and the pro region to generate the active molecules. The first 18 amino acids in FIGS. 31 and 32 represent the secretion signal sequence that is removed during secretion.

The expression of NGF and BDNF are described below and represent two exemplary methods of production for preproproteins using the methods of the present invention. Two different production methods are described because, although these molecules are very closely related, their amino acid sequences differ greatly. NGF is produced as periplasmic proprotein fusion in *E coli* because the mature form of this molecule is not susceptible to dibasic processing, allowing for the in vitro removal of the amino-terminal pro region. Mature BDNF has four internal sites that may be susceptible to the Kex2 dibasic cleavage protocol (i.e., the Lys-Arg and Arg-Arg dipeptide sequences indicated by the small boxes in FIG. 32), therefore an alternate production strategy is employed. BDNF is produced in a mammalian cell line that naturally produces high levels of furin (i.e., NIH 3T3 or COS-7) resulting in the secretion of a fusion protein comprising the mature form of BDNF linked to the carboxy-terminal affinity tail. This allows for improved yields of purified authentic molecules due to the efficient affinity isolation of fusion molecules from the growth media.

The placement of a leucine residue following the carboxy-terminal arginine residues present in the NGF and BDNF proteins prevents CPB from removing the natural arginine. This hydrophobic aliphatic residue (Leu) would also prevent any processing by furin if the carboxy-terminus contained such a recognition motif (Arg-X-Arg/Lys-Arg SEQ ID NOS:14 & 15). The carboxy-terminal 11 amino acids of the human NGF and BDNF proteins are shown below using the one letter symbol for the amino acids. Sequences shown in bold type are residues encoded by the hydrophilic linker which encodes the hydrophilic spacer which joins the protein of interest to the affinity domain (the KpnI/NheI IgG fragment) via sequences encoding an endoprotease site.

NGF: C V C V L S R K A V R L K R R-KpnI/IgG
BDNF: C V C T L T I K R G R L K K K -endoprotease-KpnI/IgG The sequence Leu-Lys-Arg-Arg (SEQ ID NO:78) represents the preferred linker when 1) the desired protein has an arginine amino acid at its natural carboxy terminus, 2) the mature protein is not susceptible to the dibasic cleavage protocol and 3) the desired host is a strain *E. coli* deficient in proteolysis (i.e., AG1). The hydrophilic spacer (Lys-Arg-Arg; SEQ ID NO:79) within the preferred linker contains two endoprotease sites susceptible to the Kex2 protease. The sequence Leu-Lys-Lys-Lys (SEQ ID NO:80) represents a preferred linker when the protein of interest ends with arginine and is going to be expressed in host that expresses furin or furin-like proteases. This linker contains a leucine residue and the hydrophilic spacer Lys-Lys-Lys (SEQ ID NO:19), both of which can be removed by CPA digestion. Authentic forms of mature NGF and BDNF are generated from the above-described fusion proteins by digestion with an endoprotease followed by digestion with one or more carboxypeptidases. The leucine residue (L) following the carboxy-terminal arginine (R) is removed from the protein of interest with a final carboxypeptidase A digestion (described in detail below).

The carboxy terminal affinity domains used herein are particularly useful in the isolation of properly folded pre-promolecules because in vivo or in vitro proteolytic processing of the amino terminal pro regions can occur without losing the ability to isolate the mature product by affinity resin chromatography.

a) Production of Mature Active NGF From an *E. coli* Source Without Refolding
i) Construction of pTV-TH-NGF DNA sequences encoding the proNGF protein (i.e., amino acid residues −104 to 108, see FIG. 31) is inserted into the pTVkIgG-1 expression vector (described in Example 4a) to produce a fusion protein containing a carboxy-terminal IgG fragment that is secreted into the periplasmic space where proper folding and disulfide bond formation may occur. The resulting expression vector is termed pTV-TH-NGF.

The fusion protein encoded by pTV-TH-NGF comprises (from amino to carboxy-terminus) the pho signal sequence, the proNGF protein sequence, a CPB terminator (Leu), a hydrophilic spacer comprising the sequence Lys-Arg-Arg (SEQ ID NO:79), and the hinge and Fc domains of human IgG1. The hydrophilic spacer in this situation is also the designed endoprotease site(s) for the Kex2 protease. The resulting fusion protein is directed to the periplasmic space due to the presence of the pho signal sequence; the pho signal sequence is cleaved from the fusion protein during transport to the periplasm. Transport to the periplasmic space allows for the proper folding and disulfide bond formation within NGF sequences (without the need to use in vitro refolding procedures). The fusion protein is recovered from the periplasmic space and affinity purified on a Protein A resin. NGF-Leu-Lys-Arg is released from the Protein A resign and separated from its pro region by recirculating a commercially available Lys-Arg and Arg-Arg specific protease (i.e., the Kex2 dibasic protease from yeast which is available from Mo Bi Tec, Gottingen, Germany) through the Protein A resin. The pro region of the proNGF protein sequences (i.e., amino acid residues −104 to −1, see FIG. 31) contains a furin processing site Arg-Ser-Lys-Arg (SEQ ID NO:39) that will be correctly cleaved at the carboxy terminal side of arginine (−1) by the Kex2 protease. Heterologous sequences present on the NGF protein contributed by the CPB terminator and hydrophilic spacer are released from the NGF protein by digestion with immobilized carboxypeptidase B and A to produce authentic NGF. pTV-TH-NGF is constructed as follows. A DNA sequence encoding the proNGF protein is isolated using the PCR. A developing human brain cDNA library (Clontech) is used as the template in the PCR. Oligonucleotide primers which bracket the sequences encoding the proNGF protein are synthesized. FIG. 31 shows the full length preproNGF protein (SEQ ID NO:75); sequences complementary to the oligonucleotide primers which are used to amplify the proNGF gene are underlined in FIG. 31.

Alternatively, RNA from a human source of Schwann cells known to contain the NGF mRNA can be used to generate first strand cDNA as described in Example 3; this single stranded cDNA preparation is then used as the template in a PCR to permit isolation of sequences encoding the proNGF protein.

The commercially available human brain phage Library (Clontech) is amplified by plating the phage at a confluent density on a lawn of lysogenic bacteria such as Y1090 (ATCC No. 37197). The amplified phage are collected from the 150 mm plates by adding 4 mls of Tris buffer to the top of the plates and placing the plates on a rotating platform for 1 hour. The lysates from 10 plates are collected and pooled, DNA is isolated from 5.0 mls of the combined amplified lysate as follows. Briefly, starting with 5 mls of phage library liquid lysate, 50 μg DNase and 250 μg RNase are added and the mixture is incubated for 1 hour at 37° C. The mixture is then centrifuged for 1.5 hours at 132,000×g at 4° C. to collect the phage particles (In addition, PEG may be added to precipitate the phage particles prior to centrifugation using standard techniques). The phage pellet is resuspended in 200 μl 50 mM Tris-HCl, pH 8.0 and transferred to a 1.5 ml microcentrifuge tube; 200 μl of buffered phenol, pH 8.0, is added and the mixture is vortexed for 20 minutes. The mixture is then centrifuged for 2 minutes at 13,000×g in a microcentrifuge and the aqueous layer is removed. Phenol extractions are repeated until the white precipitate is removed. Chloroform (200 μl) is added and the mixture shaken well and then centrifuged briefly. The DNA is precipitated by the addition of 20 μl of 3 M sodium acetate, pH 4.8 and 2 volumes of 100% ethanol at room temperature and then the mixture is centrifuged for 10 minutes at 13,000×g. The DNA pellet is washed with 70% ethanol and then resuspended in 100 μl TE, pH 8.0. The isolated phage library DNA is digested overnight with 50 units of HindIII (NEB) to decrease the viscosity of the phage DNA preparation prior to PCR amplification (HindIII is used to decrease the viscosity of the isolated phage DNA preparation because there are no HindIII sites in the NGF cDNA).

Nucleic acid sequences (e.g., cDNA) encoding the pro-protein form of NGF are isolated using the PCR as follows (it is noted that it is not necessary to isolate the DNA prior to use in the PCR as described below; a phage lysate may also be employed). A five microliter aliquot of HindIII-digested phage library DNA or first strand cDNA (prepared as described in Example 3) are amplified in a final reaction volume of 100 μl containing 10 μl 10× Pfu amplification buffer (Stratagene), 0.5 μM each primer [Ngf1 (SEQ ID NO:75) and Ngf2 (SEQ ID NO:76), 200 μM of each of the four dNTPs and 1 unit of Pfu polymerase (Stratagene). The reaction mixture is heated to 94° C. in a thermal cycler (Perkin-Elmer) for 4 minutes to completely denature the target DNA and subsequently cycled 30 times (94° C. for 90 seconds, 50° C. for 90 seconds and 72° C. for 2.5 minutes). Two microliters of the PCR products are run on a 2% agarose gel to analyze the amplified product. The PCR products may be digested with restriction enzymes; restriction digestion of the desired proNGF PCR products (which are approximately 660 bp in length) with EcoRI will produce two approximately 330 bp fragments that will appear as a doublet on the agarose gel.

Amplified proNGF DNA fragments are purified by electrophoresing the amplified reaction products on a 1.5% LMA TAE agarose gel. The approximately 660 bp DNA fragment is cut from the gel and digested with Gelase following the manufacturers protocol (Epicentre Technologies). The 5' end of the NgfI oligonucleotide (SEQ ID NO:81) primes the NGF gene at the beginning of the pro region (Glu at position −104; see FIG. 31) and because Pfu polymerase has 3'–5' exonuclease activity, it produces a blunt end product that is ready for ligation to the vector (as described below the pTVkIg-l vector is digested with HindIII and the ends are made blunt by treatment with the Klenow fragment). The Ngf2 oligonucleotide (SEQ ID NO:76) alters the nucleotide sequence at the carboxy-terminal end of the protein to create an NgoMI restriction site near the 3' end of the NGF gene; this alteration changes the native (i.e., naturally occurring) sequence of AGGA at nucleotides 703 to 706 in SEQ ID NO:74 to CGGC. This change does not alter the amino acid sequence of the NGF protein in the final construction (see below) but adds a restriction site which aids in the cloning of the desired synthetic linker encoding a hydrophilic spacer and endoprotease site.

at 30° C. The reaction is stopped by heating the mixture for 10 min at 75° C. The buffer is then changed by passing the reaction mixture through a CHROMA SPIN 1000 column (Clontech) according to the manufacturer's directions. To the flow through, 5 μl of KpnI buffer and 25 units of KpnI is added. The mixture is incubated for 90 min at 37° C. The reaction mixture is then extracted with phenol, precipitated with ethanol and resuspended in 40 μl of 20 mM Tris-HCl, pH 7.5.

The prepared insert (blunt-proNGF/linker/adapter-KpnI) is mixed with the prepared pTVkIgG-1 vector at a 3:1 (insert:vector) ratio in a 20 μl volume comprising 1× T4 ligase buffer (NEB), 50 μM ATP. T4 DNA ligase (200 units) is then added and the reaction is incubated for two hours at 16° C. The ligation products are then used to transform competent AG1 cells (Stratagene). The transformed bacteria are plated on LB plates containing ampicillin; individual ampicillin-resistant colonies are picked into 1 ml of LB/Amp medium, and grown overnight at 37° C. in a shaker incubator. Plasmid DNA is isolated using standard techniques and digested with NcoI and SmaI to identify clones with a single insert in the proper orientation. Positive clones are identified by the release of a single insert of 0.5 kb. Isolated positive colonies are screened for IgG production as described in Example 1a. Colonies containing plasmids having the desired insert (by restriction analysis) and which produce a high titer of IgG are sequenced to confirm that the inserted DNA encode the desired proNGF fusion protein.

```
NGF-TTTATCCGGATAGATACGGCCTGTGTGTGTGCTCAGCAGGAAGGCTGTGAGA

3'-AAATAGGCCTATCTATGCCGGACACACACACACGAGTCGGCCGCCC-5'  (SEQ ID NO:82)
```

The purified PCR product is digested with NgoMI (NEB) according to manufacturers protocol, phenol extracted, precipitated with 2.5 volumes of ethanol and resuspended in 20 mM Tris-HCl, pH 8.0 to generate a compatible end for the ligation of a synthetic linker/adapter formed by annealing together the NGOKP1 (SEQ ID NO:83) and NGOKP2 (SEQ ID NO:84) oligonucleotides; the annealing is conducted as described in below. The annealed oligonucleotides form the following double-stranded sequence which has a single-stranded extension at the 5' end which is compatible with NgoMI ends and a single-stranded extension at the 3' end which is compatible with KpnI ends:

5'-CCGGAAGGCTGTGAGACTTAAGCGGCGGGGT-AC-3'NGOKP1 (SEQ ID NO:83)

3'-TTCCGACACTCTGAATTCGCCGCCC-5'NGOKP2 (SEQ ID NO:84)

The NGOKP1 and NGOKP2 oligonucleotides are annealed together at a concentration of 1 μM (each) in 50 μl TE (pH 8.0), 50 mM NaCl by heating to 85° C. and slow cooling to room temperature over 2 hours. The resulting linker/adapter is ligated to the NgoMI digested proNGF PCR product to prepare the PCR product for insertion into the pTVkIgG-1 bacterial expression vector. The ligation of the synthetic linker/adapter to the NgoMI ends on the proNGF PCR product regenerates the original amino acid sequence at the carboxy-terminus of the NGF protein. The linker/adapter also truncates the natural dipeptide (Arg-Ala at position 109–110 in FIG. 31) that is not present on the mature product.

Figure 33:
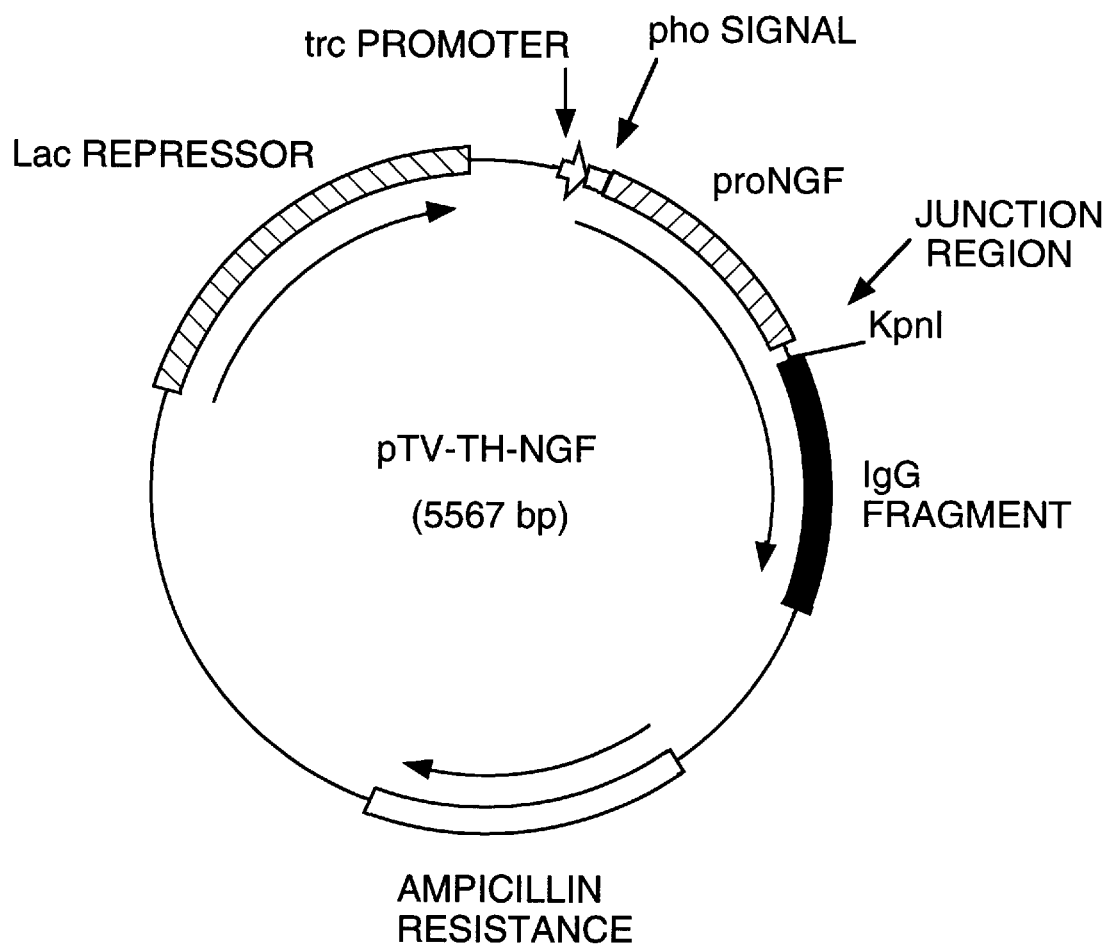
FIG. 33 provides a map of the pTV-TH-NGF vector.

The pTVkIgG-1 vector is prepared by digesting 5 μg of the vector DNA with 25 units of HindIII in a 50 μl volume for 90 minutes at 37° C. The HindIII ends are then filled in by adding 2.5 μl of 0.5 mM each dNTP and 5 units of the Klenow fragment and incubating the mixture for 15 minutes FIG. 33 provides a schematic map of the pTV-TH-NGF vector. The location of the trc promoter, the pho signal sequences, the proNGF sequences, the junction region, the IgG fragment, the ampicillin-resistance gene and the lac repressor (lacI$^q$) gene are indicated. The direction of transcription is indicated by the use of arrows inside the circle.

Figure 34:
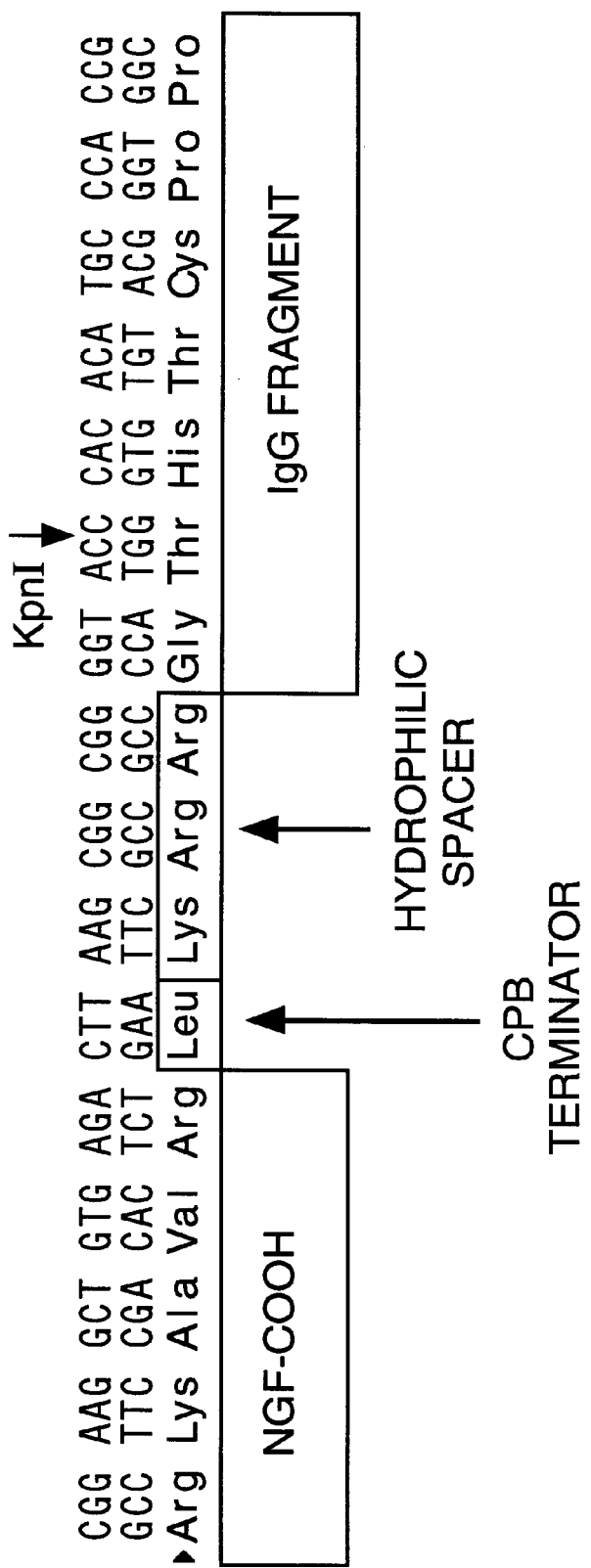
FIG. 34 depicts the junction region of the pTV-TH-NGF vector.

FIG. 34 shows the nucleotide and amino acid sequences present at the junction region in pTV-TH-NGF. Sequences present at the carboxy-terminal end of the NGF protein, the CPB terminator, the hydrophilic spacer/Kex2 protease site, and the amino-terminal end of the IgG fragment (the affinity domain) are indicated. As shown in FIG. 34, a leucine amino acid separates the hydrophilic spacer and the arginine residue which is present at the carboxy-terminus of NGF. This hydrophilic spacer separates the authentic carboxy-terminus from the KpnI-IgG Fc fragment. The carboxy-terminal sides of the arginine residues within the hydrophilic linker are both substrates for Kex2 (Lys-Arg, Arg-Arg) while the leucine residue provides a barrier to CPB digestion in order to generate authentic NGF with a final CPA digest.

ii) Large Scale Production of NGF Fusion Protein in Bacteria

One liter cultures of bacteria containing a vector encoding a NGF fusion protein are started by inoculating 100 mls of LB/Amp 100 (250 ml flask) with a single NGF positive colony from a fresh plating or from cells stored in glycerol (prepared from mid-log growths inoculated from single colonies). The inoculates are incubated at 37° C. with good aeration (250 rpm) until mid log phase is reached. One liter of LB/Amp 100 (in a 2.8 liter flask) is then inoculated with the starter culture and grown at 37° C. with good aeration to an OD$_{600}$ of 0.600; IPTG is then added to 1 mM final concentration and growth is continued for 2.5 to 3.0 hours.

The induced cells are then harvested and the periplasmic protein fraction is isolated by the cold osmotic shock method (Riggs, supra) as follows. Cells are harvested by centrifugation for 10 min at 7500×g [7000 rpm in JA-14 rotor (Beckman) at 4° C. The cell pellet is resuspended in 400 ml of 30 mM Tris-HCl (pH 8.0), 20% sucrose. Eight-tenths of a milliliter of 0.5 M EDTA (pH 8.0) is then added and the mixture is incubated for 5 to 10 minutes at room temperature with shaking. The mixture is then centrifuged for 10 min at 10,000×g at 4° C. and the pellet is resuspended in 400 ml ice-cold 5 mM magnesium sulfate. The mixture is shaken or stirred for 10 minutes in an ice bath. The mixture is then centrifuged at 10,000×g for 10 min at 4° C. and the supernatant is recovered.

Twenty milliliters of 1 M Tris-HCl (pH 8.0) and 37.8 ml of 5 M NaCl is added to the supernatant. The mixture is then prepared for chromatography on a protein A affinity column by passing the mixture through a 0.45 micron filter to remove large particulate matter. The protein concentration of the filtered mixture is measured using a Coomassie assay kit (Sigma) and the approximately 450 ml sample is passed through a 1.0 cm Protein A column as described in Example 2. The column contains 0.1 ml of immobilized Protein A per milligram of fusion protein present in the cold osmotic shock fluid (approximated using the dot blot procedure described in Example 2). The cold osmotic shock fluid is kept at 4° C. prior to flowing through the protein A column. After passing the sample through the Protein A matrix, the column is washed with 20 mls binding buffer (20 mM Tris-Cl, pH 8.0, 450 mM NaCl, 5 mM EDTA) and then with 20 mls thrombin cleavage buffer (25 mM Tris-Cl, pH 8.0, 150 mM NaCl, 2.5 mM $CaCl_2$).

Two column volumes of thrombin cleavage buffer containing 50 $\mu$g/ml of the Kex2 endoprotease (MoBiTec) is recirculated through the Protein A matrix at a flow rate of 500 $\mu$l/min for 90 minutes at 24° C. The recirculation fluid is collected at the end of the recircularization using a recircularization loop. The Protein A matrix is washed with two column volumes of thrombin buffer and the wash is combined with the recircularization digest and incubated at 30° C. for 30 minutes to any remaining pro junctions to be cleaved. The fractions are pooled and the amount of released NGF protein and the purity of the preparation is determined by electrophoresing 10 $\mu$l of the sample on a 12.5% non-reducing SDS-PAGE gel followed by staining with Coomaisse blue. Standards comprising NGF (Sigma) and molecular weight markers are included to indicate proper processing. The isolated protein is stored on ice or at −20° C. prior to removal of non-NGF amino acids from the carboxy-terminus by digestion with carboxypeptidase.

The carboxy-terminus of the isolated and Kex2-digested NGF protein has the following amino acids residues which are contributed from the CPB terminator and the hydrophilic spacer which must be removed in order to generate the authentic form of mature NGF:

(MATURE NGF)-Leu-Lys-Arg

These non-NGF protein amino acids are removed using preparations comprising immobilized carboxypeptidases. The source and purity of the carboxypeptidase enzymes used should be of highest quality available, preferably prepared chromatographically (available from Sigma). The buffer is changed by passing the sample through a Sephadex G-50 column (Pharmacia) as follows. The column is prepared using a volume of Sephadex G-50 equal to 4 times the protein sample volume and the Sephadex G-50 column is equilibrated with 100 mM Citrate/NaCl buffer, pH 5.75 (100 mM citric acid, 150 mM NaCl, pH adjusted with NaOH). The protein sample containing released NGF, the Kex2 protease and fragments of the digested pro region (two internal Kex2 sites) is passed through the gel filtration column at the maximum flow rate without increased pressure. Sample fractions are collected as the protein components elute by size: Kex2, released NGF, digested pro region fragments. Fractions containing the second elution peak (measured by absorbance at 280 nm) are pooled as released NGF.

The Kex2-digested NGF protein isolated above is concentrated to a final concentration of 2 mg/ml ([using a Centriprep-10 (Amicon)] and the solution is adjusted to pH 8.1 with NaOH. One hundred microliters of CPB-Sepharose (prepared as described below) is added per milliliter of protein solution (at 2 mg/ml, pH 8.1) and the mixture is incubated for 2 hours at 25° C. with end over end rotation.

CPB-Sepharose is prepared as described [Sassenfeld and Brewer, *Bio/Technol.* 2:76 (1984) and U.S. Pat. No. 4,532,207 to Brewer et al., the disclosure of which is herein incorporated by reference]. Briefly, 20 mg of carboxypeptidase B-DFP (i.e., diisopropyl fluorophosphate treated) Type I (Sigma) in 10 ml of 0.1 M $Na_2HCO_3$ (pH 8.3) was added to ml of CNBr-Sepharose (Pharmacia). The mixture was incubated for 16 hours at 4° C. The CPB-Sepharose is stored in PBS containing 0.1% azide at 4° C.

The above-described procedure (exposure of the Kex2-digested NGF protein to CPB-Sepharose) efficiently removes only the carboxy-terminal arginine and lysine. In preparation for CPA digestion, the pH of the sample is adjusted to 8.5 with NaOH after adding 1/10 volume 1 M ammonia carbonate, pH 8.5. Ten units of immobilized CPA (Sigma) is added to the sample for every $\mu$mol of substrate present. The reaction is incubated for 3 hours at room temperature (25° C.) with end over end rotation to insure adequate mixing of substrate with the immobilized matrix. The immobilized CPA is removed by filtration. This reaction can be monitored by the analysis of 200 $\mu$l fractions by the ninhydrin reaction for released free amino groups as described above (Doi, et al., supra). The reaction is complete when a molar equivalent of leucine residues are released to generate authentic NGF. Additional chromatography steps (i.e., ion exchange, gel filtration, RP-HPLC and/or FPLC) may be employed to gain even higher purity of the recombinant NGF.

Gel filtration on a Sephadex G-25 equilibrated 0.01 M sodium phosphate, pH 7.0, 0.1 M NaCl is used to separate the NGF molecule from the released amino acids of the carboxypeptidase digestions and prepare the sample for a final ion exchange chromatography step to separate any unprocessed protein.

b) Production of Mature BDNF in Mammalian Cells
i) Construction of an Expression Vector Encoding a BDNF/IgG Fusion Protein As shown in FIG. 32, the mature form of human BDNF ends with a carboxy-terminal arginine residue and the carboxy-terminal amino acids contain only a portion of the furin motif (e.g., Arg-Gly-Arg). Like other proteins in this family, BDNF contains hydrophilic amino acids at its carboxy-terminus therefore additional consideration in the design of the hydrophilic spacer is needed. Because of the presence of internal dibasic (Lys-Arg) sites within the mature BDNF molecules (see small boxes shown in FIG. 32), it is not a candidate for the in vitro removal of the pro region from the fusion protein as was described above for NGF. Instead, the preproBDNF protein is expressed as a fusion with the IgG fragment; the BDNF and IgG domains are joined via a hydrophilic spacer and sequences which provide a recognition site for the endoprotease renin. The expression vector encoding the BDNF fusion protein is expressed in mammalian cells which produce high levels of furin (e.g., kidney and liver cell lines). This endogenous furin is used to remove the pro region form the BDNF fusion protein in vivo; the secreted fusion protein comprises the mature form of BDNF joined to the IgG affinity domain. The affinity domain is removed from the BDNF protein by digestion with renin and authentic BDNF is then generated by treatment of the renin-digested BDNF with carboxypeptidases.

ii) Production of BDNF in Mammalian Host Cells With In Vivo Processing of the Pro Region The human brain cDNA library (Clonetech) used to amplify the gene sequences encoding NGF can also be used to amplify the gene sequence for BDNF as described above. Sequences encoding the full length gene for the preproBDNF protein are isolated from this library using PCR amplification. Two primers which are complementary to the 5' and 3' ends of the coding region were synthesized (National Biosciences). The 5' primer [BDNF-5 (SEQ ID NO:85)] begins exactly at the ATG start codon for the BDNF gene (see underlining at the 5' end of the BDNF gene shown in FIG. 32). The 3' primer [BDNF-3 (SEQ ID NO:86)] hybridizes to the first strand cDNA nine bases 5' of the stop codon (see underlining at 3' end of the BDNF gene shown in FIG. 32).

As shown below, the degeneracy of the codons allowed the creation of an MluI restriction site at the 3' end of the gene without altering the protein sequence. This internal site allows for the cloning of the modified linker required because the mature BDNF protein has an arginine at its carboxy-terminus.

Isolated BDNF PCR product is digested with MluI (NEB) to create a compatible cohesive end for ligating the BDNF/Renin linker (described below), ethanol precipitated and resuspended at a concentration of 100 ng/μl.

The BDNF/Renin linker is constructed by annealing together the complementary oligonucleotides BD/rnF (SEQ ID NO:87) and BD/rnR (SEQ ID NO:88) (both obtained from NBI); annealing is conducted as described in section (a)(i) above. The annealed oligonucleotides form the following double stranded sequence which has a single-stranded extension at the 5' end which is compatible with MluI ends and a single-stranded extension at the 3' end which is compatible with KpnI ends:

```
5'-CGCGGAAGACTTAAGAAGAAACTGCCGTTCCACCTGCTGTACGGTAC-3' BD/rnF

3'-CTTCTGAATTCTTCTTTGACGGCAAGGTGGACGACATGC-5' BD/rnR
```

The BDNF/Renin linker is ligated in excess (5×molar) to 400 ng of the MluI digested BDNF PCR product for 90 min at 20° C. in a 20 μl reaction comprising 100 units T4 ligase (NEB), 5% PEG 8000, 50 mM Tris-HCl pH 7.8, 10 mM $MgCl_2$, 1 mM ATP. Excess linker is removed by spin chromatography at 4° C. using a CHROMA SPIN 100 (Clontech) pre-equilibrated with TE buffer (pH 8.0) containing 100 mM NaCl.

The mammalian expression vector, pTVMam-Ren (Example 4b) is prepared for the insertion of the BDNF/linker insert by removing the linker present in the vector as follows. Ten micrograms of pTVMam-Ren is digested with 10 U HindIII (NEB) in a 50 μl volume for 90 min at 37° C.; the cohesive ends are then filled in by adding 5 units of Klenow fragment and 2.5 μl 0.5 mM of each dNTP. The reaction is incubated for 15 min at 30° C. The Klenow fragment is heat inactivated for 10 min at 75° C.

Ten units of KpnI is then added and the reaction is incubated for 90 min at 37° C. The vector is separated from the dNTPs, enzymes and digestion products using spin chromatography (CHROMA SPIN 1000, Clontech).

```
Native Sequence:
ARG-ILE-ASP-THR-SER-CYS-VAL-CYS-THR-LEU-THR-ILE-LYS-ARG-GLY-ARG-STOP

AGG ATA GAC ACT TCT TGT GTA TGT ACA TTG ACC ATT AAA AGG GGA AGA TAG

TCC TAT CTG TGA AGA ACA CAT ACA TGT AAC TGG TAA TTT TCC CCT TCT

Modified Sequence:
ARG-ILE-ASP-THR-SER-CYS-VAL-CYS-THR-LEU-THR-ILE-LYS-ARG-GLY-ARG-STOP

AGG ATA GAC ACT TCT TGT GTA TGT ACA TTG ACC ATT AAA CGC GTC CCA TAG

TCC TAT CTG TGA AGA ACA CAT ACA TGT AAC TGG TAA TTT GCG CAG GG
```

The PCR is conducted as follows. Reactions (100 μl final volume) are assembled which contain 1× Pfu buffer (Stratagene), 1 μm of each of the BDNF-5 and BDNF-3 primers, 200 μM of each of the four dNTPs, 1 unit Pfu polymerase (Stratagene) and 5 μl of the phage library DNA (isolated as described in section a, above; the BDNF cDNA does not contain any HindIII sites). Cycling is performed in a thermal cycler (Perkin-Elmer) for 30 cycles comprising 95° C. for 90 sec, 50° C. for 60 sec and 72° C. for 2 min.

The desired BDNF PCR product (approximately 750 bp) is confirmed by running the reaction products on a 2% low melting temperature agarose gel and isolating the 750 bp product using the Gelase protocol (Epicentre). The isolated fragment can be analyzed by digestion with NcoI which cuts the BDNF gene three times resulting in an approximately 350 bp restriction fragment on a 2% agarose gel.

Two hundred nanograms of the prepared vector is combined with 70 ng of the purified BDNF/linker insert in a 20 μl volume containing 1× ligase buffer (NEB) and 100 U of T4 ligase (NEB) and the reaction mixture is incubated at 17° C. for 12 hours. The ligation products are transformed into competent JM101 E. coli cells and the transformed cells are plated on LB/Ampicillin plates. Individual clones are picked and grown as 1 ml overnight cultures in LB/Amp media at 37° C. at 240 rpm. Plasmid DNA is isolated from several positive clones that release a 350 bp fragment as the result of NcoI restriction digests. The nucleic acid base sequence of the positive clones is determined to confirm that they contain an authentic BDNF sequence and a correct linker.

Figure 35:
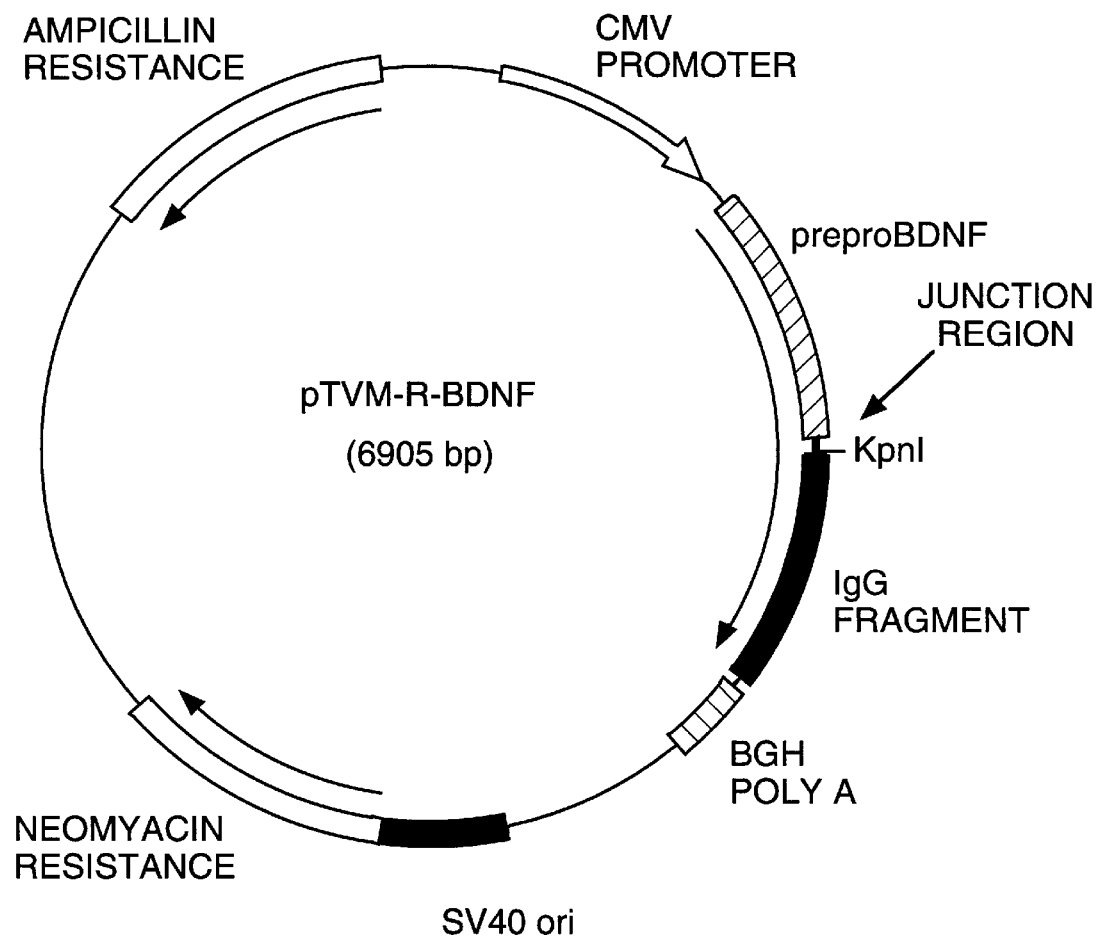
FIG. 35 provides a map of the pTVM-R-BDNF vector.

FIG. 35 provides a schematic map of the pTVM-R-BDNF vector. The location of the cytomegalovirus (CMV) promoter, the preproBDNF sequences, the junction region, the IgG fragment, the bovine growth hormone (BGH) poly A site, the SV40 origin of replication, the neomycin-resistance gene and the ampicillin-resistance gene are indicated. The direction of transcription is indicated by the use of arrows inside the circle.

Figure 36:
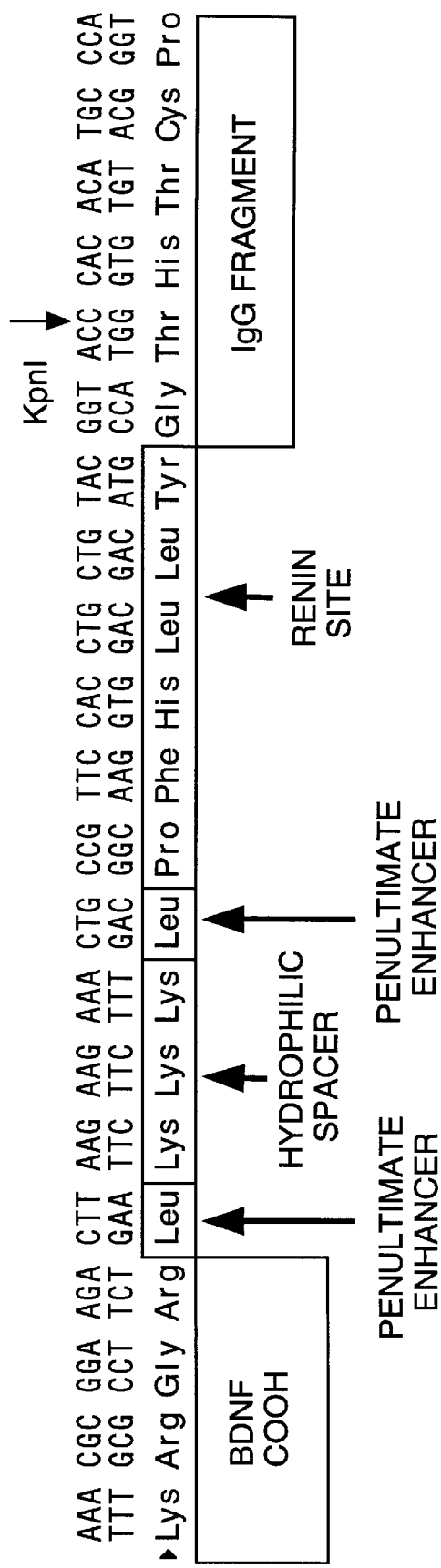
FIG. 36 depicts the junction region of the pTVM-R-BDNF vector.

FIG. 36 shows the nucleotide and amino acid sequences present at the junction region in pTVM-R-BDNF. Sequences present at the carboxy-terminal end of the BDNF protein, the hydrophilic spacer, the renin recognition site (site of cleavage is indicated by the arrow pointing between the Leu-Leu residues) and the amino-terminal end of the IgG fragment (the affinity domain) are indicated. As shown in FIG. 36, the hydrophilic spacer contains a leucine and three lysines immediately following the arginine residue which is present at the carboxy-terminus of BDNF. This hydrophilic spacer separates the authentic carboxy-terminus from the renin recognition sequence and the KpnI-IgG Fc fragment. The lysines provide a hydrophilic spacer that is resistant to carboxypeptidase Y digestion at pH 5.75 [Klarskov, *Anal. Biochem.* 180:28 (1989)], while the leucine residue provides a barrier to CPB digestion in order to generate authentic NGF with a final CPA digest.

iii) Construction of a Furin Expression Vector to Enhance Pro Processing In Vivo BDNF is expressed as a proprotein and formation of the mature, active form of BDNF requires that the pro region be proteolytically cleaved following the pro processing site comprising Arg-Val-Arg-Arg. This sequence has been well characterized as a furin recognition site [Hatsuzawa, supra and van de Ven, supra]. In experiments designed to test whether furin was responsible for the inability of LoVo cells to conduct pro processing, CHO cells were co-transfected with constructs capable of expressing wild type furin and prorenin [Takahashi, et al., *Biochem. Biophys. Res. Comm.* 195:1019 (1993)]. CHO cells were also transfected with the prorenin construct alone. The cotransfected cells showed a much greater ability to process prorenin into mature renin than did the cells transfected with the prorenin construct alone. These studies demonstrate the utility of expressing furin in cell lines used to process pro regions from the protein of interest in vivo. Accordingly, a construct capable of expressing wild type furin is co-transfected with the plasmid encoding proBDNF to ensure complete processing (it is noted that furin may be expressed from a separate plasmid or on the same plasmid as that which encodes proBDNF).

Furin is the enzyme responsible for constitutive processing and is expressed in all tissues and in most cell lines studied to date [Hatsuzawa, et al. *J Biol. Chem.* 265:22075 (1990) and Schalken et al., *J. Clin. Invest.* 80:1545 (1987)]. The cDNA sequence of human furin has been described [Van de Ouweland, et al. *Nuc. Acids Res.* 18:664 (1990). To generate a plasmid capable of expressing furin in mammalian cells, human furin cDNA sequences are cloned and inserted into an expression vector as follows.

A synthetic 30 nucleotide oligonucleotide which corresponds to the first ten amino acids of the translated furin gene is labeled with alkaline phosphatase (Lightsmith™ Luminescence Engineering System, Promega) using the manufacturer's protocols. This labeled oligonucleotide is used to screen a λgt11 human kidney cDNA library (Clontech). The sequence of this oligonucleotide is: 5'-ATGGAGCTGAGGCCCTGGTTGCTATGGGTG-3' (SEQ ID NO:89). The library is screened by hybridization of the labelled oligonucleotide to nitrocellulose filters lifted off of plates containing amplified bacteriophage plaques [the filters are generated using standard protocols such as Ausubel, et al., *Short Protocols in Molecular Biology,* Second Ed., John Wiley and Sons (1992), 6.1–6.2]. Hybridization of the alkaline phosphatase-labelled oligonucleotide to the filters is carried out using the manufacturer's protocols (Promega). Ten positive plaques are purified and DNA is isolated from each plaque. The isolated DNA is digested with SmaI to confirm the presence of the fragment containing the complete open reading frame for human furin cDNA (3209 bp). The 3.2 kb SmaI fragment is purified on a low melting temperature agarose gel and the purified fragment is ligated into the SmaI site of pUC18 to generate pUC/FUR clones (see FIG. 37) in preparation of cloning the furin cDNA into the pSV2neo vector (Clontech).

Figure 37:
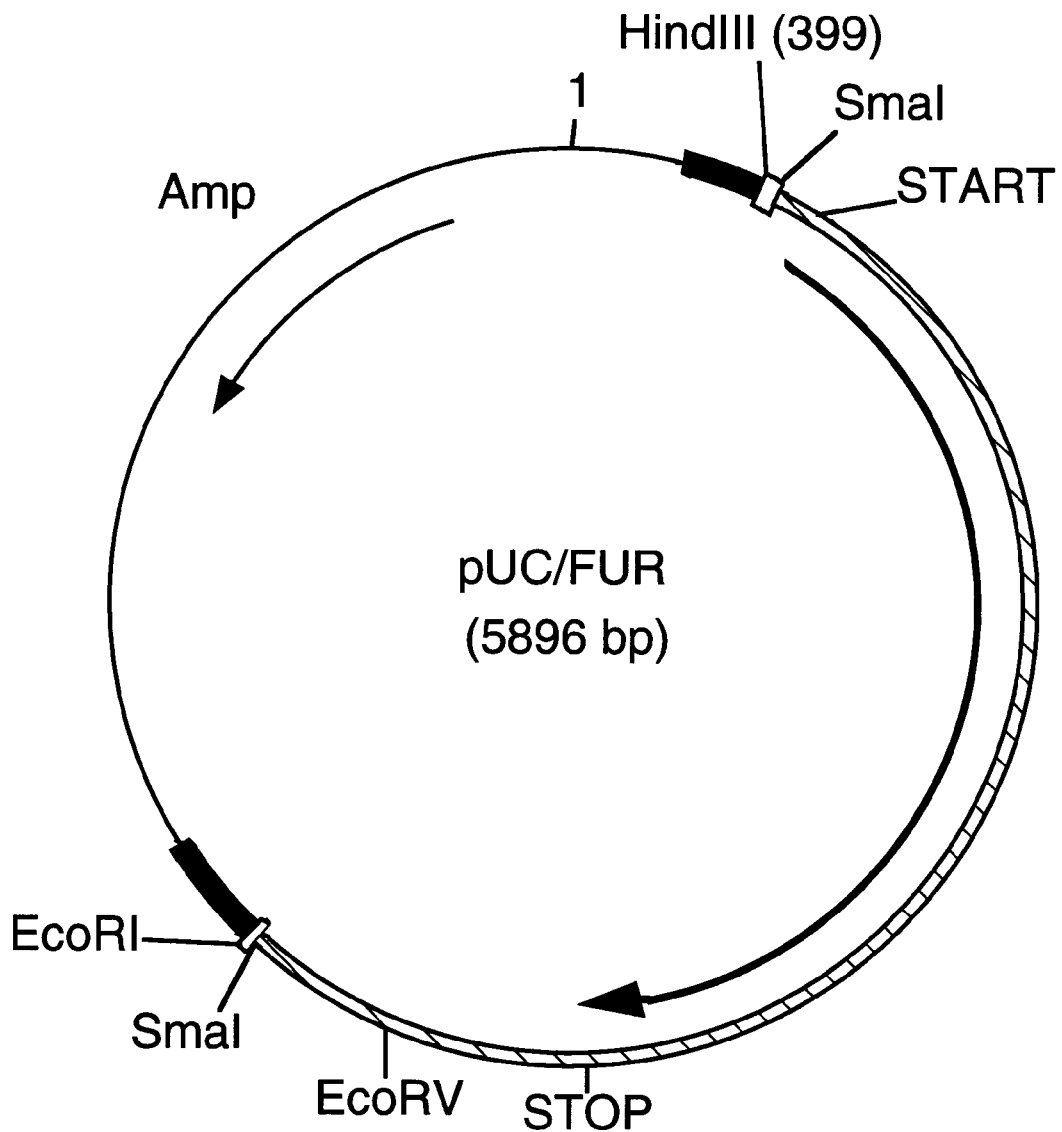
FIG. 37 provides a map of the pUC/FUR vector.

FIG. 37 provides a schematic map of the pUC/FUR construct. The location of the start (ATG) and stop codons of the furin cDNA are indicated by "START" and "STOP," respectively. The direction of transcription of the furin cDNA is indicated by the dark black arrow. The location of the ampicillin-resistance gene ("Amp") is indicated. Selected restriction endonuclease recognition sites are also indicated.

The pUC/FUR clones are screened for proper orientation of the furin cDNA within the multiple cloning site by the release of a 2902 bp fragment upon digestion with HindIII and EcoRV. The 2.9 kb HindIII/EcoRV fragment from a pUC/FUR clone containing the furin cDNA in the desired orientation is ligated into pSV2neo which has been digested with HindIII and HpaI. This manipulation replaces the neo gene of pSV2neo with the furin cDNA and allows the expression of the furin cDNA under the control of the SV40 early promoter and provides the necessary polyadenylation and processing signals. The resulting construct is termed pSV2-fur.

Figure 38:
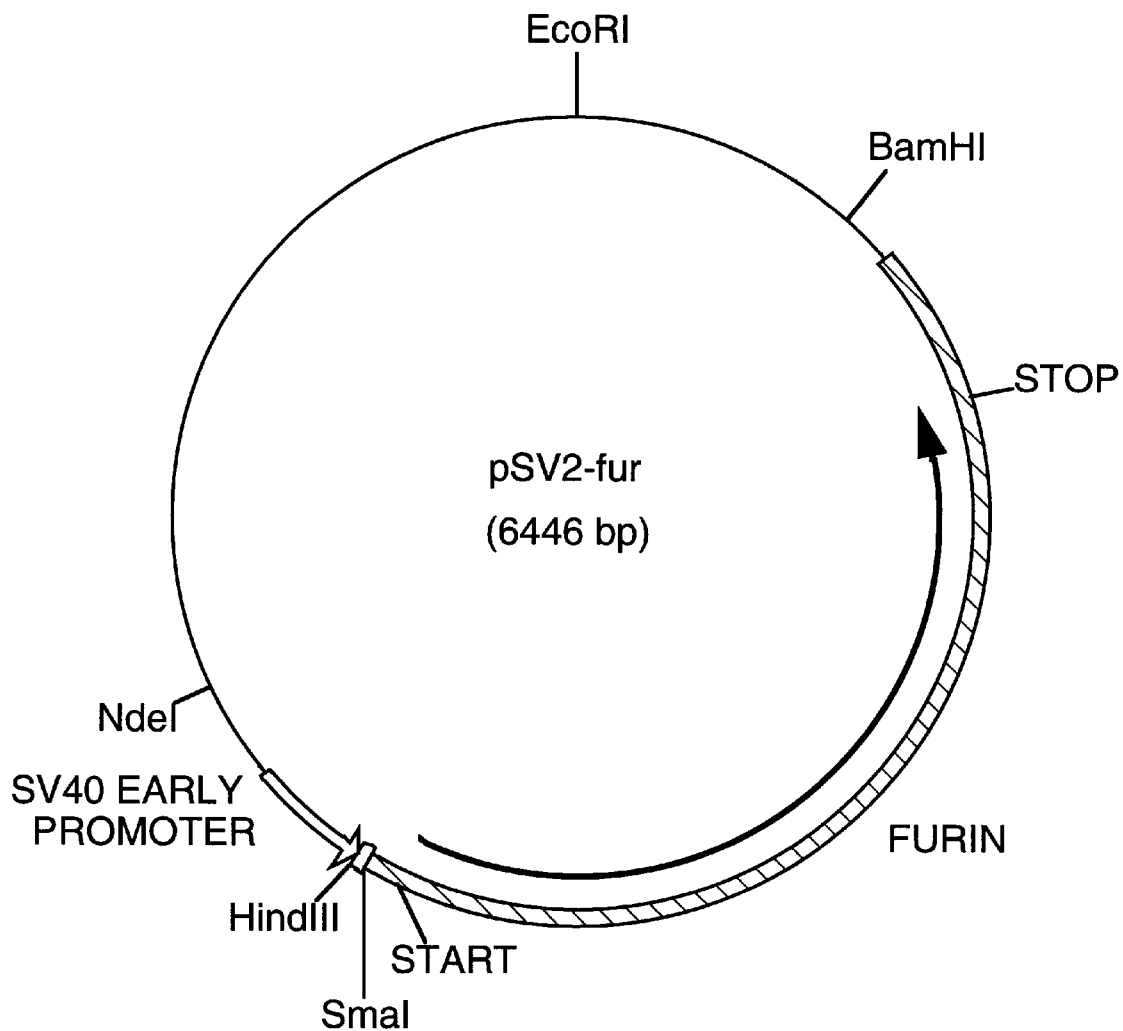
FIG. 38 provides a map of the pSV2-fur vector.

FIG. 38 a schematic map of the pSV2-fur construct. The location of the start (ATG) and stop codons of the furin cDNA are indicated by "START" and "STOP," respectively. The direction of transcription of the furin cDNA is indicated by the dark black arrow. The SV40 early promoter is represented by the open arrow. Selected restriction endonuclease recognition sites are indicated.

*E. coli* cells containing pSV2-fur are grown in LB/Amp (500 ml) and plasmid DNA is isolated using standard techniques (e.g., cesium chloride density centrifugation). The isolated pSV2-fur plasmid DNA is then digested with EcoRI in preparation for co-transfection into CHO cells as described below.

iv) Introduction of pTVM-R-BDNF and pSV2-fur Expression Vectors Into Mammalian Host Cells and Isolation of Authentic BDNF CHO cells are one of the preferred cell lines for expression of recombinant fusion proteins (other preferred cell lines include mouse myeloma Sp2/0, fibroblast cell lines and COS cells). CHO cells naturally express produce furin; however, the endogenous level of furin production is insufficient to process recombinant proproteins which are expressed at high levels using viral promoters (e.g., SV40 promoter) to drive the expression of the recombinant protein [Takahashi et al., supra and Yangita et al. *Endocrinology* 133:639 (1993)]. In order to ensure that all of the recombinantly expressed BDNF is proteolytically processed into mature BDNF in the transfected mammalian cells, a construct capable of expressing furin (e.g., pSV2-fur) is co-transfected with the BDNF expression construct (pTVM-R-BDNF). These plasmids are linearized prior to transfection into mammalian cells (the plasmids are cut with a restriction enzyme which does not cut within sequences necessary for the expression of either furin or BDNF).

CHO cells are co-transfected with equimolar amounts of the linearized pSV2-fur and pTVM-R-BDNF plasmids using the calcium phosphate co-precipitation procedure [Graham and van der Eb, Virol. 52:456 (1973)]. The transfected cells are grown in non-selective medium [Dulbecco's Modified Eagle's Medium (DMEM) (Sigma) containing 10% FBS (Gibco)] in an incubator containing 5% $CO_2$ at 37° C. for 48 hours. After 48 hours in non-selective medium, the cells are transferred into DMEM containing 10% FBS and 1.5× the killing dose of G418 (about 800 µg/ml for CHO cells; the killing dose of G418 is empirically determined for each cell line to be used). The selective medium (i.e., DMEM containing G418) is changed every 2–3 days. Cells which survive growth in the G418-containing medium for 12 days are diluted to 10 cells/ml with DMEM containing 10% FBS and G418 and 100 µl of the diluted cell mixture is placed in the wells of a 96 well plate (Costar). Cells in the wells are then grown to confluence and the levels of human IgG are determined by dot blot analysis as described in Example 1 (ammonium sulfate may be used to concentrate the culture supernatant prior to dot blot analysis).

Clones which express high levels of human IgG1 Fc fragment are expanded into 250 ml flasks; the selective medium is changed every 2 days. In the final expansion, the medium contains 10% immunoglobulin-free (<1 µg/ml) fetal bovine serum in place of 10% FBS. Media supplements such as bovine milk (Accurate Chemical and Scientific Corp., Westbury, N.Y.), serum free media (HyQTM-CCM1, HyClone Laboratories, Logan, Utah) and protein free media (JHR Biosciences, Lenexa, Kans.) can also be used. The proteases inhibitors pepstatin and leupeptin (1 µg/ml; Sigma) are included in the medium to inhibit any contaminating renin or other proteases. Complete elimination of serum immunoglobulin from the medium is not essential because the protocol used for purification of recombinant fusion protein cleaves the desired protein away from the Fc fusion molecule while the fusion protein is bound to the immobilization matrix. In this example, the specific endoprotease employed, renin, is unlikely to cleave the contaminating IgG because renin has a high degree of specificity; therefore, the contaminating IgG would remain bound to the Protein A matrix. The use of low immunoglobulin medium only reduces non-specific Protein A binding events (i.e., binding of non-fusion protein) that would saturate the IgG binding matrix very quickly if medium containing conventional serum were utilized. As an alternative to the use of low immunoglobulin medium, serum free medium may be employed. A serum free medium suitable for the growth of CHO cells is described in U.S. Pat. No. 5,122,469, the disclosure of which is herein incorporated by reference.

The desired clones are grown to confluency over 2 days and the medium is harvested and clarified by centrifugation at 1500×g. The level of production of the fusion protein is determined by assaying for human IgG1 Fc expression using the dot blot protocol described in Example 1. The supernatant is diluted with an equal volume of Tris buffer (Tris-HCl, pH 8.6, 250 mM NaCl, 0.02% sodium azide) and passed over an immobilized Protein A matrix at a rate of 1 ml/min (Protein A Actidisk, Arbor Technologies). The Protein A matrix is extensively washed with Tris buffer to remove any non-specific proteins. The matrix is washed with 10 ml of an intermediate Tris buffer of pH 7.0 (Tris-HCl, pH 7.0, 250 mM NaCl, 0.02% sodium azide) before washing with 20 ml of renin cleavage buffer (50 mM sodium phosphate, pH 6.5, 250 mM NaCl, 5 mM EGTA, 2 mM PMSF). Five milliliters of renin cleavage buffer containing 2 units renin proteases (Sigma catalog no. R2761) is circulated through the disk at 37° C. at a rate of 100 µl/min for 2 hours. The efficiency of renin cleavage is monitored by measuring protein levels (absorbance at 595 nm) in 10 µl samples of the circulating cleavage solution in 500 µl of modified Coomassie blue solution (Sigma). When expected levels of protein are released (determined by the amount of fusion protein loaded onto the matrix; this was measured in the initial dot blot assay), the circulating flow is collected and the circulating loop is washed with 3 ml of renin cleavage buffer and pooled. Collected fractions from several stable cell lines are analyzed on a 10% SDS-PAGE gel to determine whether co-transfection was successful. Released BDNF will migrate below the 16.5 kD lysozyme marker if correctly processed and above the lysozyme marker if unprocessed.

The collected fractions containing the cleaved BDNF and renin are concentrated using a Centriprep-3 (Amicon) to a concentration of 2 mg/ml and then separated by gel filtration chromatography on a Sephadex G-50 column equilibrated with ammonia carbonate buffer (50 mM ammonia carbonate pH 8.5, 150 mM NaCl, 5 mM EDTA). The processed BDNF is collected in fractions, pooled and concentrated to 1 mg/ml with using a Centriprep-3 (Amicon). The concentrated BDNF is incubated with immobilized carboxypeptidase A at 2 units enzyme/ml substrate [as described above in section (a)(ii)] for 120 minutes at 25° C. with end-over-end rotation to remove the first three amino acids of the remaining renin recognition sequence (Leu-1', His-2', Phe-3'). This reaction stops at the proline residue due to carboxypeptidase A's limited cleavage specificity (Ambler, supra). The released amino acids are removed and the buffer is changed to 100 mM sodium citrate (pH 5.75) using gel filtration chromatography on a Sephadex G-25 column. The void volume containing the cleaved BDNF is passed three times through an Actidisk containing 4 mg immobilized CPD-Y (Example 5) at a flow rate that will remove 100% of the proline residues in the first passage through the Actidisk [approximately 1 ml/min (experimental determination of the activity of each disk is required as described in Example 5)]. This procedure completely removes the proline residue that is left after the CPA digestion.

The buffer is then changed back to the ammonia carbonate buffer as described above and the sample is concentrated to 1 mg/ml using a Centricon-3 cartridge (Amicon) for the CPA digestion. The sample is incubated with immobilized CPA (2 units/ml substrate) for 180 minutes as described above to remove the leucine and lysine residues that remain after the CPD-Y flow digestion. This reaction stops at the arginine residue at the carboxy-terminal position of authentic BDNF. Released amino acids are separated from authentic BDNF by gel filtration through a Sephadex G-25 column. Additional chromatography steps (i.e., ion exchange, gel filtration, RP-HPLC and/or FPLC may be employed to gain even higher purity of the recombinant BDNF.

It is clear from the foregoing that the present invention provides compositions (fusion proteins, recombinant expression vectors) and methods which permit the production of recombinant proteins which contain only those amino acids found in the protein of interest.

I claim:

1. A fusion protein comprising three domains joined together in order from amino-terminus to carboxy-terminus of a first domain comprising a protein of interest, a second domain comprising a hydrophilic spacer, and an affinity domain, each of said three domains comprising amino acid residues, and further comprising an endoprotease recognition sequence joined to said second domain between said second domain and said affinity domain, said recognition sequence comprising at least two amino acid residues, wherein said amino acids of said hydrophilic spacer are susceptible to removal by a means for selective amino acid removal, and wherein said means for selective amino acid removal comprises a carboxypeptidase.

2. The fusion protein of claim 1 wherein said carboxypeptidase is selected from the group comprising carboxypeptidase A, carboxypeptidase B and carboxypeptidase Y.

3. The fusion protein of claim 1, wherein said susceptible amino acids of said hydrophilic spacer are selected from the group consisting of arginine, cysteine and lysine.

4. The fusion protein of claim 3, wherein said susceptible amino acids of said hydrophilic spacer have the sequence selected from the group comprising SEQ ID NOS:16–37.

5. The fusion protein of claim 1, wherein said hydrophilic spacer is an extended hydrophilic spacer.

6. The fusion protein of claim 1, further comprising a signal peptide sequence located at the amino-terminus of said fusion protein and joined to said first domain.

7. The fusion protein of claim 6, wherein said signal sequence is sequence of SEQ ID NO:61.

8. The fusion protein of claim 1, further comprising a carboxypeptidase B terminator joined to said first domain comprising said protein of interest between said first domain and said second domain comprising said hydrophilic spacer.

9. The fusion protein of claim 1, further comprising a penultimate enhancer joined to said second domain comprising said hydrophilic spacer and between said second domain and said endoprotease recognition sequence.

10. A fusion protein comprising three domains joined together in order from amino-terminus to carboxy-terminus of a first domain comprising a protein of interest, a second domain comprising a hydrophilic spacer, and an affinity domain, each of said three domains comprising amino acid residues, and further comprising an endoprotease recognition sequence joined to said second domain between said second domain and said affinity domain, said recognition sequence comprising at least two amino acid residues, wherein said hydrophilic spacer is an extended hydrophilic spacer, and wherein said extended hydrophilic spacer comprises the amino acid sequence of either SEQ ID NOS:18 or 19 joined to the carboxy-terminus of an amino acid sequence selected from the group comprising SEQ ID NOS:16–37 such that said SEQ ID NOS:18 or 19 are located between said SEQ ID NOS:16–37 and said affinity domain.

11. A recombinant DNA vector having a nucleotide sequence encoding a fusion protein comprising three domains joined together in order, from amino-terminus to carboxy-terminus, of a first domain comprising a protein of interest, a second domain comprising a hydrophilic spacer, and an affinity domain, each domain comprising amino acid residues, and further comprising an endoprotease recognition sequence joined to said second domain between said second domain and said affinity domain, said recognition sequence comprising at least two amino acid residues, wherein said amino acids of said hydrophilic spacer are susceptible to removal by a means for selective amino acid removal and wherein said means for selective amino acid removal comprises a carboxypeptidase.

12. The recombinant DNA vector of claim 11, wherein said carboxypeptidase is selected from the group comprising carboxypeptidase A, carboxypeptidase B and carboxypeptidase Y.

13. A method of producing authentic recombinant proteins of interest comprising:
  a) providing:
    i) a recombinant DNA vector encoding a fusion protein comprising three domains joined together in order from amino-terminus to carboxy-terminus of a first domain comprising a protein of interest, a second domain comprising a hydrophilic spacer having between one and five predominantly hydrophilic amino acids, a third domain comprising an endoprotease recognition sequence and an affinity domain, said recognition sequence comprising at least two amino acid residues;
    ii) host cell suitable for expressing said fusion protein encoded by said recombinant DNA vector;
    iii) an endoprotease capable of cleaving said fusion protein within said endoprotease recognition sequence;
    iv) an affinity resin capable of interacting with said affinity domain on said fusion protein; and
    v) a means for removing non-authentic amino acids from said first domain comprising said protein of interest;
  b) introducing said vector into said host cell under conditions such that said fusion protein is expressed;

c) purifying said expressed fusion protein by means of interaction of said affinity domain on said fusion protein with an affinity resin;

d) cleaving said purified fusion protein with said endoprotease to generate a released protein of interest; and e) removing any non-authentic amino acids present at the carboxy-terminus of said released protein of interest with said removal means to produce an authentic protein of interest wherein said removal means comprises at least one carboxypeptidase and said removal comprises contacting said released protein of interest with said at least one carboxypeptidase under conditions such that said non-authentic amino acids are removed to generate said authentic protein of interest.

14. The method of claim 13, wherein said affinity domain comprises a portion of the Fc domain of human IgG1.

15. The method of claim 14, wherein said affinity resin is selected from the group comprising protein A and protein G.

16. The method of claim 13, wherein said affinity domain comprises a portion of the protein glutathione-S-transferase.

17. The method of claim 16, wherein said fusion protein is purified on a glutathione resin.

18. The method of claim 13, wherein said affinity domain comprises a portion of the maltose binding protein.

19. The method of claim 18, wherein said fusion protein is purified on an amylose resin.

20. The method of claim 13, wherein said affinity domain comprises a portion of the staphylococcal protein A.

21. The method of claim 20, wherein said fusion protein is purified on an IgG resin.

22. The method of claim 13, wherein said affinity domain comprises a portion of the protein β-galactosidase.

23. The method of claim 22, wherein said fusion protein is purified on p-aminophenyl-β-D-thiogalactosidyl-succinyldiaminohexyl-Sepharose.

* * * * *

SEQUENCE LISTING (1) GENERAL INFORMATION:

(iii) NUMBER OF SEQUENCES: 90

(2) INFORMATION FOR SEQ ID NO:1:

(i) SEQUENCE CHARACTERISTICS:
        (A) LENGTH: 8 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:1:

Asp Tyr Lys Asp Asp Asp Asp Lys
1               5

(2) INFORMATION FOR SEQ ID NO:2:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:2:

Pro Xaa Gly Pro Xaa
1               5

(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:3:

Pro Phe His Leu Leu Val Tyr
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Peptide
        (B) LOCATION: 5
        (D) OTHER INFORMATION: /note= "The amino acid at this
             location can be any amino acid except proline or
             arginine."

(xi) SEQUENCE DESCRIPTION: SEQ ID NO:4:

Ile Glu Gly Arg Xaa
1               5

(2) INFORMATION FOR SEQ ID NO:5:

```
            (i) SEQUENCE CHARACTERISTICS:
                (A) LENGTH: 5 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Peptide
                (B) LOCATION: 5
                (D) OTHER INFORMATION: /note= "The amino acid at this
                    location can be any amino acid except proline or
                    arginine."

(xi) SEQUENCE DESCRIPTION: SEQ ID NO:5:

Ile Asp Gly Arg Xaa
1               5

(2) INFORMATION FOR SEQ ID NO:6:

(i) SEQUENCE CHARACTERISTICS:
                (A) LENGTH: 5 amino acids
                (B) TYPE: amino acid
                (C) STRANDEDNESS:
                (D) TOPOLOGY: unknown (ii) MOLECULE TYPE: peptide (ix) FEATURE:
                (A) NAME/KEY: Peptide
                (B) LOCATION: 5
                (D) OTHER INFORMATION: /note= "The amino acid at this
                    location can be any amino acid except proline or
                    arginine."

(xi) SEQUENCE DESCRIPTION: SEQ ID NO:6:

Ala Glu Gly Arg Xaa
1               5

(2) INFORMATION FOR SEQ ID NO:7:

(i) SEQUENCE CHARACTERISTICS:
                (A) LENGTH: 6 amino acids
                (B) TYPE: amino acid
                (C) STRANDEDNESS:
                (D) TOPOLOGY: unknown (ii) MOLECULE TYPE: peptide (xi) SEQUENCE DESCRIPTION: SEQ ID NO:7:

Leu Val Pro Arg Gly Ser
1               5

(2) INFORMATION FOR SEQ ID NO:8:

(i) SEQUENCE CHARACTERISTICS:
                (A) LENGTH: 10 amino acids
                (B) TYPE: amino acid
                (C) STRANDEDNESS:
                (D) TOPOLOGY: unknown (ii) MOLECULE TYPE: peptide (xi) SEQUENCE DESCRIPTION: SEQ ID NO:8:

Gln Gly Pro Gly Gln Lys Gln Lys Gln Lys
1               5                   10

(2) INFORMATION FOR SEQ ID NO:9:

(i) SEQUENCE CHARACTERISTICS:
```

(A) LENGTH: 4 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO:9:

Phe Arg Ser Val
1

(2) INFORMATION FOR SEQ ID NO:10:

(i) SEQUENCE CHARACTERISTICS:
          (A) LENGTH: 5 amino acids
          (B) TYPE: amino acid
          (C) STRANDEDNESS:
          (D) TOPOLOGY: unknown (ii) MOLECULE TYPE: peptide (xi) SEQUENCE DESCRIPTION: SEQ ID NO:10:

Val Pro Phe Arg Ser
1               5

(2) INFORMATION FOR SEQ ID NO:11:

(i) SEQUENCE CHARACTERISTICS:
          (A) LENGTH: 6 amino acids
          (B) TYPE: amino acid
          (C) STRANDEDNESS:
          (D) TOPOLOGY: unknown (ii) MOLECULE TYPE: peptide (ix) FEATURE:
          (A) NAME/KEY: Peptide
          (B) LOCATION: 6
          (D) OTHER INFORMATION: /note= "The amino acid at this
               location is any non-acidic amino acid."

(xi) SEQUENCE DESCRIPTION: SEQ ID NO:11:

Leu Val Pro Arg Gly Xaa
1               5

(2) INFORMATION FOR SEQ ID NO:12:

(i) SEQUENCE CHARACTERISTICS:
          (A) LENGTH: 5 amino acids
          (B) TYPE: amino acid
          (C) STRANDEDNESS:
          (D) TOPOLOGY: unknown (ii) MOLECULE TYPE: peptide (ix) FEATURE:
          (A) NAME/KEY: Peptide
          (B) LOCATION: 2
          (D) OTHER INFORMATION: /note= "The amino acid at this
               location can be either leucine, phenylanine, isoleucine,
               valine, alanine or tryptophan."

(xi) SEQUENCE DESCRIPTION: SEQ ID NO:12:

Arg Xaa Val Arg Gly
1               5

(2) INFORMATION FOR SEQ ID NO:13:

(i) SEQUENCE CHARACTERISTICS:
          (A) LENGTH: 5 amino acids
          (B) TYPE: amino acid
          (C) STRANDEDNESS:

(D) TOPOLOGY: unknown (ii) MOLECULE TYPE: peptide (xi) SEQUENCE DESCRIPTION: SEQ ID NO:13:

Asp Asp Asp Asp Lys
1               5

(2) INFORMATION FOR SEQ ID NO:14:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:14:

Arg Xaa Arg Arg
1

(2) INFORMATION FOR SEQ ID NO:15:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:15:

Arg Xaa Lys Arg
1

(2) INFORMATION FOR SEQ ID NO:16:

(i) SEQUENCE CHARACTERISTICS:
            (A) LENGTH: 3 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:16:

Arg Arg Lys
1

(2) INFORMATION FOR SEQ ID NO:17:

(i) SEQUENCE CHARACTERISTICS:
            (A) LENGTH: 3 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:17:

Arg Lys Lys
1

(2) INFORMATION FOR SEQ ID NO:18:

(i) SEQUENCE CHARACTERISTICS:
            (A) LENGTH: 3 amino acids
            (B) TYPE: amino acid
            (C) STRANDEDNESS:

(D) TOPOLOGY: unknown (ii) MOLECULE TYPE: peptide (xi) SEQUENCE DESCRIPTION: SEQ ID NO:18:

Lys Arg Lys
1

(2) INFORMATION FOR SEQ ID NO:19:

(i) SEQUENCE CHARACTERISTICS:
            (A) LENGTH: 3 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:19:

Lys Lys Lys
1

(2) INFORMATION FOR SEQ ID NO:20:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:20:

Arg Arg Arg Lys
1

(2) INFORMATION FOR SEQ ID NO:21:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:21:

Arg Arg Lys Lys
1

(2) INFORMATION FOR SEQ ID NO:22:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:22:

Lys Arg Arg Lys
1

(2) INFORMATION FOR SEQ ID NO:23:

(i) SEQUENCE CHARACTERISTICS:
            (A) LENGTH: 4 amino acids
            (B) TYPE: amino acid
            (C) STRANDEDNESS:

(D) TOPOLOGY: unknown (ii) MOLECULE TYPE: peptide (xi) SEQUENCE DESCRIPTION: SEQ ID NO:23:

Arg Lys Arg Lys
1

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:24:

Arg Lys Lys Lys
1

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:25:

Lys Arg Lys Lys
1

(2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:26:

Lys Lys Arg Lys
1

(2) INFORMATION FOR SEQ ID NO:27:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:27:

Arg Arg Arg Arg Lys
1               5

(2) INFORMATION FOR SEQ ID NO:28:

(i) SEQUENCE CHARACTERISTICS:
        (A) LENGTH: 5 amino acids
        (B) TYPE: amino acid
        (C) STRANDEDNESS:

(D) TOPOLOGY: unknown (ii) MOLECULE TYPE: peptide (xi) SEQUENCE DESCRIPTION: SEQ ID NO:28:

Arg Arg Arg Lys Lys
1               5

(2) INFORMATION FOR SEQ ID NO:29:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:29:

Arg Arg Lys Arg Lys
1               5

(2) INFORMATION FOR SEQ ID NO:30:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:30:

Arg Lys Arg Arg Lys
1               5

(2) INFORMATION FOR SEQ ID NO:31:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:31:

Lys Arg Arg Arg Lys
1               5

(2) INFORMATION FOR SEQ ID NO:32:

(i) SEQUENCE CHARACTERISTICS:
        (A) LENGTH: 5 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:32:

Arg Arg Lys Lys Lys
1               5

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS:

(D) TOPOLOGY: unknown (ii) MOLECULE TYPE: peptide (xi) SEQUENCE DESCRIPTION: SEQ ID NO:33:

Arg Lys Arg Lys Lys
1               5

(2) INFORMATION FOR SEQ ID NO:34:

(i) SEQUENCE CHARACTERISTICS:
            (A) LENGTH: 5 amino acids
            (B) TYPE: amino acid
            (C) STRANDEDNESS:
            (D) TOPOLOGY: unknown
        (ii) MOLECULE TYPE: peptide (xi) SEQUENCE DESCRIPTION: SEQ ID NO:34:

Arg Lys Lys Arg Lys
1               5

(2) INFORMATION FOR SEQ ID NO:35:

(i) SEQUENCE CHARACTERISTICS:
            (A) LENGTH: 5 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:35:

Lys Arg Arg Lys Lys
1               5

(2) INFORMATION FOR SEQ ID NO:36:

(i) SEQUENCE CHARACTERISTICS:
            (A) LENGTH: 5 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:36:

Lys Arg Lys Arg Lys
1               5

(2) INFORMATION FOR SEQ ID NO:37:

(i) SEQUENCE CHARACTERISTICS:
            (A) LENGTH: 5 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:37:

Lys Arg Arg Lys Lys
1               5

(2) INFORMATION FOR SEQ ID NO:38:

(i) SEQUENCE CHARACTERISTICS:
            (A) LENGTH: 5 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:38:

Arg Lys Lys Lys Lys
1               5

(2) INFORMATION FOR SEQ ID NO:39:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:39:

Arg Ser Lys Arg
1

(2) INFORMATION FOR SEQ ID NO:40:

(i) SEQUENCE CHARACTERISTICS:
            (A) LENGTH: 4 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:40:

Arg Xaa Xaa Arg
1

(2) INFORMATION FOR SEQ ID NO:41:

(i) SEQUENCE CHARACTERISTICS:
            (A) LENGTH: 9 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:41:

Arg Arg Lys Leu Asp Asp Asp Asp Lys
1               5

(2) INFORMATION FOR SEQ ID NO:42:

(i) SEQUENCE CHARACTERISTICS:
            (A) LENGTH: 8 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:42:

Arg Lys Lys Lys Leu Val Pro Arg
1               5

(2) INFORMATION FOR SEQ ID NO:43:

(i) SEQUENCE CHARACTERISTICS:
            (A) LENGTH: 6 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:43:

Leu Val Pro Arg Gly Thr
1               5

(2) INFORMATION FOR SEQ ID NO:44:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:44:

CCGGGCGCGC GCGC                                                             14

(2) INFORMATION FOR SEQ ID NO:45:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:45:

CGTTTCGCCG GCTGGTTCCG CGGGGTCGAC GGATTCAGCT AGCA                             44

(2) INFORMATION FOR SEQ ID NO:46:

(i) SEQUENCE CHARACTERISTICS:
            (A) LENGTH: 52 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:46:

AGCTTGCTAG CTGAATCCGT CGACCCCGCG GAACCAGCCG GCGAAACGAG CT                    52

(2) INFORMATION FOR SEQ ID NO:47:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:47:

CGTTTAAAAA GAAACCGCGG GGCCCGGGTA C                                          31

(2) INFORMATION FOR SEQ ID NO:48:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:48:

CCGGGCCCCG CGGTTTCTTT TTAAACGAGC T                                31

(2) INFORMATION FOR SEQ ID NO:49:

(i) SEQUENCE CHARACTERISTICS:
        (A) LENGTH: 699 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..699

(xi) SEQUENCE DESCRIPTION: SEQ ID NO:49:

```
GAG CCC AAA TCT TGT GAC AAA ACT CAC ACA TGC CCA CCG TGC CCA GCA      48
Glu Pro Lys Ser Cys Asp Lys Thr His Thr Cys Pro Pro Cys Pro Ala
 1               5                  10                  15

CCA GAA CTC CTG GGG GGA CCG TCA GTC TTC CTC TTC CCC CCA AAA CCC      96
Pro Glu Leu Leu Gly Gly Pro Ser Val Phe Leu Phe Pro Pro Lys Pro
             20                  25                  30

AAG GAC ACC CTC ATG ATC TCC CGG ACC CCT GAG GTC ACA TGC GTG GTG     144
Lys Asp Thr Leu Met Ile Ser Arg Thr Pro Glu Val Thr Cys Val Val
         35                  40                  45

GTG GAC GTG AGC CAC GAA GAC CCT GAG GTC AAG TTC AAC TGG TAC GTG     192
Val Asp Val Ser His Glu Asp Pro Glu Val Lys Phe Asn Trp Tyr Val
 50                  55                  60

GAC GGC GTG GAG GTG CAT AAT GCC AAG ACA AAG CCG CGG GAG GAG CAG     240
Asp Gly Val Glu Val His Asn Ala Lys Thr Lys Pro Arg Glu Glu Gln
 65                  70                  75                  80

TAC AAC AGC ACG TAC CGG GTG GTC AGC GTC CTC ACC GTC CTG CAC CAG     288
Tyr Asn Ser Thr Tyr Arg Val Val Ser Val Leu Thr Val Leu His Gln
             85                  90                  95

GAC TGG CTG AAT GGC AAG GAG TAC AAG TGC AAG GTC TCC AAC AAA GCC     336
Asp Trp Leu Asn Gly Lys Glu Tyr Lys Cys Lys Val Ser Asn Lys Ala
                100                 105                 110

CTC CCA GCC CCC ATC GAG AAA ACC ATC TCC AAA GCC AAA GGG CAG CCC     384
Leu Pro Ala Pro Ile Glu Lys Thr Ile Ser Lys Ala Lys Gly Gln Pro
            115                 120                 125

CGA GAA CCA CAG GTG TAC ACC CTG CCC CCA TCC CGG GAT GAG CTG ACC     432
Arg Glu Pro Gln Val Tyr Thr Leu Pro Pro Ser Arg Asp Glu Leu Thr
130                 135                 140

AAG AAC CAG GTC AGC CTG ACC TGC CTG GTC AAA GGC TTC TAT CCC AGC     480
Lys Asn Gln Val Ser Leu Thr Cys Leu Val Lys Gly Phe Tyr Pro Ser
145                 150                 155                 160

GAC ATC GCC GTG GAG TGG GAG AGC AAT GGG CAG CCG GAG AAC AAC TAC     528
Asp Ile Ala Val Glu Trp Glu Ser Asn Gly Gln Pro Glu Asn Asn Tyr
                165                 170                 175

AAG ACC ACG CCT CCC GTG CTG GAC TCC GAC GGC TCC TTC TTC CTC TAC     576
Lys Thr Thr Pro Pro Val Leu Asp Ser Asp Gly Ser Phe Phe Leu Tyr
            180                 185                 190

AGC AAG CTC ACC GTG GAC AAG AGC AGG TGG CAG CAG GGG AAC GTC TTC     624
Ser Lys Leu Thr Val Asp Lys Ser Arg Trp Gln Gln Gly Asn Val Phe
        195                 200                 205

TCA TGC TCC GTG ATG CAT GAG GCT CTG CAC AAC CAC TAC ACG CAG AAG     672
Ser Cys Ser Val Met His Glu Ala Leu His Asn His Tyr Thr Gln Lys
    210                 215                 220

AGC CTC TCC CTG TCT CCG GGT AAA TGA                                 699
Ser Leu Ser Leu Ser Pro Gly Lys *
225                 230
```

(2) INFORMATION FOR SEQ ID NO:50:

(i) SEQUENCE CHARACTERISTICS:
        (A) LENGTH: 232 amino acids
        (B) TYPE: amino acid
        (D) TOPOLOGY: linear (ii) MOLECULE TYPE: protein (xi) SEQUENCE DESCRIPTION: SEQ ID NO:50:

```
Glu Pro Lys Ser Cys Asp Lys Thr His Thr Cys Pro Pro Cys Pro Ala
  1               5                  10                  15
Pro Glu Leu Leu Gly Gly Pro Ser Val Phe Leu Phe Pro Pro Lys Pro
                 20                  25                  30
Lys Asp Thr Leu Met Ile Ser Arg Thr Pro Glu Val Thr Cys Val Val
             35                  40                  45
Val Asp Val Ser His Glu Asp Pro Glu Val Lys Phe Asn Trp Tyr Val
         50                  55                  60
Asp Gly Val Glu Val His Asn Ala Lys Thr Lys Pro Arg Glu Glu Gln
 65                  70                  75                  80
Tyr Asn Ser Thr Tyr Arg Val Val Ser Val Leu Thr Val Leu His Gln
                 85                  90                  95
Asp Trp Leu Asn Gly Lys Glu Tyr Lys Cys Lys Val Ser Asn Lys Ala
            100                 105                 110
Leu Pro Ala Pro Ile Glu Lys Thr Ile Ser Lys Ala Lys Gly Gln Pro
        115                 120                 125
Arg Glu Pro Gln Val Tyr Thr Leu Pro Pro Ser Arg Asp Glu Leu Thr
130                 135                 140
Lys Asn Gln Val Ser Leu Thr Cys Leu Val Lys Gly Phe Tyr Pro Ser
145                 150                 155                 160
Asp Ile Ala Val Glu Trp Glu Ser Asn Gly Gln Pro Glu Asn Asn Tyr
                165                 170                 175
Lys Thr Thr Pro Pro Val Leu Asp Ser Asp Gly Ser Phe Phe Leu Tyr
            180                 185                 190
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230
```

(2) INFORMATION FOR SEQ ID NO:51:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CCCCCGCCGG CACACATGCC CACCGTCGCC AGCA                              34

(2) INFORMATION FOR SEQ ID NO:52:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

CCCCCGTCGA CGGACATGCC CACCGTGCCC A                                    31

(2) INFORMATION FOR SEQ ID NO:53:

(i) SEQUENCE CHARACTERISTICS:
             (A) LENGTH: 35 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:53:

GGGGTACCCA CACATGCCCA CCGTGCCCAG CACCT                                35

(2) INFORMATION FOR SEQ ID NO:54:

(i) SEQUENCE CHARACTERISTICS:
             (A) LENGTH: 35 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:54:

CCCCCGCTAG CGTCATTTAC CCGGAGACAG GGAGA                                35

(2) INFORMATION FOR SEQ ID NO:55:

(i) SEQUENCE CHARACTERISTICS:
             (A) LENGTH: 35 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:55:

CATGGACTGA AAGCTTGACG GTACCTGAGC TAGCT                                35

(2) INFORMATION FOR SEQ ID NO:56:

(i) SEQUENCE CHARACTERISTICS:
             (A) LENGTH: 35 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:56:

AGCTAGCTAG CTCAGGTACC GTCAAGCTTT CAGTC                                35

(2) INFORMATION FOR SEQ ID NO:57:

(i) SEQUENCE CHARACTERISTICS:
             (A) LENGTH: 34 base pairs
             (B) TYPE: nucleic acid
             (C) STRANDEDNESS: single
             (D) TOPOLOGY: linear (ii) MOLECULE TYPE: DNA (genomic)

(xi) SEQUENCE DESCRIPTION: SEQ ID NO:57:

```
CATGAAACAA AGCACTATTG CACTGGCTTT ACCG                                34
```

(2) INFORMATION FOR SEQ ID NO:58:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
TTACTGTTTA CCCCTGTGAC AAA                                            23
```

(2) INFORMATION FOR SEQ ID NO:59:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

```
AGCTTTTGTC ACAGGGGTAA ACAGTAACGG TAAAGC                              36
```

(2) INFORMATION FOR SEQ ID NO:60:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
CAGTGCAATA GTGCTTTGTT T                                              21
```

(2) INFORMATION FOR SEQ ID NO:61:

(i) SEQUENCE CHARACTERISTICS:
        (A) LENGTH: 20 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:61:

```
Met Lys Gln Ser Thr Ile Ala Leu Ala Leu Pro Leu Leu Phe Thr Pro
1               5                   10                  15

Val Thr Lys Ala
            20
```

(2) INFORMATION FOR SEQ ID NO:62:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

```
CTAGCTGATC GCGAAAGAAG CTGCCGTTCC ACCTGCTGGT GTACGGTAC                49
```

(2) INFORMATION FOR SEQ ID NO:63:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

CGTACACCAG CAGGTGGAAC GGCAGCTTCT TTCGCGATCA G               41

(2) INFORMATION FOR SEQ ID NO:64:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GATCTTCGCG AAAGAAGAAG CTTCCGTTTC ACCTGCTGGT CTACGGTAC       49

(2) INFORMATION FOR SEQ ID NO:65:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

CGTAGACCAG CAGGTGAAAC GGAAGCTTCT TCTTTCGCGA A               41

(2) INFORMATION FOR SEQ ID NO:66:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

CTAGCCCCCC                                                    10

(2) INFORMATION FOR SEQ ID NO:67:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

GATCGGGGGG                                                    10

(2) INFORMATION FOR SEQ ID NO:68:

(i) SEQUENCE CHARACTERISTICS:

(A) LENGTH: 37 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:68:

GATCTTCGCG AAAGAAGAAG CTGGTTCCGC GGGGTAC                             37

(2) INFORMATION FOR SEQ ID NO:69:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:69:

CCCGCGGAAC CAGCTTCTTC TTTCGCGAA                                     29

(2) INFORMATION FOR SEQ ID NO:70:

(i) SEQUENCE CHARACTERISTICS:
            (A) LENGTH: 12 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:70:

Ala Leu Lys Asp Ala Gln Thr Asn Ser Ser Ser Phe
1               5                   10

(2) INFORMATION FOR SEQ ID NO:71:

(i) SEQUENCE CHARACTERISTICS:
            (A) LENGTH: 7 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:71:

Phe Leu Ala Pro Arg Gly Thr
1               5

(2) INFORMATION FOR SEQ ID NO:72:

(i) SEQUENCE CHARACTERISTICS:
            (A) LENGTH: 6 amino acids
            (B) TYPE: amino acid
            (C) STRANDEDNESS:
            (D) TOPOLOGY: unknown (ii) MOLECULE TYPE: peptide (xi) SEQUENCE DESCRIPTION: SEQ ID NO:72:

Ala Pro Tyr Gly Pro Pro
1               5

(2) INFORMATION FOR SEQ ID NO:73:

(i) SEQUENCE CHARACTERISTICS:
            (A) LENGTH: 10 amino acids
            (B) TYPE: amino acid (C) STRANDEDNESS:
                    (D) TOPOLOGY: unknown (ii) MOLECULE TYPE: peptide (xi) SEQUENCE DESCRIPTION: SEQ ID NO:73:

Pro Leu Ser Arg Leu Ser Val Ala Lys Lys
1               5                   10

(2) INFORMATION FOR SEQ ID NO:74:

(i) SEQUENCE CHARACTERISTICS:
                    (A) LENGTH: 726 base pairs
                    (B) TYPE: nucleic acid
                    (C) STRANDEDNESS: double
                    (D) TOPOLOGY: linear (ii) MOLECULE TYPE: cDNA (ix) FEATURE:
                    (A) NAME/KEY: CDS
                    (B) LOCATION: 1..726

(xi) SEQUENCE DESCRIPTION: SEQ ID NO:74:

```
ATG TCC ATG TTG TTC TAC ACT CTG ATC ACA GCT TTT CTG ATC GGC ATA        48
Met Ser Met Leu Phe Tyr Thr Leu Ile Thr Ala Phe Leu Ile Gly Ile
1               5                   10                  15

CAG GCG GAA CCA CAC TCA GAG AGC AAT GTC CCT GCA GGA CAC ACC ATC        96
Gln Ala Glu Pro His Ser Glu Ser Asn Val Pro Ala Gly His Thr Ile
                20                  25                  30

CCC CAA GTC CAC TGG ACT AAA CTT CAG CAT TCC CTT GAC ACT GCC CTT       144
Pro Gln Val His Trp Thr Lys Leu Gln His Ser Leu Asp Thr Ala Leu
            35                  40                  45

CGC AGA GCC CGC AGC GCC CCG GCA GCG GCG ATA GCT GCA CGC GTG GCG       192
Arg Arg Ala Arg Ser Ala Pro Ala Ala Ala Ile Ala Ala Arg Val Ala
    50                  55                  60

GGG CAG ACC CGC AAC ATT ACT GTG GAC CCC AGG CTG TTT AAA AAG CGG       240
Gly Gln Thr Arg Asn Ile Thr Val Asp Pro Arg Leu Phe Lys Lys Arg
65                  70                  75                  80

CGA CTC CGT TCA CCC CGT GTG CTG TTT AGC ACC CAG CCT CCC CGT GAA       288
Arg Leu Arg Ser Pro Arg Val Leu Phe Ser Thr Gln Pro Pro Arg Glu
                85                  90                  95

GCT GCA GAC ACT CAG GAT CTG GAC TTC GAG GTC GGT GGT GCT GCC CCC       336
Ala Ala Asp Thr Gln Asp Leu Asp Phe Glu Val Gly Gly Ala Ala Pro
                100                 105                 110

TTC AAC AGG ACT CAC AGG AGC AAG CGG TCA TCA TCC CAT CCC ATC TTC       384
Phe Asn Arg Thr His Arg Ser Lys Arg Ser Ser Ser His Pro Ile Phe
            115                 120                 125

CAC AGG GGC GAA TTC TCG GTG TGT GAC AGT GTC AGC GTG TGG GTT GGG       432
His Arg Gly Glu Phe Ser Val Cys Asp Ser Val Ser Val Trp Val Gly
    130                 135                 140

GAT AAG ACC ACC GCC ACA GAC ATC AAG GGC AAG GAG GTG ATG GTG TTG       480
Asp Lys Thr Thr Ala Thr Asp Ile Lys Gly Lys Glu Val Met Val Leu
145                 150                 155                 160

GGA GAG GTG AAC ATT AAC AAC AGT GTA TTC AAA CAG TAC TTT TTT GAG       528
Gly Glu Val Asn Ile Asn Asn Ser Val Phe Lys Gln Tyr Phe Phe Glu
                165                 170                 175

ACC AAG TGC CGG GAC CCA AAT CCC GTT GAC AGC GGG TGC CGG GGC ATT       576
Thr Lys Cys Arg Asp Pro Asn Pro Val Asp Ser Gly Cys Arg Gly Ile
                180                 185                 190

GAC TCA AAG CAC TGG AAC TCA TAT TGT ACC ACG ACT CAC ACC TTT GTC       624
Asp Ser Lys His Trp Asn Ser Tyr Cys Thr Thr Thr His Thr Phe Val
            195                 200                 205
```

```
AAG GCG CTG ACC ATG GAT GGC AAG CAG GCT GCC TGG CGG TTT ATC CGG    672
Lys Ala Leu Thr Met Asp Gly Lys Gln Ala Ala Trp Arg Phe Ile Arg
210                 215                 220

ATA GAT ACG GCC TGT GTG TGT GTG CTC AGC AGG AAG GCT GTG AGA AGA    720
Ile Asp Thr Ala Cys Val Cys Val Leu Ser Arg Lys Ala Val Arg Arg
225                 230                 235                 240

GCC TGA                                                             726
Ala *
```

(2) INFORMATION FOR SEQ ID NO:75:

(i) SEQUENCE CHARACTERISTICS:
        (A) LENGTH: 241 amino acids
        (B) TYPE: amino acid
        (D) TOPOLOGY: linear (ii) MOLECULE TYPE: protein (xi) SEQUENCE DESCRIPTION: SEQ ID NO:75:

```
Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
                20                  25                  30

Pro Gln Val His Trp Thr Lys Leu Gln His Ser Leu Asp Thr Ala Leu
            35                  40                  45

Arg Arg Ala Arg Ser Ala Pro Ala Ala Ile Ala Ala Arg Val Ala
        50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
                100                 105                 110

Phe Asn Arg Thr His Arg Ser Lys Arg Ser Ser His Pro Ile Phe
            115                 120                 125

His Arg Gly Glu Phe Ser Val Cys Asp Ser Val Ser Val Trp Val Gly
        130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
                180                 185                 190

Asp Ser Lys His Trp Asn Ser Tyr Cys Thr Thr Thr His Thr Phe Val
            195                 200                 205

Lys Ala Leu Thr Met Asp Gly Lys Gln Ala Ala Trp Arg Phe Ile Arg
        210                 215                 220

Ile Asp Thr Ala Cys Val Cys Val Leu Ser Arg Lys Ala Val Arg Arg
225                 230                 235                 240

Ala
```

(2) INFORMATION FOR SEQ ID NO:76:

(i) SEQUENCE CHARACTERISTICS:
        (A) LENGTH: 744 base pairs
        (B) TYPE: nucleic acid
        (C) STRANDEDNESS: double
        (D) TOPOLOGY: linear (ii) MOLECULE TYPE: cDNA (ix) FEATURE:
    (A) NAME/KEY: CDS
    (B) LOCATION: 1..744

(xi) SEQUENCE DESCRIPTION: SEQ ID NO:76:

| | | | | | | | | | | | | | | | | |
|---|---|---|---|---|---|---|---|---|---|---|---|---|---|---|---|---|
| ATG | ACC | ATC | CTT | TTC | CTT | ACT | ATG | GTT | ATT | TCA | TAC | TTT | GGT | TGC | ATG | 48 |
| Met | Thr | Ile | Leu | Phe | Leu | Thr | Met | Val | Ile | Ser | Tyr | Phe | Gly | Cys | Met | |
| 1 | | | | 5 | | | | | 10 | | | | | 15 | | |
| AAG | GCT | GCC | CCC | ATG | AAA | GAA | GCA | AAC | ATC | CGA | GGA | CAA | GGT | GGC | TTG | 96 |
| Lys | Ala | Ala | Pro | Met | Lys | Glu | Ala | Asn | Ile | Arg | Gly | Gln | Gly | Gly | Leu | |
| | | | 20 | | | | | 25 | | | | | 30 | | | |
| GCC | TAC | CCA | GGT | GTG | CGG | ACC | CAT | GGG | ACT | CTG | GAG | AGC | GTG | AAT | GGG | 144 |
| Ala | Tyr | Pro | Gly | Val | Arg | Thr | His | Gly | Thr | Leu | Glu | Ser | Val | Asn | Gly | |
| | | 35 | | | | | 40 | | | | | 45 | | | | |
| CCC | AAG | GCA | GGT | TCA | AGA | GGC | TTG | ACA | TCA | TTG | GCT | GAC | ACT | TTC | GAA | 192 |
| Pro | Lys | Ala | Gly | Ser | Arg | Gly | Leu | Thr | Ser | Leu | Ala | Asp | Thr | Phe | Glu | |
| | 50 | | | | | 55 | | | | | 60 | | | | | |
| CAC | GTG | ATA | GAA | GAG | CTG | TTG | GAT | GAG | GAC | CAG | AAA | GTT | CGG | CCC | AAT | 240 |
| His | Val | Ile | Glu | Glu | Leu | Leu | Asp | Glu | Asp | Gln | Lys | Val | Arg | Pro | Asn | |
| 65 | | | | | 70 | | | | | 75 | | | | | 80 | |
| GAA | GAA | AAC | AAT | AAG | GAC | GCA | GAC | TTG | TAC | ACG | TCC | AGG | GTG | ATG | CTC | 288 |
| Glu | Glu | Asn | Asn | Lys | Asp | Ala | Asp | Leu | Tyr | Thr | Ser | Arg | Val | Met | Leu | |
| | | | | 85 | | | | | 90 | | | | | 95 | | |
| AGT | AGT | CAA | GTG | CCT | TTG | GAG | CCT | CCT | CTT | CTC | TTT | CTG | CTG | GAG | GAA | 336 |
| Ser | Ser | Gln | Val | Pro | Leu | Glu | Pro | Pro | Leu | Leu | Phe | Leu | Leu | Glu | Glu | |
| | | | 100 | | | | | 105 | | | | | 110 | | | |
| TAC | AAA | AAT | TAC | CTA | GAT | GCT | GCA | AAC | ATG | TCC | ATG | AGG | GTC | CGG | CGC | 384 |
| Tyr | Lys | Asn | Tyr | Leu | Asp | Ala | Ala | Asn | Met | Ser | Met | Arg | Val | Arg | Arg | |
| | | 115 | | | | | 120 | | | | | 125 | | | | |
| CAC | TCT | GAC | CCT | GCC | CGC | CGA | GGG | GAG | CTG | AGC | GTG | TGT | GAC | AGT | ATT | 432 |
| His | Ser | Asp | Pro | Ala | Arg | Arg | Gly | Glu | Leu | Ser | Val | Cys | Asp | Ser | Ile | |
| | 130 | | | | | 135 | | | | | 140 | | | | | |
| AGT | GAG | TGG | GTA | ACG | GCG | GCA | GAC | AAA | AAG | ACT | GCA | GTG | GAC | ATG | TCG | 480 |
| Ser | Glu | Trp | Val | Thr | Ala | Ala | Asp | Lys | Lys | Thr | Ala | Val | Asp | Met | Ser | |
| 145 | | | | | 150 | | | | | 155 | | | | | 160 | |
| GGC | GGG | ACG | GTC | ACA | GTC | CTT | GAA | AAG | GTC | CCT | GTA | TCA | AAA | GGC | CAA | 528 |
| Gly | Gly | Thr | Val | Thr | Val | Leu | Glu | Lys | Val | Pro | Val | Ser | Lys | Gly | Gln | |
| | | | | 165 | | | | | 170 | | | | | 175 | | |
| CTG | AAG | CAA | TAC | TTC | TAC | GAG | ACC | AAG | TGC | AAT | CCC | ATG | GGT | TAC | ACA | 576 |
| Leu | Lys | Gln | Tyr | Phe | Tyr | Glu | Thr | Lys | Cys | Asn | Pro | Met | Gly | Tyr | Thr | |
| | | | 180 | | | | | 185 | | | | | 190 | | | |
| AAA | GAA | GGC | TGC | AGG | GGC | ATA | GAC | AAA | AGG | CAT | TGG | AAC | TCC | CAG | TGC | 624 |
| Lys | Glu | Gly | Cys | Arg | Gly | Ile | Asp | Lys | Arg | His | Trp | Asn | Ser | Gln | Cys | |
| | | 195 | | | | | 200 | | | | | 205 | | | | |
| CGA | ACT | ACC | CAG | TCG | TAC | GTG | CGG | GCC | CTT | ACC | ATG | GAT | AGC | AAA | AAG | 672 |
| Arg | Thr | Thr | Gln | Ser | Tyr | Val | Arg | Ala | Leu | Thr | Met | Asp | Ser | Lys | Lys | |
| | 210 | | | | | 215 | | | | | 220 | | | | | |
| AGA | ATT | GGC | TGG | CGA | TTC | ATA | AGG | ATA | GAC | ACT | TCT | TGT | GTA | TGT | ACA | 720 |
| Arg | Ile | Gly | Trp | Arg | Phe | Ile | Arg | Ile | Asp | Thr | Ser | Cys | Val | Cys | Thr | |
| 225 | | | | | 230 | | | | | 235 | | | | | 240 | |
| TTG | ACC | ATT | AAA | AGG | GGA | AGA | TAG | | | | | | | | | 744 |
| Leu | Thr | Ile | Lys | Arg | Gly | Arg | * | | | | | | | | | |
| | | | | 245 | | | | | | | | | | | | |

(2) INFORMATION FOR SEQ ID NO:77:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:77:

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
            35                  40                  45

Pro Lys Ala Gly Ser Arg Gly Leu Thr Ser Leu Ala Asp Thr Phe Glu
            50                  55                  60

His Val Ile Glu Glu Leu Leu Asp Glu Asp Gln Lys Val Arg Pro Asn
65                  70                  75                  80

Glu Glu Asn Asn Lys Asp Ala Asp Leu Tyr Thr Ser Arg Val Met Leu
                85                  90                  95

Ser Ser Gln Val Pro Leu Glu Pro Pro Leu Leu Phe Leu Leu Glu Glu
                100                 105                 110

Tyr Lys Asn Tyr Leu Asp Ala Ala Asn Met Ser Met Arg Val Arg Arg
            115                 120                 125

His Ser Asp Pro Ala Arg Arg Gly Glu Leu Ser Val Cys Asp Ser Ile
            130                 135                 140

Ser Glu Trp Val Thr Ala Ala Asp Lys Lys Thr Ala Val Asp Met Ser
145                 150                 155                 160

Gly Gly Thr Val Thr Val Leu Glu Lys Val Pro Val Ser Lys Gly Gln
            165                 170                 175

Leu Lys Gln Tyr Phe Tyr Glu Thr Lys Cys Asn Pro Met Gly Tyr Thr
            180                 185                 190

Lys Glu Gly Cys Arg Gly Ile Asp Lys Arg His Trp Asn Ser Gln Cys
            195                 200                 205

Arg Thr Thr Gln Ser Tyr Val Arg Ala Leu Thr Met Asp Ser Lys Lys
            210                 215                 220

Arg Ile Gly Trp Arg Phe Ile Arg Ile Asp Thr Ser Cys Val Cys Thr
225                 230                 235                 240

Leu Thr Ile Lys Arg Gly Arg
                245

(2) INFORMATION FOR SEQ ID NO:78:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:78:

Leu Lys Arg Arg
1

(2) INFORMATION FOR SEQ ID NO:79:

(i) SEQUENCE CHARACTERISTICS:
        (A) LENGTH: 3 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:79:

Lys Arg Arg
1

(2) INFORMATION FOR SEQ ID NO:80:

(i) SEQUENCE CHARACTERISTICS:
        (A) LENGTH: 4 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:80:

Leu Lys Lys Lys
1

(2) INFORMATION FOR SEQ ID NO:81:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:81:

GAACCACACT CAGAGAGCAA TGTCCCTGCA GGACACACCA T                    41

(2) INFORMATION FOR SEQ ID NO:82:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:82:

CCCGCCGGCT GAGCACACAC ACACAGGCCG TATCTATCCG GATAAA              46

(2) INFORMATION FOR SEQ ID NO:83:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

CCGGAAGGCT GTGAGACTTA AGCGGCGGGG TAC                             33

(2) INFORMATION FOR SEQ ID NO:84:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

CCCGCCGCTT AAGTCTCACA GCCTT                                      25

(2) INFORMATION FOR SEQ ID NO:85:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

ATGACCATCC TTTTCCTTAC TATGGTTATT TCATACTTTG GT                42

(2) INFORMATION FOR SEQ ID NO:86:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

GGGACGCGTT TAATGGTCAA TGTACATACA CAAGAAGTGC TTATCCT            47

(2) INFORMATION FOR SEQ ID NO:87:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:87:

CGCGGAAGAC TTAAGAAGAA ACTGCCGTTC CACCTGCTGT ACGGTAC            47

(2) INFORMATION FOR SEQ ID NO:88:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:88:

CGTACAGCAG GTGGAACGGC AGTTTCTTCT TAAGTCTTC                    39

(2) INFORMATION FOR SEQ ID NO:89:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:89:

ATGGAGCTGA GGCCCTGGTT GCTATGGGTG                            30

(2) INFORMATION FOR SEQ ID NO:90:

(i) SEQUENCE CHARACTERISTICS:

-continued

```
        (A) LENGTH: 6 amino acids
        (B) TYPE: amino acid
        (C) STRANDEDNESS:
        (D) TOPOLOGY: unknown (ii) MOLECULE TYPE: peptide (ix) FEATURE:
        (A) NAME/KEY: Peptide
        (B) LOCATION: 5..6
        (D) OTHER INFORMATION: /note= "The glutamine and lysine
            residues at this location may be repeated as a unit 1 to 5
            times."

(xi) SEQUENCE DESCRIPTION: SEQ ID NO:90:

Gln Gly Pro Gly Gln Lys
1               5
```